(12) United States Patent
Imai et al.

(10) Patent No.: US 6,458,908 B1
(45) Date of Patent: Oct. 1, 2002

(54) SULFUR-CONTAINING UNSATURATED CARBOXYLATE COMPOUND AND ITS CURED PRODUCTS

(75) Inventors: Masao Imai; Kenichi Sugimoto; Kenichi Fujii; Atsuo Otsuji, all of Kanagawa; Tadashi Ohkuma, Chiba; Masatoshi Takagi, Kanagawa; Rihoko Suzuki, Chiba; Keisuke Takuma, Kanagawa, all of (JP)

(73) Assignee: Mitsui Chemicals, Inc. (JP)

( * ) Notice: Subject to any disclaimer, the term of this patent is extended or adjusted under 35 U.S.C. 154(b) by 22 days.

(21) Appl. No.: 09/583,469

(22) Filed: May 31, 2000

(30) Foreign Application Priority Data

| Jun. 1, 1999 | (JP) | ............................................. 11-153389 |
| Jun. 16, 1999 | (JP) | ............................................. 11-169511 |
| Dec. 20, 1999 | (JP) | ............................................. 11-360634 |
| Jan. 11, 2000 | (JP) | ............................................. 2000-002329 |
| Feb. 1, 2000 | (JP) | ............................................. 2000-024152 |
| Feb. 23, 2000 | (JP) | ............................................. 2000-045348 |

(51) Int. Cl.$^7$ .................... C08F 28/06; C08F 26/06; C07C 69/34; C07D 277/60; C07D 341/00
(52) U.S. Cl. ................ 526/259; 526/260; 526/284; 526/286; 526/289; 526/296; 526/256; 548/150; 548/159; 548/160; 548/201; 548/215; 548/217; 549/19; 549/20; 549/22; 549/35; 549/39; 549/79; 560/201; 560/195; 560/196; 560/205; 560/220; 560/221; 560/222; 560/224
(58) Field of Search .................. 548/150, 159, 548/160, 201, 215, 217; 549/19, 20, 22, 35, 36, 39, 71, 79; 560/195, 196, 201, 205, 220, 221, 222, 224; 526/256, 259, 260, 284, 286, 289, 296

(56) References Cited

FOREIGN PATENT DOCUMENTS

| JP | 58130450 | | 8/1983 |
|---|---|---|---|
| JP | 58137150 | | 8/1983 |
| JP | 60135901 | | 7/1985 |
| JP | 60202557 | | 10/1985 |
| JP | 60203414 | | 10/1985 |
| JP | 62280008 | | 12/1987 |
| JP | 63248814 | | 10/1988 |
| JP | 03217412 | | 9/1991 |
| JP | 04161410 | | 6/1992 |
| JP | 10067736 | | 3/1998 |
| JP | 10130250 | | 5/1998 |
| JP | 226438 | * | 8/2001 |

OTHER PUBLICATIONS

V. N. Rajasekharan Pillai et al, "New, Easily Removable Poly(ethylene glycol) Supports for the Liquid Phase Method of Peptide Synthesis", J. Org. Chem., vol. 45, pp. 5364–5370, 1980.

A. Okamoto et al, "Effect of Polymer as Cosolvent on Chemical Reactions in Solution", Eur. Polym. J., vol. 19, No. 5, pp. 399–403, 1983.

Jikken Kagaku Koza, 4$^{th}$ ed., vol. 20, pp. 49–51.

Synthesis, p. 763, 1986.

\* cited by examiner

*Primary Examiner*—Christopher Henderson
(74) *Attorney, Agent, or Firm*—Burns, Doane, Swecker, & Mathis, L.L.P.

(57) ABSTRACT

A sulfur-containing unsaturated carboxylate compound comprising a sulfur-containing substituent and at least two α,β-unsaturated carboxylic acid residues, which are each attached to a secondary or tertiary carbon atom via an oxygen atom; a polymerizable composition comprising the sulfur-containing unsaturated carboxylate compound; a cured product prepared by polymerizing the polymerizable composition; an optical component consisting of the cured product; and novel intermediate compounds for preparation of the above carboxylate.

29 Claims, No Drawings

SULFUR-CONTAINING UNSATURATED CARBOXYLATE COMPOUND AND ITS CURED PRODUCTS

BACKGROUND OF THE INVENTION

1. Field of the Invention

This invention relates to a sulfur-containing unsaturated carboxylate comprising a sulfur-containing substituent and at least two α,β-unsaturated carboxylic acid residues via an oxygen atom attached to a secondary or tertiary carbon atom. This invention also relates to a polymerizable composition comprising the sulfur-containing unsaturated carboxylate compound and to an optical component produced by polymerizing the polymerizable composition.

A sulfur-containing unsaturated carboxylate compound according to this invention has a structural feature that it intramolecularly comprises a sulfur-containing substituent and at least two α,β-unsaturated carboxylic acid residues, which are each attached to a secondary or tertiary carbon atom via an oxygen atom.

The sulfur-containing unsaturated carboxylate compound is useful as a monomer for a polymerizable composition which is photocurable or thermosetting, and is suitably used in a variety of materials such as optical materials and dental materials. An optical component produced by curing the polymerizable composition has excellent optical, thermal and mechanical properties; can be produced in an improved yield; has a higher refractive index; and is useful in various applications such as a variety of plastic lenses (typically, an orthodontic eyeglass), optical information recording media, plastic substrates for a liquid crystal cell and optical-fiber coatings.

2. Description of the Prior Art

Inorganic glasses have a number of excellent physical properties such as excellent transparency and a reduced optical anisotropy, and thus has been used as a transparent optical material in various applications. The glasses, however, have problems such as fragility due to their heavy weight and a poor productivity, leading to recent intensive attempts for developing an optical resin as a substitute for an inorganic glass.

An essential property is transparency for an optical material. To date, various industrial resins with good transparency are known; for example, polymethyl methacrylate (PMMA), bisphenol-A-polycarbonate (BPA-PC), polystyrene (PS), methyl methacrylate-styrene copolymer (MS), styrene-acrylonitrile copolymer (SAN), poly(4-methylpentene-1) (TPX), polycycloolefin (COP), poly(diethyleneglycol bisallylcarbonate) (EGAC) and polythiourethane (PTU).

PMMA exhibits good transparency, weather resistance and moldability, but has drawbacks such as a lower refractive index ($n_d$) of 1.49 and a higher absorbency.

BPA-PC exhibits good transparency, heat resistance and shock resistance and a higher refractive index, but a larger chromatic aberration, which limits its application.

PS and MS exhibit good moldability and transparency as well as have a lower absorbency and a higher refractive index, but exhibit lower shock resistance, weather resistance and heat resistance. They have been, therefore, rarely used as an optical resin in practice.

SAN is believed to have a relatively higher refractive index and well-balanced mechanical properties, but it is inadequately heat resistant (heat-distortion point: 80 to 90° C.) to be used as an optical resin.

TPX and COP exhibit good transparency, lower absorbency and good heat resistance, but have drawbacks such as a lower refractive index ($n_d$=1.47 to 1.53), lower shock resistance, lower gas barrier property and poor dye-affinity.

EGAC is a thermosetting resin from diethyleneglycol bisallylcarbonate monomer, which is most frequently used for a general-purpose eyeglass. It exhibits good transparency, good heat resistance and a minimal chromatic aberration, but has drawbacks such as a lower refractive index ($n_d$=1.50) and lower shock resistance.

PTU is a thermosetting resin prepared by reaction of a diisocyanate with a polythiol, which is most frequently used for a superhigh refractive index eyeglass. It is an excellent material with good transparency, good shock resistance, a higher refractive index and a lower chromatic aberration, but has only one drawback of a longer duration for thermal-polymerization molding (1 to 3 days); i.e. , there is a problem in productivity.

To reduce duration for polymerization or curing for improving the above yield, various procedures have been suggested, including a process for manufacturing an optical lens by optical polymerization using bromine- or sulfur-containing acrylates; for example, JP-A 4-161410 and JP-A 3-217412. According to the process, polymerization can be conducted in a reduced period, but an obtained resin is not satisfactory as an optical component. For example, when it is used as an eyeglass, a resin with a higher refractive index is fragile and has a higher specific gravity. Thus, a material has been earnestly desired, which can solve these problems.

As described above, optical resins of the prior art have good properties, but they have their specific problems to be solved. Thus, it has been earnestly desired to develop an optical resin with good optical, mechanical and thermal properties as well as a good productivity and a higher refractive index.

SUMMARY OF THE INVENTION

Thus, an object of this invention for solving the drawbacks in a conventional optical resin is to provide an optical resin with good optical, mechanical and thermal properties as well as a good productivity and a higher refractive index.

We have intensely attempted to solve the problems to achieve this invention.

This invention provides the followings:

<1> A sulfur-containing unsaturated carboxylate compound comprising a sulfur-containing substituent and at least two α,β-unsaturated carboxylic acid residues, which are each attached to a secondary or tertiary carbon atom via an oxygen atom.

<2> A sulfur-containing unsaturated carboxylate compound represented by general formula (1).

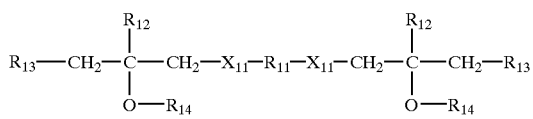

(1)

wherein $R_{11}$ represents a bivalent organic group; each $X_{11}$ independently represents oxygen, sulfur, —COO— or —$(CH_2)_l X_{12}$— ($X_{12}$ represents oxygen or sulfur and l is an integer of 1 to 3); each $R_{12}$ independently represents hydrogen or alkyl; each $R_{13}$ independently represents a sulfur-containing substituent; and each $R_{14}$ independently represents an α,β-unsaturated carboxylate residue.

<3> The sulfur-containing unsaturated carboxylate compound described in <2> prepared by reacting a sulfur-containing dihydroxy compound with an α,β-unsaturated carboxylic acid derivative represented by general formula (2):

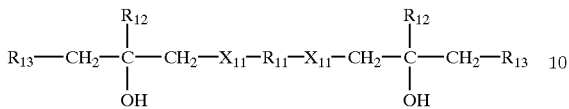

(2)

wherein $R_{11}$ represents a bivalent organic group; each Xll independently represents oxygen, sulfur, —COO— or —$(CH_2)_l X_{12}$— ($X_{12}$ represents oxygen or sulfur and l is an integer of 1 to 3); each $R_{12}$ independently represents hydrogen or alkyl;,and each $R_{13}$ independently represents a sulfur-containing substituent.

<4> The sulfur-containing unsaturated carboxylate compound described in <2> where the α,β-unsaturated carboxylate residue is selected from the group consisting of (meth) acrylic acid, crotonic acid, tiglic acid, 3,3-dimethylacrylic acid, maleic acid, citraconic acid, 2,3-dimethylmaleic acid, itaconic acid and cinnamic acid residues.

<5> The sulfur-containing unsaturated carboxylate compound described in <2> where the bivalent organic group $R_{11}$ is a moiety represented by a formula selected from the group of formulas (3-a), (4-a), (5-a) and (6-a):

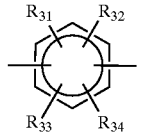

(3-a)

wherein $R_{31}$, $R_{32}$, $R_{33}$ and $R_{34}$ independently represent hydrogen, alkyl, alkoxy, nitro or halogen;

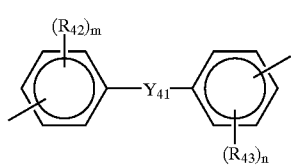

(4-a)

wherein $Y_{41}$ represents a single bond, —$C(R_{41})_2$— (each $R_{41}$ independently represents hydrogen or methyl), —O—, —S— or —$SO_2$—; $R_{42}$ and $R_{43}$ independently represent alkyl, alkenyl, aralkyl, aryl, alkoxy, alkylthio, nitro or halogen; m and n independently represent an integer of 0 to 4;

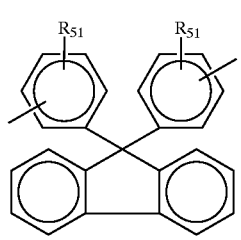

(5-a)

wherein each $R_{51}$ independently represents hydrogen or alkyl;

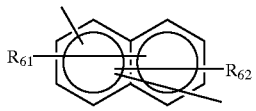

(6-a)

wherein $R_{61}$ and $R_{62}$ independently represent hydrogen or alkyl.

<6> The sulfur-containing unsaturated carboxylate compound described in <2> where the sulfur-containing substituent $R_{13}$ is a moiety represented by formula (7-a) or (8-a)

$$R_{71}-O- \quad (7\text{-}a)$$

wherein $R_{71}$ is a monovalent organic group containing at least one sulfur atom;

$$R_{81}-S- \quad (8\text{-}a)$$

wherein $R_{81}$ is a monovalent organic group optionally containing a sulfur atom.

<7> The sulfur-containing unsaturated carboxylate compound described in <2> where the sulfur-containing substituent $R_{13}$ is a moiety represented by formula (9-a):

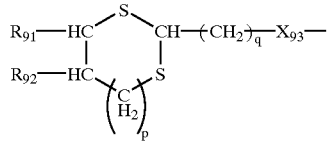

(9-a)

wherein $R_{91}$ and $R_{92}$ independently represent hydrogen or alkyl or $R_{91}$ and $R_{92}$ may be linked together to form a ring; $X_{93}$ represents oxygen or sulfur; p represents an integer of 0 to 3; and q represents an integer of 1 to 4.

<8> The sulfur-containing unsaturated carboxylate compound described in <2> where the bivalent organic group $R_{11}$ is represented by formula (3-a-i); $X_{11}$ is oxygen, —COO— or —$(CH_2)_l X_{12}$— ($X_{12}$ represents oxygen or sulfur and l is an integer of 1 to 3); $R_{13}$ is represented by formula (7-a) or (8-a); and $R_{14}$ is a (meth)acrylic acid residue.

(3-a-i)

<9> The sulfur-containing unsaturated carboxylate compound described in <2> where the bivalent organic group $R_{11}$ is represented by formula (4-a-i), (4-a-ii) or (4-a-iii); $X_{11}$ is oxygen; $R_{13}$ is represented by formula (7-a) or (8-a); and $R_{14}$ is a (meth)acrylic acid residue;

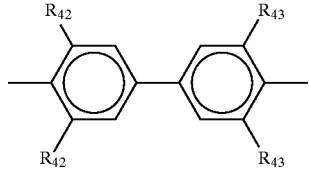

(4-a-i)

wherein $R_{42}$ and $R_{43}$ independently represent hydrogen or methyl;

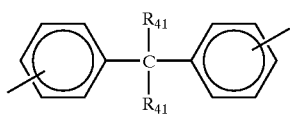

(4-a-ii)

wherein each $R_{41}$ independently represents hydrogen or methyl;

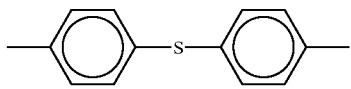

(4-a-iii)

<10> The sulfur-containing unsaturated carboxylate compound described in <2> where the bivalent organic group $R_{11}$ is represented by formula (5-a-i); $X_{11}$ is oxygen; $R_{13}$ is represented by formula (7-a) or (8-a); and $R_{14}$ is a (meth)acrylic acid residue.

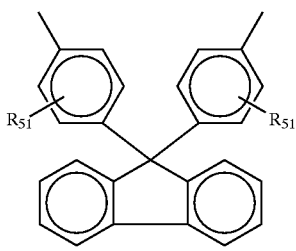

(5-a-i)

wherein each $R_{51}$ independently represents hydrogen or alkyl.

<11> The sulfur-containing unsaturated carboxylate compound described in <2> where the bivalent organic group $R_{11}$ is represented by formula (6-a-i); $X_{11}$ is oxygen or —COO—; $R_{13}$ is represented by formula (7-a) or (8-a); and $R_{14}$ is a (meth)acrylic acid residue.

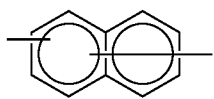

(6-a-i)

<12> A polymerizable composition comprising the sulfur-containing unsaturated carboxylate compound described in any of <1> to <11>.

<13> A cured product prepared by polymerizing the polymerizable composition described in <12>.

<14> An optical component consisting of the cured product described in <13>.

This invention also provides the following intermediates for preparing the sulfur-containing unsaturated carboxylate compound described in any of <1> to <11>:

<15> A hydroxy compound represented by general formula (2):

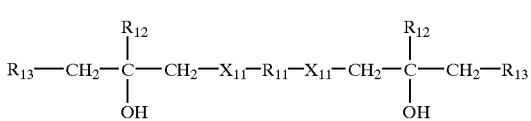

(2)

wherein $R_{11}$ represents a bivalent organic group; each $X_{11}$ independently represents oxygen, sulfur, —COO— or —(CH$_2$)$_l$X$_{12}$— ($X_{12}$ represents oxygen or sulfur and l is an integer of 1 to 3); each $R_{12}$ independently represents hydrogen or alkyl; each $R_{13}$ independently represents a sulfur-containing substituent.

<16> The hydroxy compound described in <16> where the bivalent organic group $R_{11}$ is a moiety represented by a formula selected from the group of formulas (3-a), (4-a), (5-a) and (6-a):

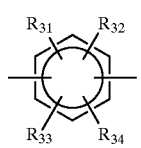

(3-a)

wherein $R_{31}$, $R_{32}$, $R_{33}$ and $R_{34}$ independently represent hydrogen, alkyl, alkoxy, nitro or halogen;

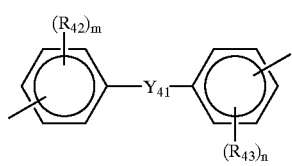

(4-a)

wherein $Y_{41}$ represents a single bond, —C($R_{41}$)$_2$— (each $R_{41}$ independently represents hydrogen or methyl), —O—, —S— or —SO$_2$—; $R_{42}$ and $R_{43}$ independently represent alkyl, alkenyl, aralkyl, aryl, alkoxy, alkylthio, nitro or halogen; m and n independently represent an integer of 0 to 4;

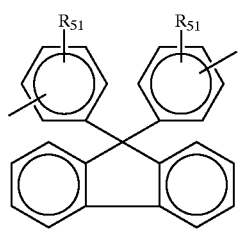

(5-a)

wherein each $R_{51}$ independently represents hydrogen or alkyl;

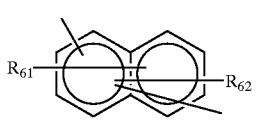

(6-a)

wherein $R_{61}$ and $R_{62}$ independently represent hydrogen or alkyl.

<17> A sulfur-containing compound represented by formula (9):

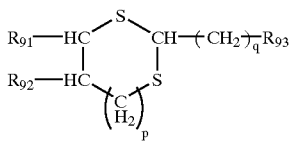

(9)

wherein $R_{91}$ and $R_{92}$ independently represent hydrogen or alkyl or $R_{91}$ and $R_{92}$ may be linked together to form a ring; $R_{93}$ represents halogen atom, hydroxyl group or thiol group; p represents an integer of 0 to 3; and q represents an integer of 1 to 4.

The sulfur-containing unsaturated carboxylate compound according to this invention is useful as a monomer for a photocurable polymerizable composition in a variety of applications such as optical materials and dental materials. An optical component produced by curing the polymerizable composition has excellent optical, thermal and mechanical properties; can be produced in an improved yield; has a higher refractive index; and is useful in various applications such as a variety of plastic lenses (typically, an orthodontic eyeglass), substrates for optical information recording media, plastic substrates for a liquid crystal cell and coatings for optical-fibers.

Furthermore, this invention can provide a novel sulfur-containing dihydroxy compound represented by general formula (2) and a novel sulfur-containing compound represented by formula (9) which are very useful as a preparation material for a starting monomer for the above optical resin.

DETAILED DESCRIPTION OF PREFERRED EMBODIMENTS

This invention will be described in detail.

A sulfur-containing unsaturated carboxylate compound according to this invention is a novel compound having a structural feature that it intramolecularly comprises a sulfur-containing substituent and at least two α,β-unsaturated carboxylic acid residues, which are each attached to a secondary or tertiary carbon atom via an oxygen atom.

The sulfur-containing unsaturated carboxylate compound of this invention is, although described in later, an unsaturated carboxylate compound typically obtained by an esterified reaction of a sulfur-containing hydroxyl compound having two or more hydroxyl groups which are bonded to a secondary or tertiary carbon atom with α,β-unsaturated carboxylic acids.

The term "α,β-unsaturated carboxylic acid residue" means a group derived from α,β-unsaturated carboxylic acids which are one of the starting material, i.e., an acyl residue of which a hydroxyl group is eliminated from a carboxyl group in the α,β-unsaturated carboxylic acid. In the case that the α,β-unsaturated carboxylic acid has 2 or more (plurality) of carboxyl groups, the term means an acyl residue of which a hydroxyl group is eliminated from only one carboxyl group among those.

The sulfur-containing unsaturated carboxylate compound of this invention has two or more of the above unsaturated carboxylic acid residues in its molecule.

The number of the unsaturated carboxylic acid residues is preferably two to five, more preferably two to four, further preferably two or three. Particularly, it is the most preferable that the number of the unsaturated carboxylic acid residues is two.

Another structural feature of the present sulfur-containing unsaturated carboxylate compound is to have a substituent containing sulfur atom. The number of the substituents containing sulfur atom is preferably 2 to 10, more preferably 2 to 8, further preferably 2 to 4.

In the light of desired effects of this invention, the sulfur-containing unsaturated carboxylate according to this invention intramolecularly comprises preferably at least 2, more preferably at least 3, further preferably at least 4 sulfur atoms.

When the sulfur-containing unsaturated carboxylate compound according to this invention is used as an optical component such as a lens, it preferably has a property that a cured product prepared by curing a polymerizable composition comprising the compound has a refractive index (nd) of 1.58 or higher. A refractive index for the cured product is more preferably 1.59 or higher, further preferably 1.60 or higher.

When the sulfur-containing unsaturated carboxylate compound according to this invention is used as an optical component such as a lens, it preferably has a property that a cured product prepared by curing a polymerizable composition comprising the compound has an Abbe number (vd) of 28 or higher, more preferably 30 or higher, further preferably 33 or higher.

A typical example of the sulfur-containing unsaturated carboxylate compound is a sulfur-containing unsaturated carboxylate compound represented by general formula (1).

The sulfur-containing unsaturated carboxylate represented by general formula (1) will be described in detail.

In general formula (1), $R_{11}$ represents a bivalent organic group, particularly a bivalent aliphatic or aromatic group or a combination thereof. The bivalent organic group $R_{11}$ may have a substituent or substituents comprising, in addition to carbon and hydrogen atoms, hetero atoms such as oxygen, sulfur and nitrogen atoms. Particularly, it is preferable that a sulfur atom is contained, for achieving a higher refractive index and a higher Abbe number which constitute desired effects of this invention.

The organic group is more preferably selected from the group of $C_2$–$C_{30}$ alkylenes which are straight, circular or a combination thereof; $C_5$–$C_{30}$ aralkylenes; $C_4$–$C_{30}$ arylenes; and moieties where at least two arylenes above are linked via at least one bivalent linker.

When the organic group $R_{11}$ has a substituent, the substituent may be, for example, selected from the group of alkyl, alkoxy, alkylthio, nitro or halogen (e.g., bromine, iodine or chlorine atom); preferably, $C_1$–$C_4$ alkyl, $C_1$–$C_4$ alkoxy, $C_1$–$C_4$ alkylthio, bromine and iodine; more preferably methyl, methoxy, methylthio and bromine.

The organic group $R_{11}$ may include, but not limited to, methylene, 1,2-ethylene, 1,1-ethylene, 1-methyl-1,2-ethylene, 1,2-dimethyl-1,2-ethylene, 1,3-trimethylene,

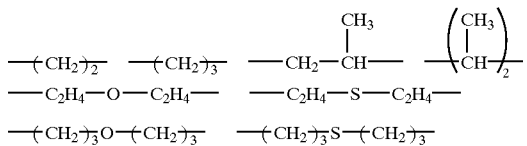

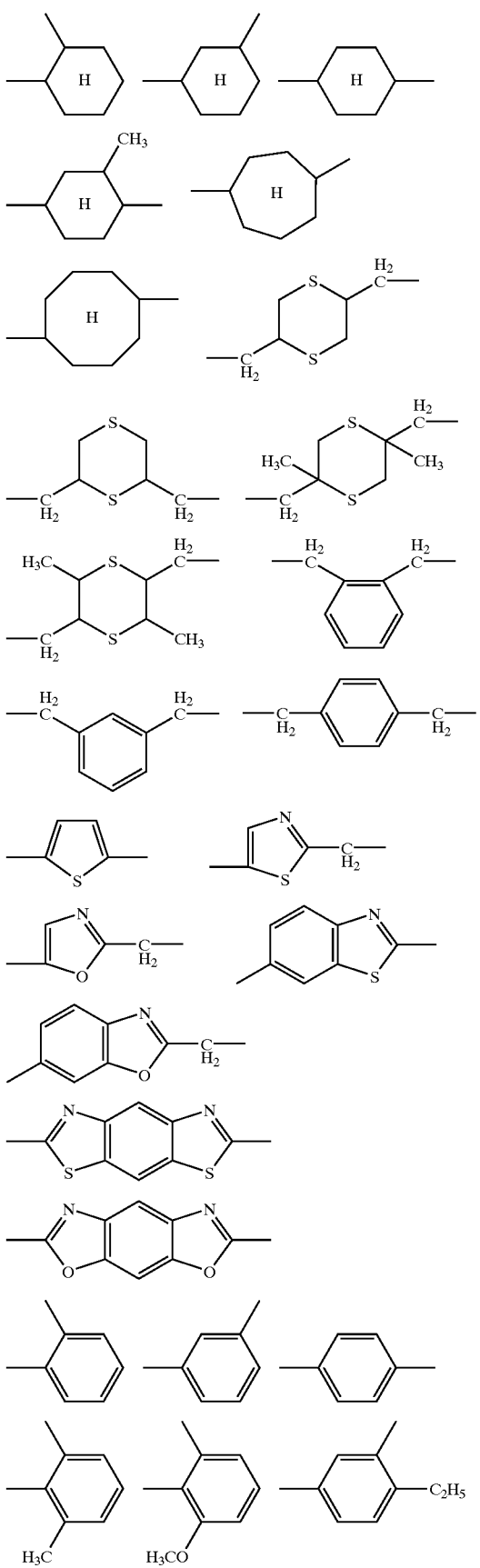
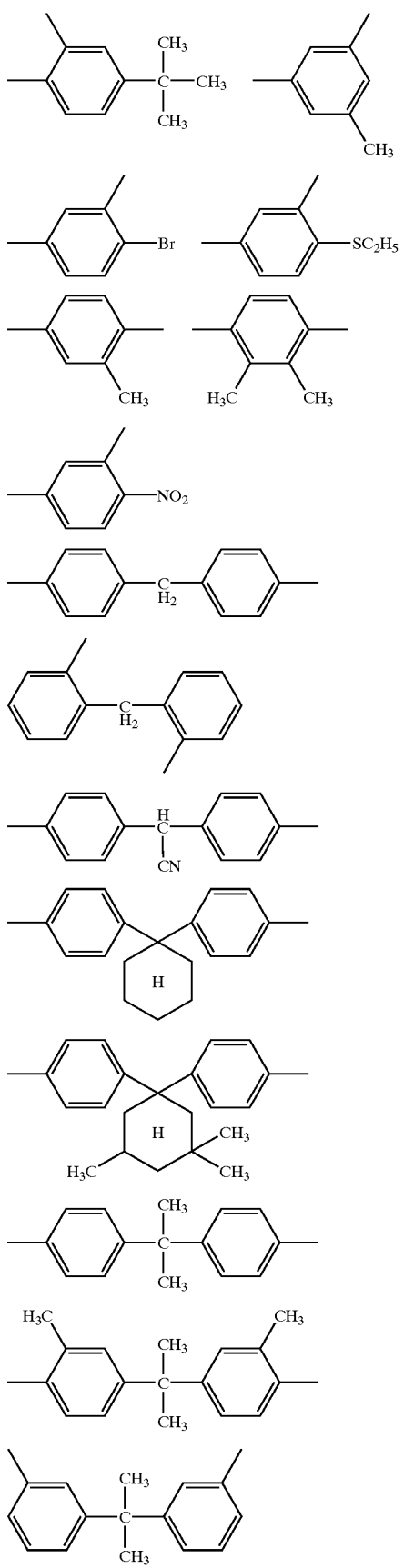

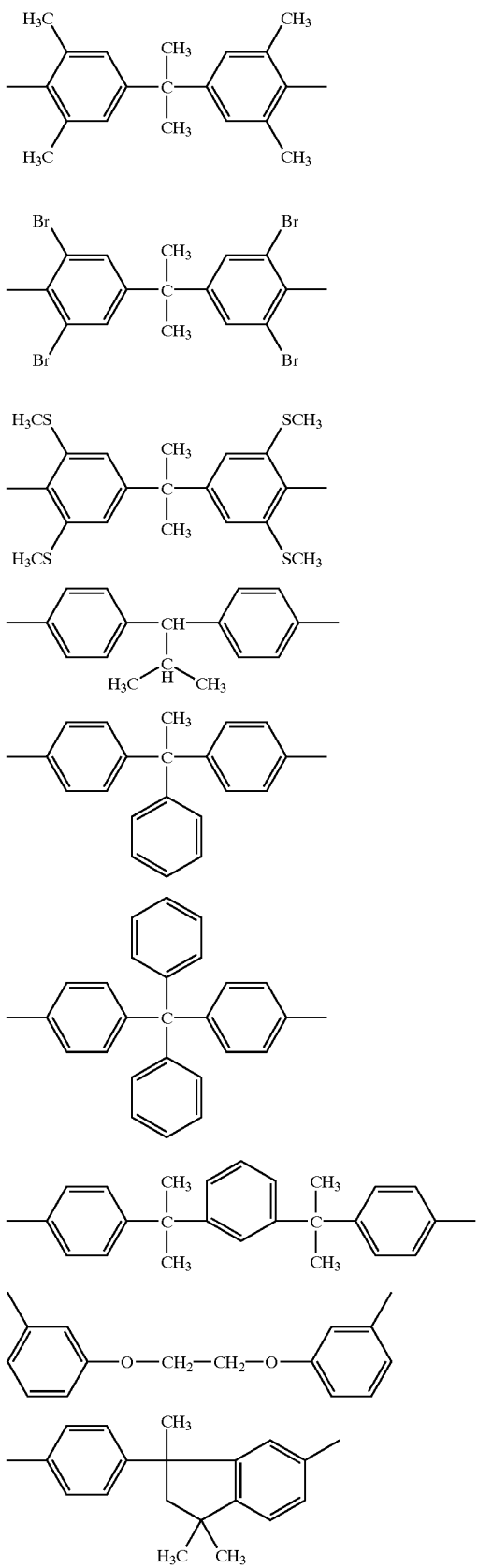
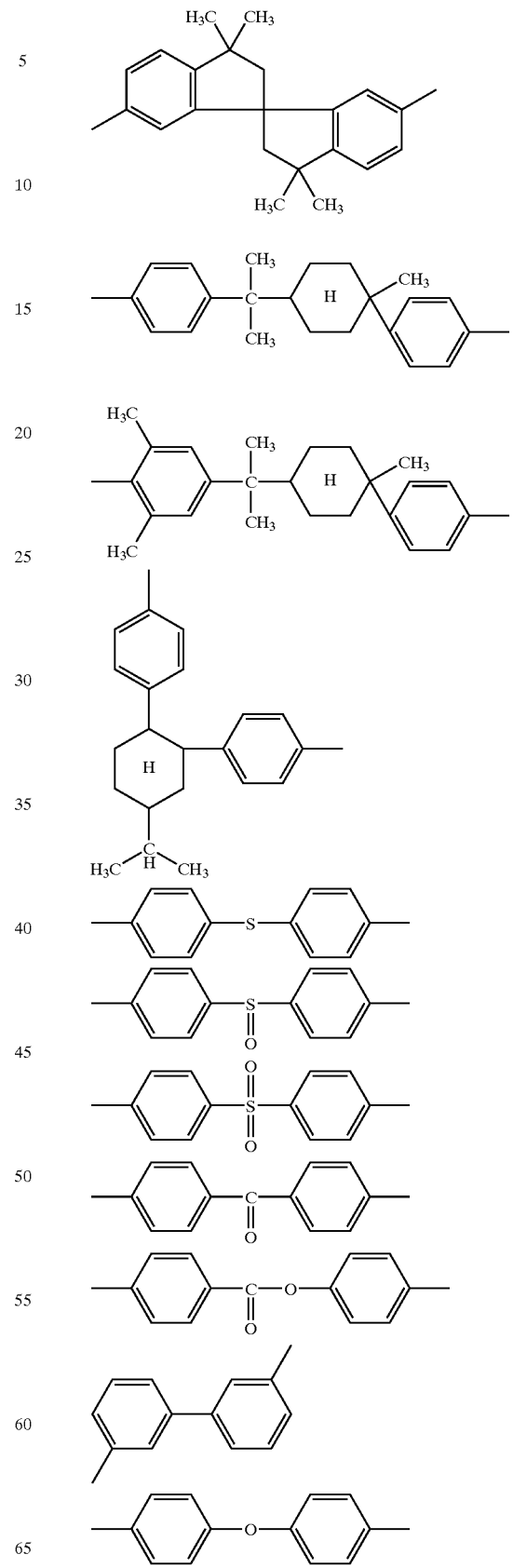

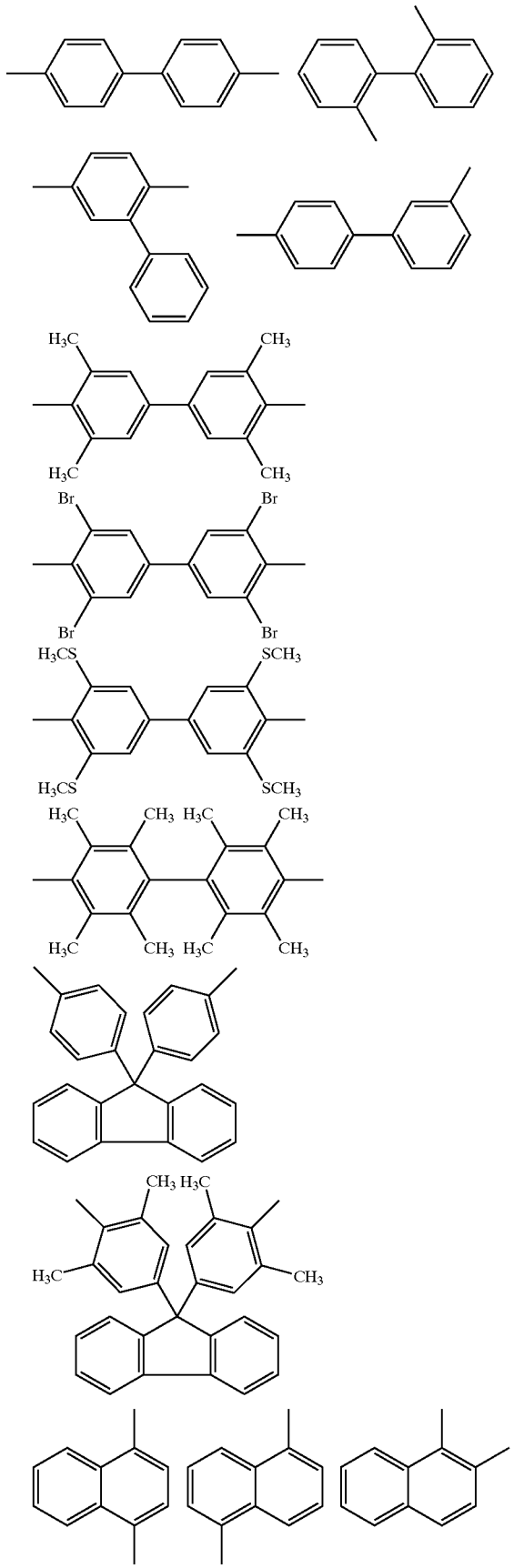

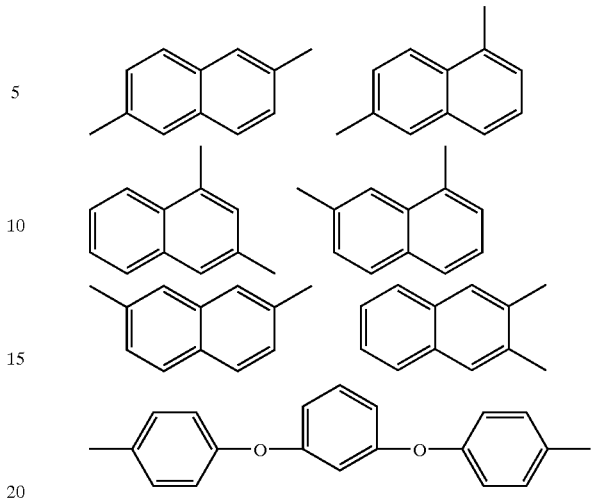

Among these bivalent organic groups, the organic group $R_{11}$ is more preferably a group represented by formula (3-a), (4-a), (5-a) or (6-a);

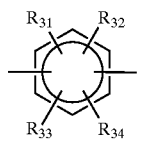
(3-a)

wherein $R_{31}$, $R_{32}$, $R_{33}$ and $R_{34}$ independently represent hydrogen, alkyl, alkoxy, nitro or halogen;

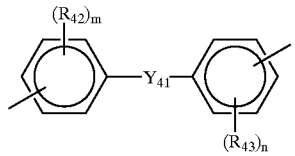
(4-a)

wherein $Y_{41}$ represents a single bond, —C($R_{41}$)$_2$— (each $R_{41}$ independently represents hydrogen or methyl), —O—, —S— or —SO$_2$—; $R_{42}$ and $R_{43}$ independently represent alkyl, alkenyl, aralkyl, aryl, alkoxy, alkylthio, nitro or halogen; m and n independently represent an integer of 0 to 4;

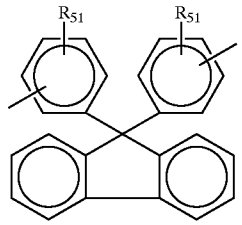
(5-a)

wherein each $R_{51}$ independently represents hydrogen or alkyl;

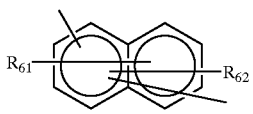

wherein $R_{61}$ and $R_{62}$ independently represent hydrogen or alkyl.

The bivalent organic group represented by one of formulas (3-a) to (6-a).

In formula (3-a), $R_{31}$, $R_{32}$, $R_{33}$ and $R_{34}$ independently represent hydrogen, alkyl, alkoxy, nitro or halogen; preferably, hydrogen, optionally substituted straight, branched or circular alkyl, optionally substituted straight, branched or circular alkoxy, nitro or halogen; more preferably, optionally substituted straight, branched or circular $C_1$–$C_{20}$ alkyl, optionally substituted straight, branched or circular $C_1$–$C_{20}$ alkoxy, nitro or halogen.

Specific examples of $R_{31}$, $R_{32}$, $R_{33}$ and $R_{34}$ include hydrogen, methyl, ethyl, n-propyl, isopropyl, n-butyl, isobutyl, sec-butyl, tert-butyl, n-pentyl, n-hexyl, 2-ethylhexyl, n-octyl, n-decyl, n-dodecyl, n-tetradecyl, n-octadecyl, cyclopentyl, cyclohexyl, 4-tert-butylcyclohexyl, cycloheptyl, cyclooctyl, cyclohexylmethyl, cyclohexylethyl, tetrahydrofurfuryl, 2-methoxyethyl, 2-ethoxyethyl, 2-n-butoxyethyl, 3-methoxypropyl, 3-ethoxypropyl, 3-n-propoxypropyl, 3-n-butoxypropyl, 3-n-hexyloxypropyl, 2-methoxyethoxyethyl, 2-ethoxyethoxyethyl, phenoxymethyl, 2-phenoxyethoxyethyl, chlolromethyl, 2-chloroethyl, 3-chloropropyl, 2,2,2-trichloroethyl, methoxy, ethoxy, n-propoxy, isopropoxy, n-butoxy, isobutoxy, sec-butoxy, n-pentyloxy, n-hexyloxy, 2-ethylhexyloxy, n-octyloxy, n-decyloxy, n-dodecyloxy, n-tetradecyloxy, n-octadecyloxy, cyclopentyloxy, cyclohexyloxy, 4-tert-butylcyclohexyloxy, cycloheptyloxy, cyclooctyloxy, cyclohexylmethoxy, cyclohexylethoxy, 2-methoxyethoxy, 2-ethoxyethoxy, 2-n-butoxyethoxy, 3-methoxypropoxy, 3-ethoxypropoxy, 3-n-propoxypropoxy, 3-n-butoxypropoxy, 3-n-hexyloxypropoxy, 2-methoxyethoxyethoxy, phenoxymethoxy, 2-phenoxyethoxyethoxy, chloromethoxy, 2-chloroethoxy, 3-chloropropoxy, 2,2,2-trichloroethoxy, nitro, fluorine, chlorine, bromine and iodine.

$R_{31}$, $R_{32}$, $R_{33}$ and $R_{34}$ are more preferably selected from hydrogen, $C_1$–$C_{10}$ unsubstituted straight or branched alkyl, $C_1$–$C_{10}$ unsubstituted straight or branched alkoxy, nitro, chlorine and bromine; further preferably, hydrogen, methyl, ethyl, n-propyl, isopropyl, n-butyl, isobutyl, tert-butyl, methoxy, ethoxy, n-propoxy, isopropoxy, n-butoxy, isobutoxy, tert-butoxy, nitro, bromine and iodine.

Particularly, $R_{31}$, $R_{32}$, $R_{33}$ and $R_{34}$ are hydrogen.

In formula (4-a), $Y_{41}$ represents a single bond, —C(R$_{41}$)$_2$— (each $R_{41}$ independently represents hydrogen or methyl), —O—, —S— or —SO$_2$—.

$Y_{41}$ in formula (4-a) preferably represents a single bond, methylene, ethylidene, isopropylidene, —S— or —SO$_2$—; more preferably, a single bond, methylene, isopropylidene, —S— or —SO$_2$—; further preferably, a single bond, methylene, isopropylidene or —S—.

In formula (4-a), $R_{42}$ and $R_{43}$ independently represent alkyl, alkenyl, aralkyl, aryl, alkoxy, alkylthio, nitro or halogen.

$R_{42}$ and $R_{43}$ are preferably $C_1$–$C_4$ straight alkyl, $C_5$–$C_{10}$ circular alkyl, $C_2$–$C_6$ straight or circular alkenyl, $C_5$–$C_{20}$ aralkyl, $C_6$–$C_{20}$ aryl, $C_1$–$C_4$ straight alkoxy, $C_5$–$C_{12}$ circular alkoxy, $C_1$–$C_4$ alkylthio, nitro, bromine or iodine; more preferably, methyl, allyl, benzyl, phenyl, methoxy, methylthio or bromine.

In formula (4-a), m and n independently represent an integer of 0 to 4; preferably 0 to 3; more preferably 0 to 2.

A preferable group represented by formula (4-a) is one represented by formula (4-a-i), (4-a-ii) or (4-a-iii);

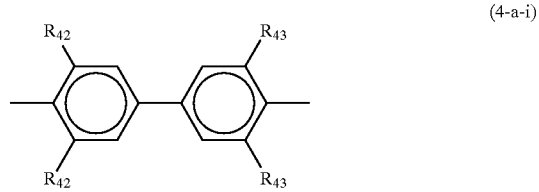

wherein $R_{42}$ and $R_{43}$ independently represent hydrogen or methyl;

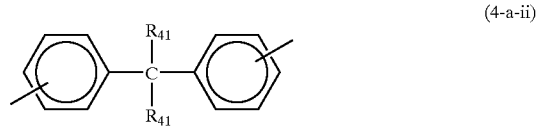

wherein each $R_{41}$ represents hydrogen or methyl;

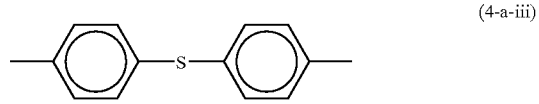

In formula (5-a), each $R_{51}$ independently represents hydrogen or alkyl; preferably, hydrogen or $C_1$–$C_4$ straight alkyl; more preferably, hydrogen or methyl.

In formula (6-a), $R_{61}$ and $R_{62}$ independently represent hydrogen or alkyl; preferably, hydrogen or $C_1$–$C_4$ straight alkyl; more preferably, hydrogen or methyl.

In general formula (1), each substituent $R_{12}$ independently represents hydrogen or alkyl; more preferably, hydrogen or methyl; further preferably, hydrogen.

In general formula (1), each $R_{13}$ independently represents a sulfur-containing substituent comprising at least one sulfur atom.

The substituent $R_{13}$ is preferably a group represented by formula (7-a):

wherein $R_{71}$ is a monovalent organic group containing at least one sulfur atom; or (8-a):

wherein $R_{81}$ is a monovalent organic group optionally containing a sulfur atom.

In the above formula, the substituent $R_{71}$ is a monovalent organic group containing at least one sulfur atom. The substituent $R_{71}$ is preferably alkyl, aralkyl, aryl or acyl containing at least one sulfur atom; more preferably, straight, branched or circular $C_1$–$C_{20}$ alkyl, $C_5$–$C_{20}$ aralkyl, $C_4$–$C_{20}$ aryl or $C_2$–$C_{20}$ acyl containing at least one sulfur atom. These monovalent organic groups may have a substituent and a hetero atom other than sulfur; e.g., a substituent comprising a heterocycle.

In the above formula, the substituent $R_{81}$ is a monovalent organic group optionally containing a sulfur atom. The substituent R$_{81}$ is preferably alkyl, aralkyl, aryl or acyl optionally containing a sulfur atom; more preferably, straight, branched or circular C$_1$–C$_{20}$ alkyl, C$_5$–C$_{20}$ aralkyl, C$_4$–C$_{20}$ aryl or C$_2$–C$_{20}$ acyl optionally containing a sulfur atom. These monovalent organic groups may have a substituent and a hetero atom other than sulfur; e.g., a substituent comprising a heterocycle. More preferably, the substituent R$_{81}$ contains a sulfur atom, for achieving desired effects of this invention such as a higher refractive index and a higher Abbe number.

The substituent R$_{13}$ is more preferably straight, branched or circular alkoxy containing at least one sulfur atom; aralkyloxy containing at least one sulfur atom; aryloxy containing at least one sulfur atom; acyloxy containing at least one sulfur atom; straight, branched or circular alkylthio optionally containing a sulfur atom; aralkylthio optionally containing a sulfur atom; arylthio optionally containing a sulfur atom; or acylthio optionally containing a sulfur atom.

Specific examples of the substituent R$_{13}$ include, but not limited to, methylthioethoxy, ethylthioethoxy, propylthioethoxy, butylthioethoxy, methylthioethylthioethoxy, methylthioethylthioethylthioethoxy, 2,2-di(methylthio)ethoxy, 2,2-di(ethylthio)ethoxy, 2,2-di(propylthio)ethoxy, 2,2-di(butylthio)-ethoxy, 3,3-di(methylthio)propoxy, 3,3-di(ethylthio)propoxy, 3,3-di(propylthio)ethoxy, 3,3-di(butylthio)ethoxy, (1,3-dithiolan-2-yl)methoxy, 2-(1,3-dithiolan-2-yl)ethoxy, 3-(1,3-dithiolan-2-yl)propoxy, (1,3-dithiolan-4-yl)methoxy, 2-(1,3-dithiolan-4-yl)ethoxy, 3-(1,3-dithiolan-4-yl)propoxy, (1,4-dithian-2-yl)methoxy, 2-(1,4-dithian-2-yl)ethoxy, 3-(1,4-dithian-2-yl)propoxy, (1,3,5-trithian-2-yl)methoxy, 2-(1,3,5-trithian-2-yl)ethoxy, 3-(1,3,5-trithian-2-yl)propoxy, 4-methylthiobenzyloxy, 3-methylthiobenzyloxy, 2-methylthiobenzyloxy, 2,4-di(methylthio)benzyloxy, 3,4-di(methylthio)benzyloxy, 2,4,6-tri(methylthio)benzyloxy, (4-methylthiophenyl)ethoxy, (3-methylthiophenyl)ethoxy, (2-methylthiophenyl)ethoxy, [2,4-di(methylthio)phenyl]ethoxy, [3,4-di(methylthio)phenyl]ethoxy, [2,4,6-tri(methylthio)phenyl]ethoxy, 4-methylthiophenyloxy, 3-methylthiophenyloxy, 2-methylthiophenyloxy, 2,4-di(methylthio)phenyloxy, 2,5-di(methylthio)phenyloxy, 2,6-di(methylthio)phenyloxy, 3,4-di(methylthio)phenyloxy, 3,5-di(methylthio)phenyloxy, 2,4,6-tri(methylthio)phenyloxy, 2,3,4,5,6-penta(methylthio)phenyloxy, methylthio, ethylthio, propylthio, butylthio, methoxyethylthio, butoxyethylthio, methoxypropylthio, cyclohexylthio, 2-methylthioethylthio, 2-ethylthioethylthio, 2-propylthioethylthio, 2-butylthioethylthio, methylthioethylthioethylthio, methylthioethylthioethylthioethylthio, 2,2-di(methylthio)ethylthio, 2,2-di(ethylthio)ethylthio, 2,2-di(propylthio)ethylthio, 2,2-di(butylthio)ethylthio, 3,3-di(methylthio)propylthio, 3,3-di(ethylthio)propylthio, 3,3-di(propylthio)propylthio, 3,3-di(butylthio)propylthio, (1,3-dithiolan-2-yl)methylthio, 2-(1,3-dithiolan-2-yl)ethylthio, 3-(1,3-dithiolan-2-yl)propylthio, (1,3-dithiolan-4-yl)methylthio, 2-(1,3-dithiolan-4-yl)ethylthio, 3-(1,3-dithiolan-4-yl)propylthio, (1,3-dithian-2-yl)methylthio, 2-(1,3-dithian-2-yl)ethylthio, 3-(1,3-dithian-2-yl)propylthio, (1,4-dithian-2-yl)methylthio, 2-(1,4-dithian-2-yl)ethylthio, 3-(1,4-dithian-2-yl)propylthio, (1,3,5-trithian-2-yl)methylthio, 2-(1,3,5-trithian-2-yl)ethylthio, 3-(1,3,5-trithian-2-yl)propylthio, benzylthio, 4-methylbenzylthio, 4-methoxybenzylthio, 4-methylthiobenzylthio, 3-methylthiobenzylthio, 2-methylthiobenzylthio, 2,4-di(methylthio)benzylthio, 3,4-di(methylthio)benzylthio, 2,4,6-tri(methylthio)benzylthio, (4-methylthiophenyl)ethylthio, (3-methylthiophenyl)ethylthio, (2-methylthiophenyl)ethylthio, [2,4-di(methylthio)phenyl]elthylthio, [3,4-di(methylthio)phenyl]ethylthio, [2,4,6-tri(methylthio)phenyl]ethylthio, phenylthio, 4-methylphenylthio, 4-methoxyphenylthio, 4-methylthiophenylthio, 3-methylthiophenylthio, 2-methylthiophenylthio, 2,4-di(methylthio)phenylthio, 2,5-di(methylthio)phenylthio, 2,6-di(methylthio)phenylthio, 3,4-di(methylthio)phenylthio, 3,5-di(methylthio)phenylthio, 2,4,6-tri(methylthio)phenylthio, 2,3,4,5,6-penta(methylthio)phenylthio, thiazolin-2-yl-thio, methylthiomethylcarbonyloxy, methylthioethylcarbonyloxy, (1,3-dithiolan-2-yl)carbonyloxy, (1,3-dithiolan-4-yl)carbonyloxy, (1,3-dithian-2-yl)carbonyloxy, (1,4-dithian-2-yl)carbonyloxy, (1,3,5-trithian-2-yl)carbonyloxy, 4-methylthiobenzoyloxy, thiophene-2-carbonyloxy, thiazole-2-carbonyloxy, methylthiomethylcarbonylthio, methylthioethylcarbonylthio, (1,3-dithiolan-2-yl)carbonylthio, (1,3-dithiolan-4-yl)carbonylthio, (1,3-dithian-2-yl)carbonylthio, (1,4-dithian-2-yl)carbonylthio, (1,3,5-trithian-2-yl)carbonylthio, benzoylthio, 4-methylthiobenzoylthio, thiophene-2-carbonylthio and thiazole-2-carbonylthio.

The substituent R$_{13}$ is particularly preferably a group represented by formula (9-a):

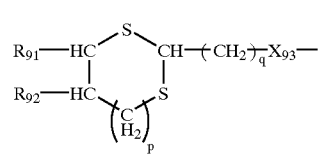

(9-a)

wherein R$_{91}$ and R$_{92}$ independently represent hydrogen or alkyl or R$_{91}$ and R$_{92}$ may be linked together to form a ring; X$_{93}$ represents oxygen or sulfur; p represents an integer of 0 to 3; and q represents an integer of 1 to 4.

In general formula (1), each substituent R$_{14}$ independently represents an α,β-unsaturated carboxylate residue. As detailed later, a sulfur-containing unsaturated carboxylate compound represented by general formula (1) can be prepared typically by reacting a hydroxy compound represented by general formula (2) with an α,β-unsaturated carboxylic acid, wherein the substituent R$_{14}$ is a group derived from the reactant, the α,β-unsaturated carboxylic acid. The substituent R$_{14}$ is preferably, (meth)acrylic acid, crotonic acid, tiglic acid, 3,3-dimethylacrylic acid, maleic acid, citraconic acid, 2,3-dimethylmaleic acid, itaconic acid or cinnamic acid residue. Among these, the substituent R$_{14}$ is particularly preferably (meth)acrylic acid residue.

Preferable sulfur-containing unsaturated carboxylate compounds represented by general formula (1) include those represented by formulas (1-a), (1-b), (1-c), (1-d), (1-e), (1-f), (1-g), (1-h), (1-i), (1-j) and (1-k).

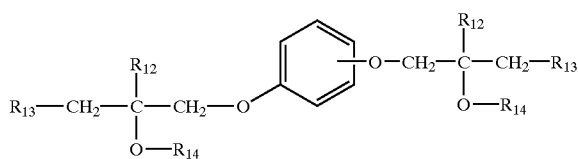 (1-a)
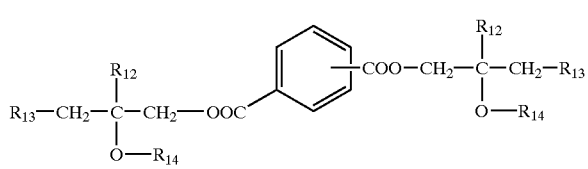 (1-b)
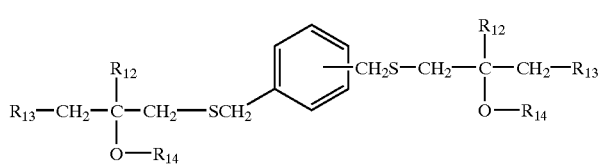 (1-c)
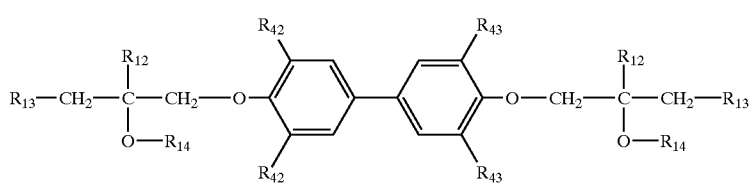 (1-d)
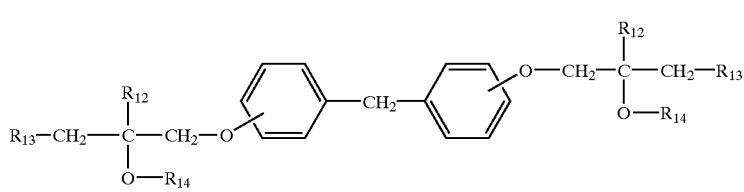 (1-e)
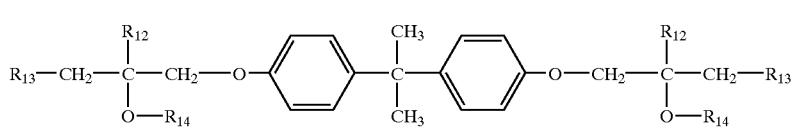 (1-f)
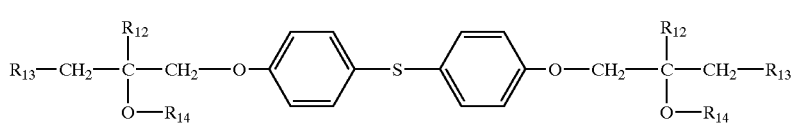 (1-g)
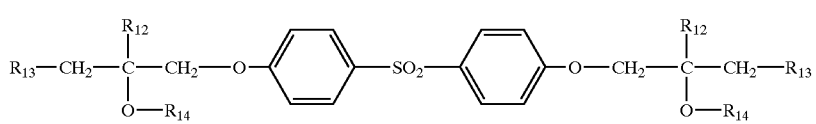 (1-h)
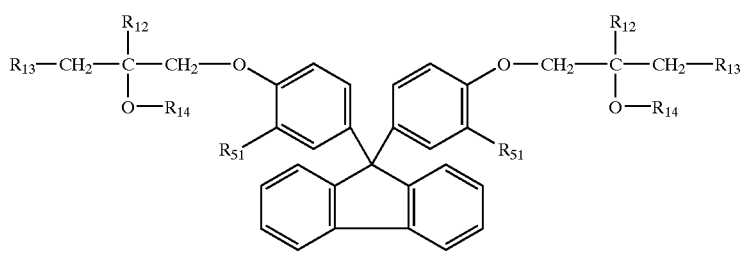 (1-i)
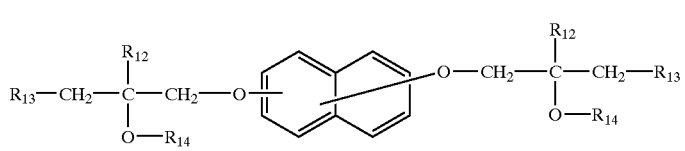 (1-j)

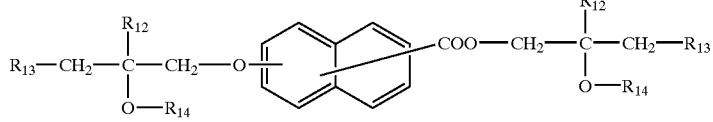

(1-k)

wherein $R_{12}$, $R_{13}$ and $R_{14}$ are as defined above; $R_{42}$ and $R_{43}$ are each independently hydrogen or methyl; and $R_{51}$ is independently hydrogen or methyl.

The compound is more preferably one represented by formula (1-a), (1-c), (1-d), (1-e) (1-f), (1-g), (1-h) or (1-i); further preferably one represented by formula (1-a), (1-d), (1-e), (1-f), (1-g), (1-h) or (1-i); particularly preferably one represented by formula (1-a), (1-d) or (1-f).

Specific examples of a sulfur-containing unsaturated carboxylate compounds represented by general formula (1) according to this invention are listed in Table 1 below, but this invention is not limited to those compounds.

TABLE 1
| No. of exemplified compounds | Structure |
|---|---|
| 1 | 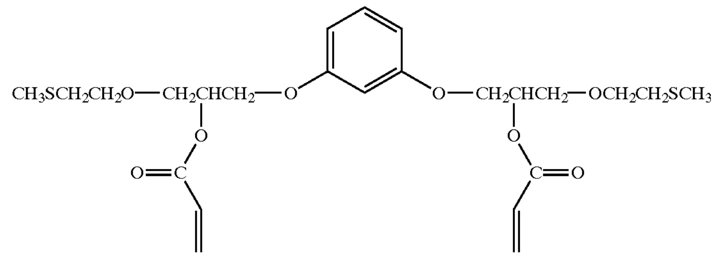 |
| 2 | 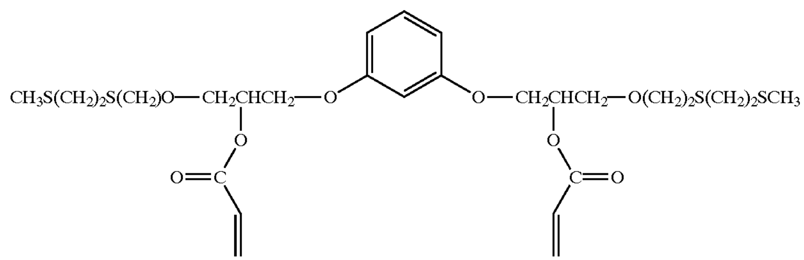 |
| 3 | 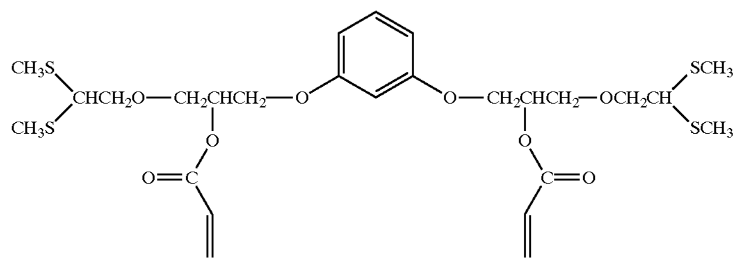 |

TABLE 1-continued
| No. of exemplified compounds | Structure |
|---|---|
| 4 | 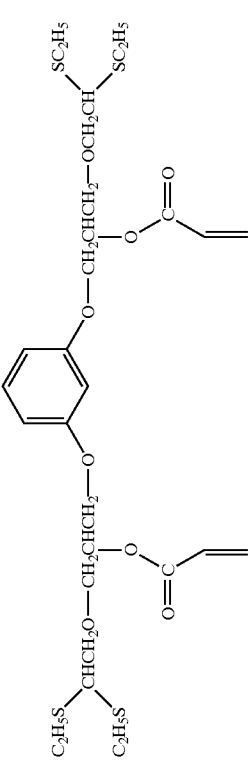 |
| 5 | 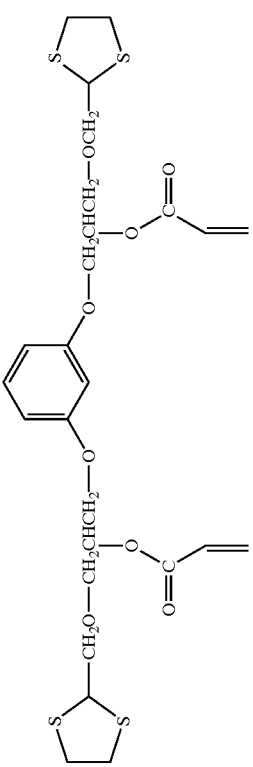 |
| 6 | 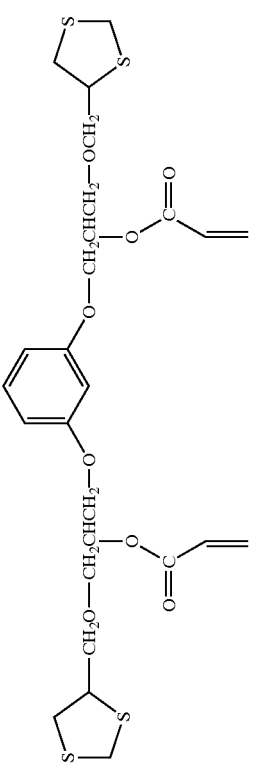 |

TABLE 1-continued
| No. of exemplified compounds | Structure |
|---|---|
| 7 | 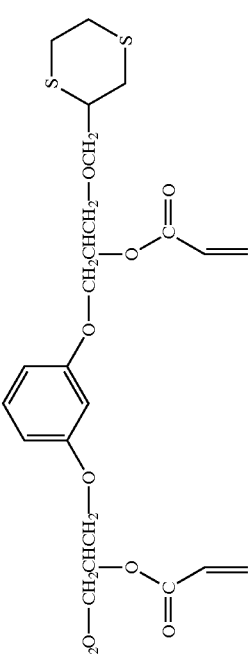 |
| 8 | 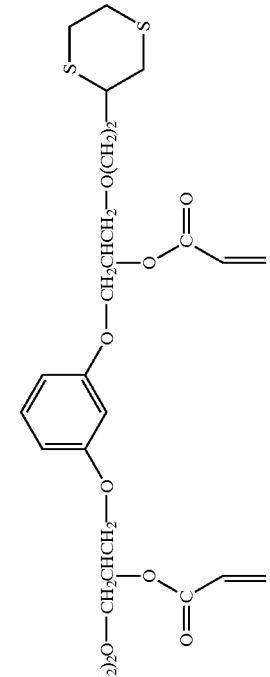 |
| 9 | 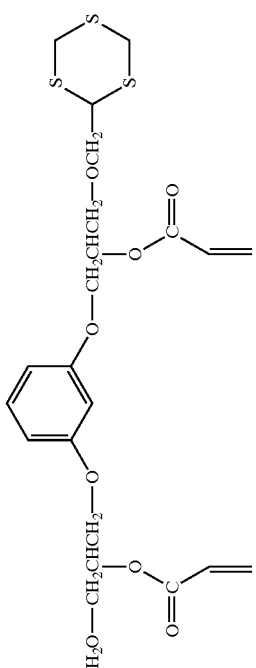 |

TABLE 1-continued
| No. of exemplified compounds | Structure |
|---|---|
| 10 | 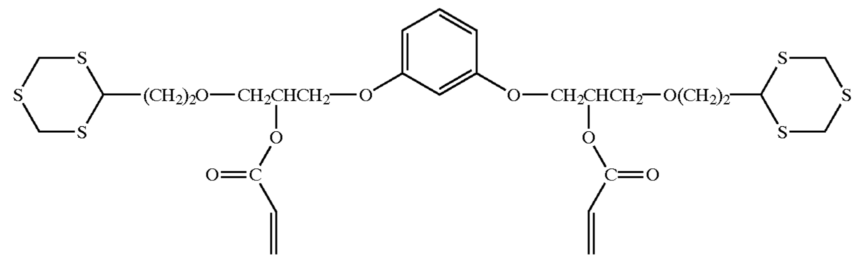 |
| 11 | 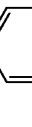 |
| 12 | 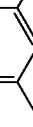 |

TABLE 1-continued
| No. of exemplified compounds | Structure |
|---|---|
| 13 | 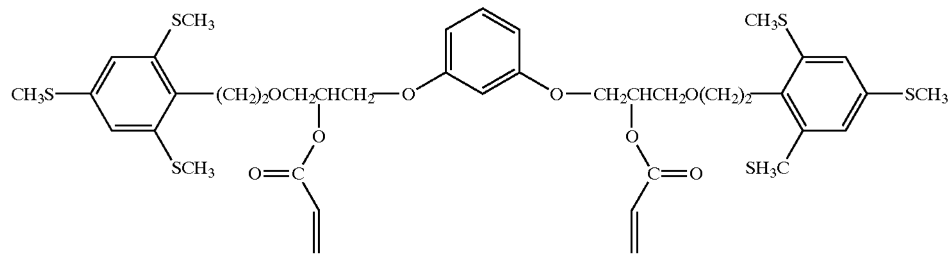 |
| 14 | 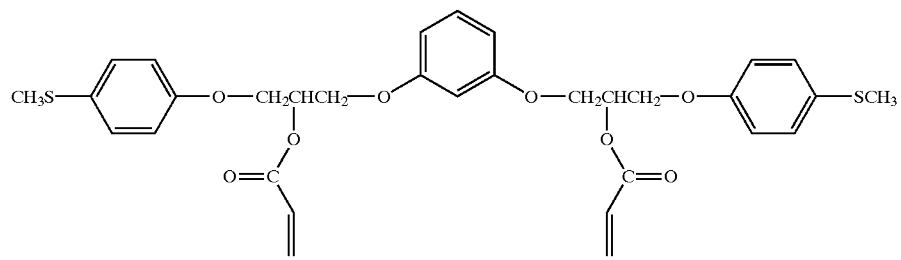 |
| 15 | 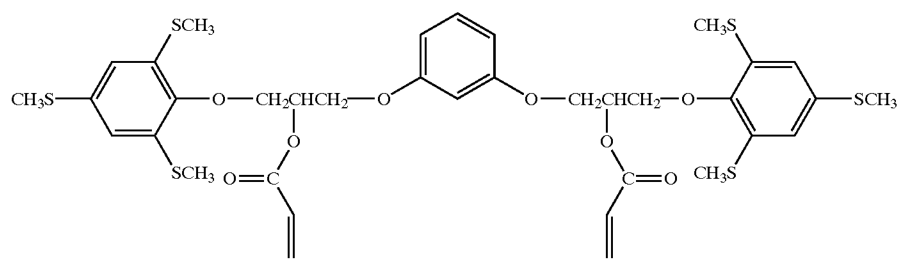 |

TABLE 1-continued

| No. of exemplified compounds | Structure |
|---|---|
| 16 | CH₃S—CH₂CHCH₂—O—[benzene]—O—CH₂CHCH₂—SCH₃ with acrylate groups |
| 17 | C₂H₅S—CH₂CHCH₂—O—[benzene]—O—CH₂CHCH₂—SC₂H₅ with acrylate groups |
| 18 | CH₃O(CH₂)₂S—CH₂CHCH₂—O—[benzene]—O—CH₂CHCH₂—S(CH₂)₂OCH₃ with acrylate groups |

TABLE 1-continued
| No. of exemplified compounds | Structure |
|---|---|
| 19 | 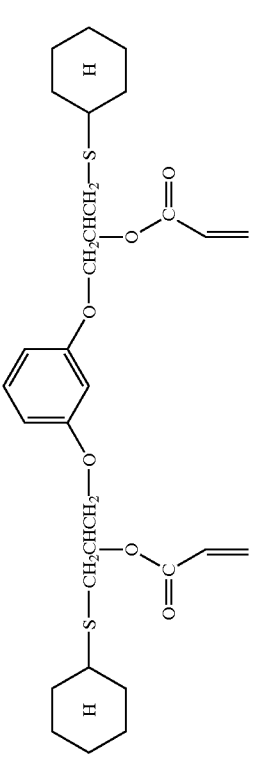 |
| 20 | 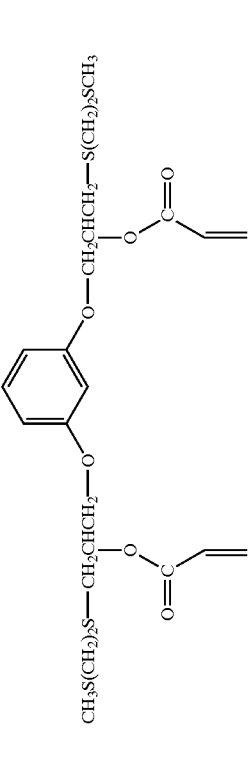 |
| 21 | 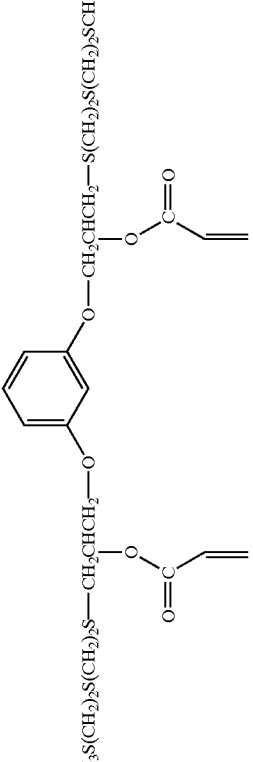 |

TABLE 1-continued
| No. of exemplified compounds | Structure |
|---|---|
| 22 | 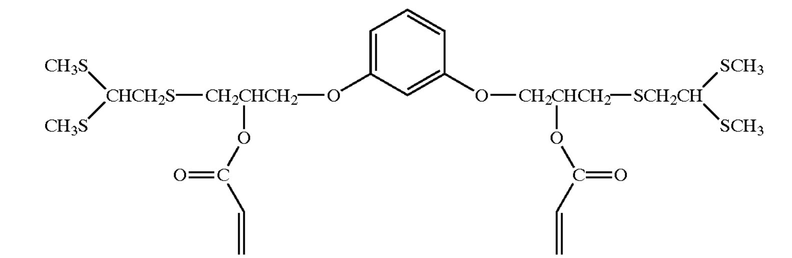 |
| 23 | 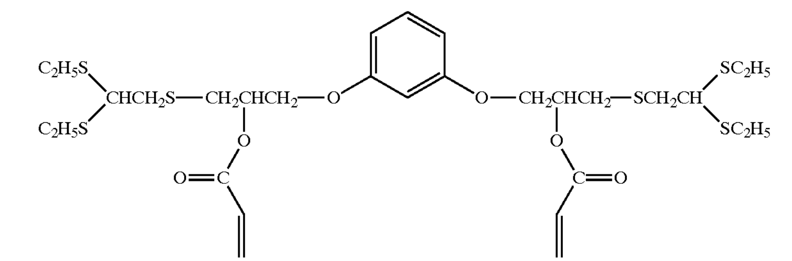 |
| 24 | 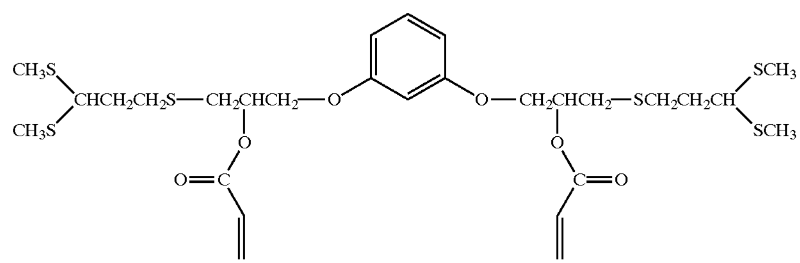 |

TABLE 1-continued
| No. of exemplified compounds | Structure |
| --- | --- |
| 25 | 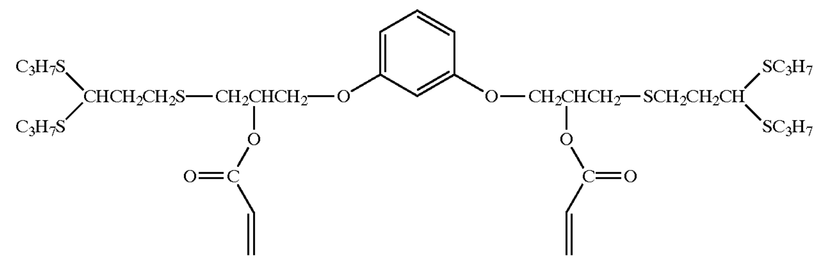 |
| 26 | 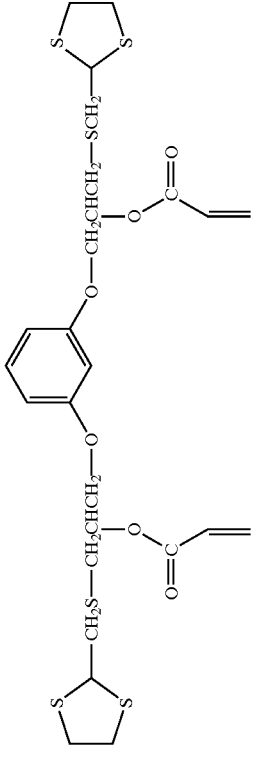 |
| 27 | 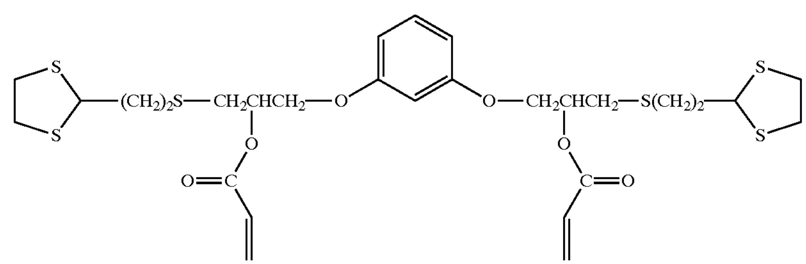 |

TABLE 1-continued
| No. of exemplified compounds | Structure |
|---|---|
| 28 | 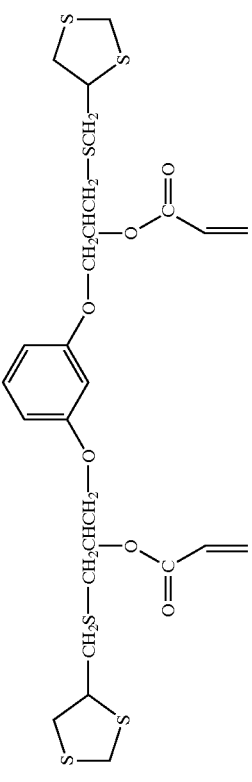 |
| 29 | 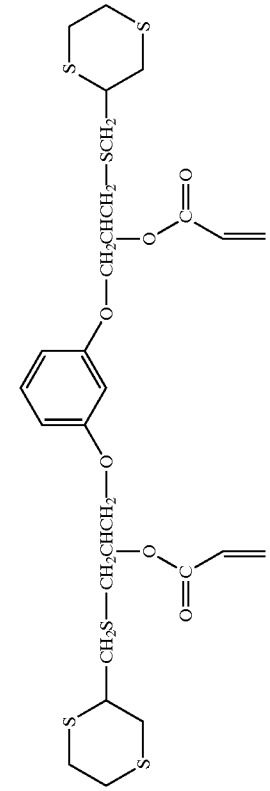 |
| 30 | 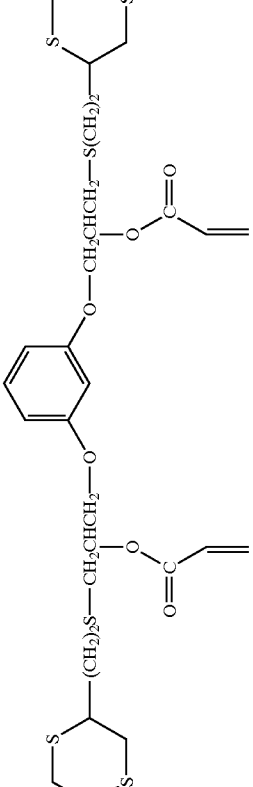 |

TABLE 1-continued
| No. of exemplified compounds | Structure |
|---|---|
| 31 | 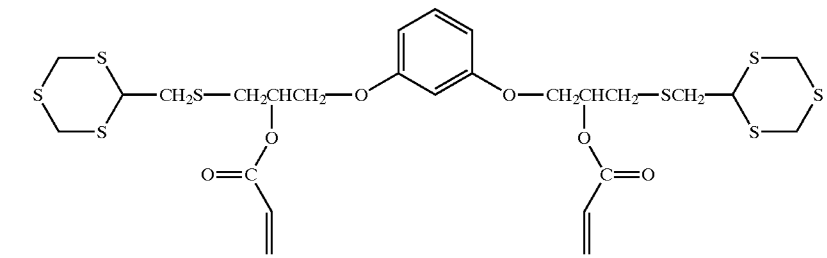 |
| 32 | 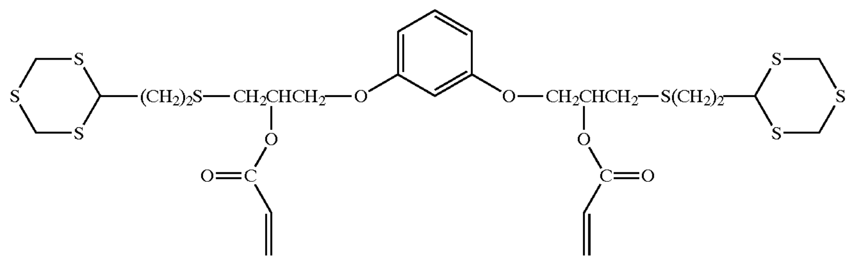 |
| 33 | 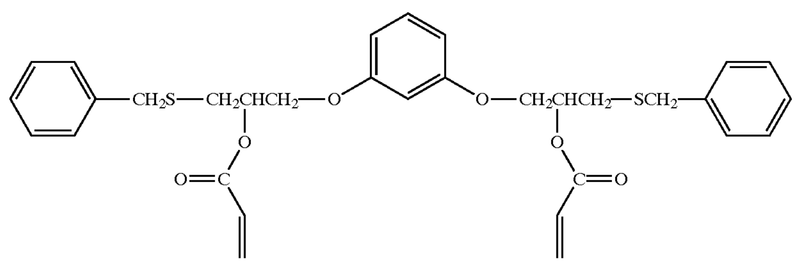 |

TABLE 1-continued
| No. of exemplified compounds | Structure |
|---|---|
| 34 | 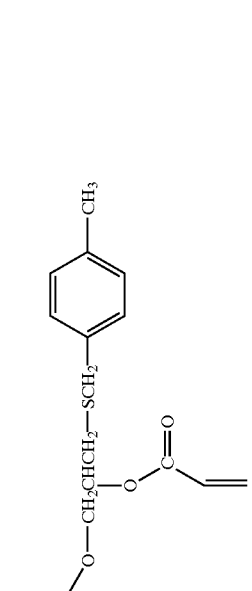 |
| 35 | 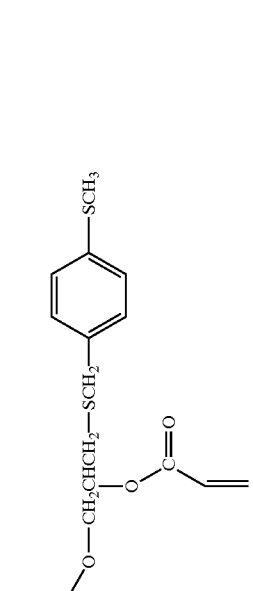 |
| 36 | 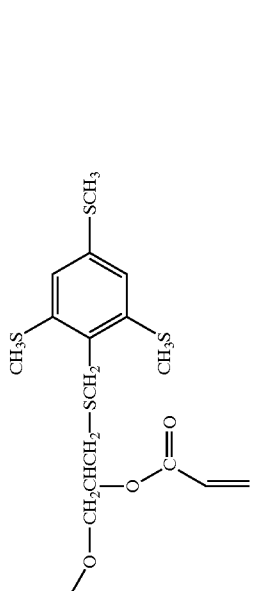 |

TABLE 1-continued
| No. of exemplified compounds | Structure |
|---|---|
| 37 | 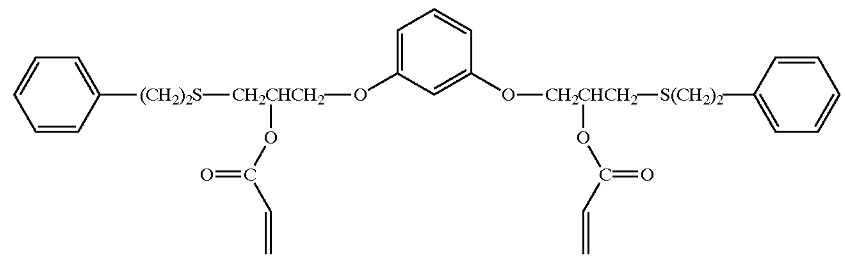 |
| 38 | 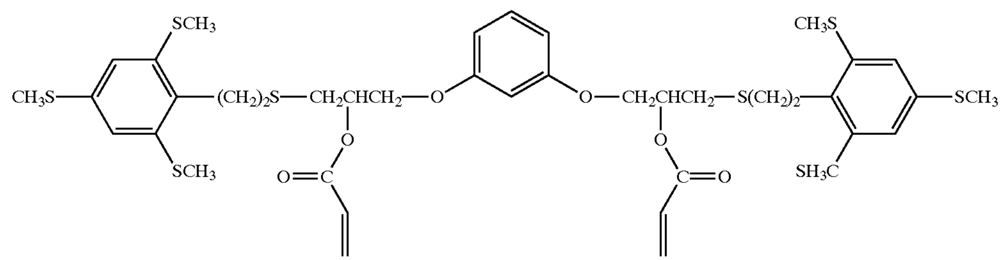 |
| 39 | 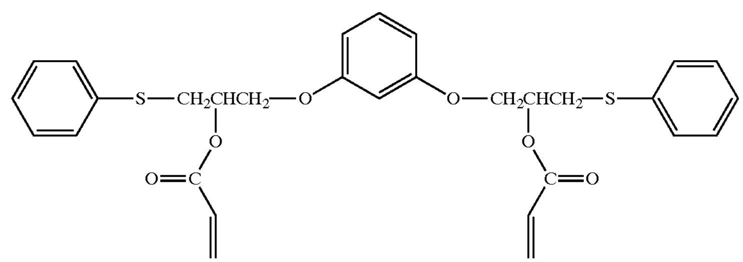 |

TABLE 1-continued

| No. of exemplified compounds | Structure |
|---|---|
| 40 | (structure with 1,3-phenylene bis(oxy-CH₂CHCH₂-acrylate) with S-C₆H₄-CH₃ groups) |
| 41 | (structure with 1,3-phenylene bis(oxy-CH₂CHCH₂-acrylate) with S-C₆H₄-OCH₃ groups) |
| 42 | (structure with 1,3-phenylene bis(oxy-CH₂CHCH₂-acrylate) with S-C₆H₄-SCH₃ groups) |

TABLE 1-continued
| No. of exemplified compounds | Structure |
|---|---|
| 43 | 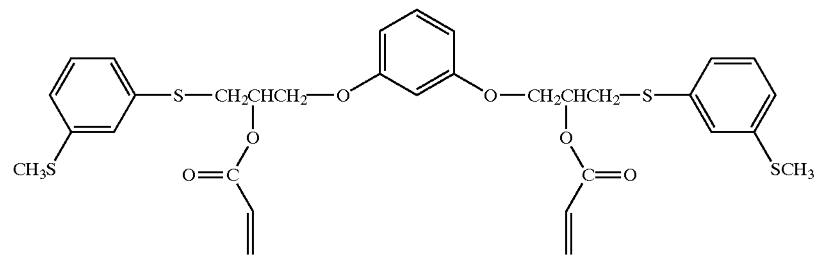 |
| 44 | 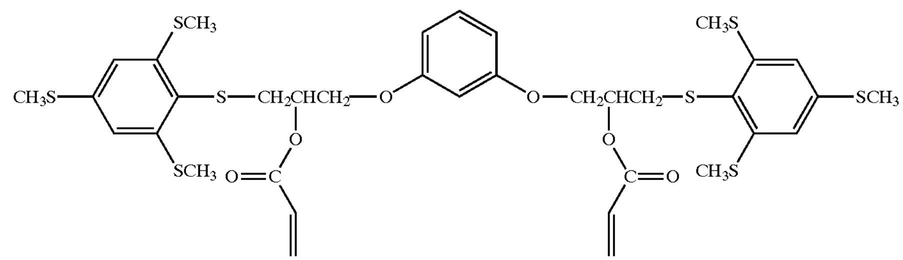 |
| 45 | 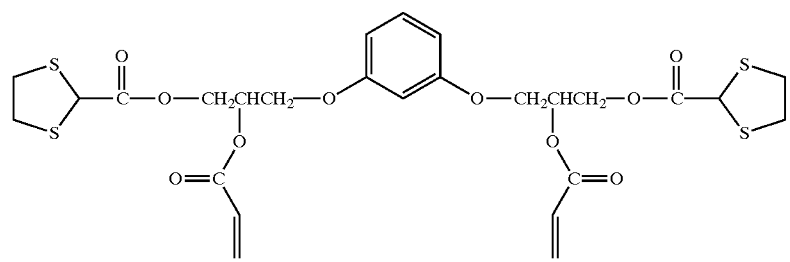 |

TABLE 1-continued
| No. of exemplified compounds | Structure |
|---|---|
| 46 | 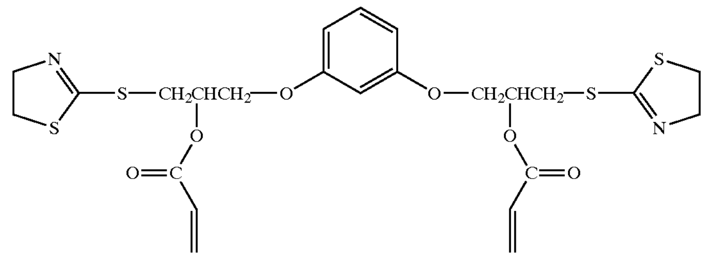 |
| 47 | 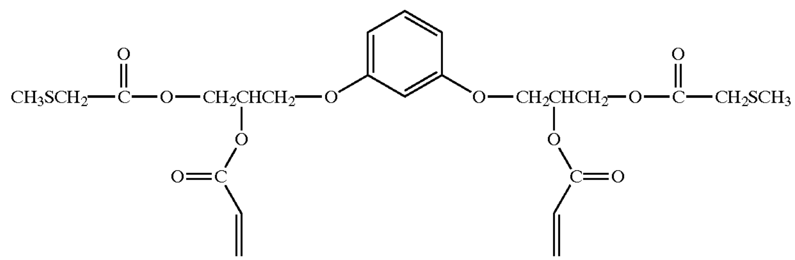 |
| 48 | 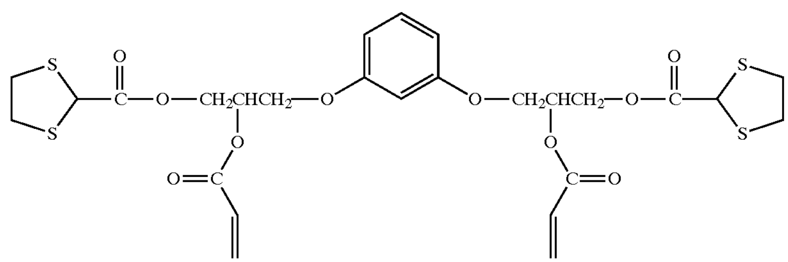 |

TABLE 1-continued
| No. of exemplified compounds | Structure |
|---|---|
| 49 | 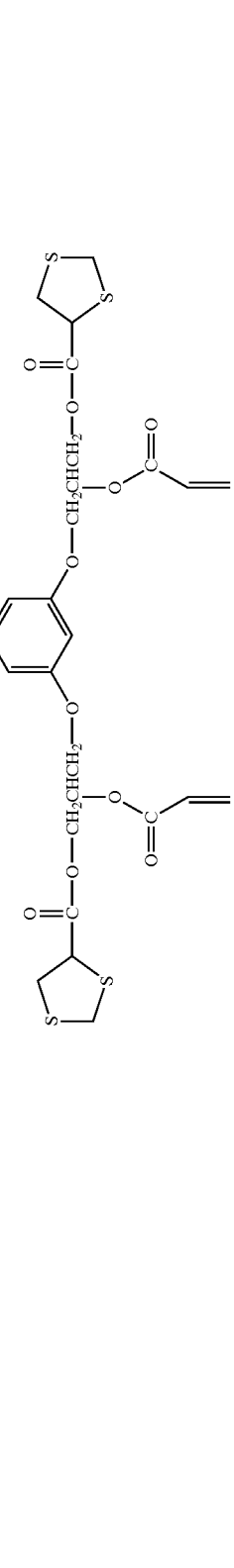 |
| 50 | 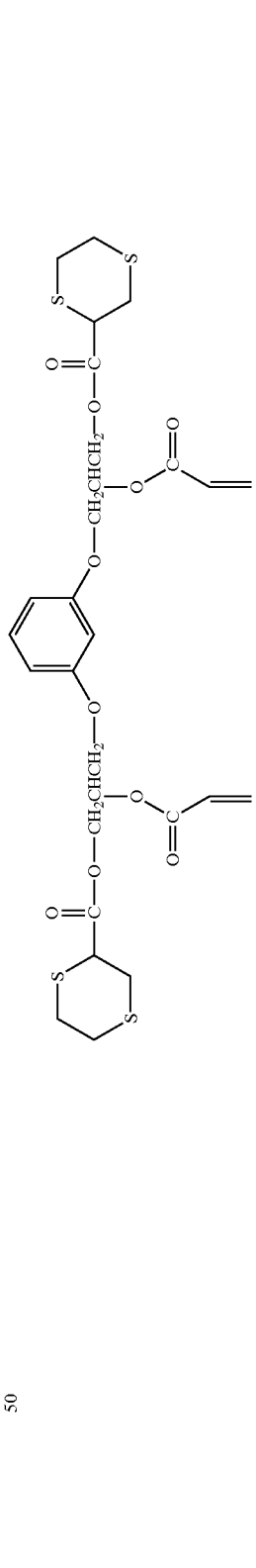 |
| 51 | 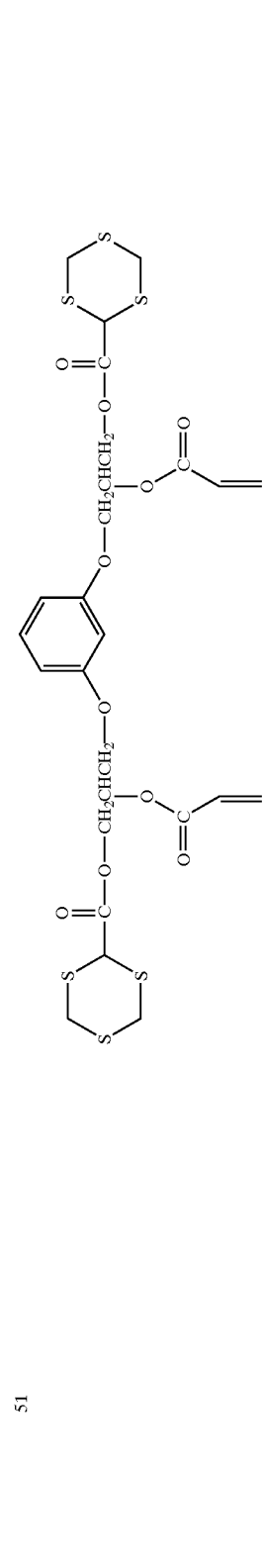 |

TABLE 1-continued
| No. of exemplified compounds | Structure |
|---|---|
| 52 | 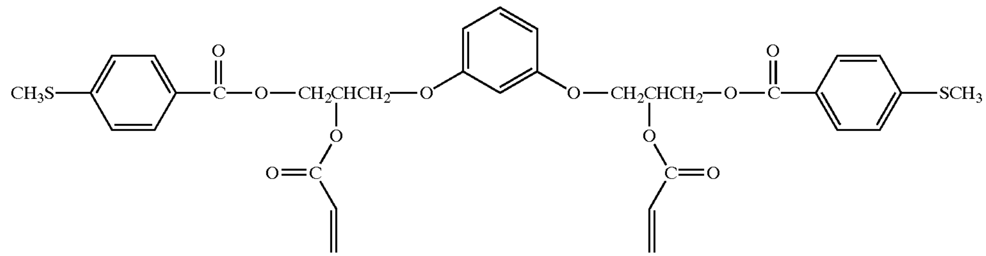 |
| 53 | 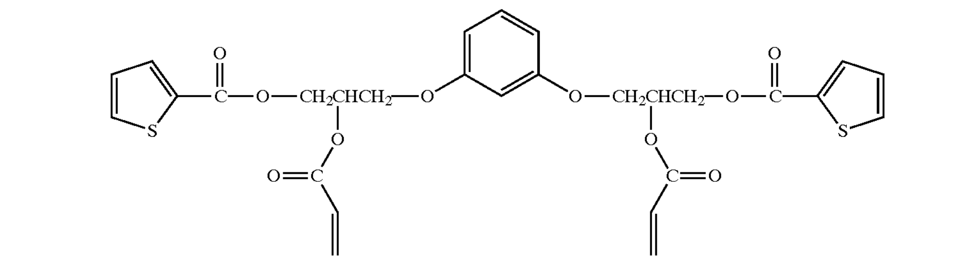 |
| 54 | 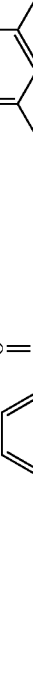 |

TABLE 1-continued

| No. of exemplified compounds | Structure |
|---|---|
| 55 | 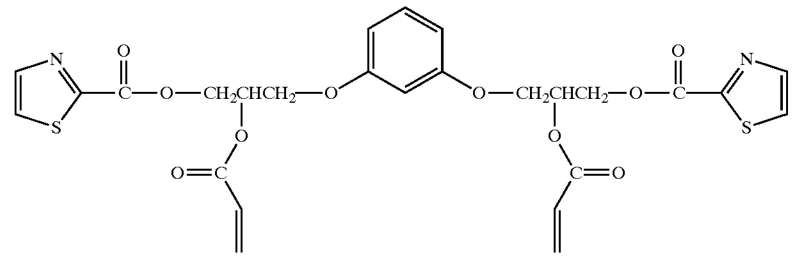 |
| 56 | 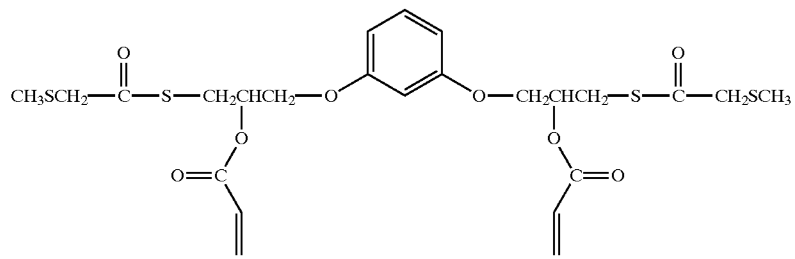 |
| 57 | 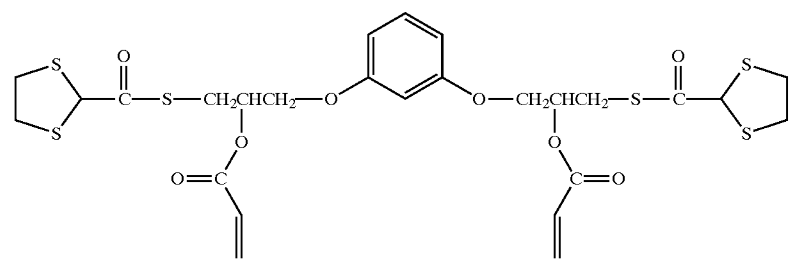 |

TABLE 1-continued
| No. of exemplified compounds | Structure |
|---|---|
| 58 | 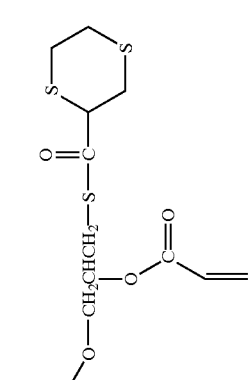 |
| 59 | 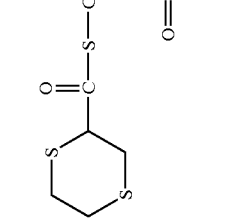 |
| 60 | 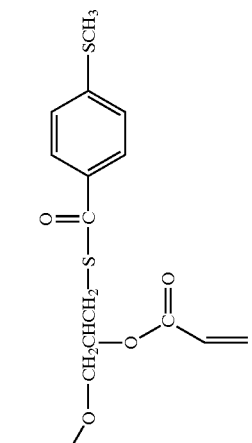 |

TABLE 1-continued
| No. of exemplified compounds | Structure |
|---|---|
| 61 | 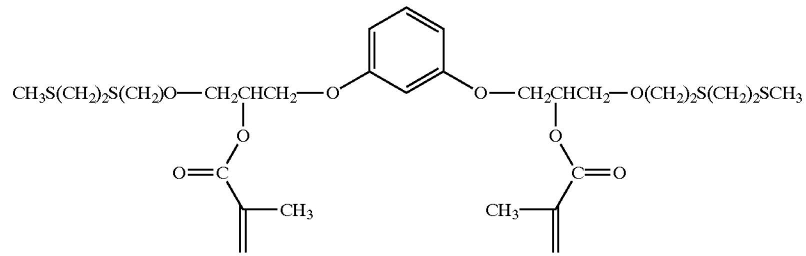 |
| 62 | 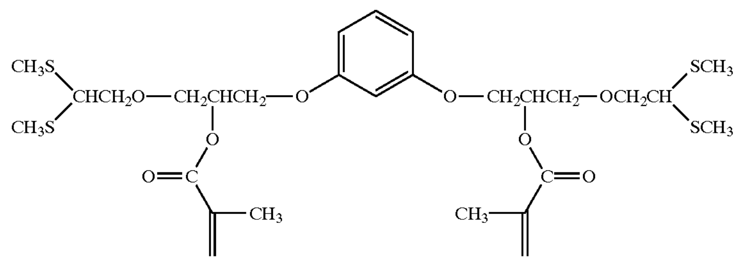 |
| 63 | 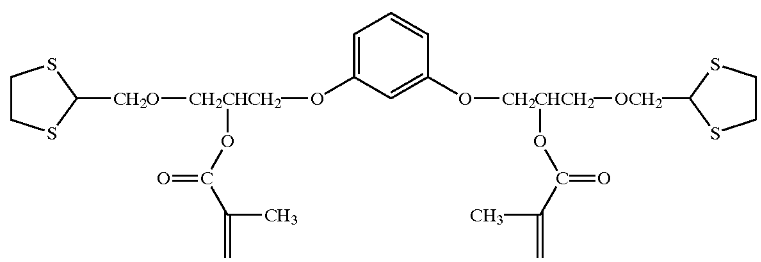 |

TABLE 1-continued

| No. of exemplified compounds | Structure |
|---|---|
| 64 | (structure) |
| 65 | (structure) |
| 66 | (structure) |

TABLE 1-continued
| No. of exemplified compounds | Structure |
|---|---|
| 67 | 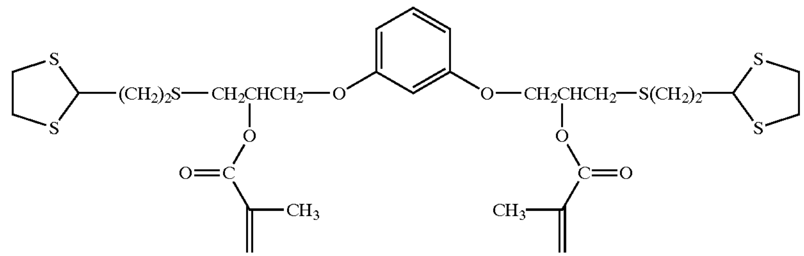 |
| 68 | 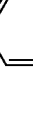 |
| 69 | 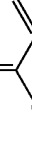 |

TABLE 1-continued
| No. of exemplified compounds | Structure |
|---|---|
| 70 | 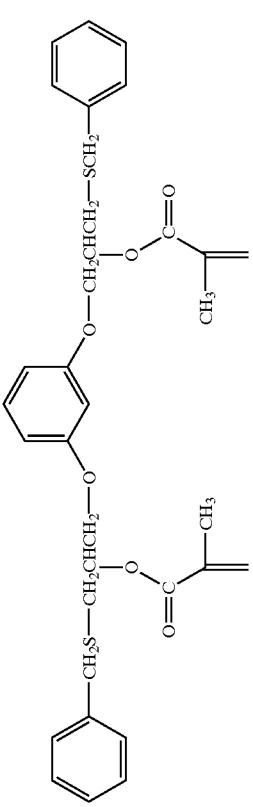 |
| 71 | 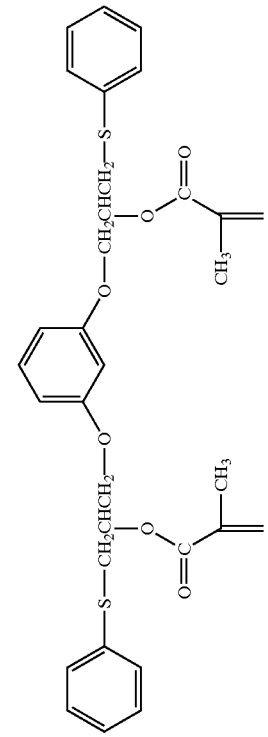 |
| 72 | 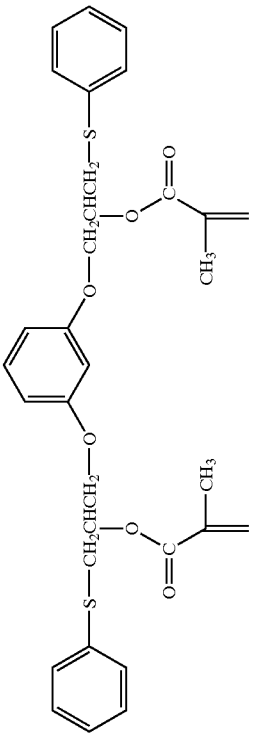 |

TABLE 1-continued
| No. of exemplified compounds | Structure |
|---|---|
| 73 | 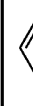 |
| 74 | 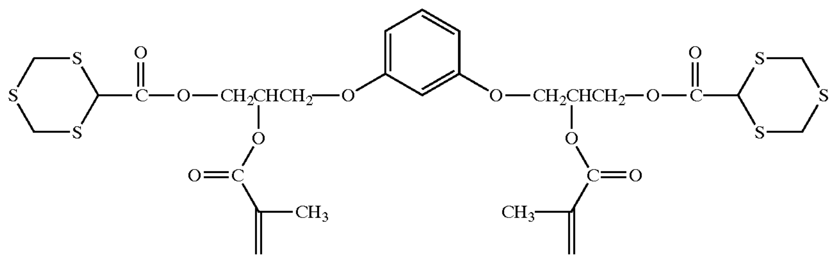 |
| 75 | 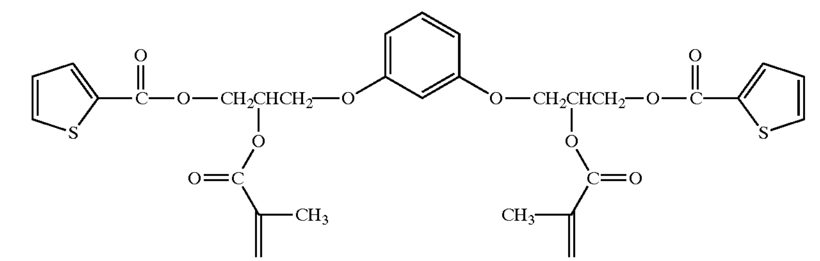 |

TABLE 1-continued
| No. of exemplified compounds | Structure |
|---|---|
| 76 | 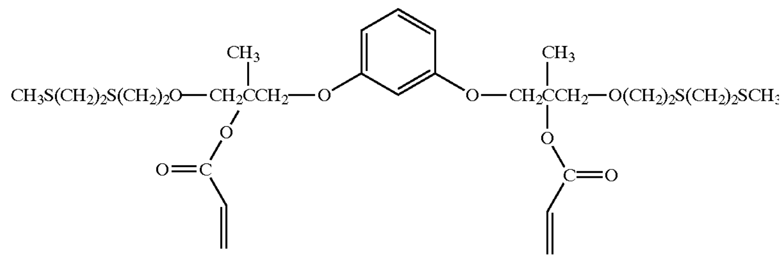 |
| 77 | 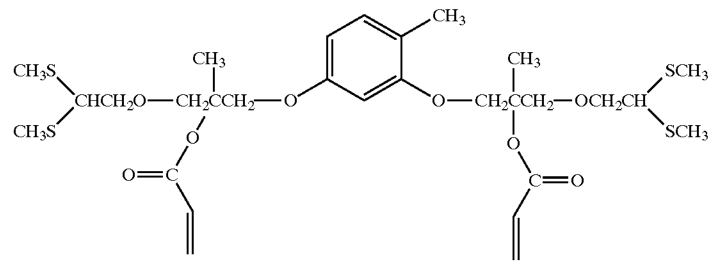 |
| 78 | 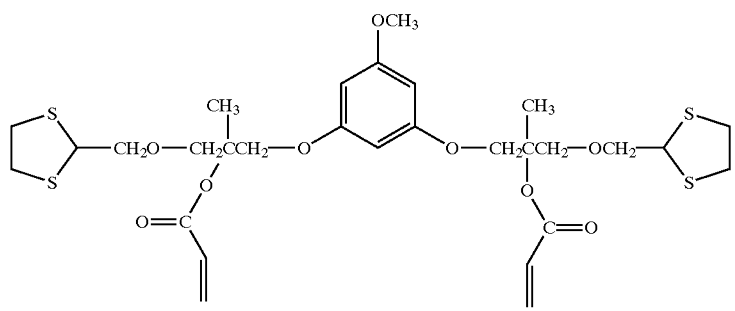 |

TABLE 1-continued

| No. of exemplified compounds | Structure |
|---|---|
| 79 | 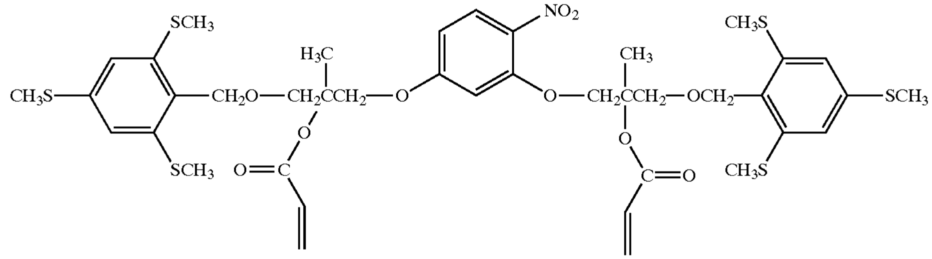 |
| 80 | 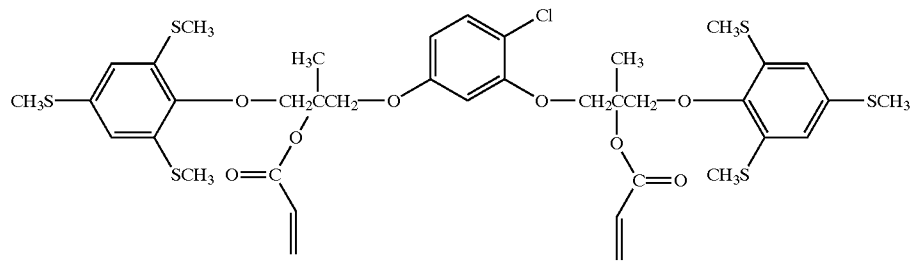 |
| 81 | 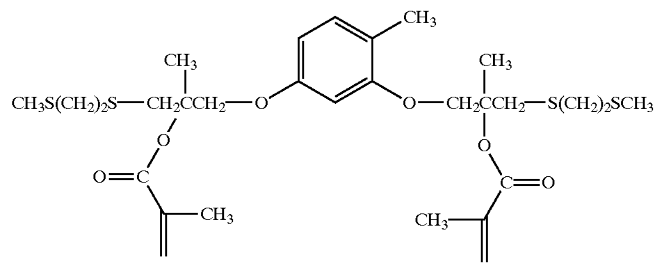 |

TABLE 1-continued

| No. of exemplified compounds | Structure |
|---|---|
| 82 | 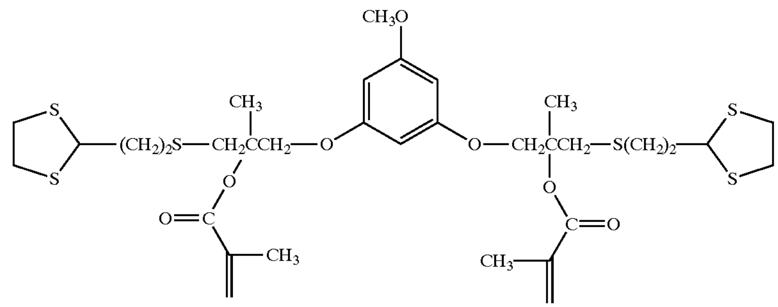 |
| 83 | 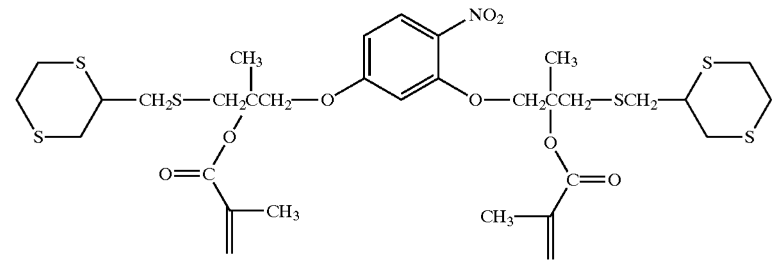 |
| 84 | 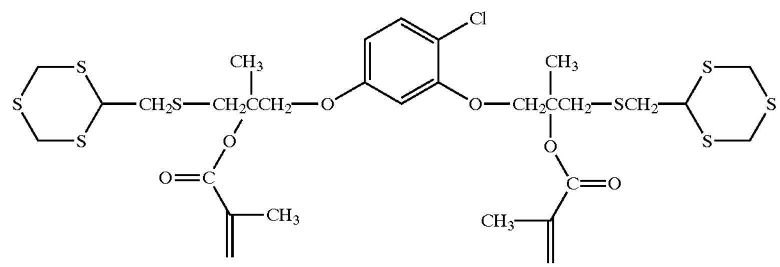 |

TABLE 1-continued
| No. of exemplified compounds | Structure |
|---|---|
| 85 | 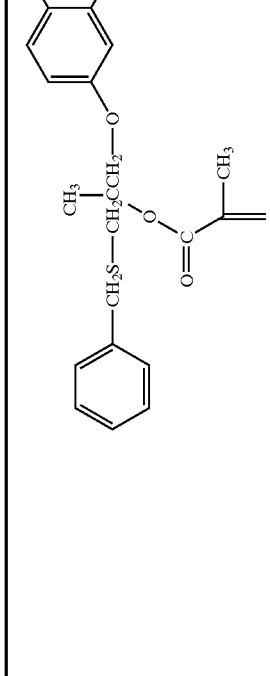 |
| 86 | 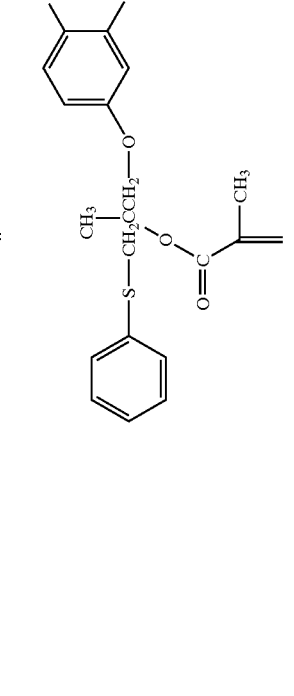 |
| 87 | 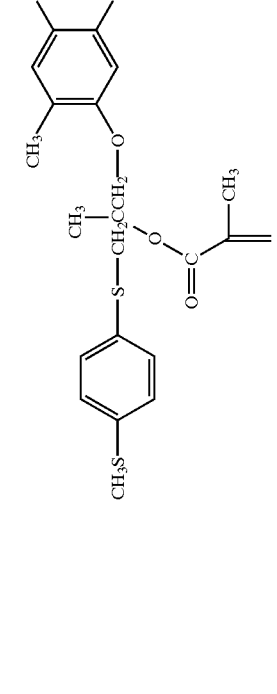 |

TABLE 1-continued

| No. of exemplified compounds | Structure |
|---|---|
| 88 | (structure) |
| 89 | (structure) |
| 90 | (structure) |

TABLE 1-continued

| No. of exemplified compounds | Structure |
|---|---|
| 91 | (structure) |
| 92 | (structure) |
| 93 | (structure) |
| 94 | (structure) |

TABLE 1-continued
| No. of exemplified compounds | Structure |
|---|---|
| 95 | 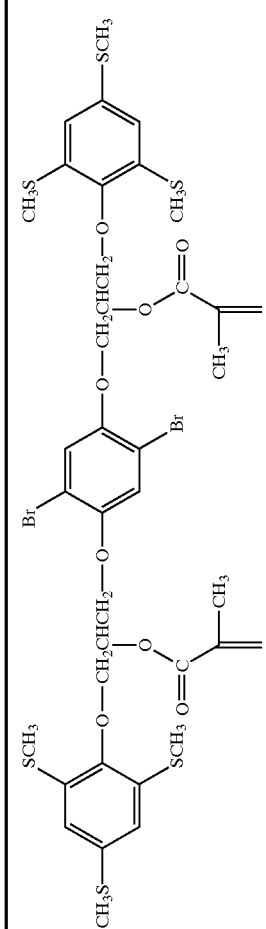 |
| 96 | 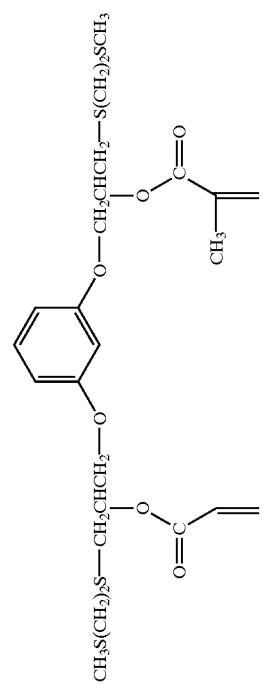 |
| 97 | 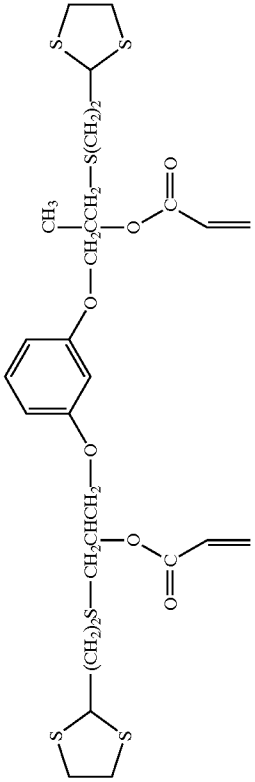 |

TABLE 1-continued

| No. of exemplified compounds | Structure |
|---|---|
| 98 | (structure) |
| 99 | (structure) |
| 100 | (structure) |
| 101 | (structure) |

TABLE 1-continued

| No. of exemplified compounds | Structure |
|---|---|
| 102 | Compound with 4,4'-biphenyl core, bearing -O-CH₂CHCH₂-O(CH₂)₂S(CH₂)₂SCH₃ and acrylate (O-C(=O)-CH=CH₂) on one ring, and -O-CH₂CHCH₂-O-CH₂CH₂S(CH₂)₂SCH₃ with acrylate on the other ring |
| 103 | 3,3',5,5'-tetramethylbiphenyl core with -O-CH₂CHCH₂-OCH₂CH(SCH₃)₂ and acrylate groups on both rings |
| 104 | 3,3',5,5'-tetramethylbiphenyl core with -O-CH₂CHCH₂-OCH₂CH(SC₂H₅)₂ and acrylate groups on both rings |
| 105 | 3,3',5,5'-tetramethylbiphenyl core with -O-CH₂CHCH₂-OCH₂-(1,3-dithiolan-2-yl) and acrylate groups on both rings |

TABLE 1-continued

| No. of exemplified compounds | Structure |
|---|---|
| 106 | 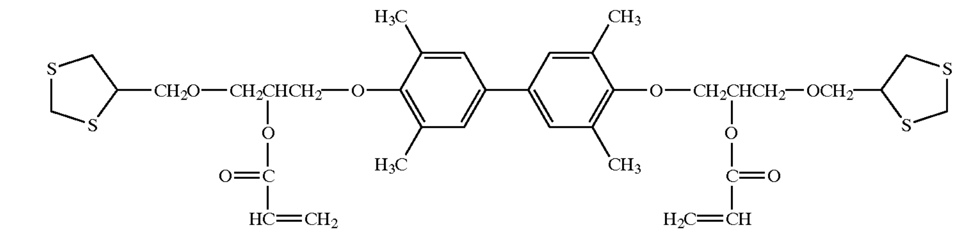 |
| 107 | 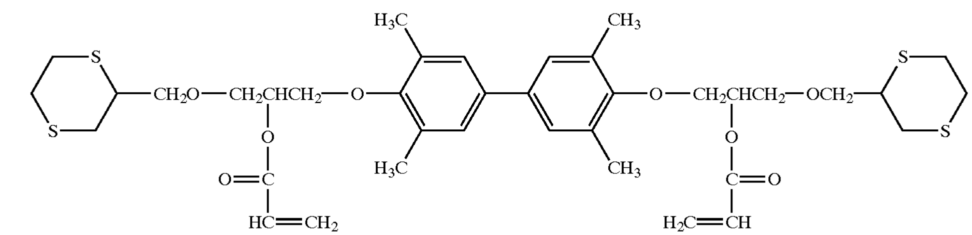 |
| 108 | 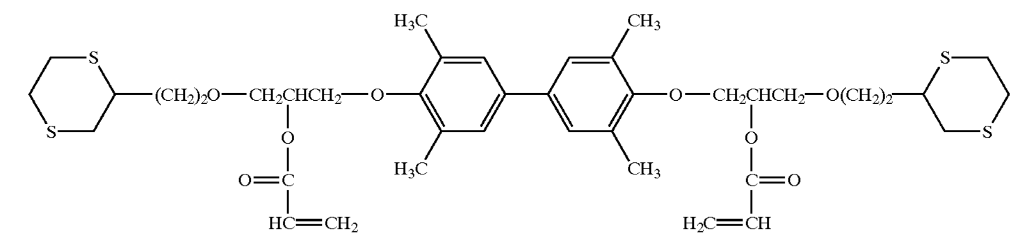 |
| 109 | 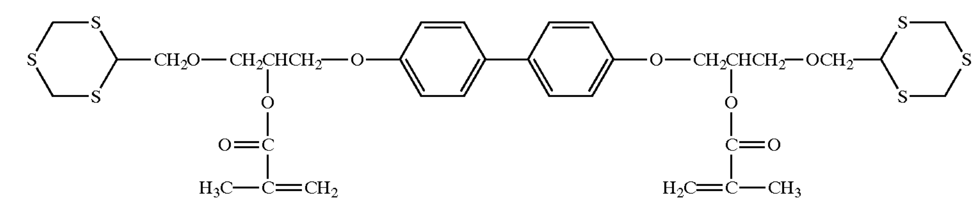 |

TABLE 1-continued

| No. of exemplified compounds | Structure |
|---|---|
| 110 | (chemical structure) |
| 111 | (chemical structure) |
| 112 | (chemical structure) |
| 113 | (chemical structure) |

TABLE 1-continued

| No. of exemplified compounds | Structure |
|---|---|
| 114 | 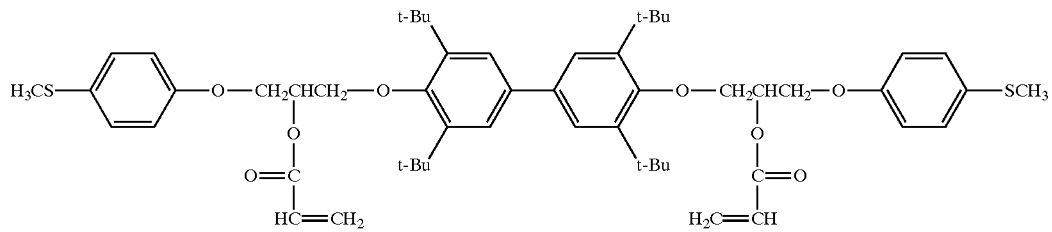 |
| 115 | 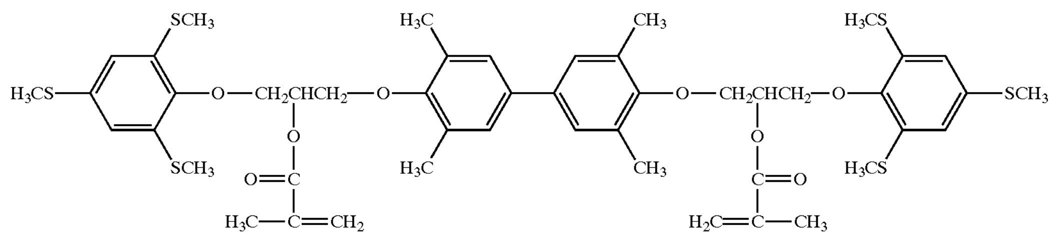 |
| 116 | 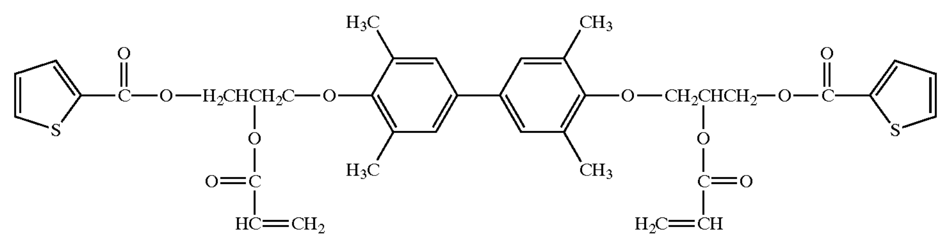 |
| 117 | 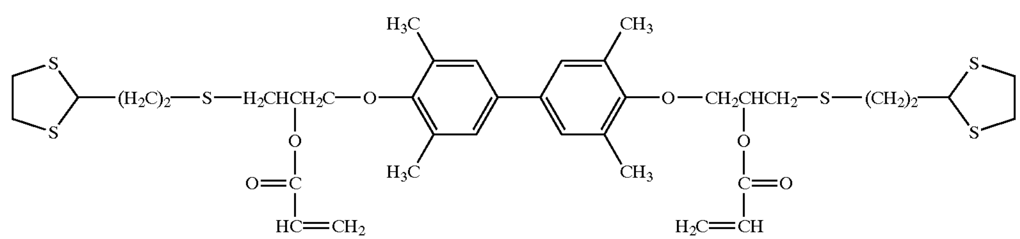 |

TABLE 1-continued

| No. of exemplified compounds | Structure |
|---|---|
| 118 | (structure) |
| 119 | (structure) |
| 120 | (structure) |
| 121 | (structure) |

TABLE 1-continued

| No. of exemplified compounds | Structure |
|---|---|
| 122 | 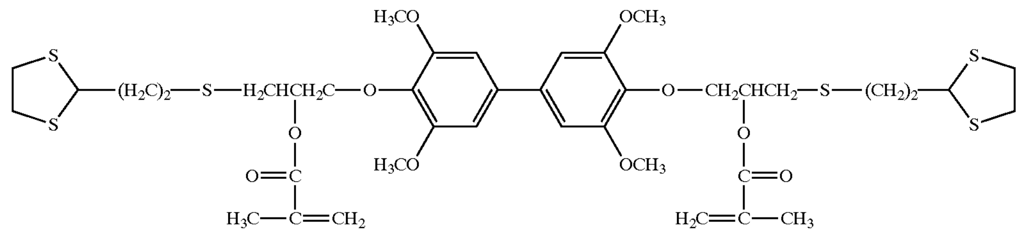 |
| 123 | 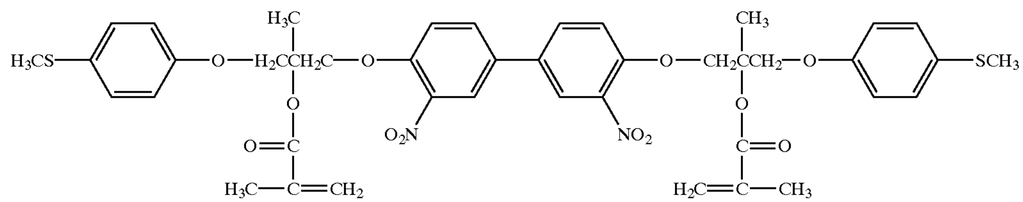 |
| 124 | 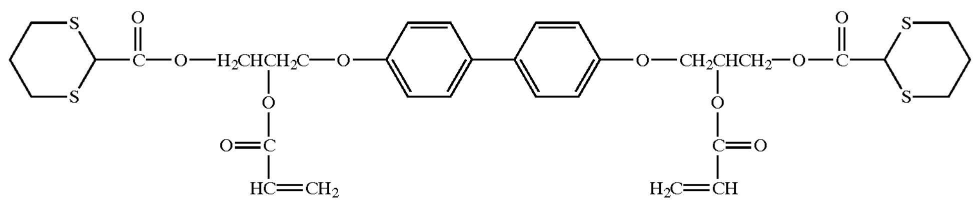 |
| 125 | 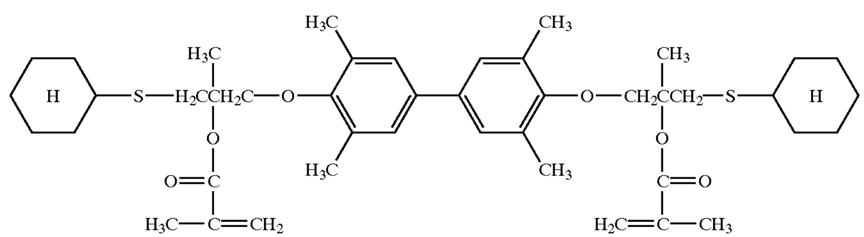 |

TABLE 1-continued

| No. of exemplified compounds | Structure |
|---|---|
| 126 | 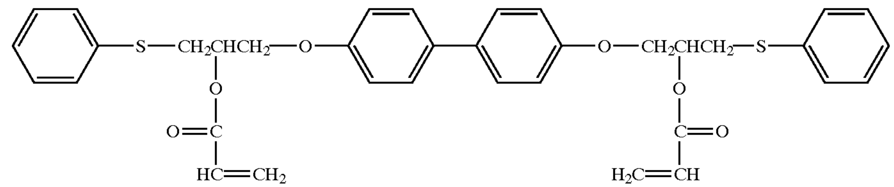 |
| 127 | 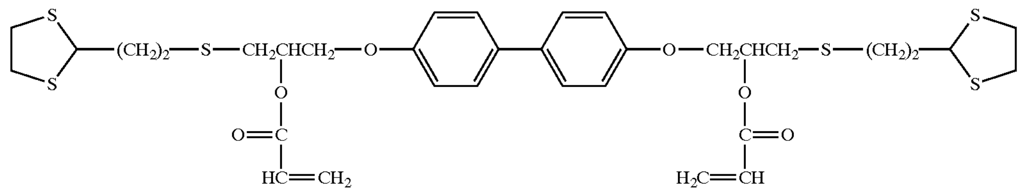 |
| 128 | 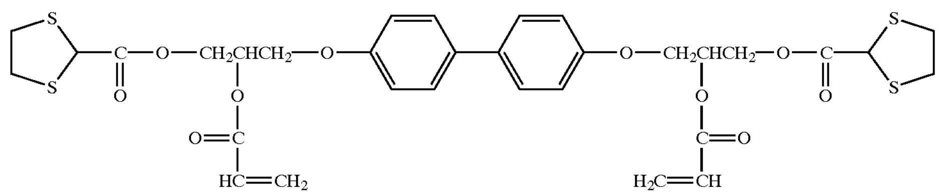 |
| 129 | 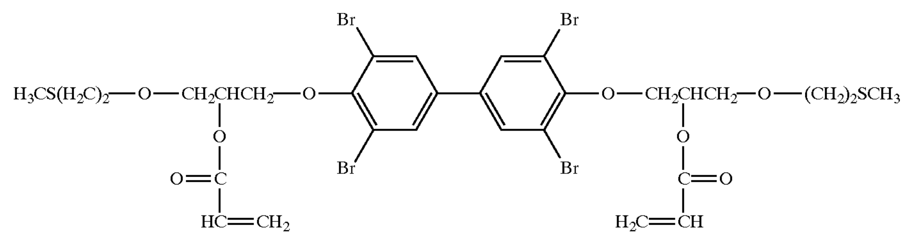 |

TABLE 1-continued
| No. of exemplified compounds | Structure |
|---|---|
| 130 | 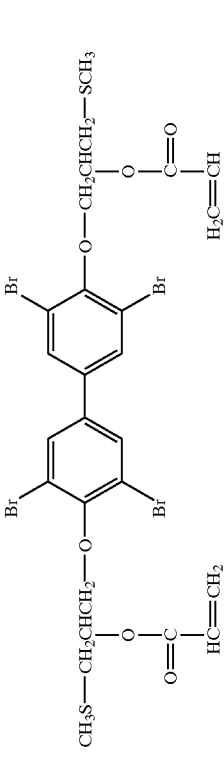 |
| 131 | 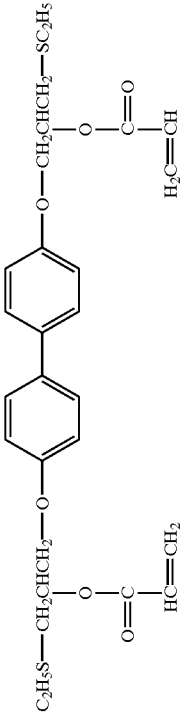 |
| 132 | 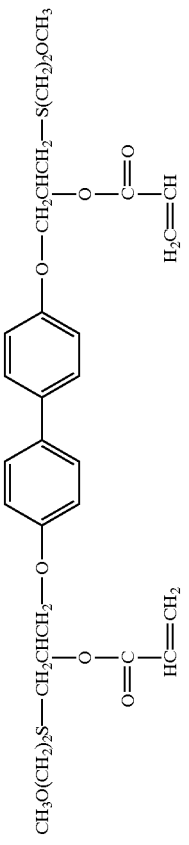 |
| 133 | 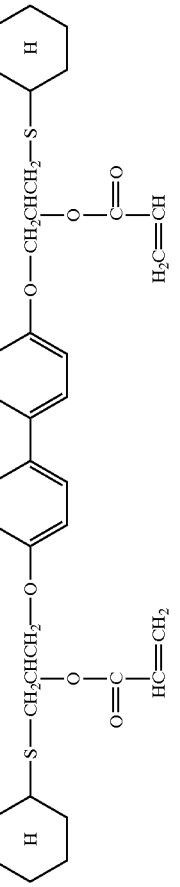 |

TABLE 1-continued

| No. of exemplified compounds | Structure |
|---|---|
| 134 | (structure with dimethyl-biphenyl core, bearing CH₃S(CH₂)₂S—CH₂CHCH₂—O—C(=O)—CH=CH₂ and O—CH₂CHCH₂—S(CH₂)₂SCH₃ with acrylate group) |
| 135 | (structure analogous to 134 with CH₃S(CH₂)₂S(CH₂)₂S— chains) |
| 136 | (biphenyl core with H₃CS/H₃CS—CHCH₂—SCH₂CHCH₂—O—C(=O)—CH=CH₂ substituents) |
| 137 | (biphenyl core with C₂H₅S/C₂H₅S—CHCH₂—SCH₂CHCH₂—O—C(=O)—CH=CH₂ substituents) |

TABLE 1-continued

| No. of exemplified compounds | Structure |
|---|---|
| 138 | 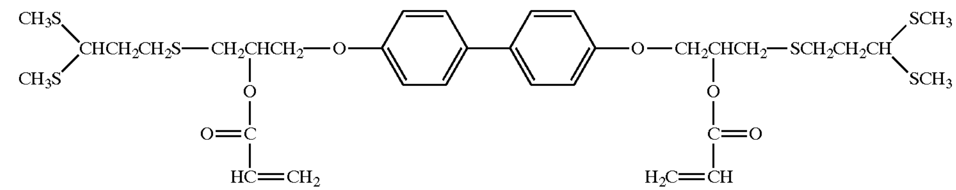 |
| 139 | 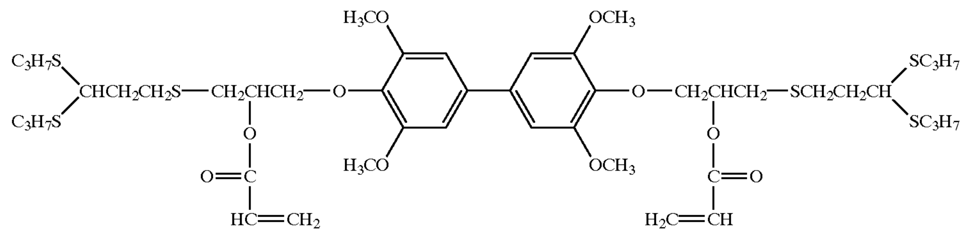 |
| 140 | 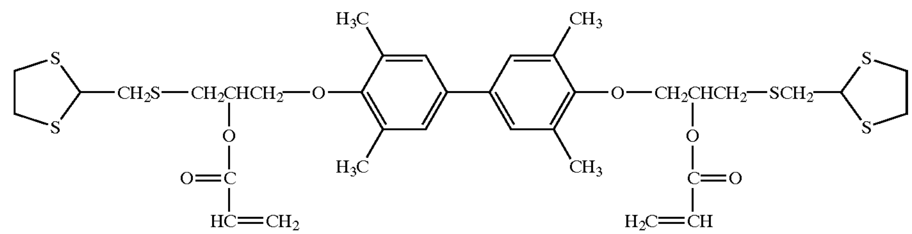 |
| 141 | 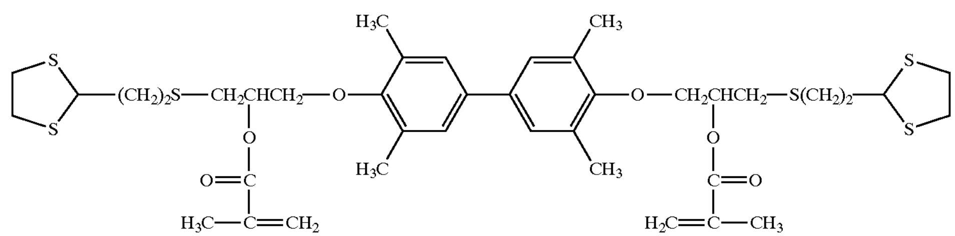 |

TABLE 1-continued

| No. of exemplified compounds | Structure |
|---|---|
| 142 | 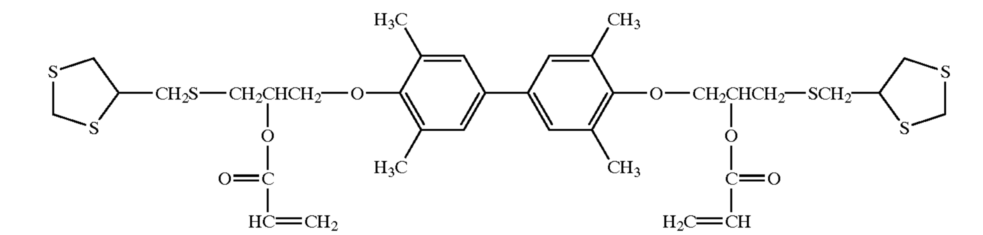 |
| 143 | 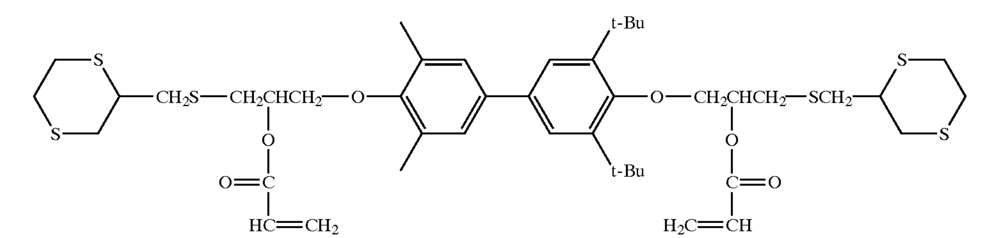 |
| 144 | 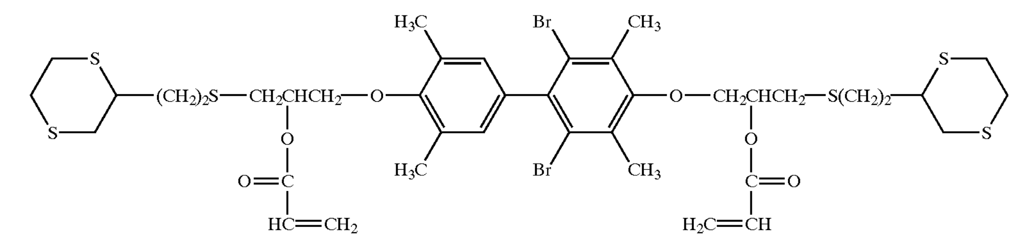 |
| 145 | 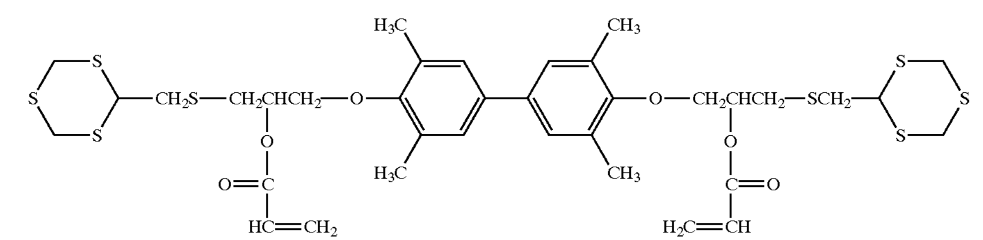 |

TABLE 1-continued
| No. of exemplified compounds | Structure |
|---|---|
| 146 | 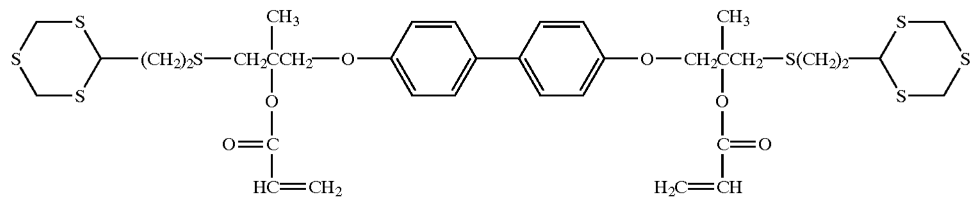 |
| 147 | 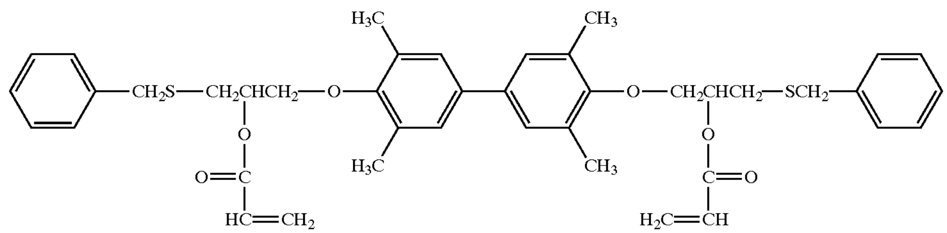 |
| 148 | 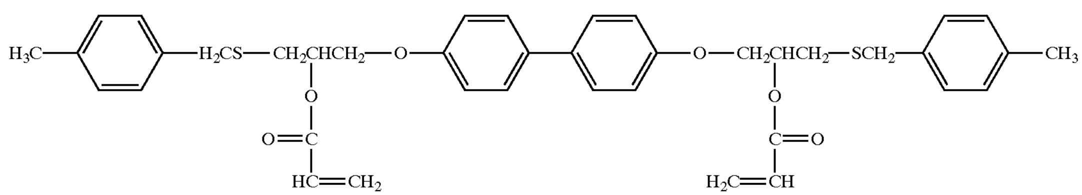 |
| 149 | 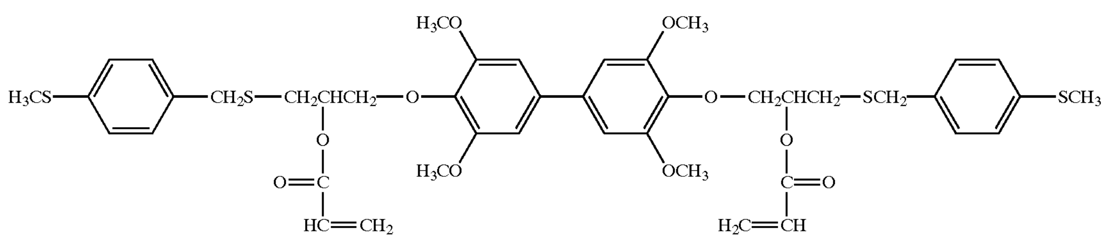 |
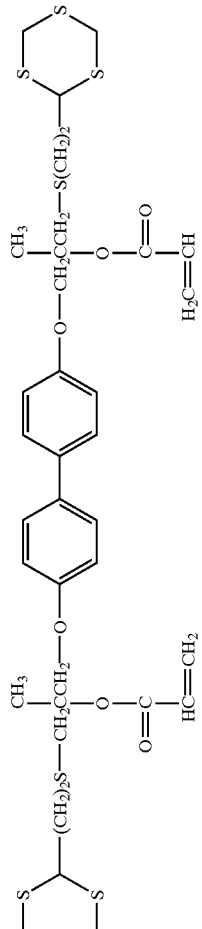

TABLE 1-continued

| No. of exemplified compounds | Structure |
|---|---|
| 150 | (structure) |
| 151 | (structure) |
| 152 | (structure) |
| 153 | (structure) |

TABLE 1-continued

| No. of exemplified compounds | Structure |
|---|---|
| 154 | 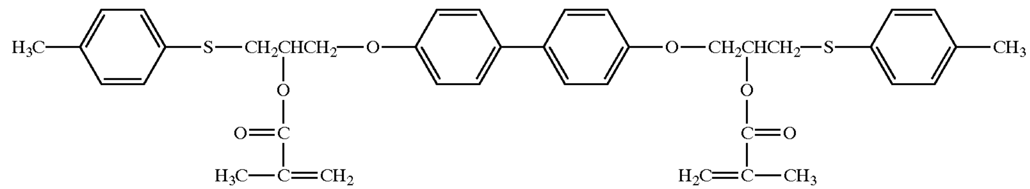 |
| 155 | 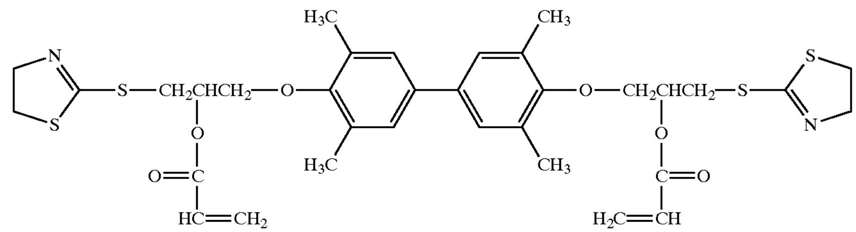 |
| 156 | 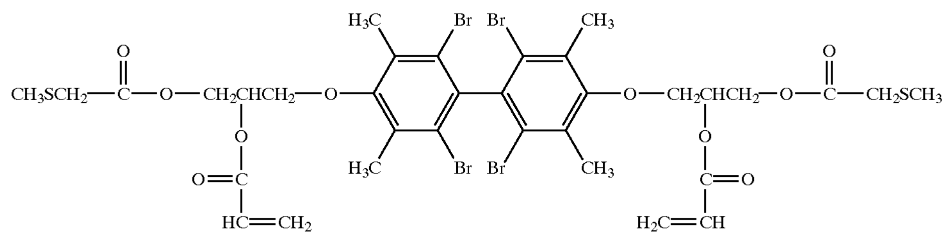 |
| 157 | 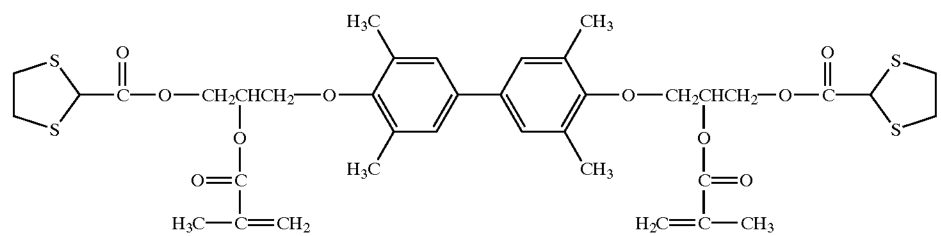 |

TABLE 1-continued

| No. of exemplified compounds | Structure |
| --- | --- |
| 158 | 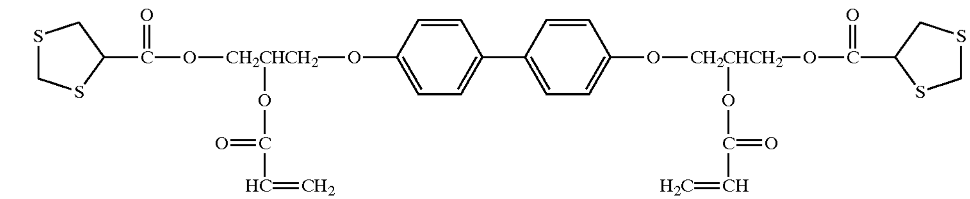 |
| 159 | 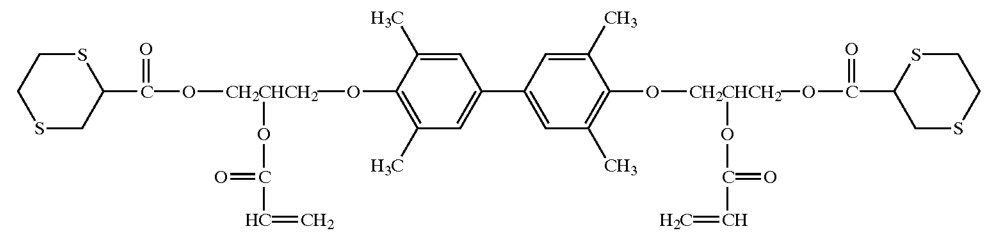 |
| 160 | 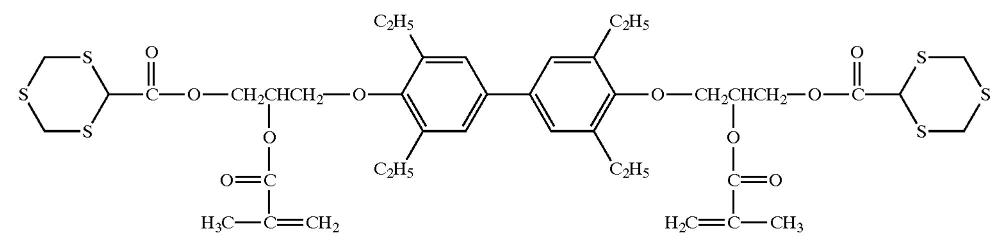 |
| 161 | 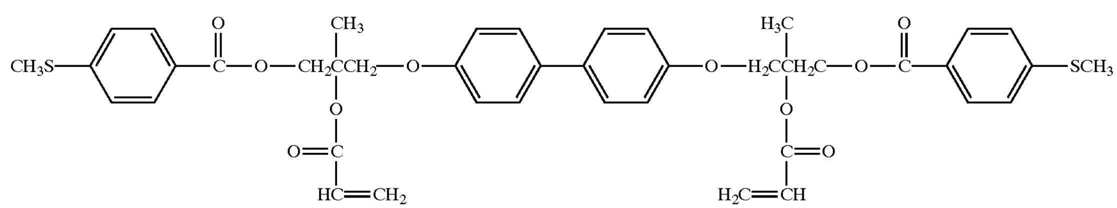 |

TABLE 1-continued

| No. of exemplified compounds | Structure |
|---|---|
| 162 | 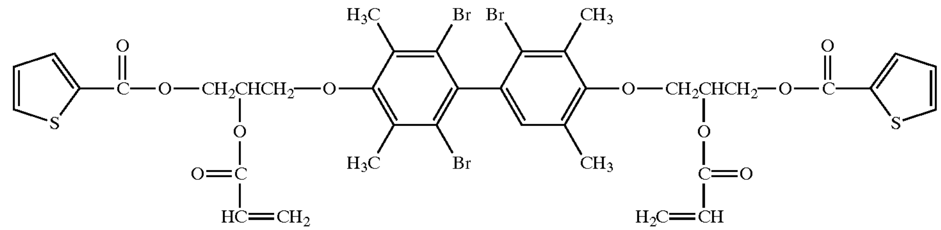 |
| 163 | 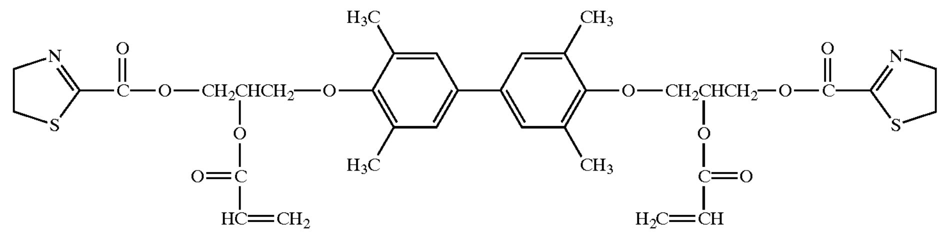 |
| 164 | 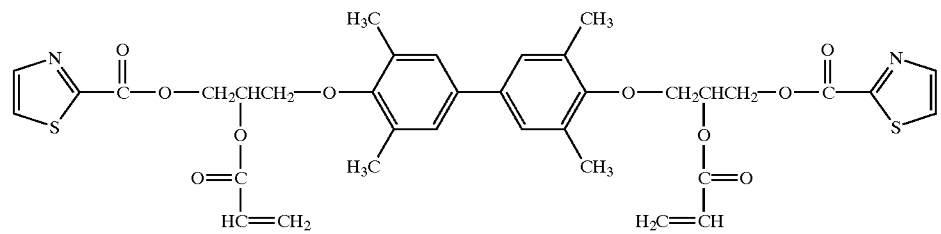 |
| 165 | 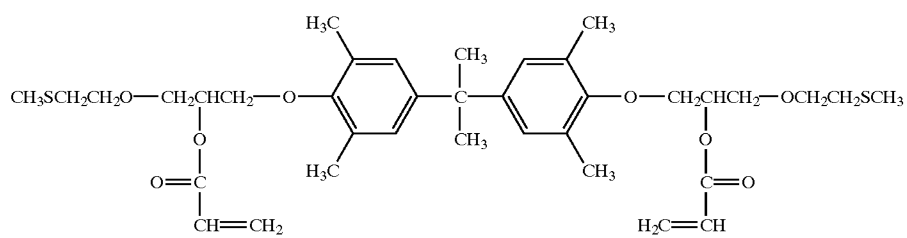 |

TABLE 1-continued

| No. of exemplified compounds | Structure |
| --- | --- |
| 166 | (structure) |
| 167 | (structure) |
| 168 | (structure) |
| 169 | (structure) |

TABLE 1-continued

| No. of exemplified compounds | Structure |
|---|---|
| 170 | 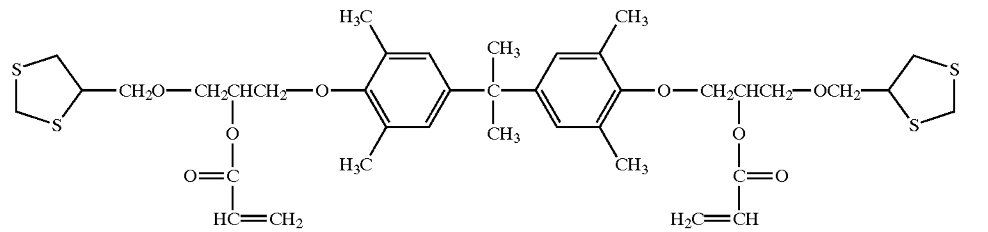 |
| 171 | 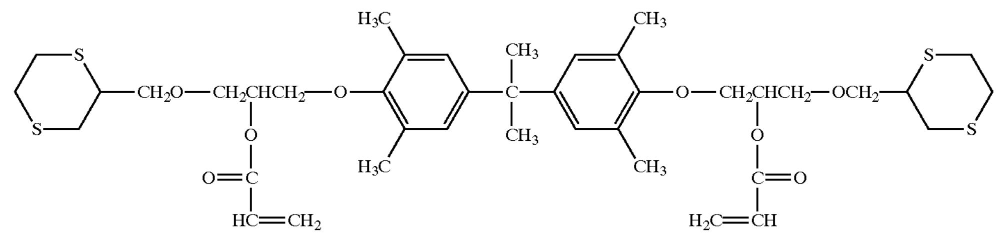 |
| 172 | 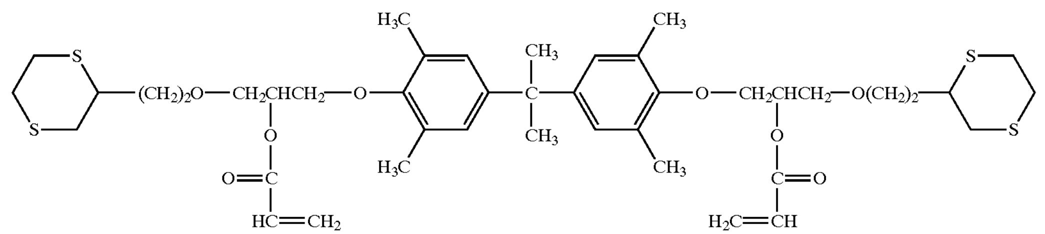 |
| 173 | 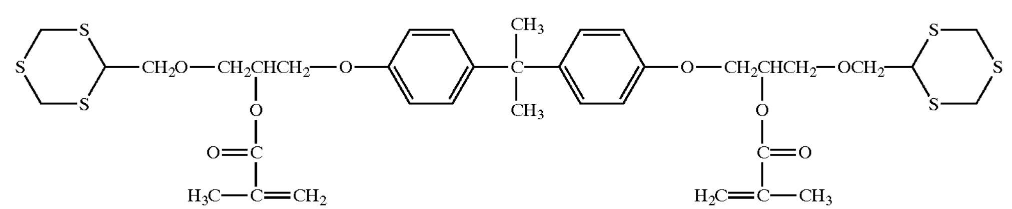 |

TABLE 1-continued

| No. of exemplified compounds | Structure |
|---|---|
| 174 | (structure) |
| 175 | (structure) |
| 176 | (structure) |
| 177 | (structure) |

TABLE 1-continued

| No. of exemplified compounds | Structure |
|---|---|
| 178 | (structure) |
| 179 | (structure) |
| 180 | (structure) |
| 181 | (structure) |

TABLE 1-continued

| No. of exemplified compounds | Structure |
|---|---|
| 182 | (structure) |
| 183 | (structure) |
| 184 | (structure) |
| 185 | (structure) |

TABLE 1-continued

| No. of exemplified compounds | Structure |
|---|---|
| 186 | 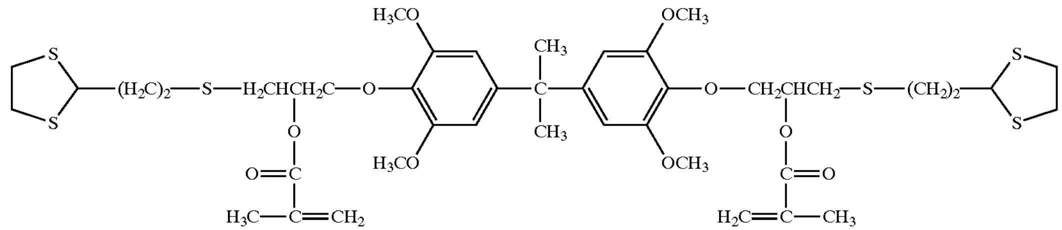 |
| 187 | 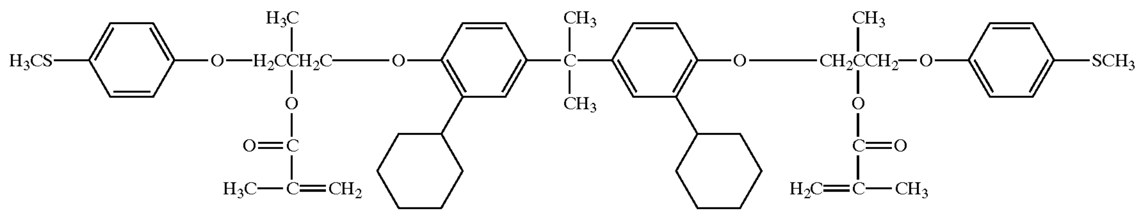 |
| 188 | 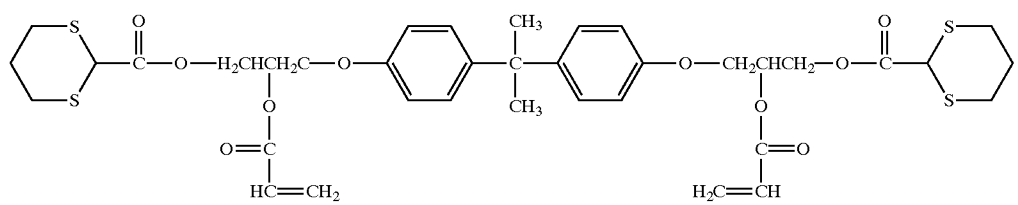 |
| 189 | 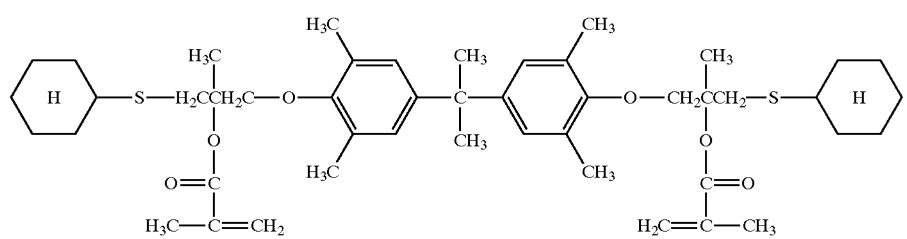 |

TABLE 1-continued

| No. of exemplified compounds | Structure |
|---|---|
| 190 | (structure) |
| 191 | (structure) |
| 192 | (structure) |
| 193 | (structure) |

TABLE 1-continued
| No. of exemplified compounds | Structure |
|---|---|
| 194 | 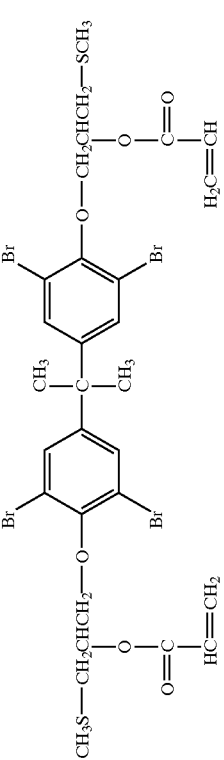 |
| 195 | 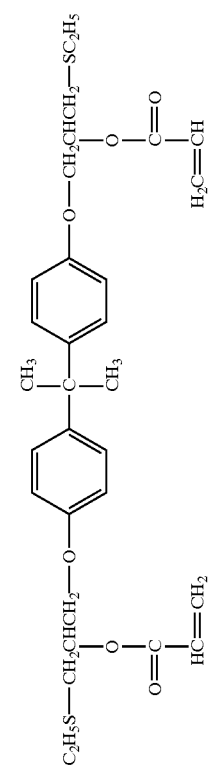 |
| 196 | 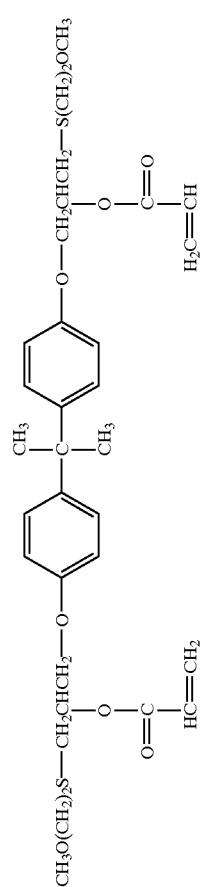 |
| 197 | 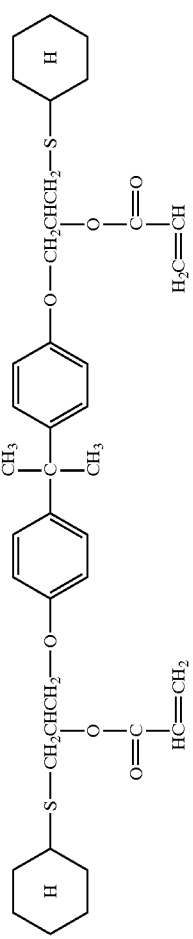 |

TABLE 1-continued

| No. of exemplified compounds | Structure |
|---|---|
| 198 | (structure) |
| 199 | (structure) |
| 200 | (structure) |
| 201 | (structure) |

TABLE 1-continued

| No. of exemplified compounds | Structure |
|---|---|
| 202 | (structure) |
| 203 | (structure) |
| 204 | (structure) |
| 205 | (structure) |

TABLE 1-continued
| No. of exemplified compounds | Structure |
|---|---|
| 206 | 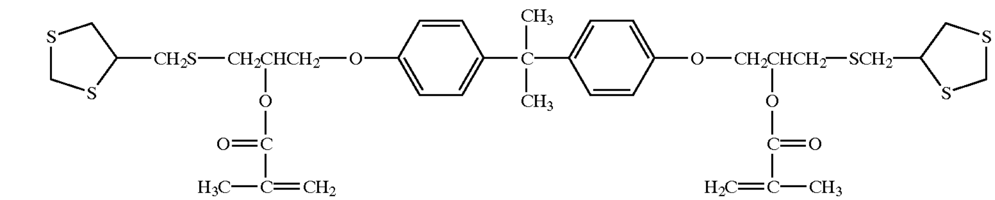 |
| 207 | 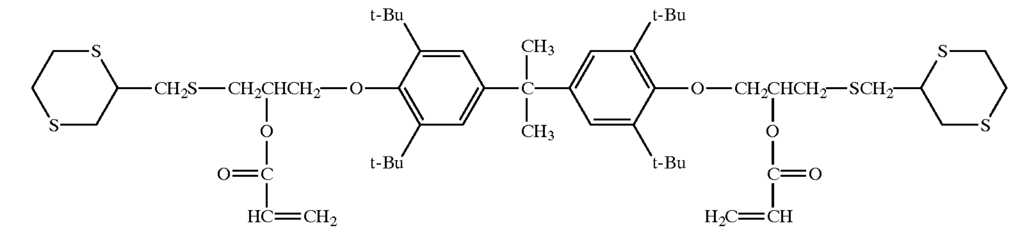 |
| 208 | 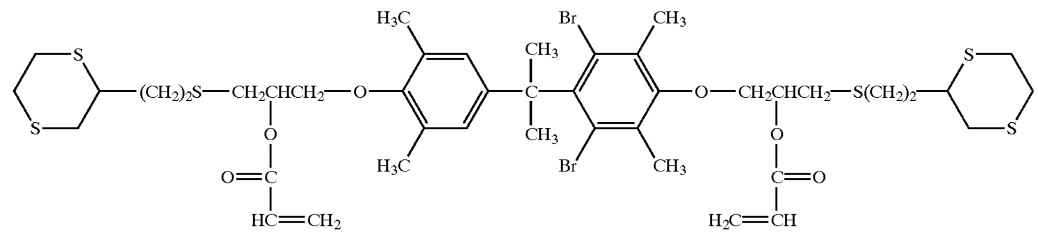 |
| 209 | 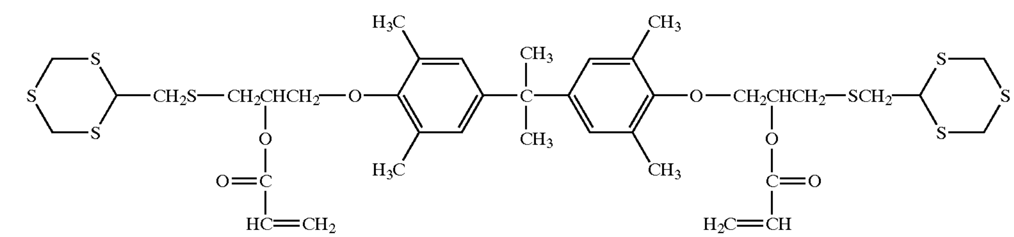 |

TABLE 1-continued

| No. of exemplified compounds | Structure |
|---|---|
| 210 | 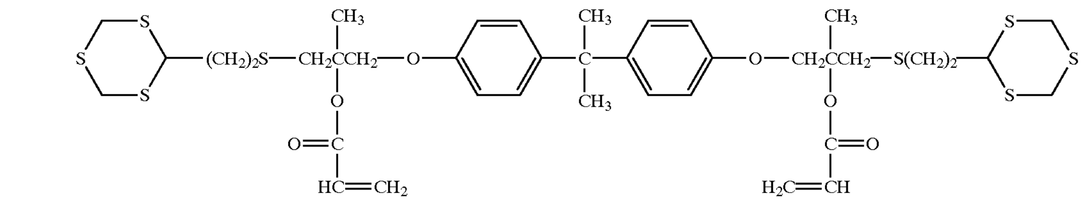 |
| 211 | 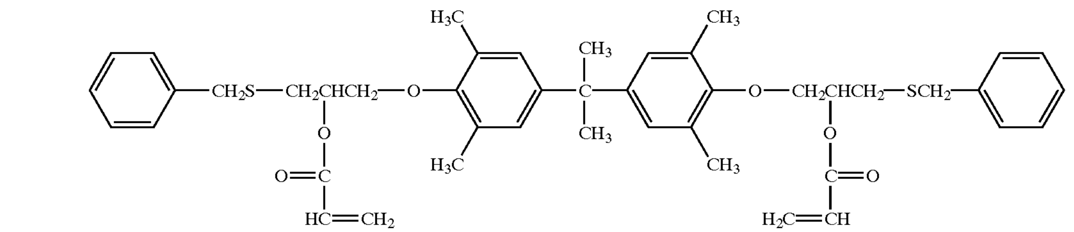 |
| 212 | 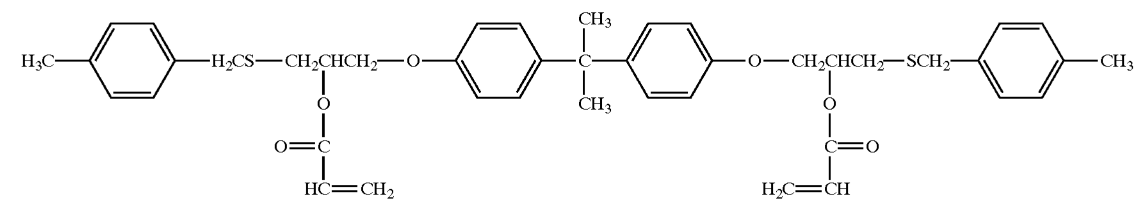 |
| 213 | 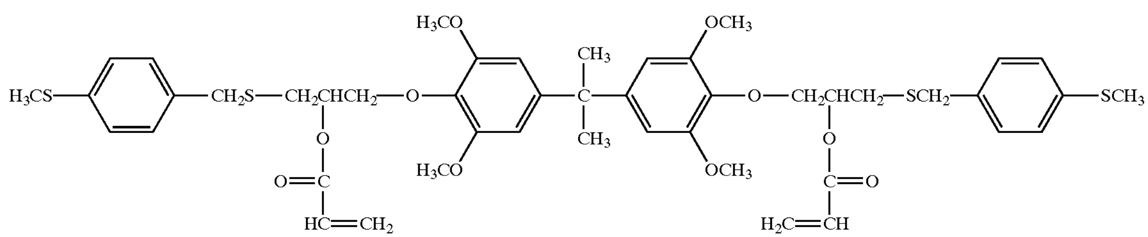 |

TABLE 1-continued
| No. of exemplified compounds | Structure |
|---|---|
| 214 | 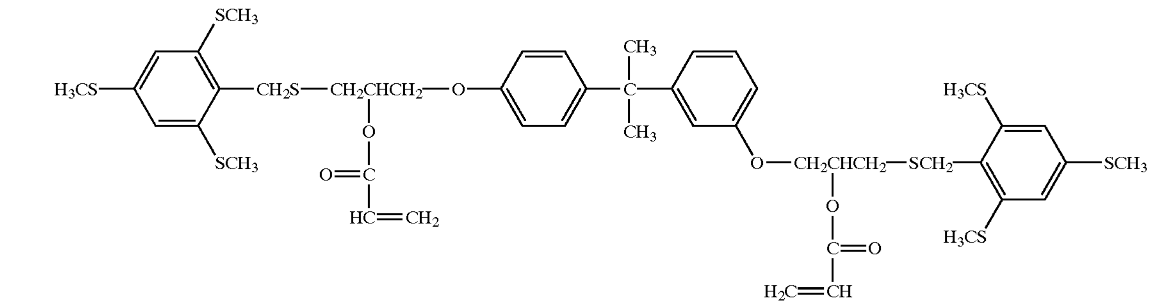 |
| 215 | 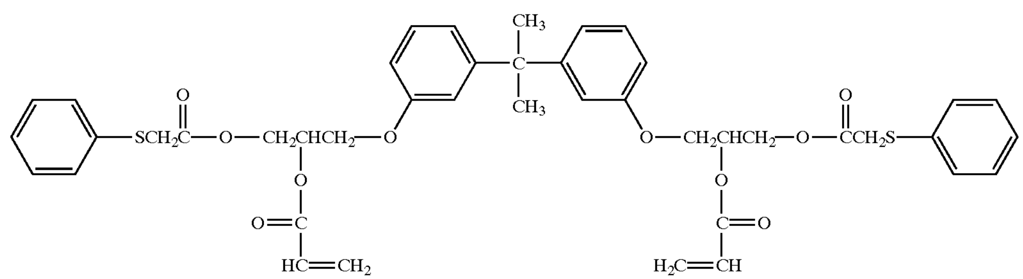 |
| 216 | 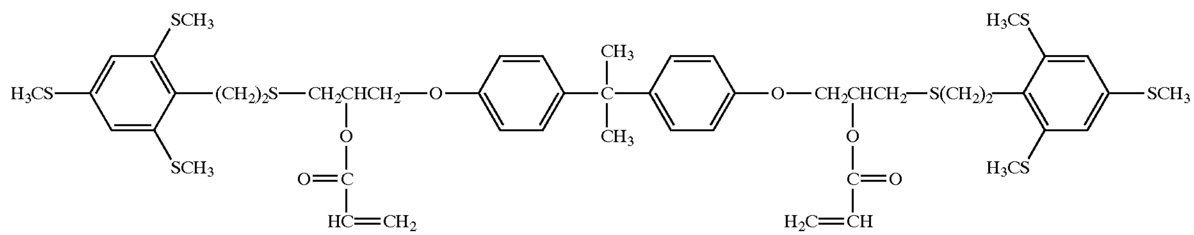 |
| 217 | 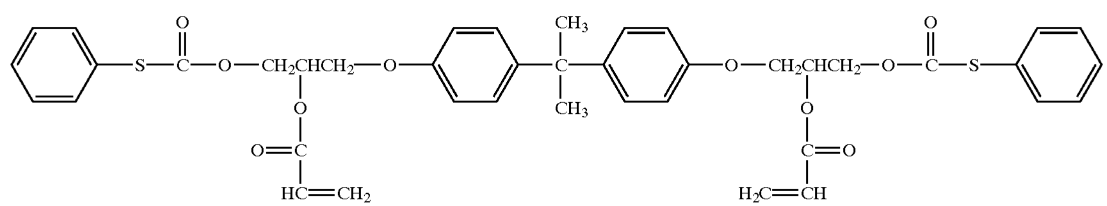 |

TABLE 1-continued

| No. of exemplified compounds | Structure |
|---|---|
| 218 | (structure) |
| 219 | (structure) |
| 220 | (structure) |
| 221 | (structure) |

TABLE 1-continued
| No. of exemplified compounds | Structure |
|---|---|
| 222 | 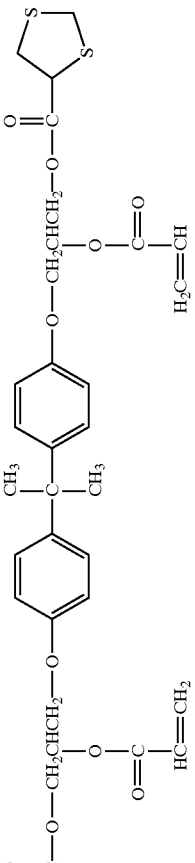 |
| 223 | 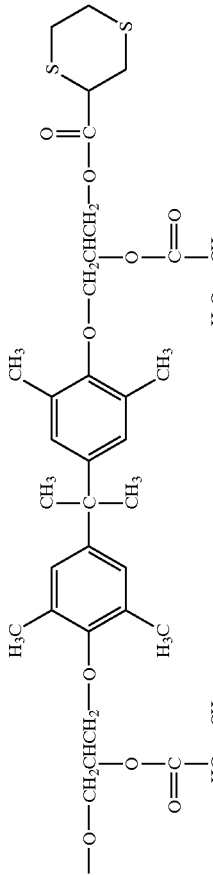 |
| 224 | 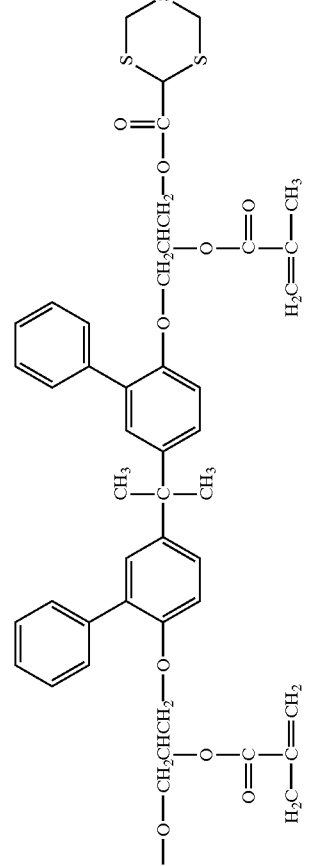 |
| 225 | 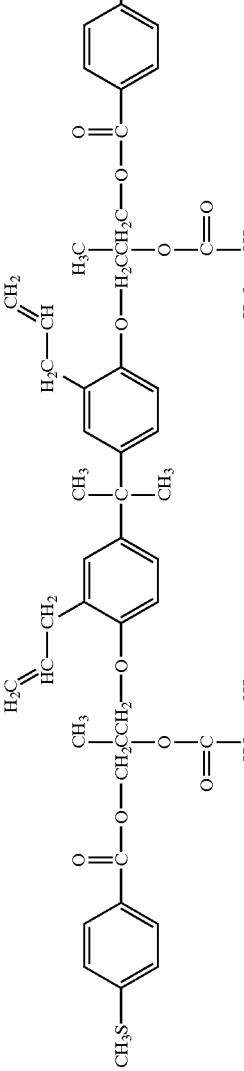 |

TABLE 1-continued

| No. of exemplified compounds | Structure |
|---|---|
| 226 | 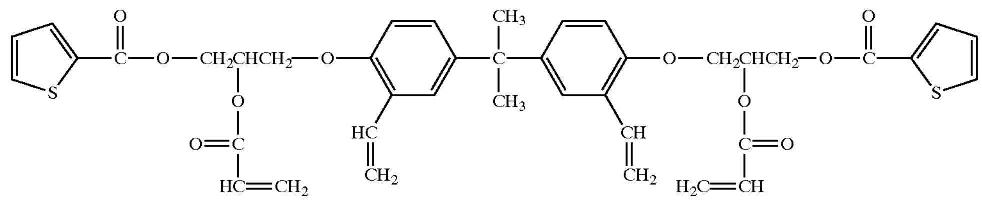 |
| 227 | 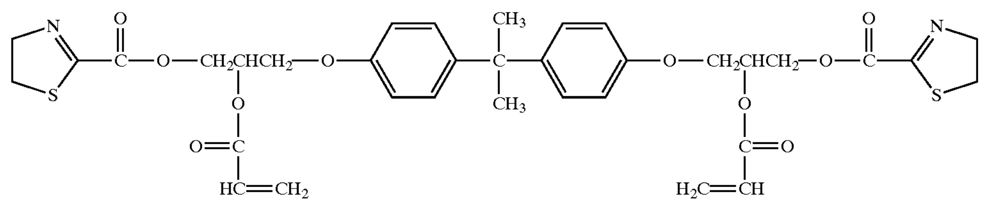 |
| 228 | 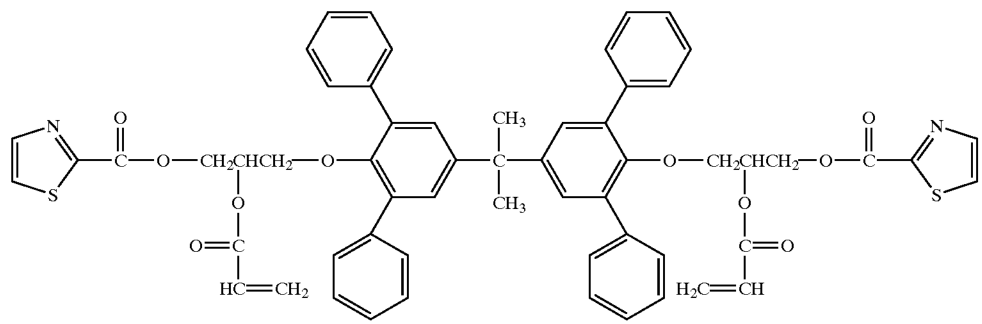 |
| 229 | 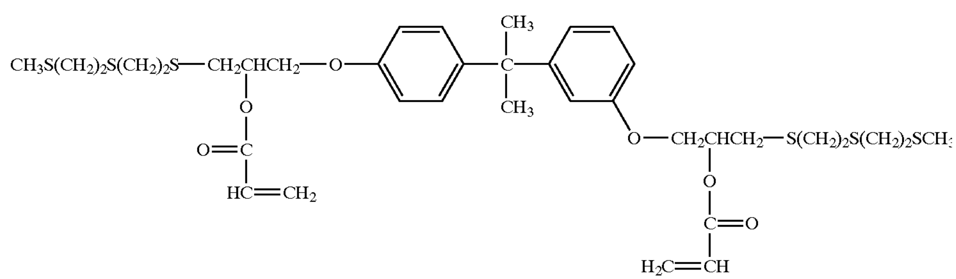 |

TABLE 1-continued
| No. of exemplified compounds | Structure |
|---|---|
| 230 | 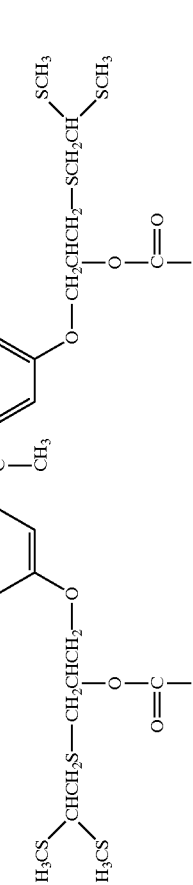 |
| 231 | 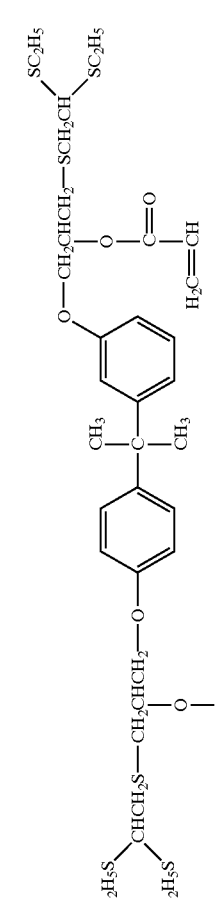 |
| 232 | 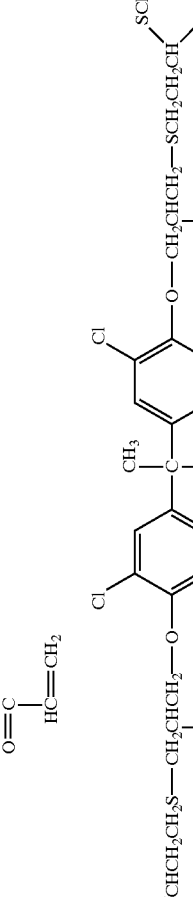 |
| 233 | 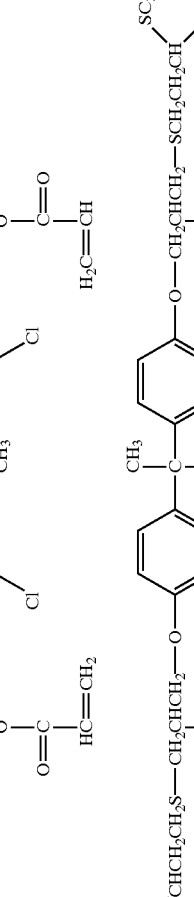 |

TABLE 1-continued
| No. of exemplified compounds | Structure |
|---|---|
| 234 | 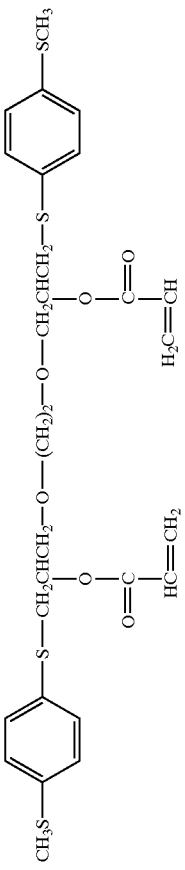 |
| 235 | 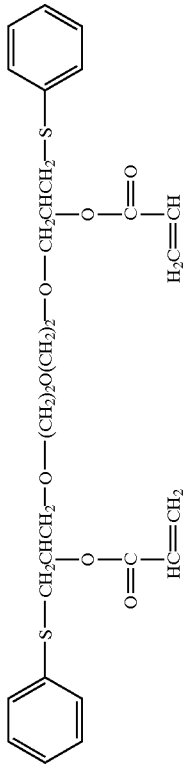 |
| 236 | 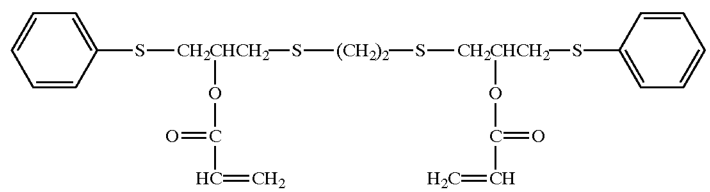 |
| 237 | 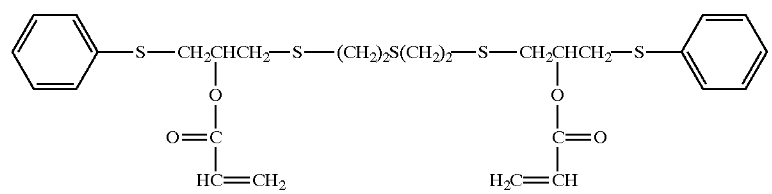 |
| 238 | 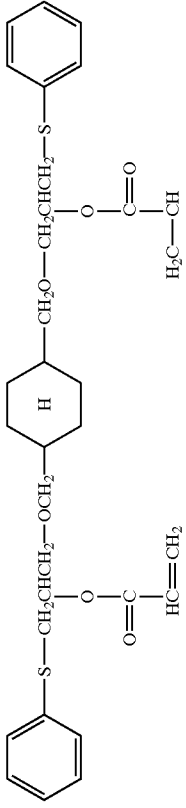 |

TABLE 1-continued

| No. of exemplified compounds | Structure |
|---|---|
| 239 | 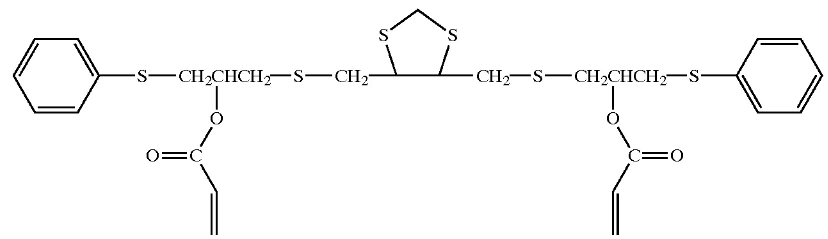 |
| 240 | 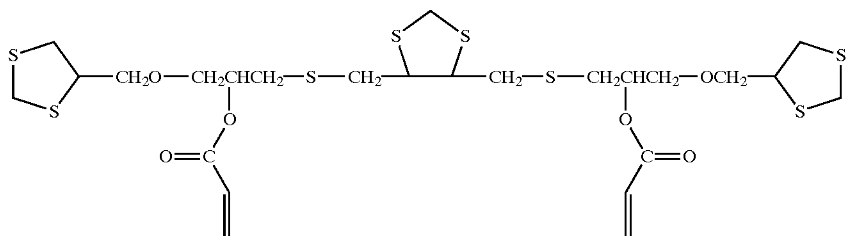 |
| 241 | 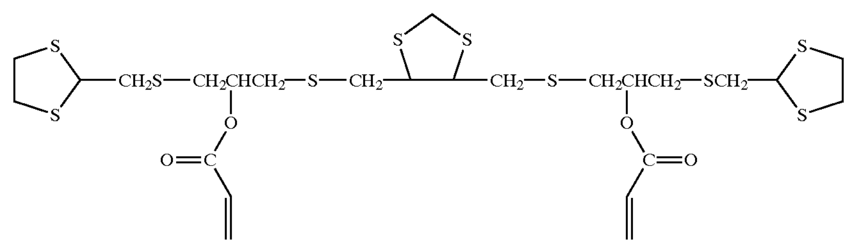 |
| 242 | 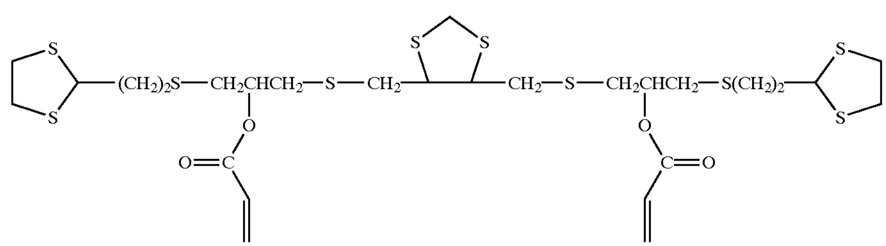 |

TABLE 1-continued

| No. of exemplified compounds | Structure |
|---|---|
| 243 | 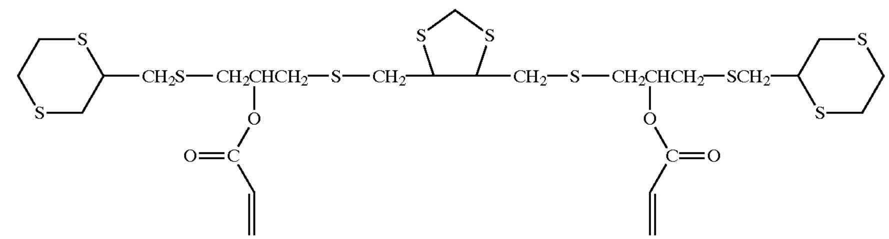 |
| 245 | 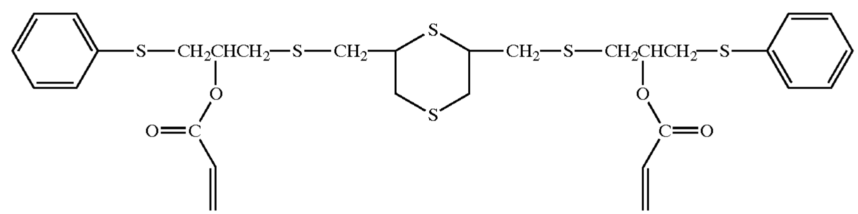 |
| 246 | 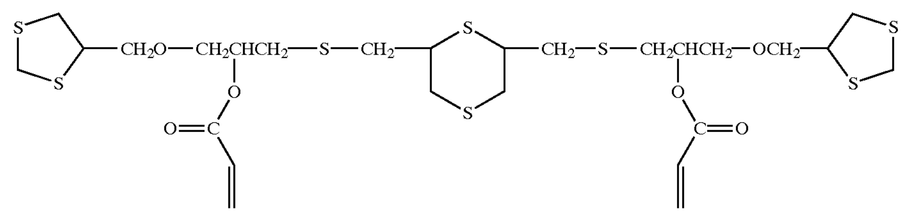 |
| 247 | 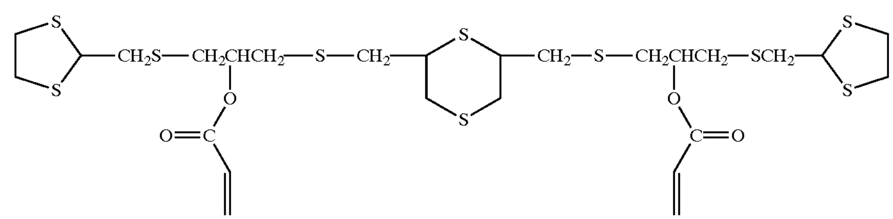 |

TABLE 1-continued

| No. of exemplified compounds | Structure |
|---|---|
| 248 | (structure) |
| 249 | (structure) |
| 250 | (structure) |
| 251 | (structure) |

TABLE 1-continued
| No. of exemplified compounds | Structure |
|---|---|
| 252 | 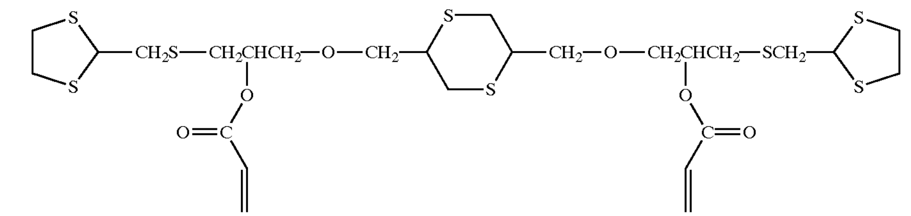 |
| 253 | 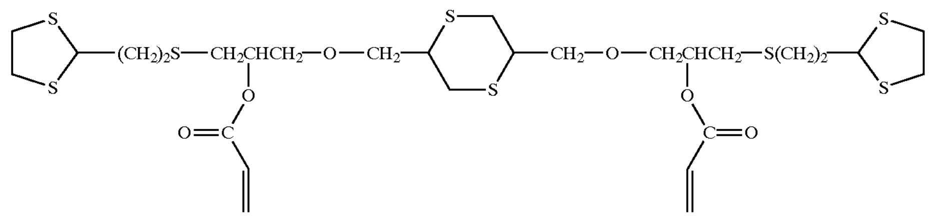 |
| 254 | 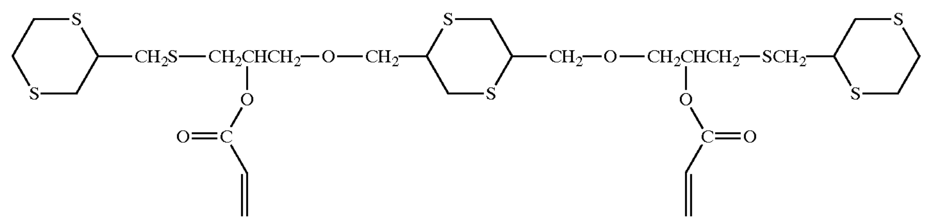 |
| 255 | 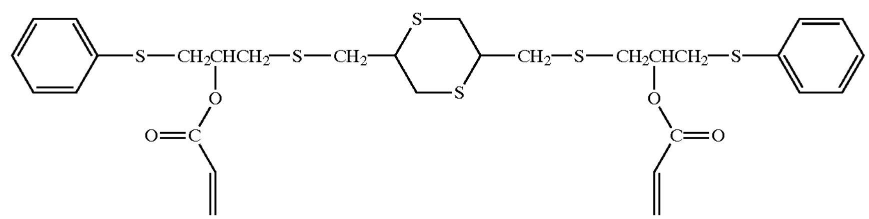 |

TABLE 1-continued
| No. of exemplified compounds | Structure |
|---|---|
| 256 | 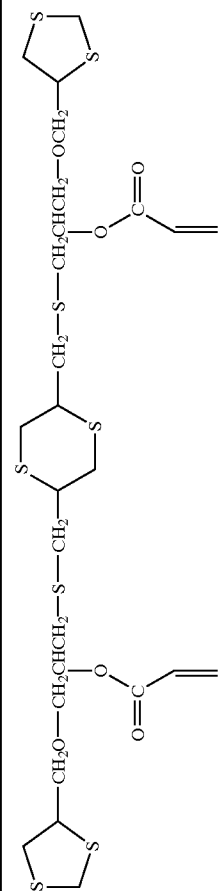 |
| 257 | 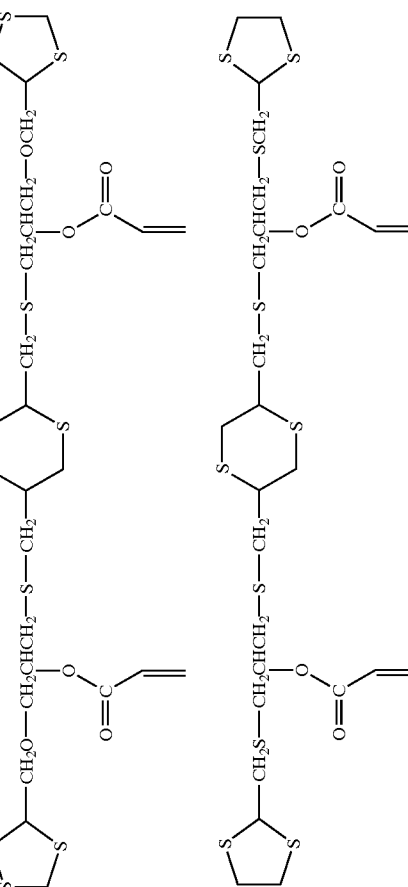 |
| 258 | 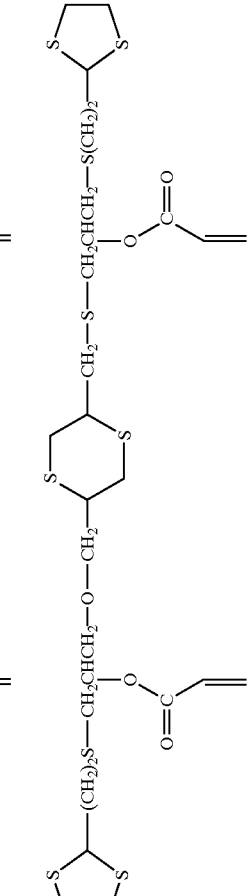 |
| 259 | 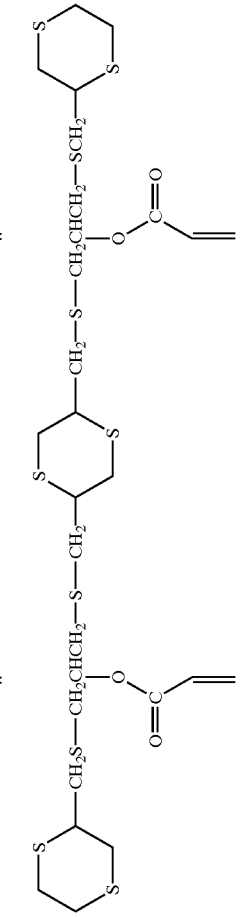 |

TABLE 1-continued

| No. of exemplified compounds | Structure |
|---|---|
| 260 | 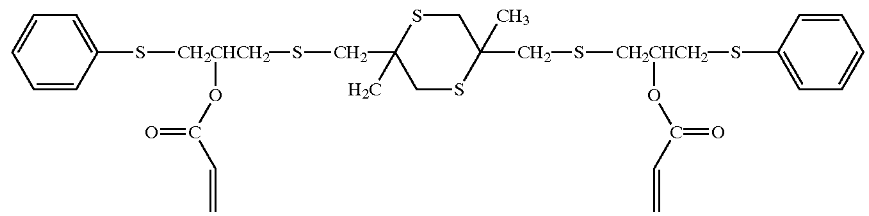 |
| 261 | 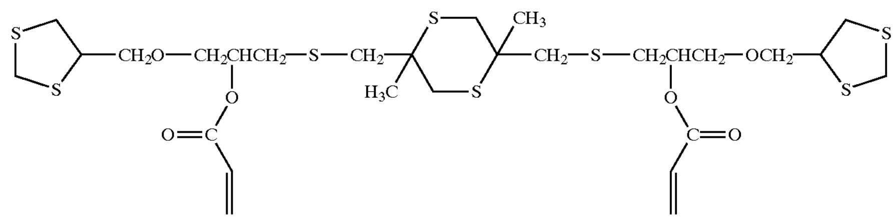 |
| 262 | 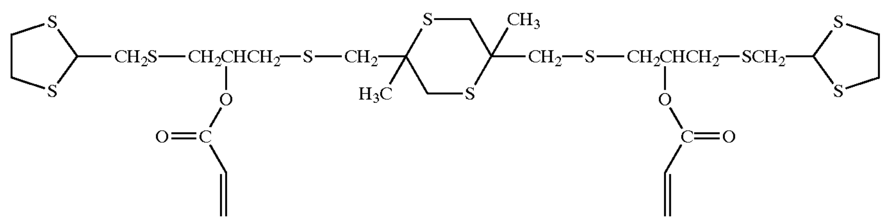 |
| 263 | 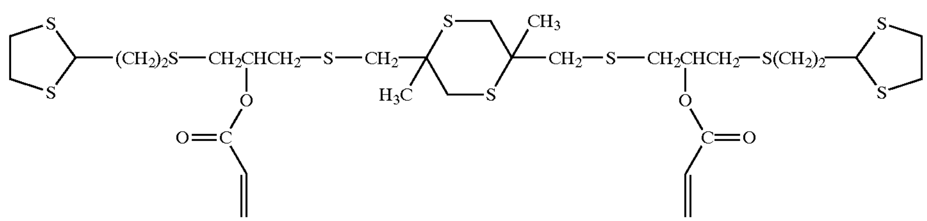 |

TABLE 1-continued

| No. of exemplified compounds | Structure |
|---|---|
| 264 | (structure) |
| 265 | (structure) |
| 266 | (structure) |
| 267 | (structure) |

TABLE 1-continued
| No. of exemplified compounds | Structure |
|---|---|
| 268 | 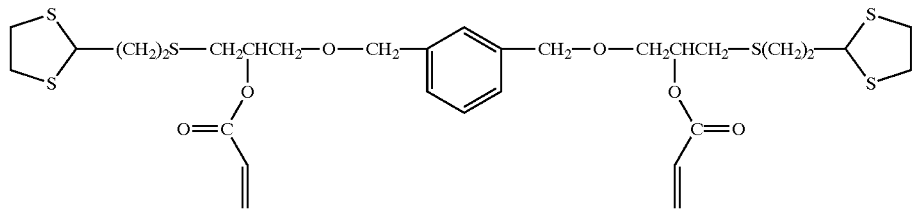 |
| 269 | 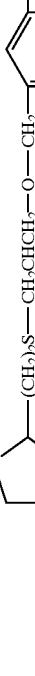 |
| 270 | 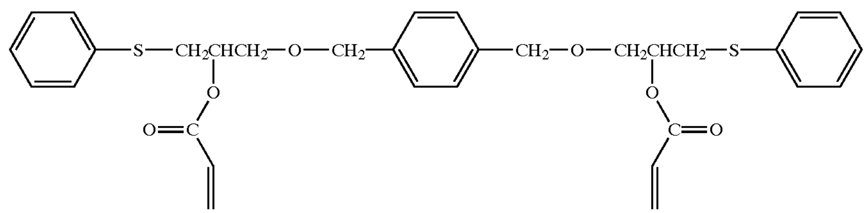 |
| 271 | 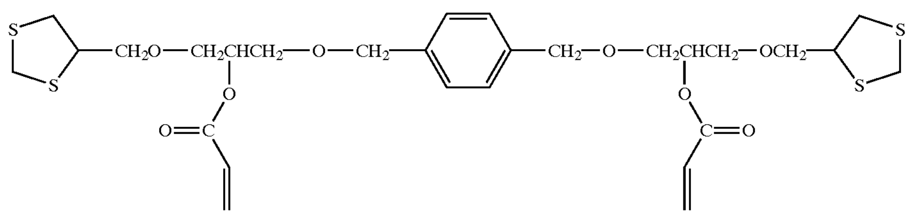 |

TABLE 1-continued

| No. of exemplified compounds | Structure |
|---|---|
| 272 | (1,3-dithiolan-2-yl)-CH₂S—CH₂CHCH₂—O—CH₂—(p-C₆H₄)—CH₂—O—CH₂CHCH₂—SCH₂-(1,3-dithiolan-2-yl), with both CHCH₂ bearing O—C(=O)—CH=CH₂ (acrylate) groups |
| 273 | (1,3-dithiolan-2-yl)-(CH₂)₂S—CH₂CHCH₂—O—CH₂—(p-C₆H₄)—CH₂—O—CH₂CHCH₂—S(CH₂)₂-(1,3-dithiolan-2-yl), with both CHCH₂ bearing acrylate groups |
| 274 | (1,3-dithian-2-yl)-CH₂S—CH₂CHCH₂—O—CH₂—(p-C₆H₄)—CH₂—O—CH₂CHCH₂—SCH₂-(1,3-dithian-2-yl), with both CHCH₂ bearing acrylate groups |
| 275 | C₆H₅—S—CH₂CHCH₂—S—CH₂—(C₆H₄)—CH₂—S—CH₂CHCH₂—S—C₆H₅, with both CHCH₂ bearing acrylate groups |

TABLE 1-continued
| No. of exemplified compounds | Structure |
|---|---|
| 276 | 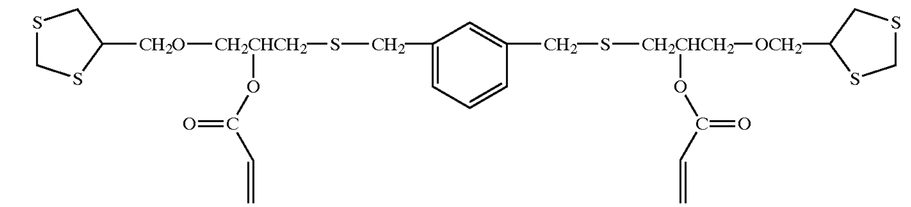 |
| 277 | 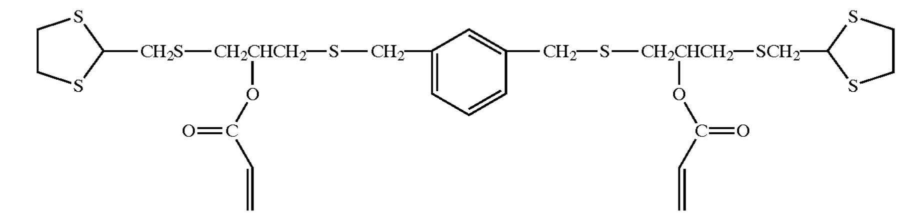 |
| 278 | 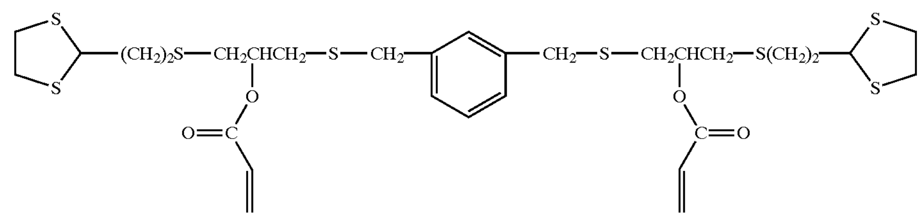 |
| 279 | 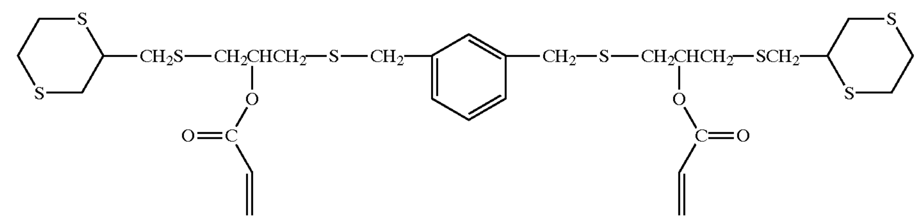 |

TABLE 1-continued
| No. of exemplified compounds | Structure |
|---|---|
| 280 | 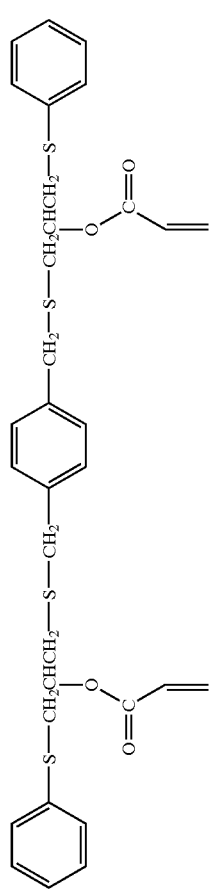 |
| 281 | 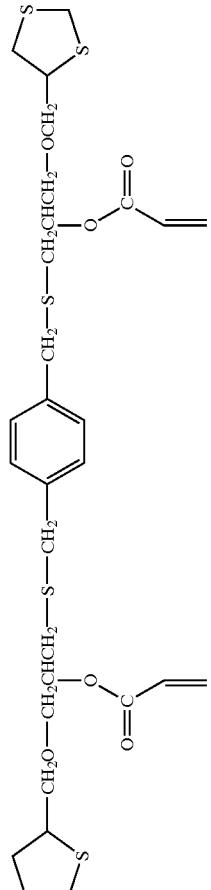 |
| 282 | 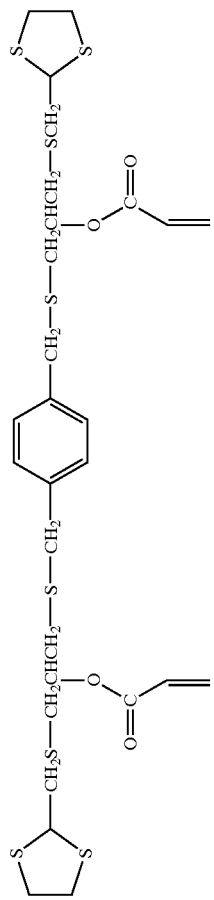 |
| 283 | 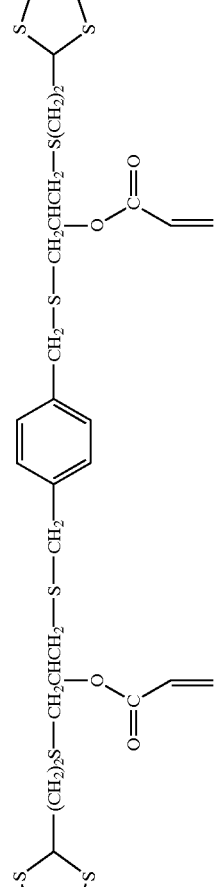 |

TABLE 1-continued
| No. of exemplified compounds | Structure |
|---|---|
| 284 | 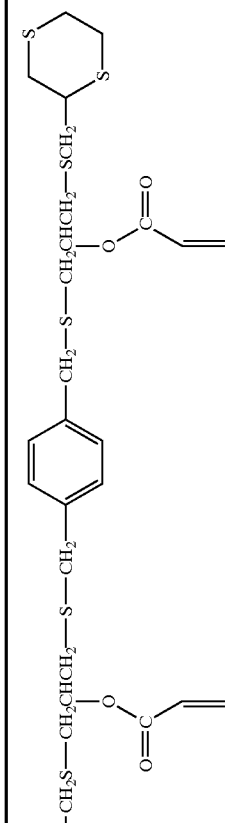 |
| 285 | 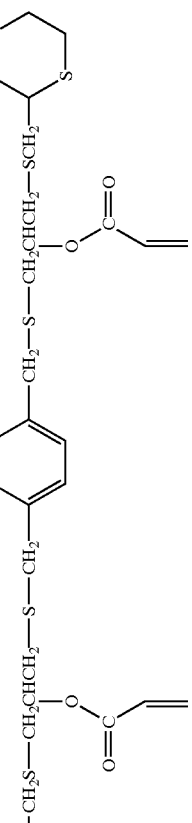 |
| 286 | 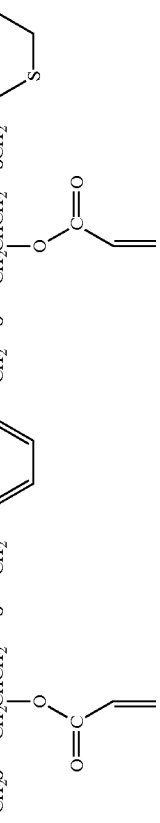 |
| 287 | 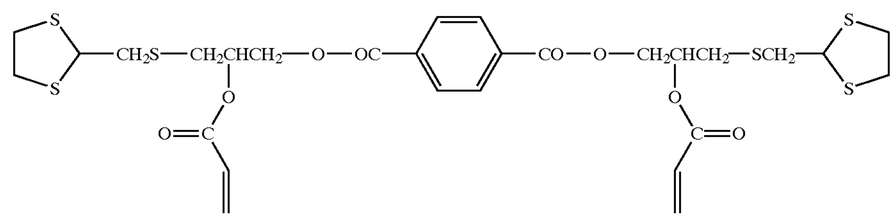 |

TABLE 1-continued
| No. of exemplified compounds | Structure |
|---|---|
| 288 | 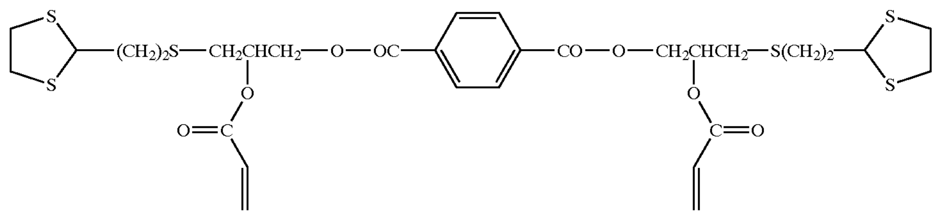 |
| 289 | 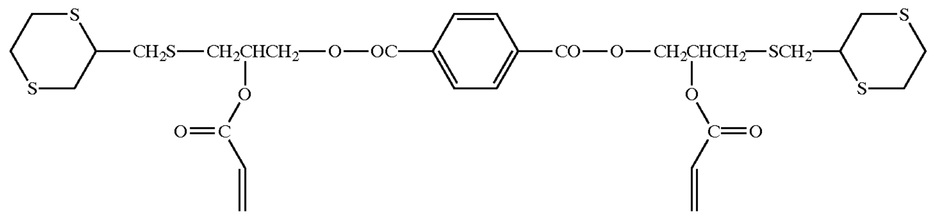 |
| 290 | 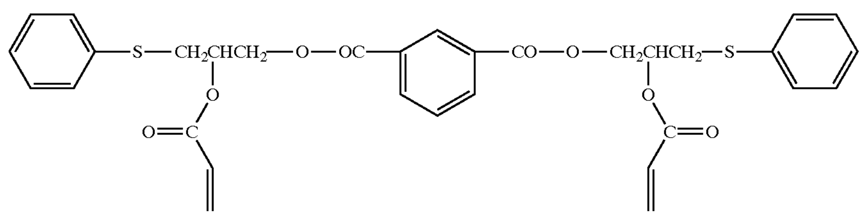 |
| 291 | 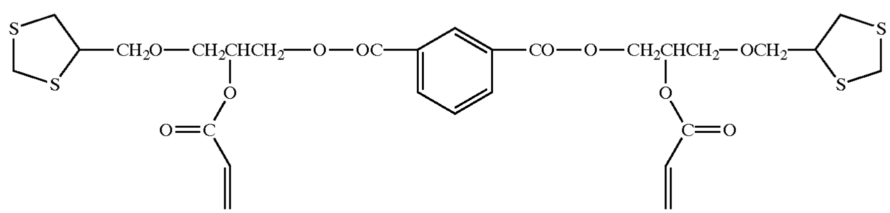 |

TABLE 1-continued
| No. of exemplified compounds | Structure |
|---|---|
| 292 | 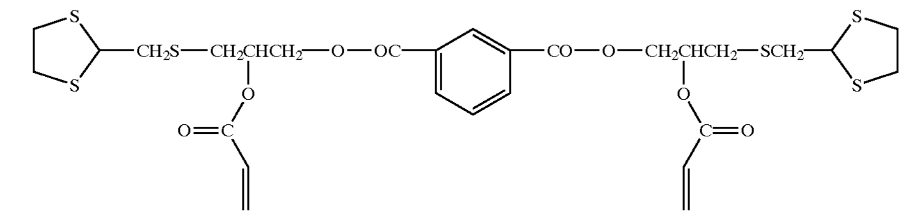 |
| 293 | 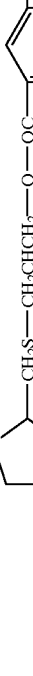 |
| 294 | 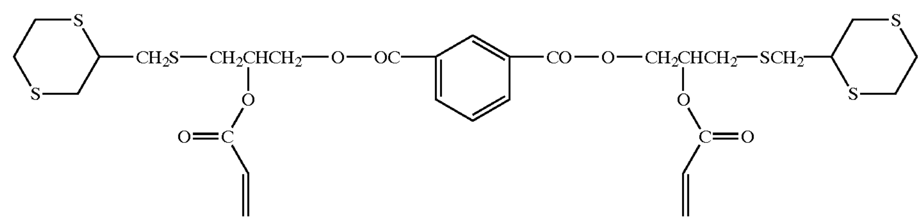 |
| 295 | 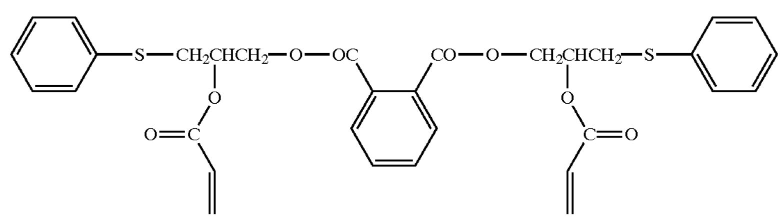 |

TABLE 1-continued
| No. of exemplified compounds | Structure |
|---|---|
| 296 | 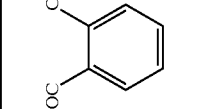 |
| 297 | 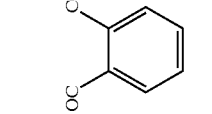 |
| 298 | 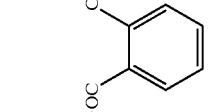 |
| 299 | 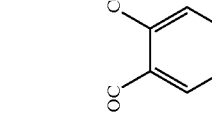 |

TABLE 1-continued

| No. of exemplified compounds | Structure |
|---|---|
| 300 | (structure) |
| 301 | (structure) |
| 302 | (structure) |
| 303 | (structure) |
| 304 | (structure) |

TABLE 1-continued

| No. of exemplified compounds | Structure |
|---|---|
| 305 | (structure) |
| 306 | (structure) |
| 307 | (structure) |
| 308 | (structure) |
| 309 | (structure) |

TABLE 1-continued

| No. of exemplified compounds | Structure |
|---|---|
| 310 | (structure) |
| 311 | (structure) |
| 312 | (structure) |
| 313 | (structure) |
| 314 | (structure) |

TABLE 1-continued

| No. of exemplified compounds | Structure |
|---|---|
| 315 | (structure) |
| 316 | (structure) |
| 317 | (structure) |
| 318 | (structure) |
| 319 | (structure) |

TABLE 1-continued

| No. of exemplified compounds | Structure |
|---|---|
| 320 | 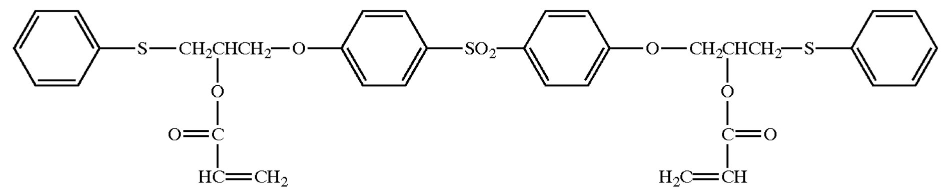 |
| 321 | 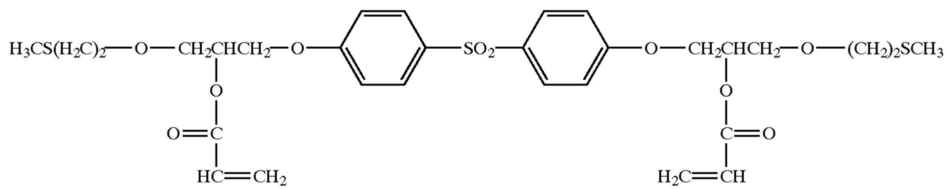 |
| 322 | 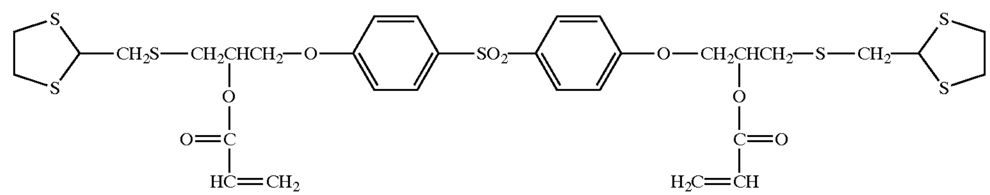 |
| 323 | 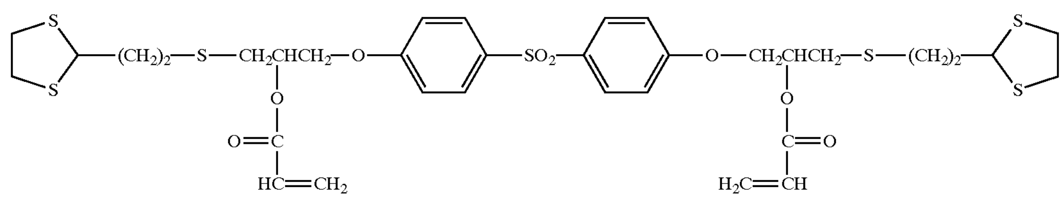 |
| 324 | 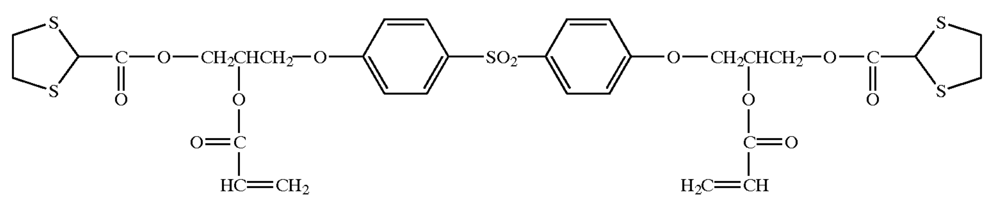 |

TABLE 1-continued
| No. of exemplified compounds | Structure |
|---|---|
| 325 | 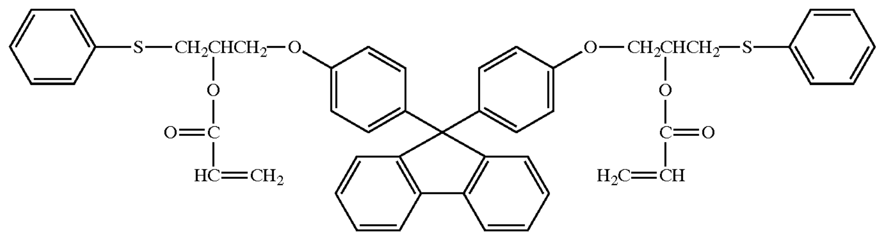 |
| 326 | 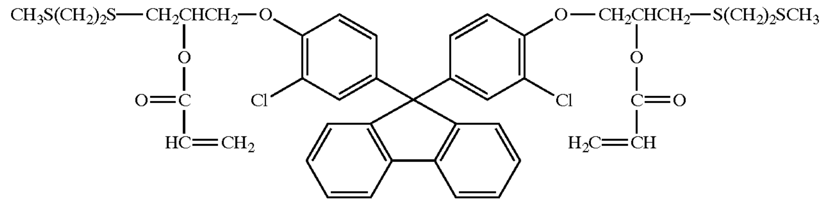 |
| 327 | 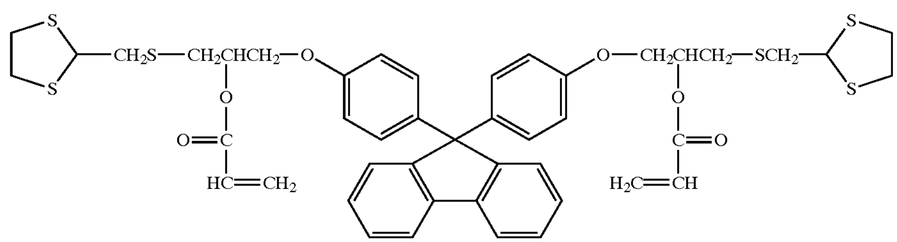 |
| 328 | 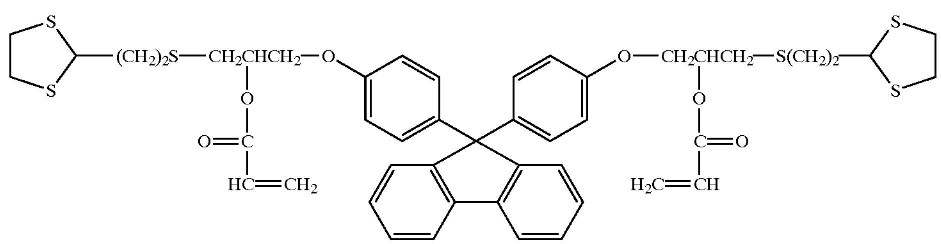 |

TABLE 1-continued

| No. of exemplified compounds | Structure |
|---|---|
| 329 | (structure) |
| 330 | (structure) |
| 331 | (structure) |
| 332 | (structure) |

TABLE 1-continued

| No. of exemplified compounds | Structure |
|---|---|
| 333 | (structure) |
| 334 | (structure) |
| 335 | (structure) |
| 336 | (structure) |

TABLE 1-continued
| No. of exemplified compounds | Structure |
|---|---|
| 337 | 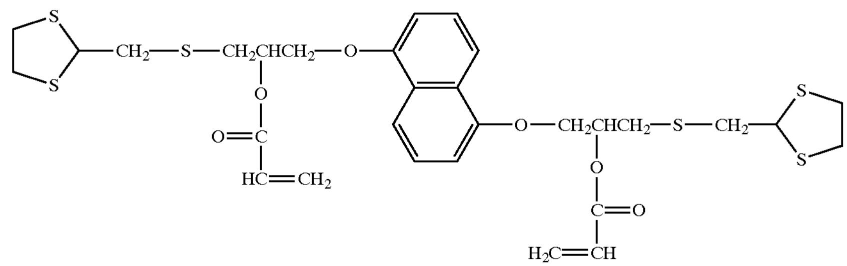 |
| 338 | 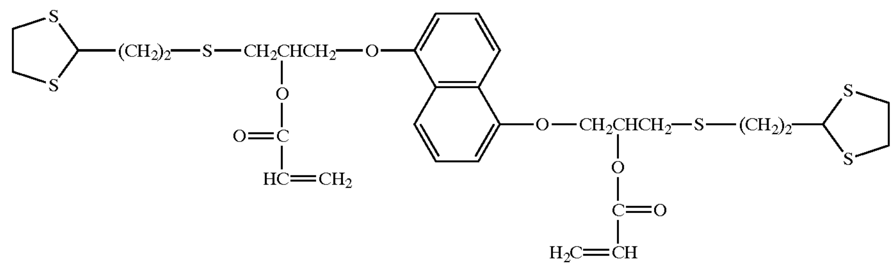 |
| 339 | 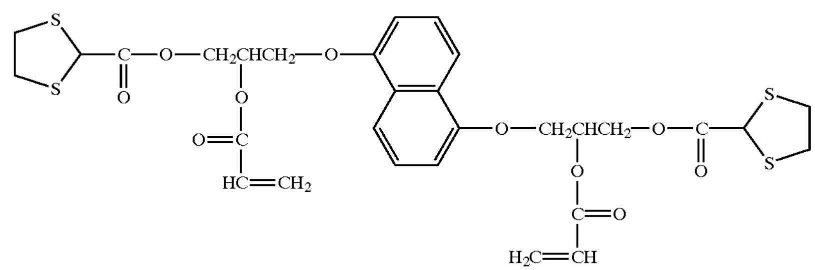 |

TABLE 1-continued

| No. of exemplified compounds | Structure |
|---|---|
| 340 | (naphthalene structure with phenyl-S-CH₂CHCH₂-O-C(=O)-CH=CH₂ and COO-CH₂CHCH₂-S-phenyl with O-C(=O)-CH=CH₂ substituents) |
| 341 | (naphthalene structure with H₃CS(H₂C)₂-O-CH₂CHCH₂-O-C(=O)-CH=CH₂ and COO-CH₂CHCH₂-O-(CH₂)₂SCH₃ with O-C(=O)-CH=CH₂ substituents) |
| 342 | (naphthalene structure with 1,3-dithiolane-CH₂-S-CH₂CHCH₂-O-C(=O)-CH=CH₂ and COO-CH₂CHCH₂-S-CH₂-1,3-dithiolane with O-C(=O)-CH=CH₂ substituents) |
| 343 | (naphthalene structure with 1,3-dithiolane-(CH₂)₂-S-CH₂CHCH₂-O-C(=O)-CH=CH₂ and COO-CH₂CHCH₂-S-(CH₂)₂-1,3-dithiolane with O-C(=O)-CH=CH₂ substituents) |

TABLE 1-continued

| No. of exemplified compounds | Structure |
|---|---|
| 344 | 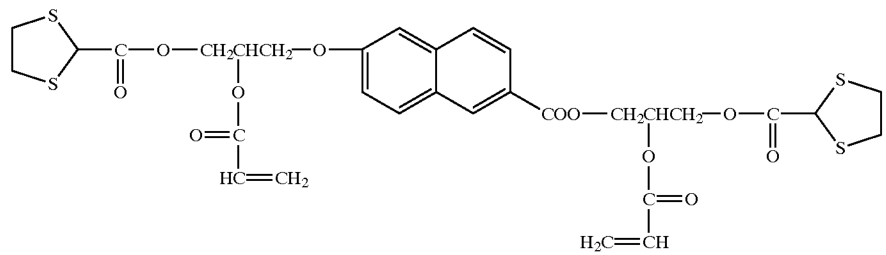 |
| 345 | 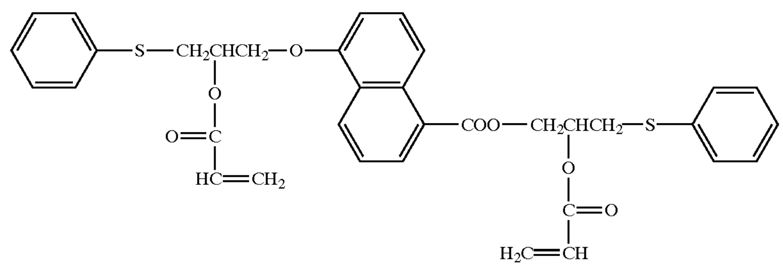 |
| 346 | 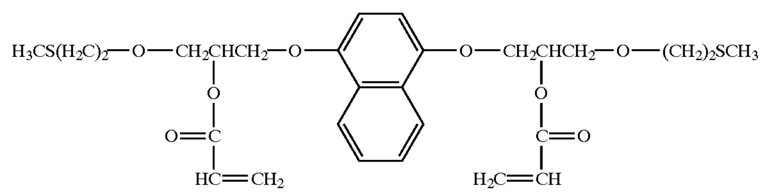 |
| 347 | 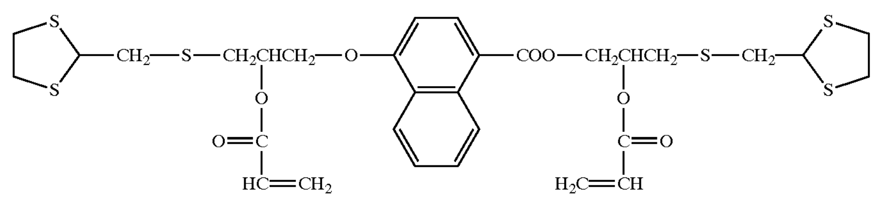 |

TABLE 1-continued
| No. of exemplified compounds | Structure |
|---|---|
| 348 | 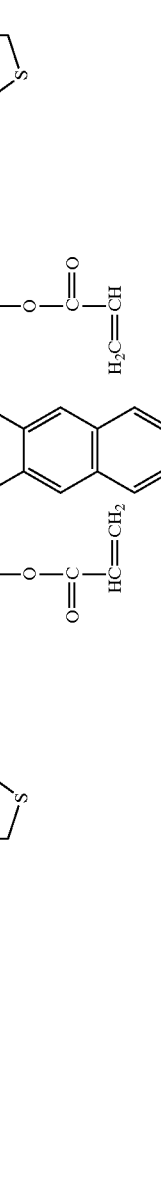 |
| 349 | 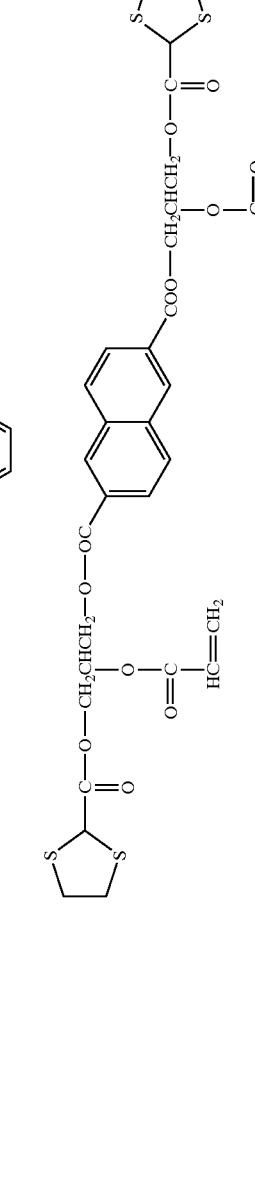 |
| 350 | 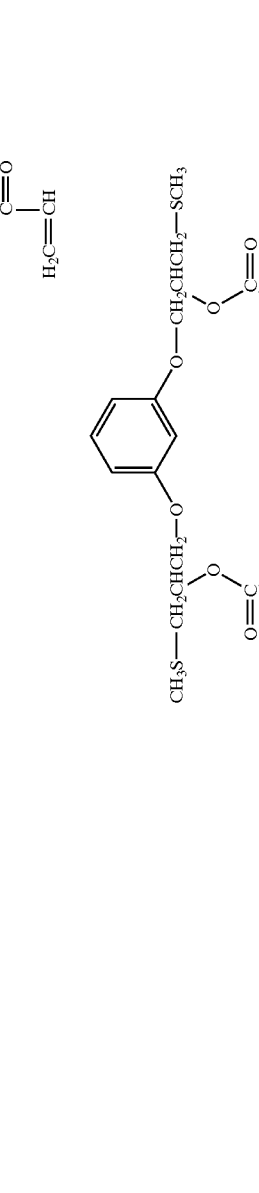 |

TABLE 1-continued
| No. of exemplified compounds | Structure |
|---|---|
| 351 | 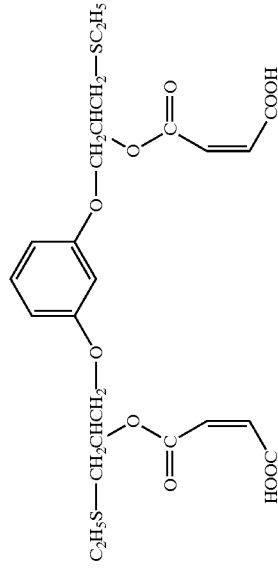 |
| 352 | 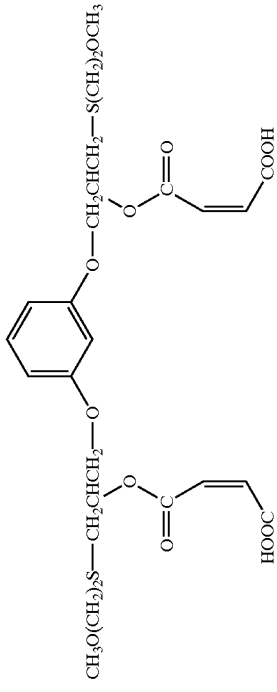 |
| 353 | 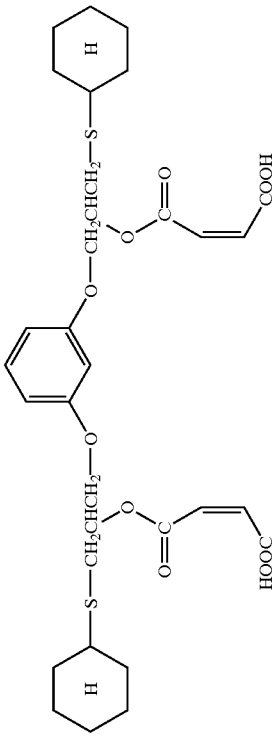 |

TABLE 1-continued
| No. of exemplified compounds | Structure |
|---|---|
| 354 | 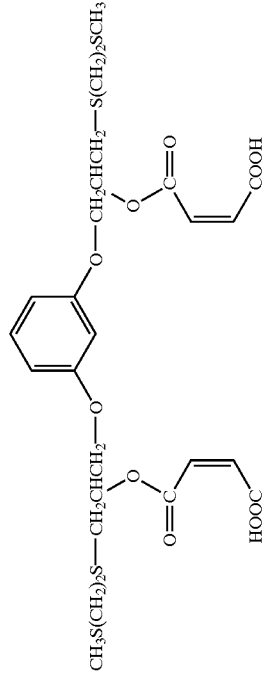 |
| 355 | 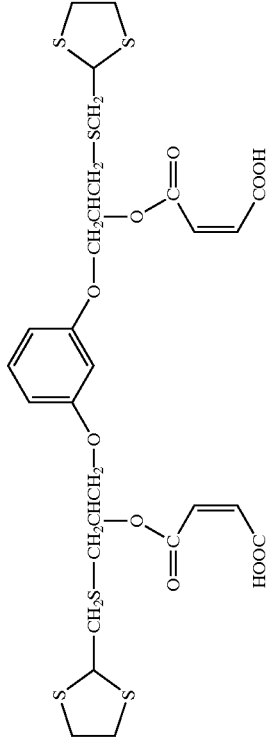 |
| 356 | 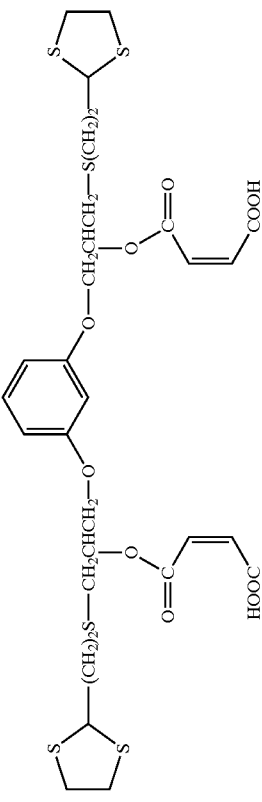 |

TABLE 1-continued

| No. of exemplified compounds | Structure |
|---|---|
| 357 | (structure) |
| 358 | (structure) |
| 359 | (structure) |

TABLE 1-continued

| No. of exemplified compounds | Structure |
|---|---|
| 360 | (structure with 1,3-phenylene bis(O-CH₂CH₂-S-phenyl) ether, with maleate ester groups bearing COOH) |
| 361 | (structure with 1,3-phenylene bis(O-CH₂CH₂-S-(4-OCH₃-phenyl)) ether, with maleate ester groups bearing COOH) |
| 362 | (structure with 1,3-phenylene bis(O-CH₂CH₂-S-(4-SCH₃-phenyl)) ether, with maleate ester groups bearing COOH) |

TABLE 1-continued

| No. of exemplified compounds | Structure |
|---|---|
| 363 | 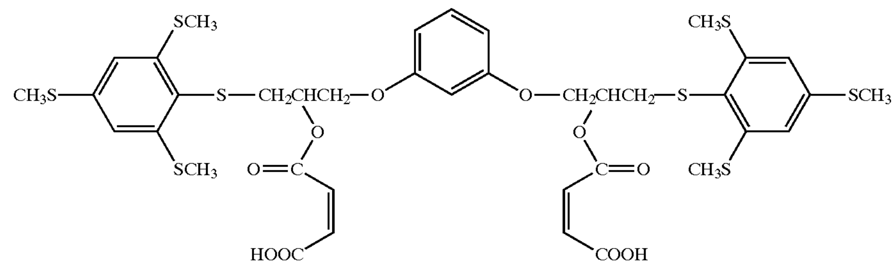 |
| 364 | 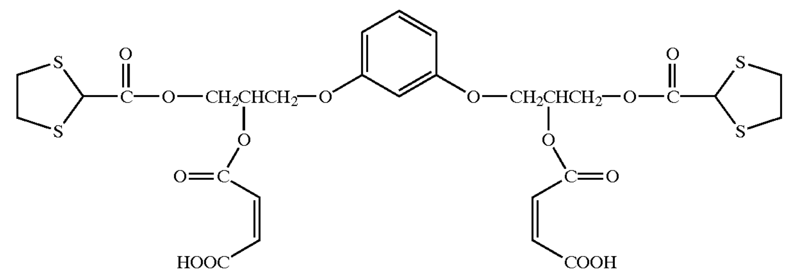 |
| 365 | 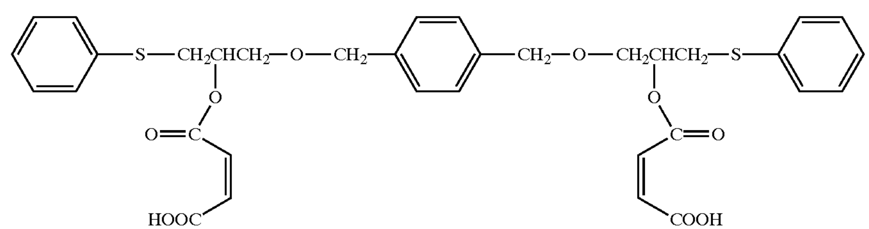 |
| 366 | 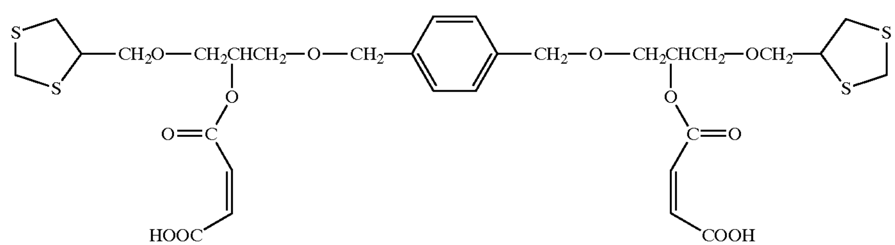 |

TABLE 1-continued
| No. of exemplified compounds | Structure |
|---|---|
| 367 | 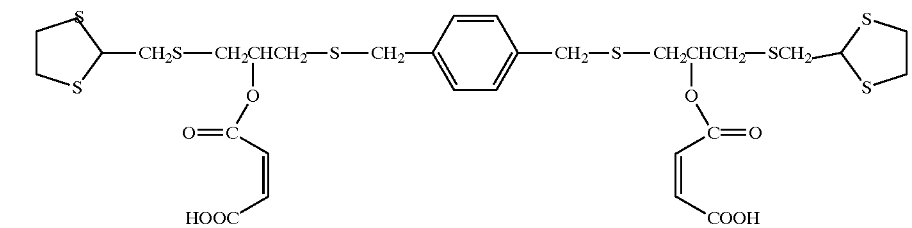 |
| 368 | 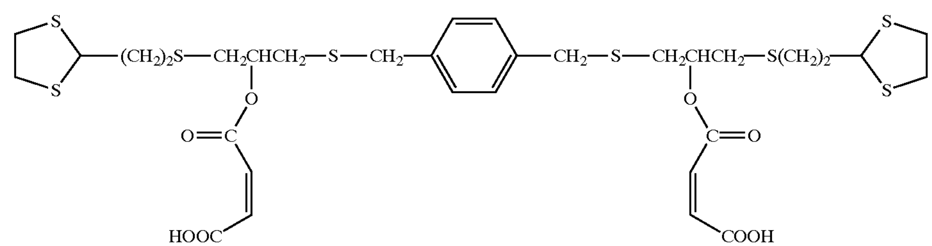 |
| 369 | 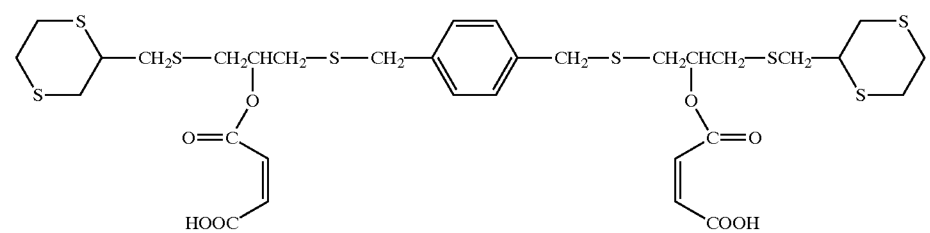 |
| 370 | 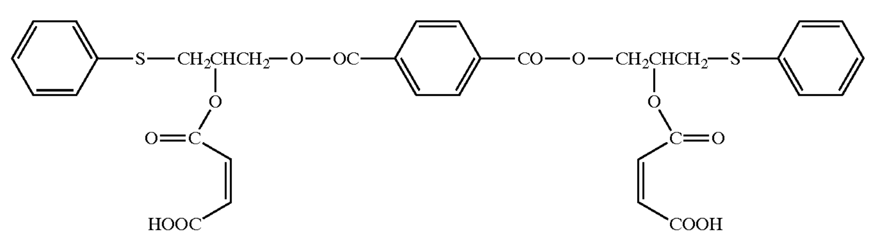 |

TABLE 1-continued
| No. of exemplified compounds | Structure |
|---|---|
| 371 | 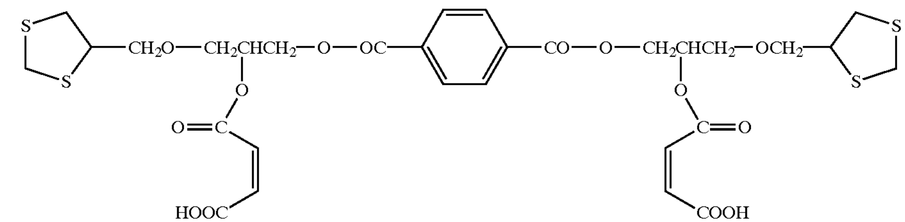 |
| 372 | 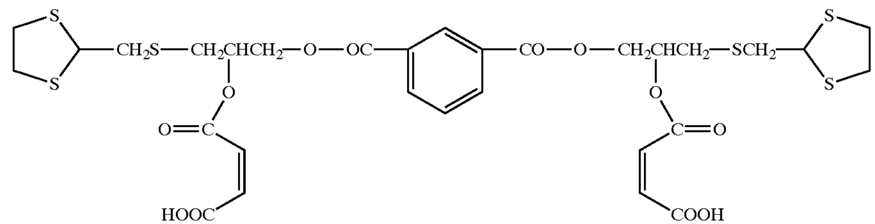 |
| 373 | 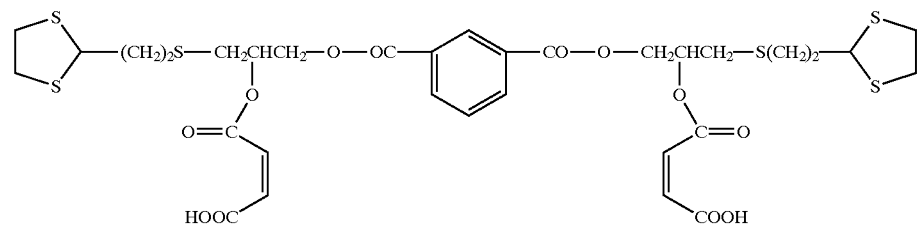 |
| 374 | 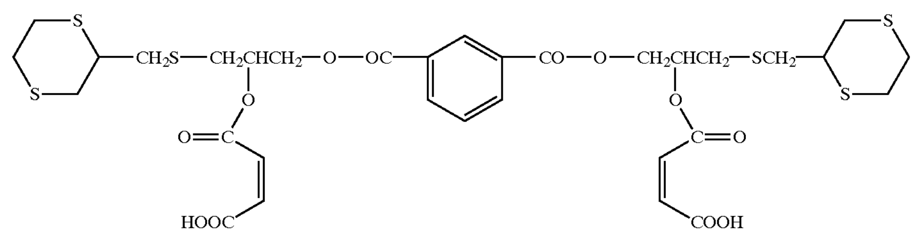 |

TABLE 1-continued

| No. of exemplified compounds | Structure |
|---|---|
| 375 | 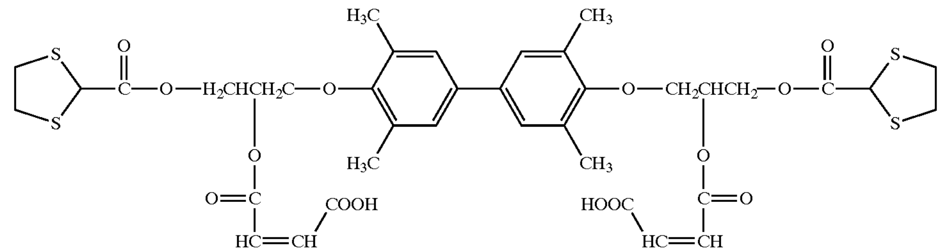 |
| 376 | 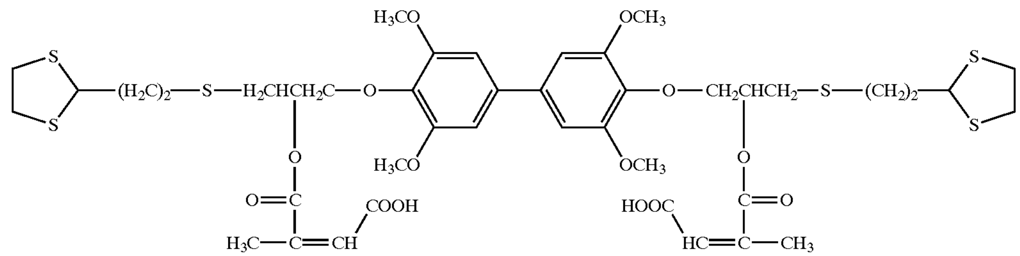 |
| 377 | 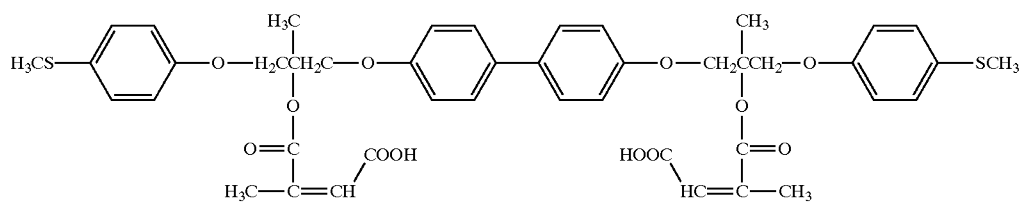 |
| 378 | 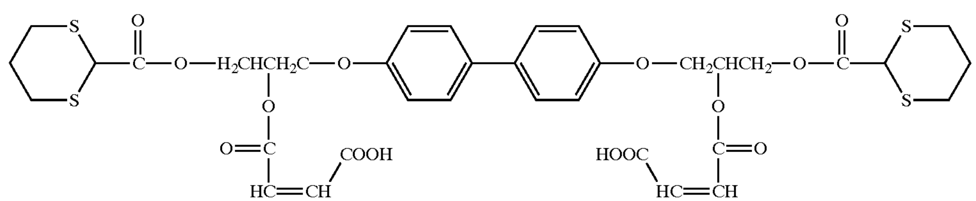 |

TABLE 1-continued

| No. of exemplified compounds | Structure |
|---|---|
| 379 | 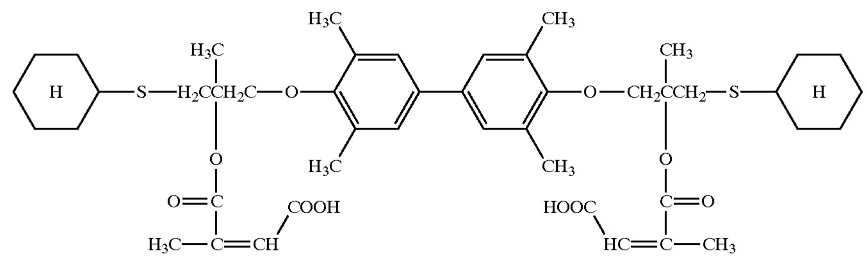 |
| 380 | 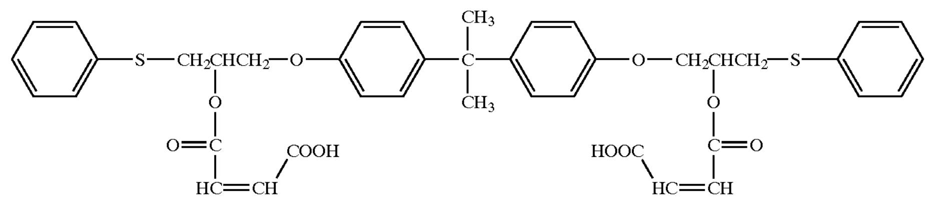 |
| 381 | 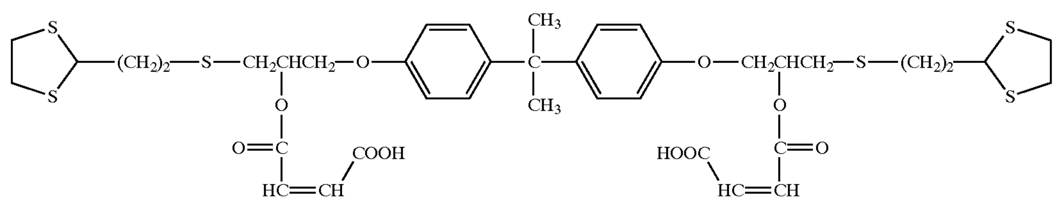 |
| 382 | 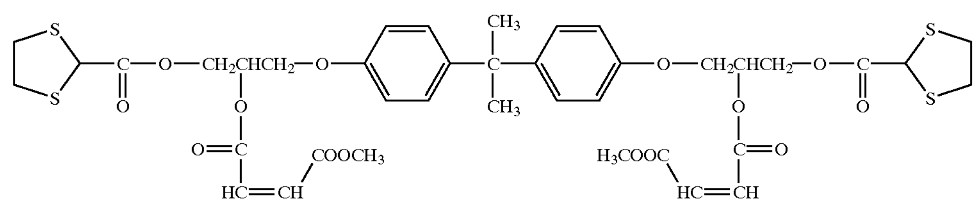 |

TABLE 1-continued

| No. of exemplified compounds | Structure |
|---|---|
| 383 | (structure) |
| 384 | (structure) |
| 385 | (structure) |
| 386 | (structure) |
| 387 | (structure) |

TABLE 1-continued

| No. of exemplified compounds | Structure |
|---|---|
| 388 | (structure) |
| 389 | (structure) |
| 390 | (structure) |
| 391 | (structure) |

TABLE 1-continued

| No. of exemplified compounds | Structure |
|---|---|
| 392 | 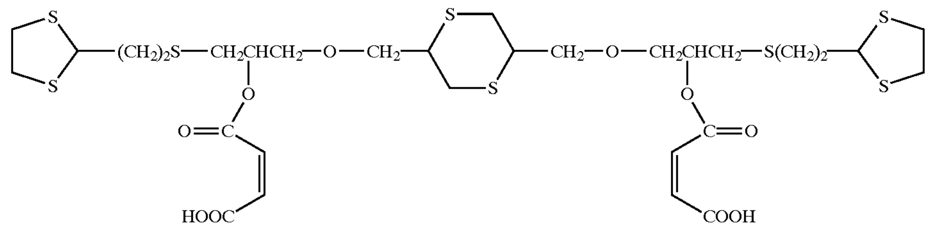 |
| 393 | 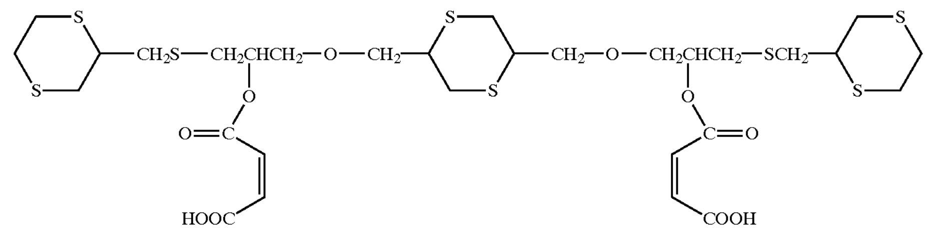 |
| 394 | 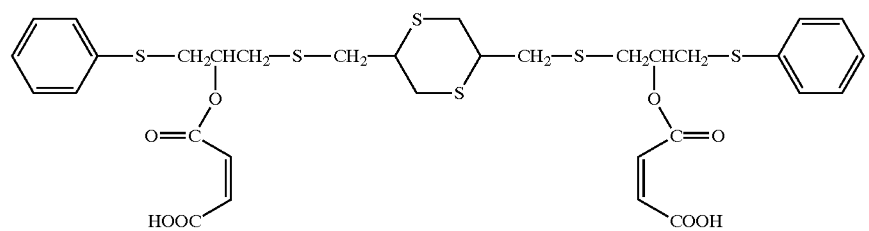 |
| 395 | 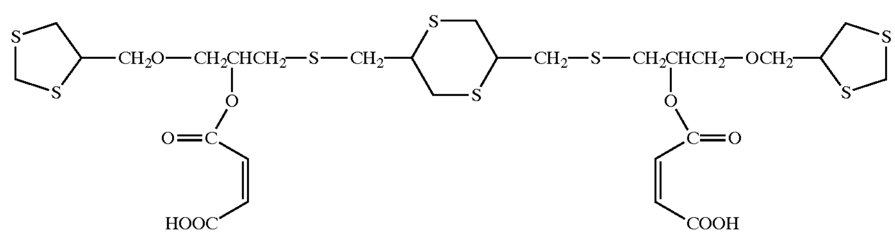 |

TABLE 1-continued

| No. of exemplified compounds | Structure |
|---|---|
| 396 | 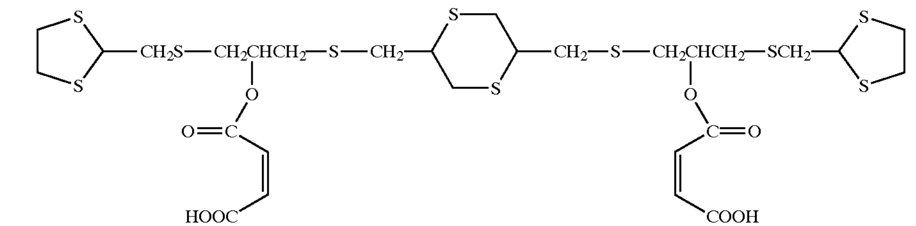 |
| 397 | 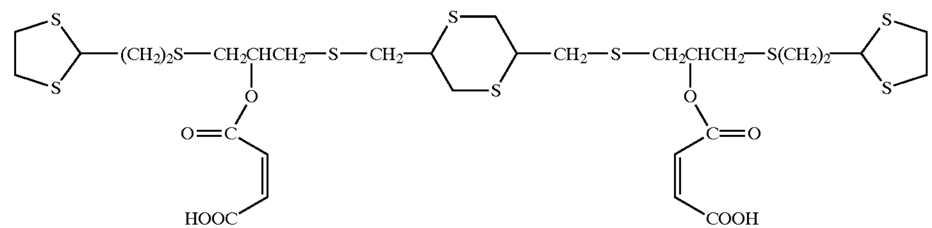 |
| 398 | 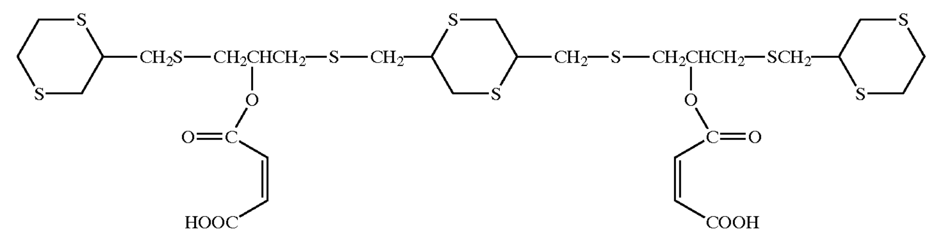 |
| 399 | 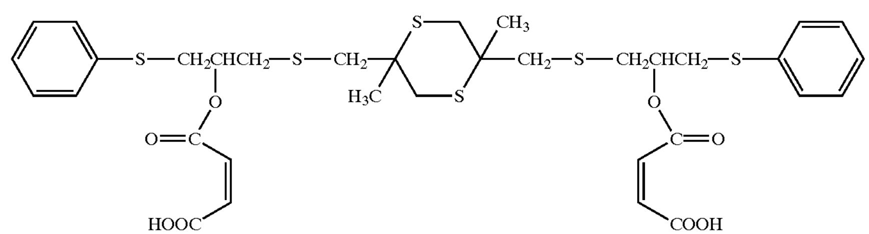 |

TABLE 1-continued
| No. of exemplified compounds | Structure |
|---|---|
| 400 | 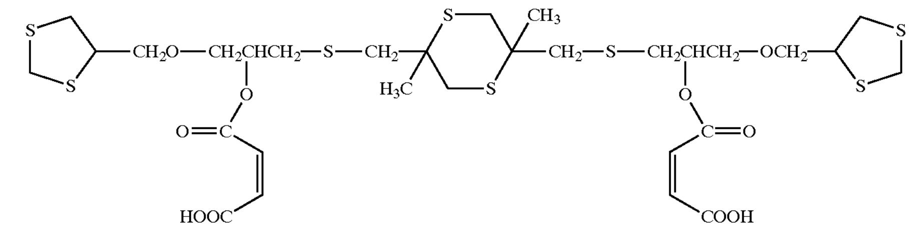 |
| 401 | 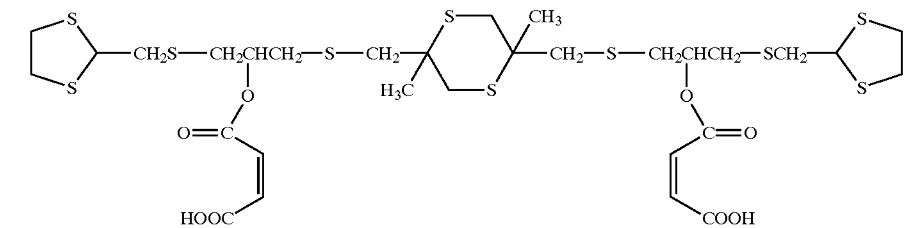 |
| 402 | 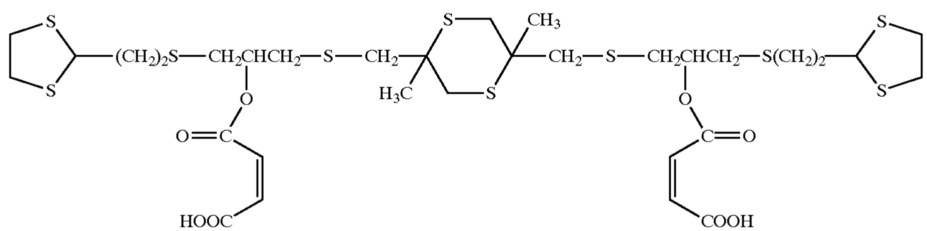 |
| 403 | 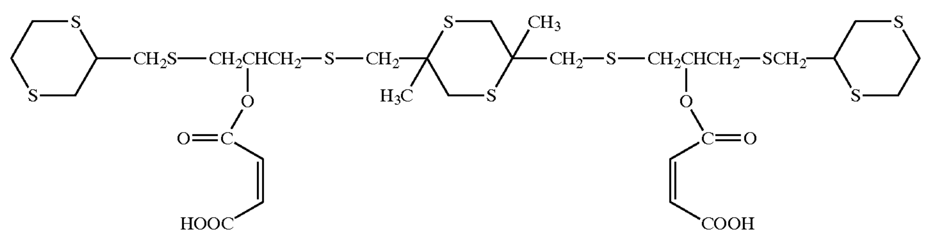 |

TABLE 1-continued
| No. of exemplified compounds | Structure |
|---|---|
| 404 | 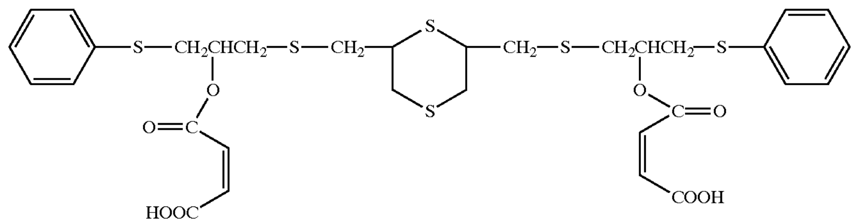 |
| 405 | 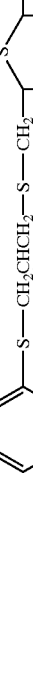 |
| 406 | 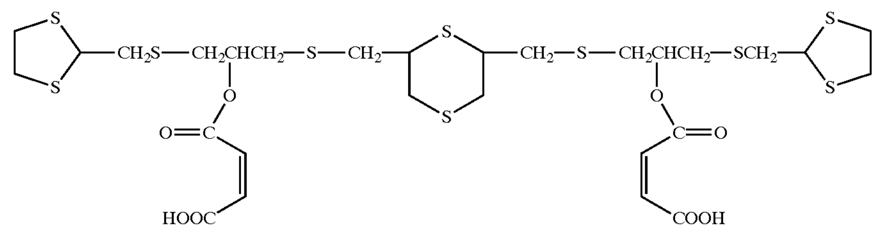 |
| 407 | 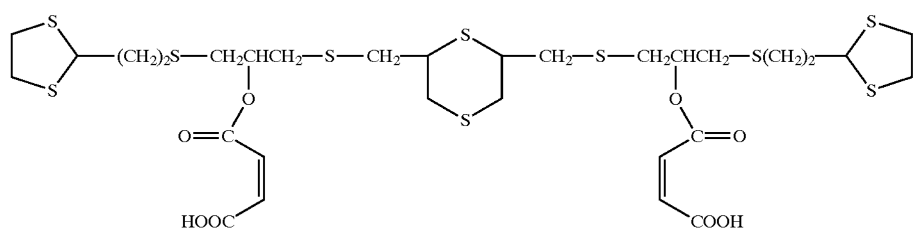 |

TABLE 1-continued

| No. of exemplified compounds | Structure |
|---|---|
| 408 | 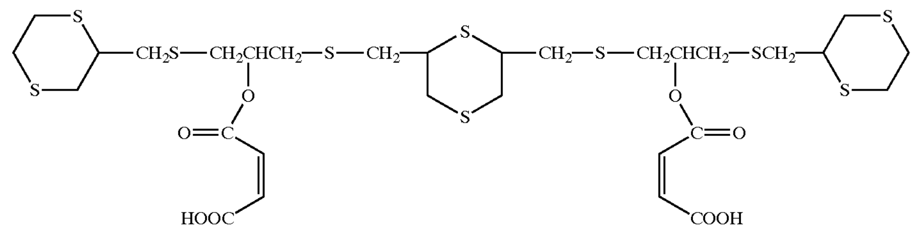 |
| 409 | 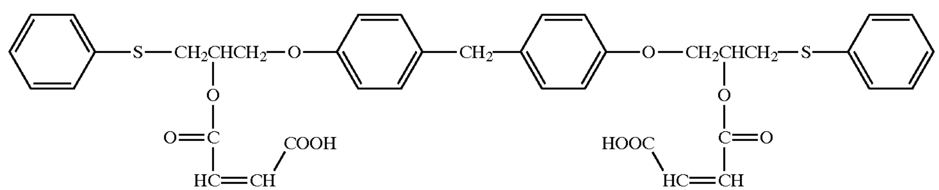 |
| 410 | 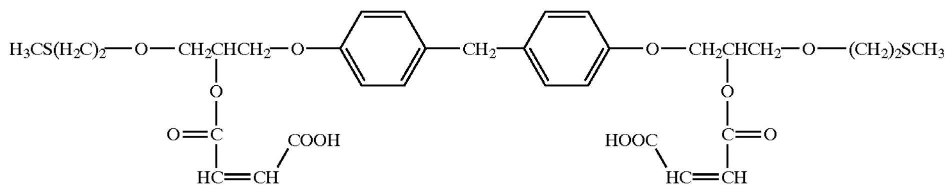 |
| 411 | 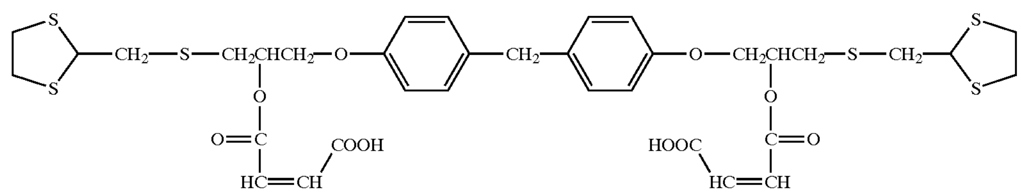 |
| 412 | 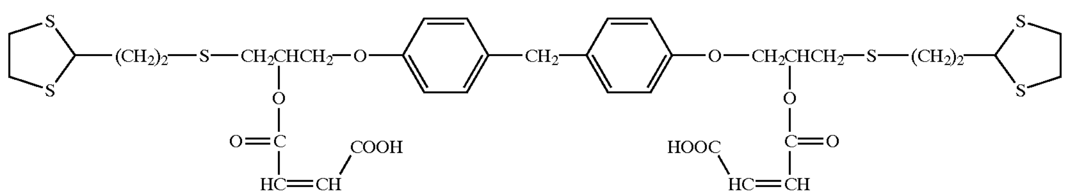 |

TABLE 1-continued

| No. of exemplified compounds | Structure |
|---|---|
| 413 | 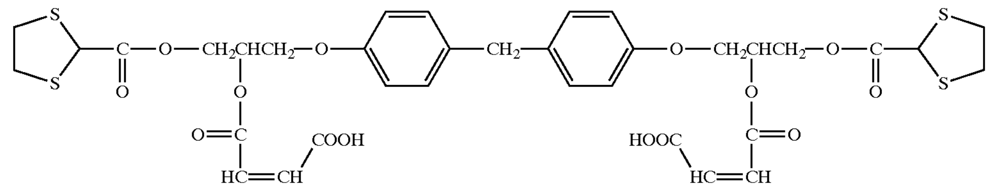 |
| 414 | 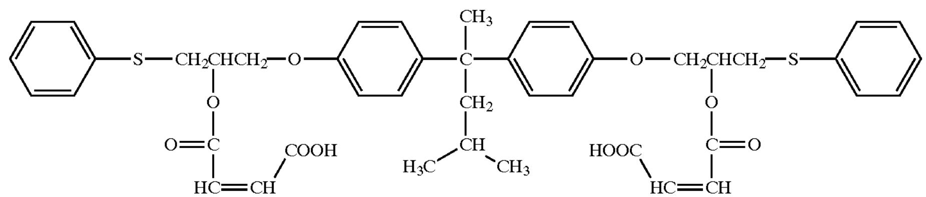 |
| 415 | 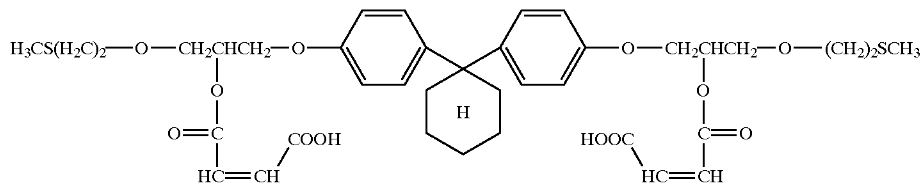 |
| 416 | 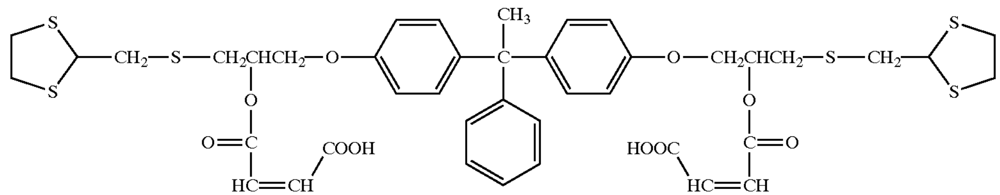 |
| 417 | 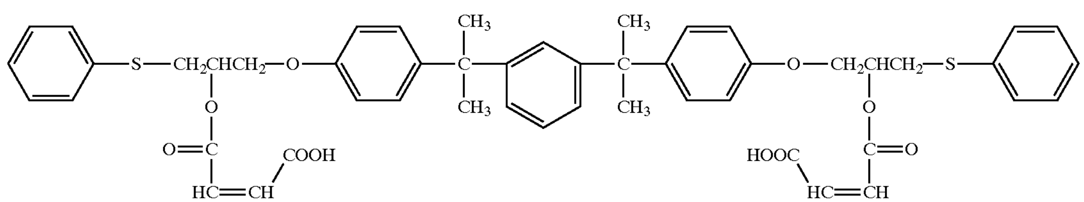 |

TABLE 1-continued

| No. of exemplified compounds | Structure |
|---|---|
| 418 | (complex structure) |
| 419 | (complex structure) |
| 420 | (complex structure) |
| 421 | (complex structure) |
| 422 | (complex structure) |

TABLE 1-continued

| No. of exemplified compounds | Structure |
|---|---|
| 423 | 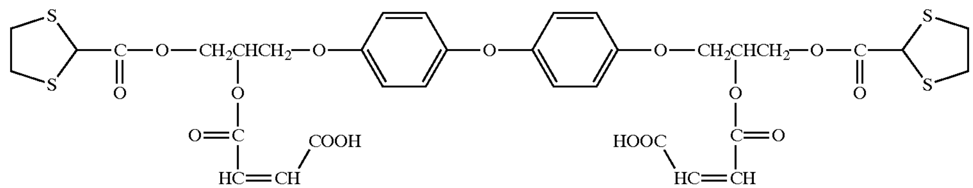 |
| 424 | 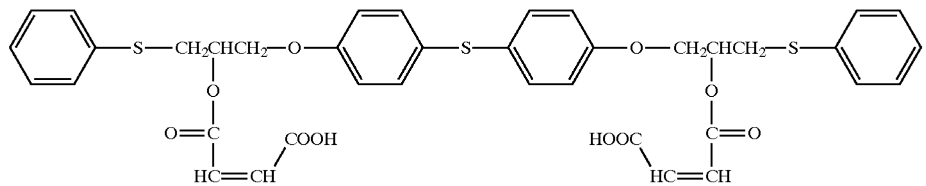 |
| 425 | 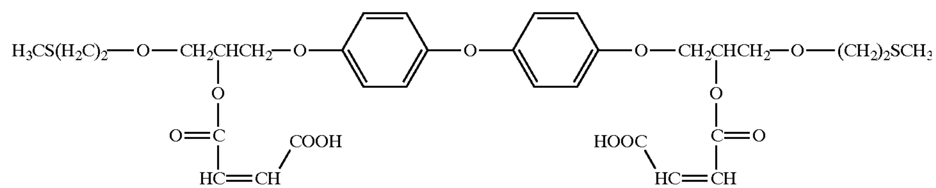 |
| 426 | 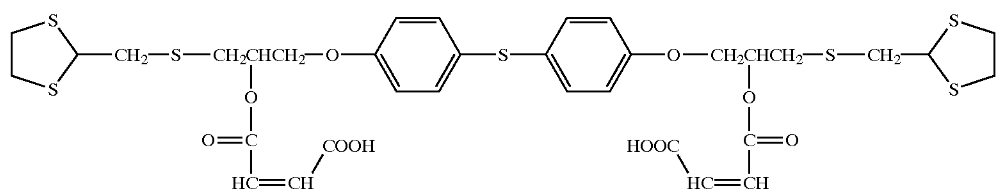 |
| 427 | 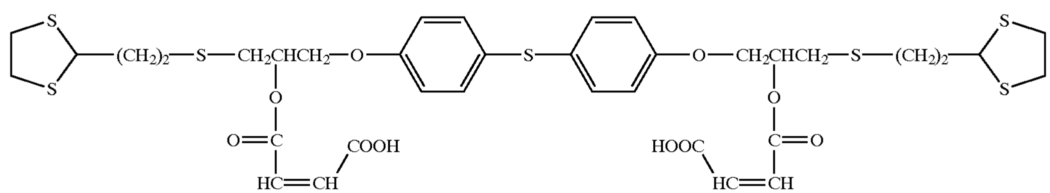 |

TABLE 1-continued

| No. of exemplified compounds | Structure |
|---|---|
| 428 | 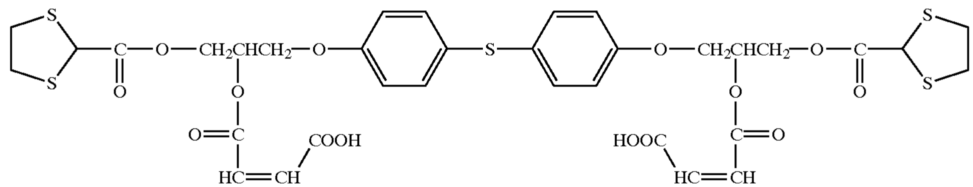 |
| 429 | 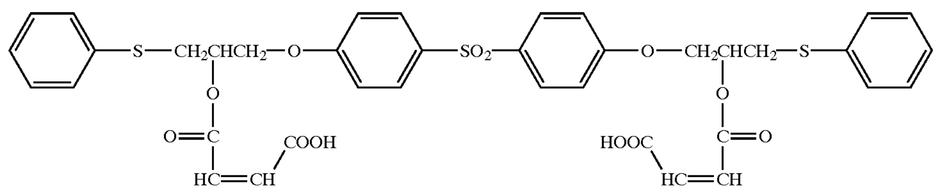 |
| 430 | 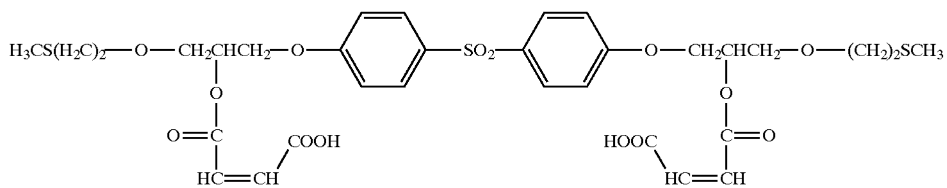 |
| 431 | 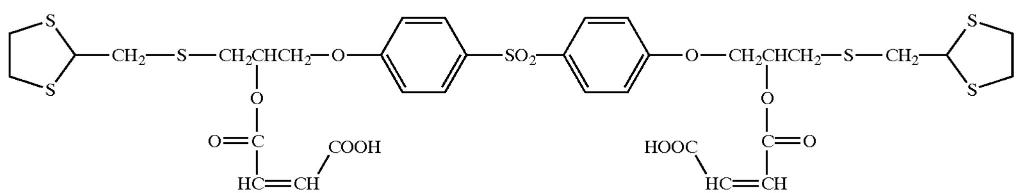 |
| 432 | 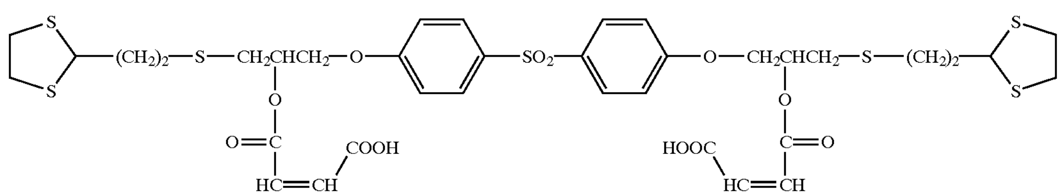 |

TABLE 1-continued
| No. of exemplified compounds | Structure |
|---|---|
| 433 | 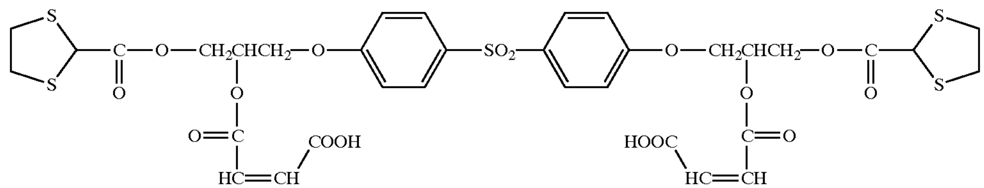 |
| 434 | 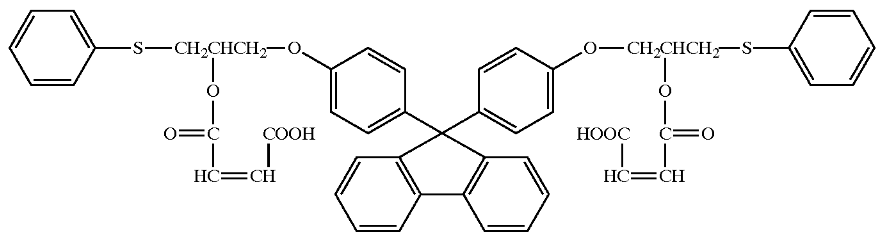 |
| 435 | 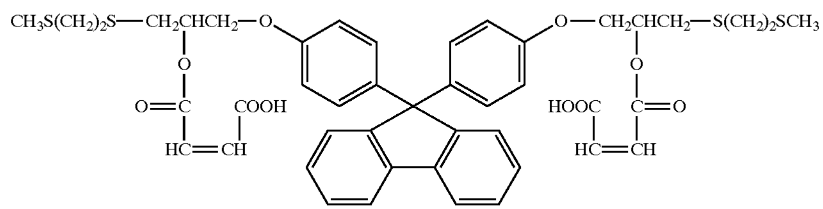 |
| 436 | 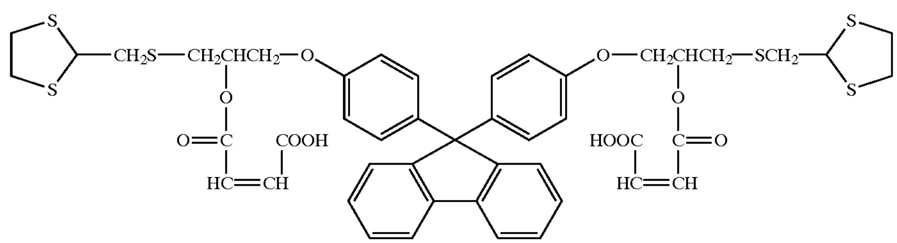 |

TABLE 1-continued
| No. of exemplified compounds | Structure |
|---|---|
| 437 | 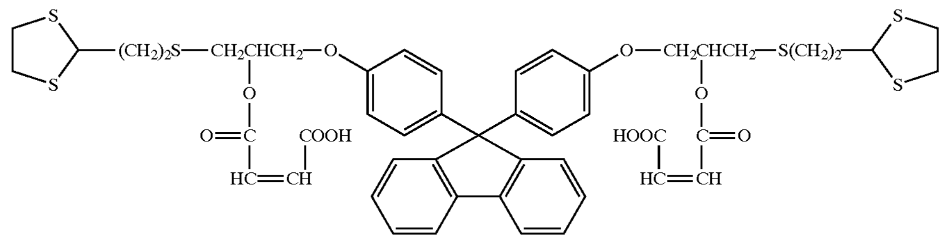 |
| 438 | 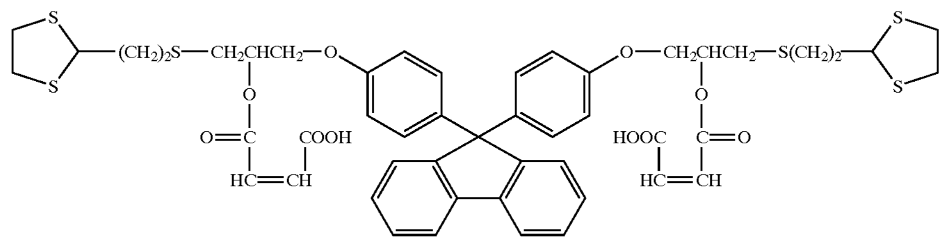 |
| 439 | 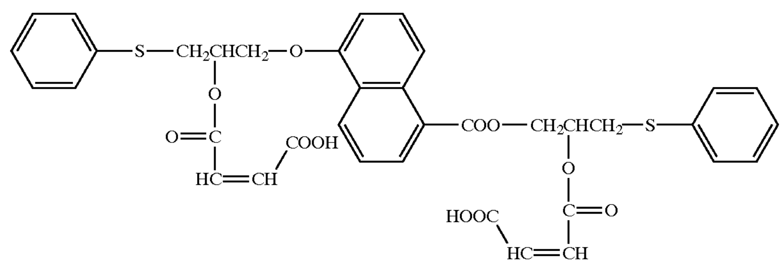 |
| 440 | 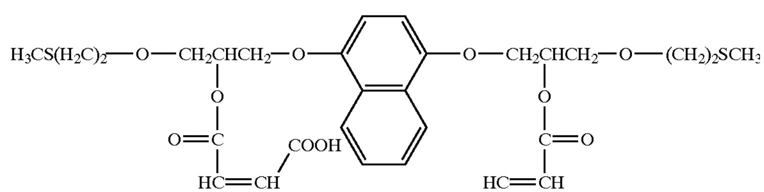 |

TABLE 1-continued

| No. of exemplified compounds | Structure |
|---|---|
| 441 | 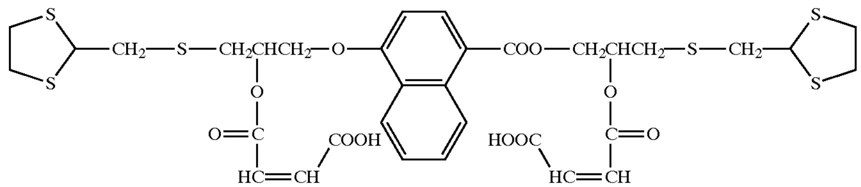 |
| 442 | 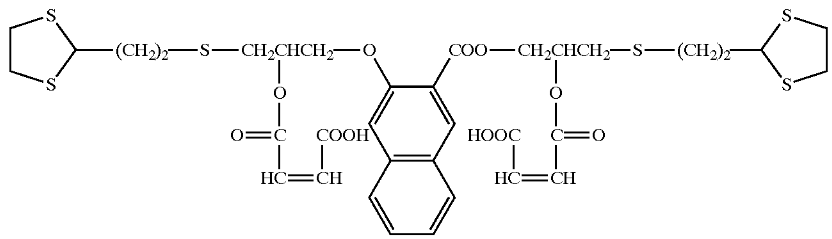 |
| 443 | 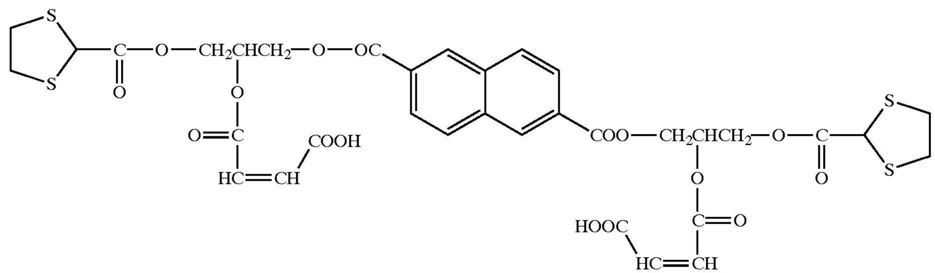 |
| 444 | 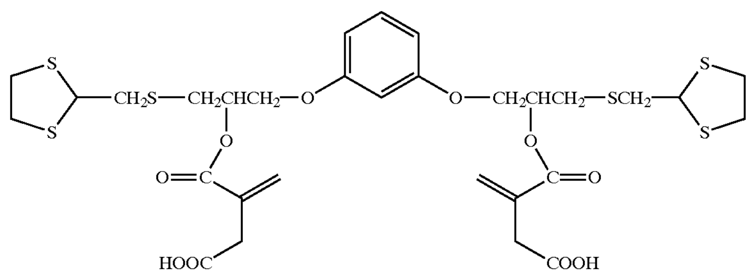 |

TABLE 1-continued

| No. of exemplified compounds | Structure |
|---|---|
| 445 | 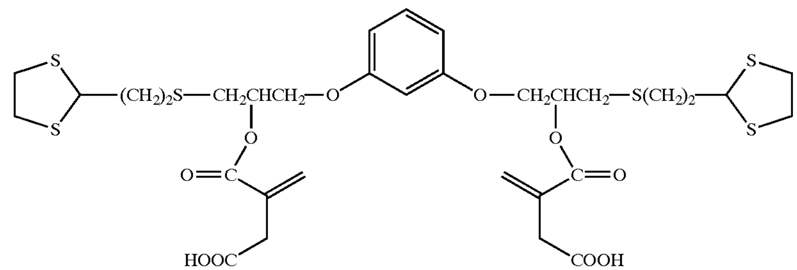 |
| 446 | 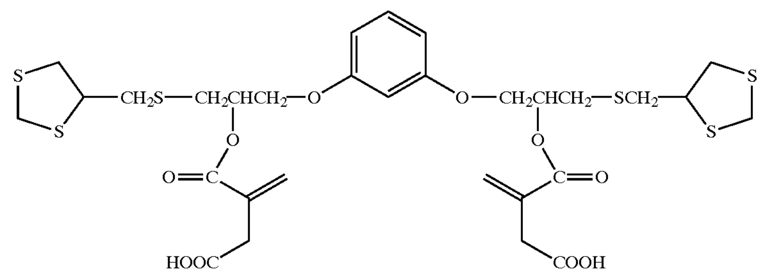 |
| 447 | 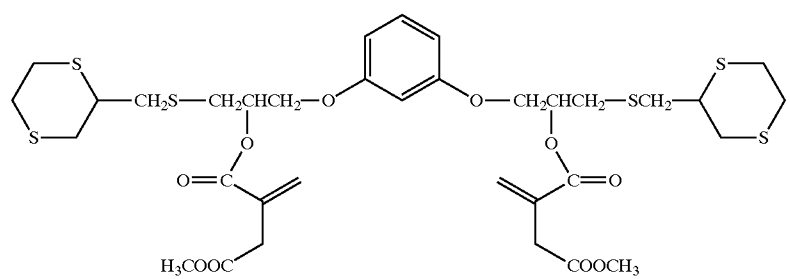 |

TABLE 1-continued
| No. of exemplified compounds | Structure |
|---|---|
| 448 | 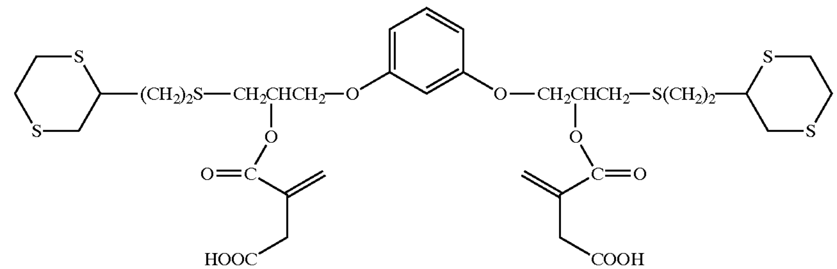 |
| 449 | 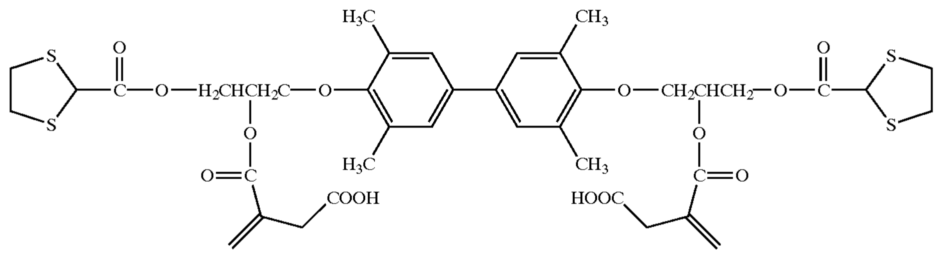 |
| 450 | 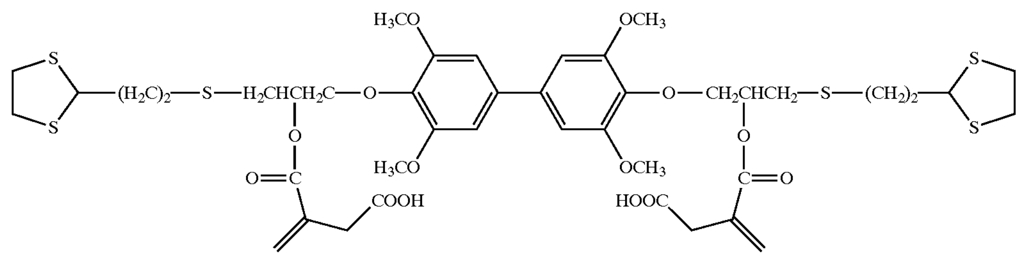 |
| 451 | 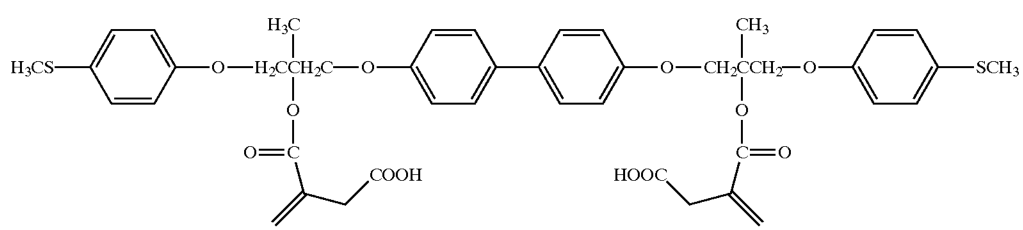 |

TABLE 1-continued

| No. of exemplified compounds | Structure |
|---|---|
| 452 | 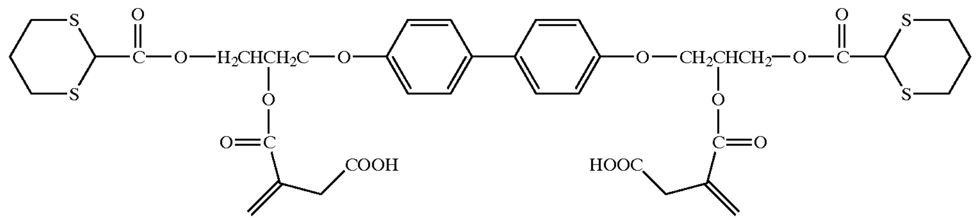 |
| 453 | 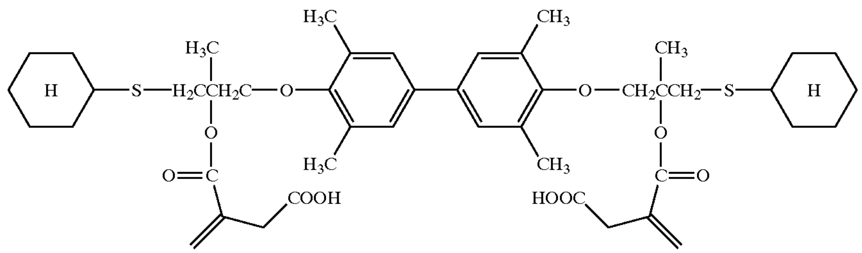 |
| 454 | 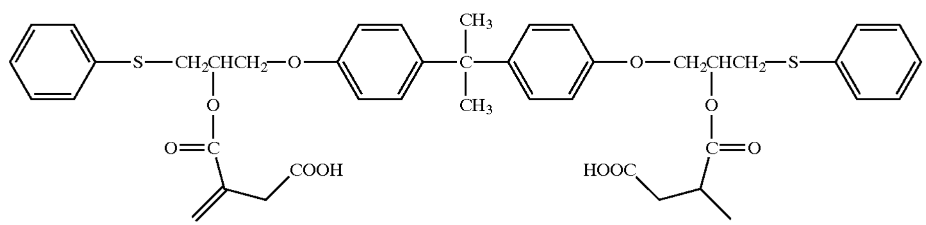 |
| 455 | 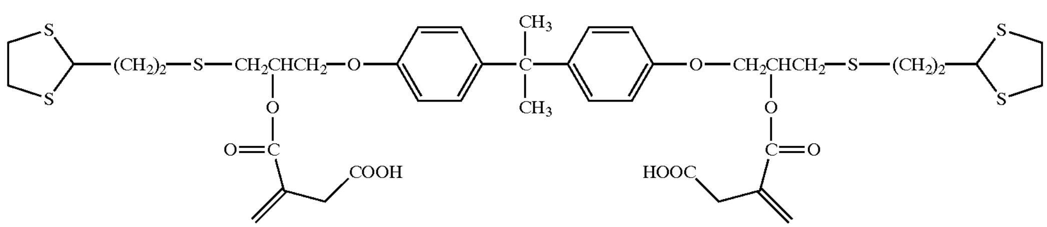 |

TABLE 1-continued

| No. of exemplified compounds | Structure |
|---|---|
| 456 | 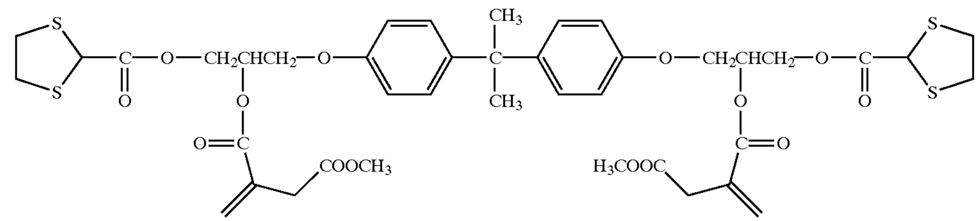 |
| 457 | 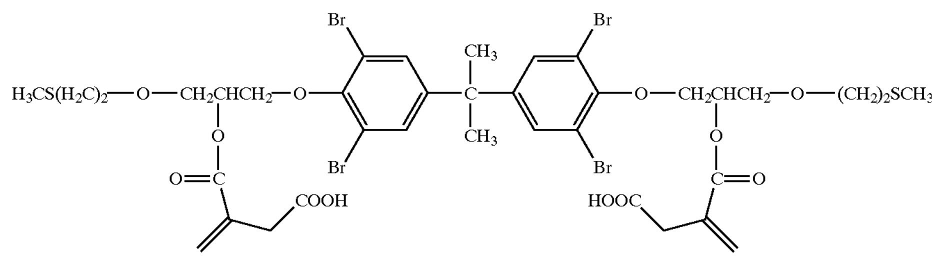 |
| 458 | 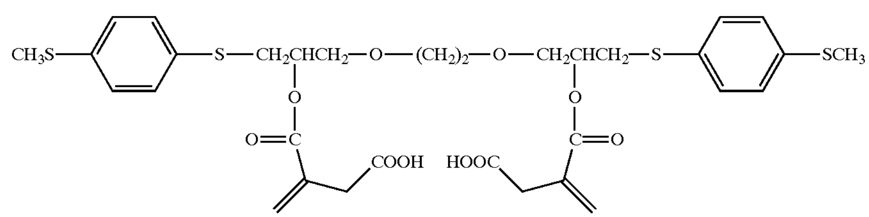 |
| 459 | 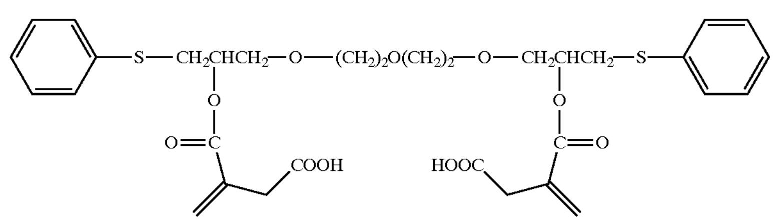 |

TABLE 1-continued
| No. of exemplified compounds | Structure |
|---|---|
| 460 | 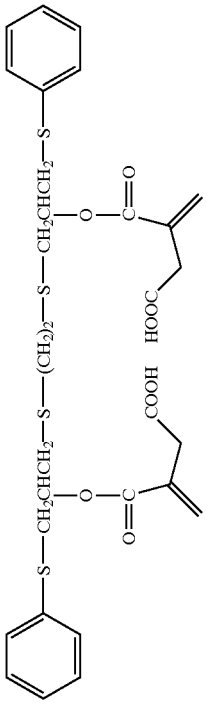 |
| 461 | 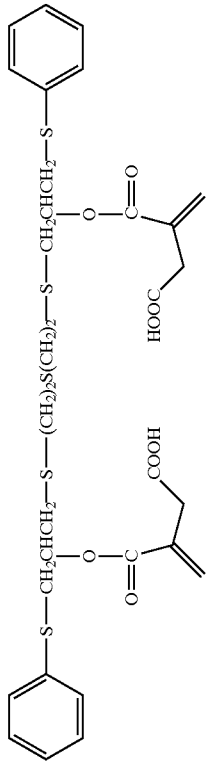 |
| 462 | 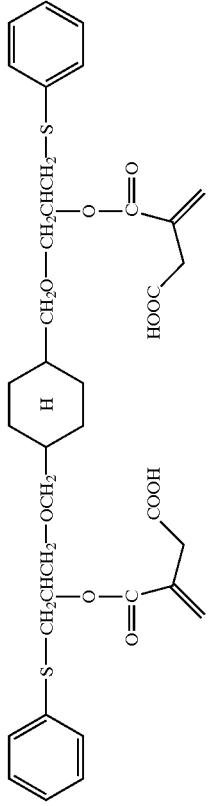 |
| 463 | 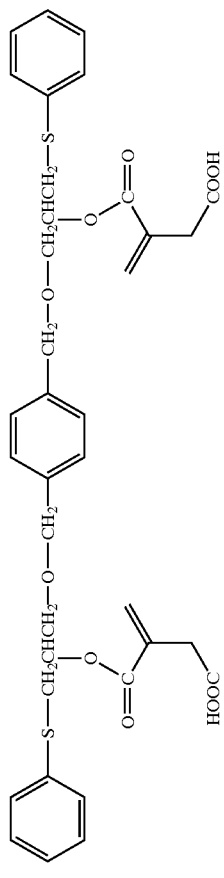 |

TABLE 1-continued

| No. of exemplified compounds | Structure |
|---|---|
| 464 | 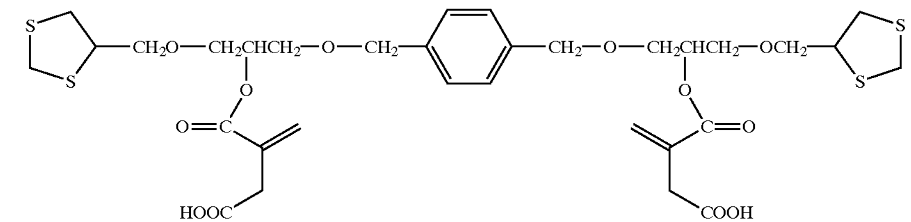 |
| 465 | 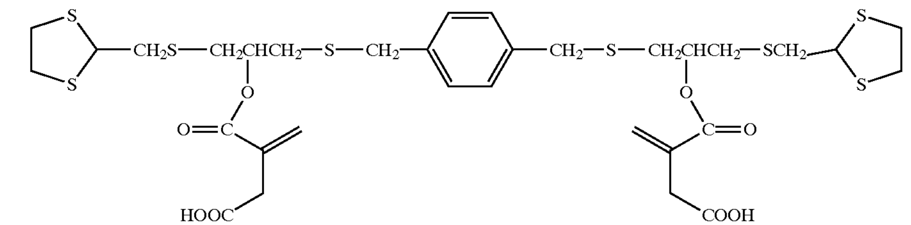 |
| 466 | 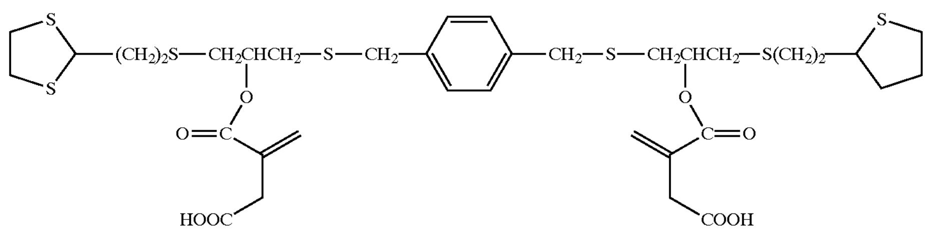 |
| 467 | 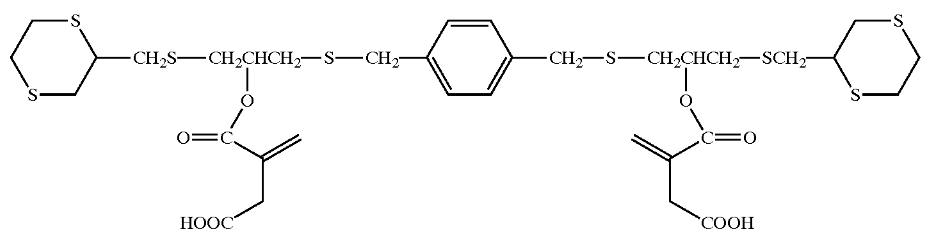 |

TABLE 1-continued

| No. of exemplified compounds | Structure |
|---|---|
| 468 | 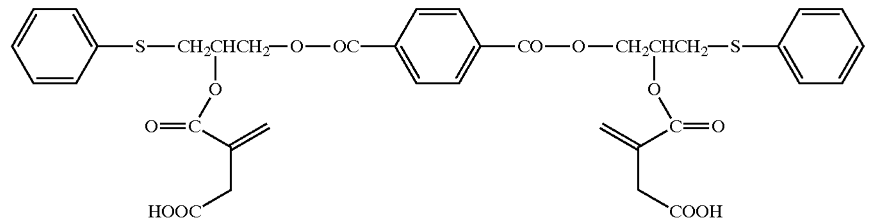 |
| 469 | 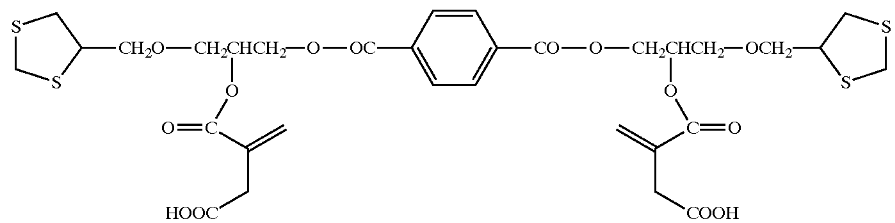 |
| 470 | 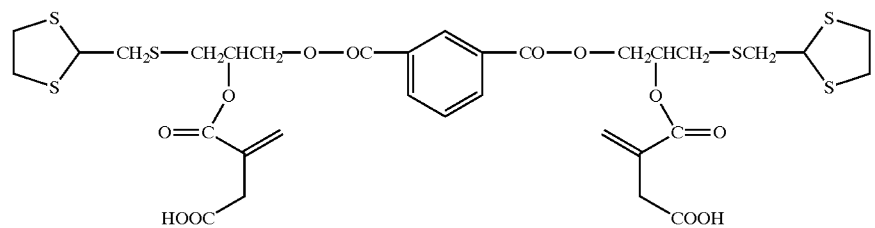 |
| 471 | 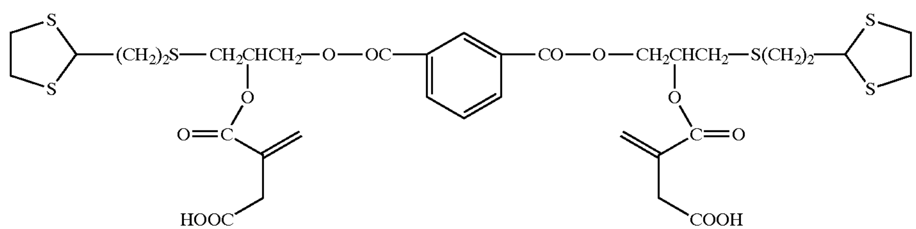 |

TABLE 1-continued

| No. of exemplified compounds | Structure |
|---|---|
| 472 | 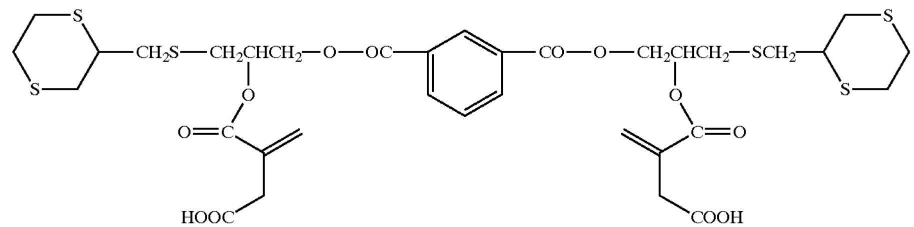 |
| 473 | 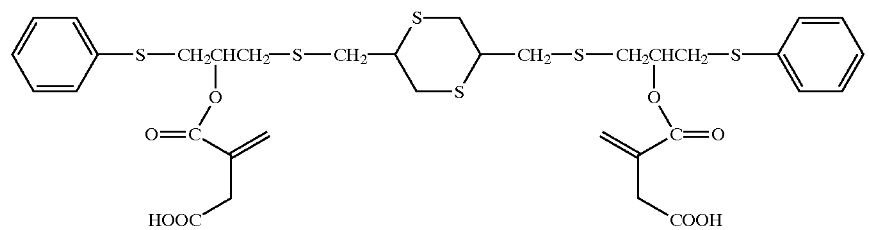 |
| 474 | 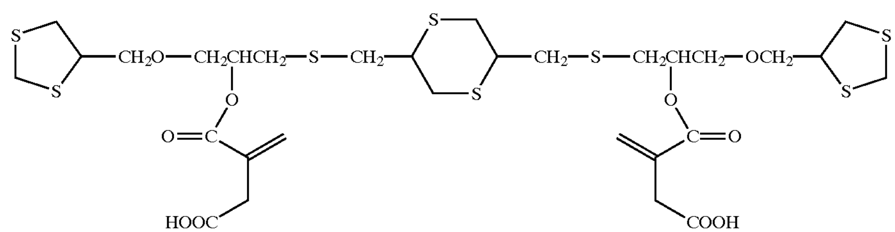 |
| 475 | 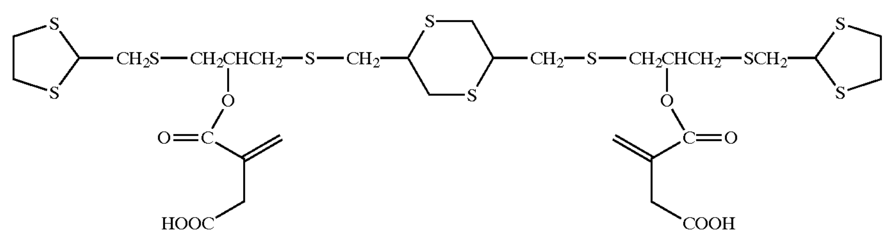 |

TABLE 1-continued
| No. of exemplified compounds | Structure |
|---|---|
| 476 | 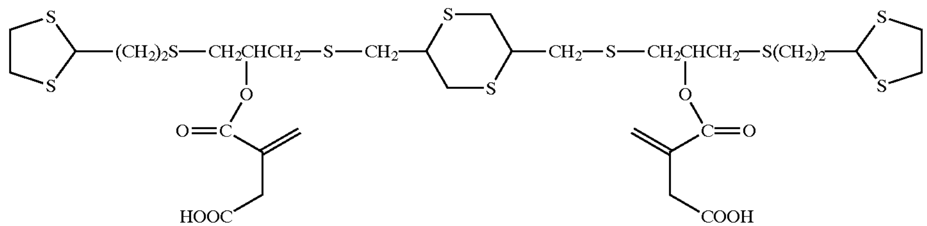 |
| 477 | 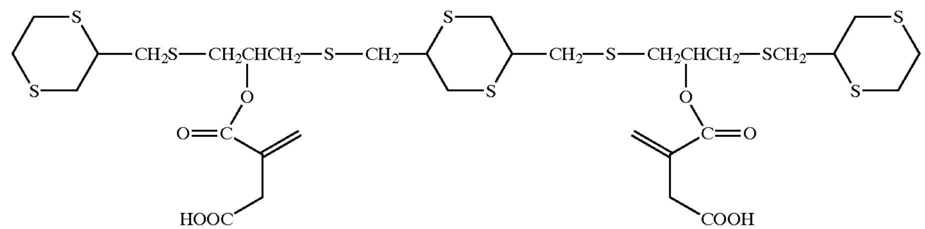 |
| 478 | 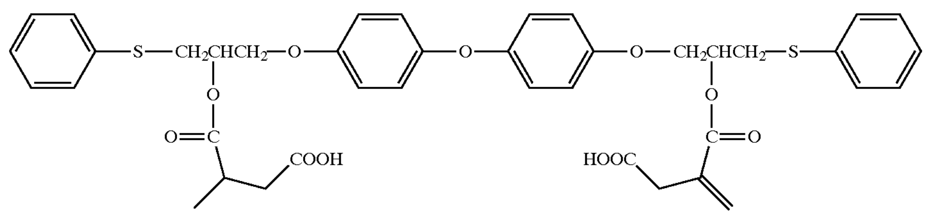 |
| 479 | 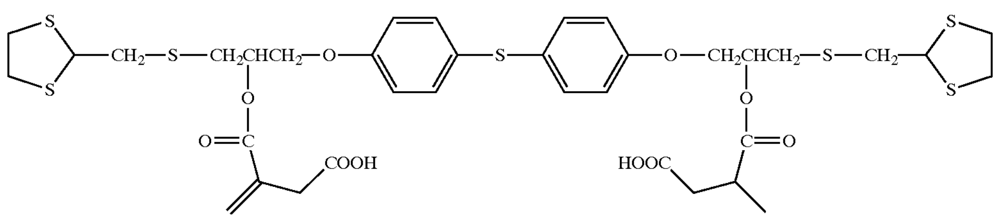 |

TABLE 1-continued
| No. of exemplified compounds | Structure |
|---|---|
| 480 | 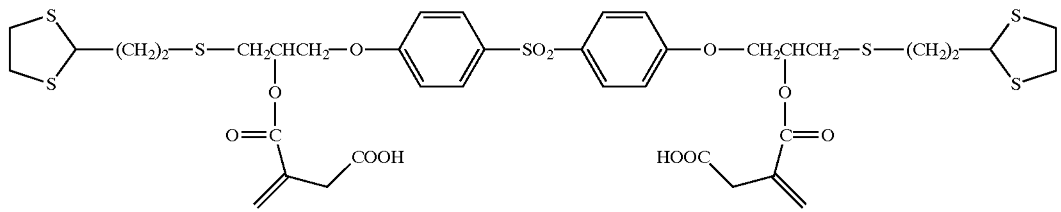 |
| 481 | 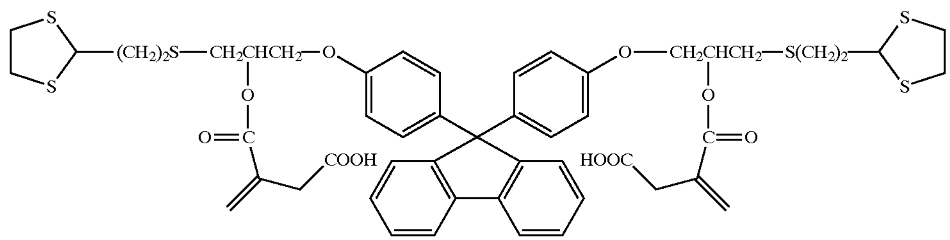 |
| 482 | 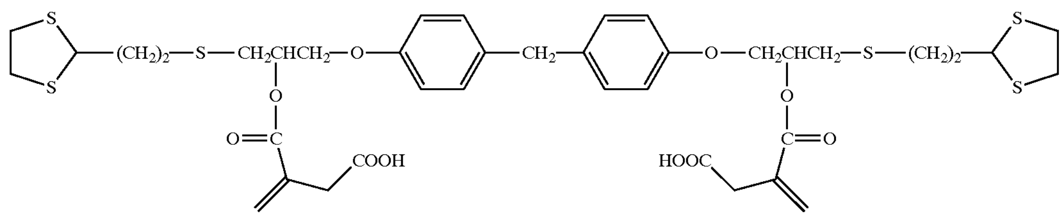 |
| 483 | 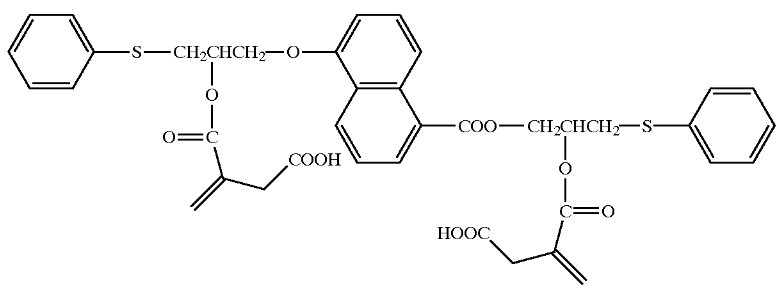 |

TABLE 1-continued

| No. of exemplified compounds | Structure |
|---|---|
| 484 | 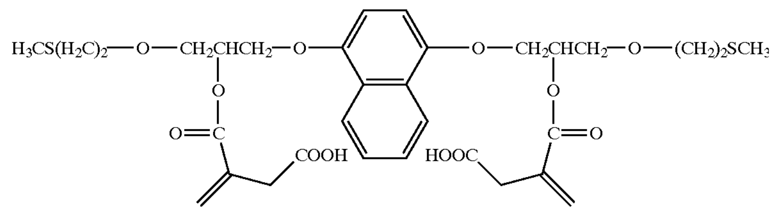 |
| 485 | 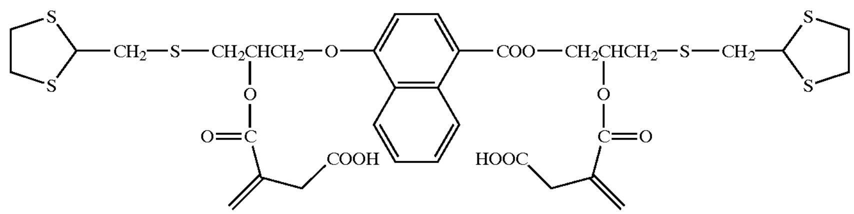 |
| 486 | 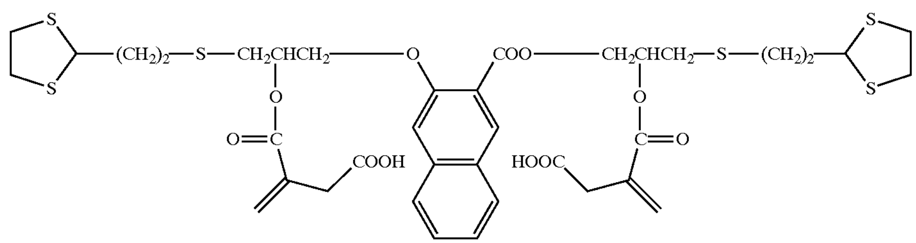 |
| 487 | 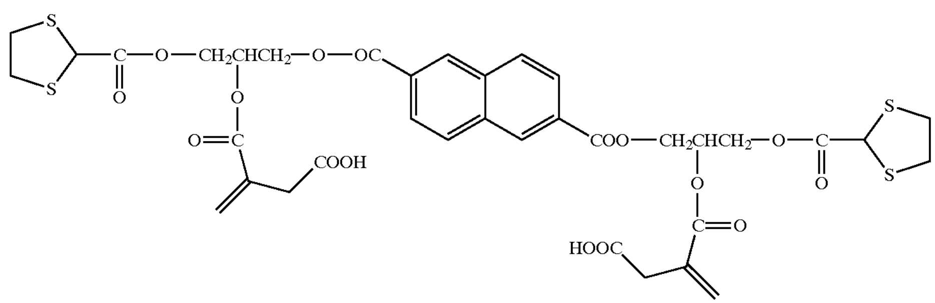 |

TABLE 1-continued
| No. of exemplified compounds | Structure |
|---|---|
| 488 | 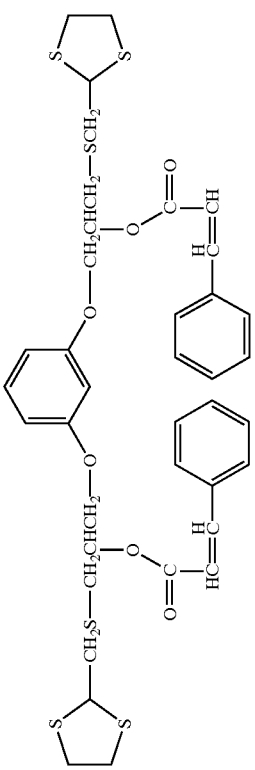 |
| 489 | 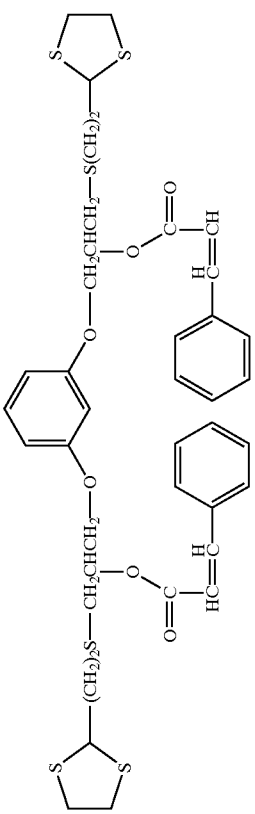 |
| 490 | 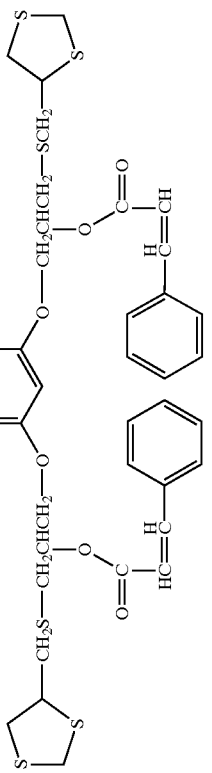 |

TABLE 1-continued

| No. of exemplified compounds | Structure |
|---|---|
| 491 | (structure) |
| 492 | (structure) |
| 493 | (structure) |
| 494 | (structure) |

TABLE 1-continued

| No. of exemplified compounds | Structure |
|---|---|
| 495 | 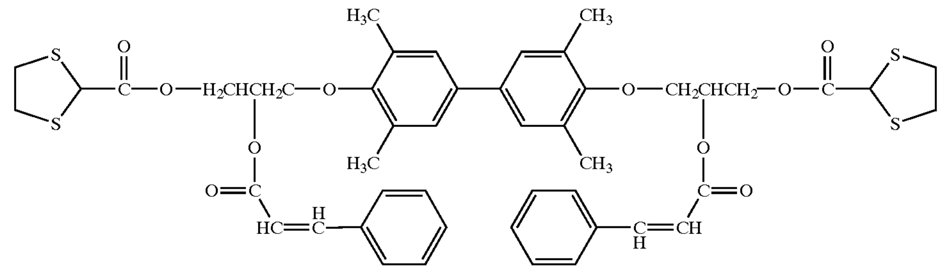 |
| 496 | 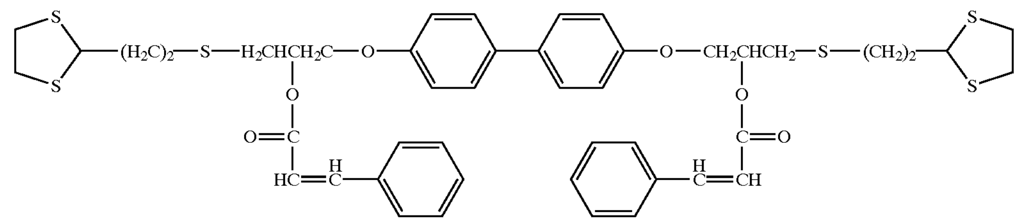 |
| 497 | 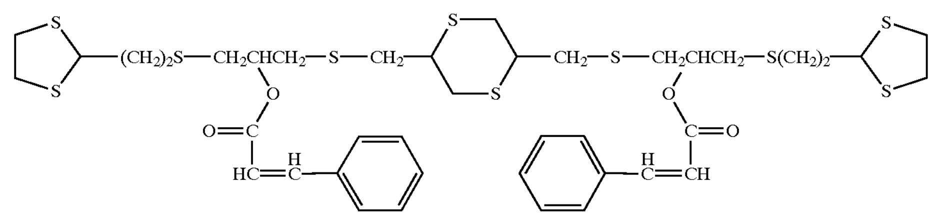 |
| 498 | 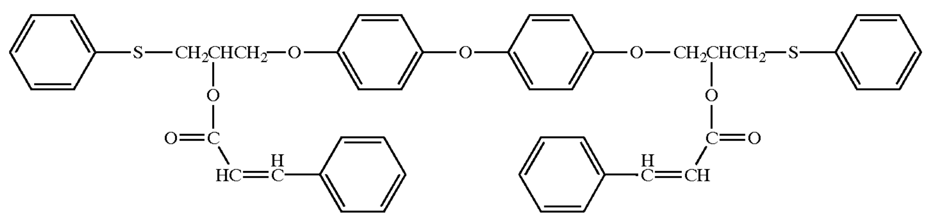 |

TABLE 1-continued

| No. of exemplified compounds | Structure |
|---|---|
| 499 | 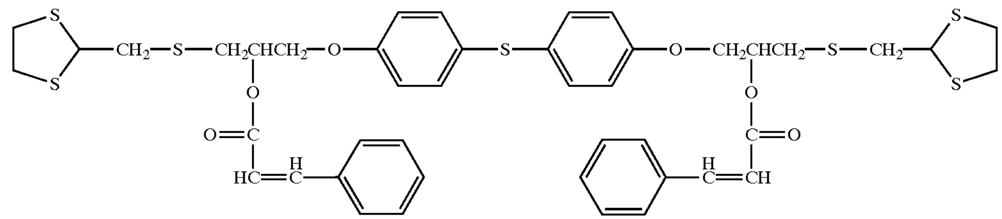 |
| 500 | 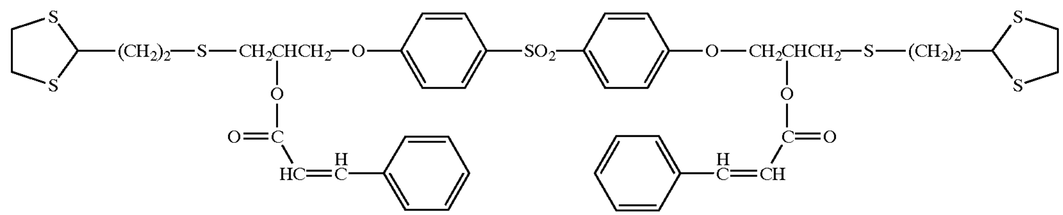 |
| 501 | 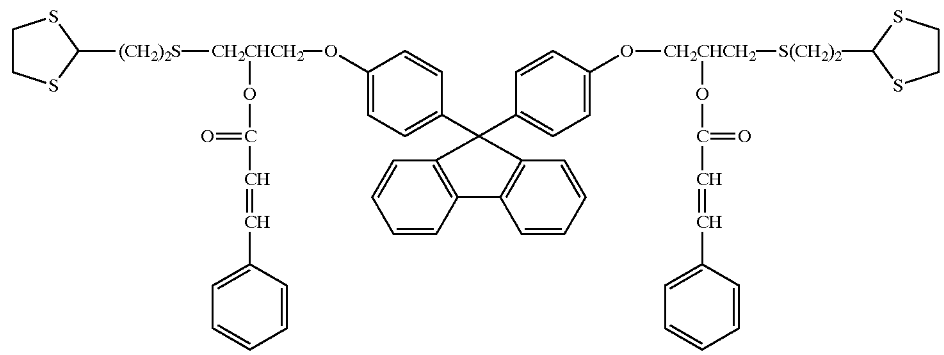 |
| 502 | 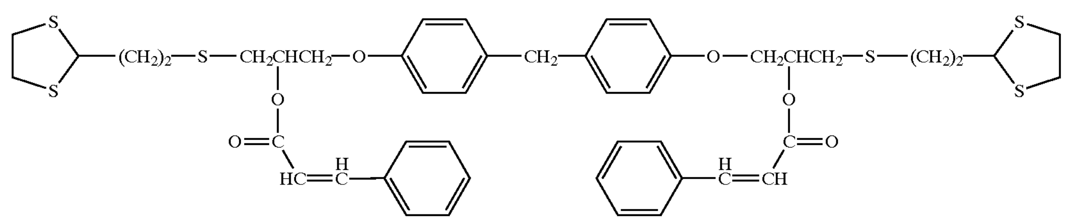 |

TABLE 1-continued

| No. of exemplified compounds | Structure |
|---|---|
| 503 | (structure) |
| 504 | (structure) |
| 505 | (structure) |
| 506 | (structure) |

TABLE 1-continued

| No. of exemplified compounds | Structure |
|---|---|
| 507 | 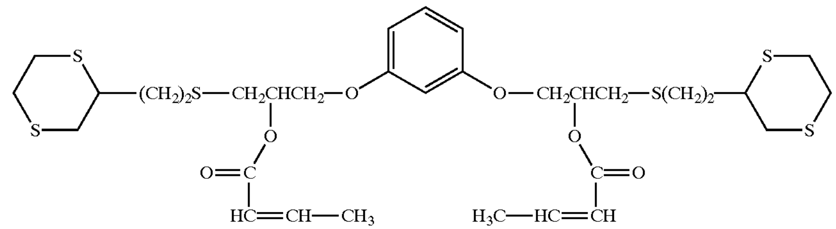 |
| 508 | 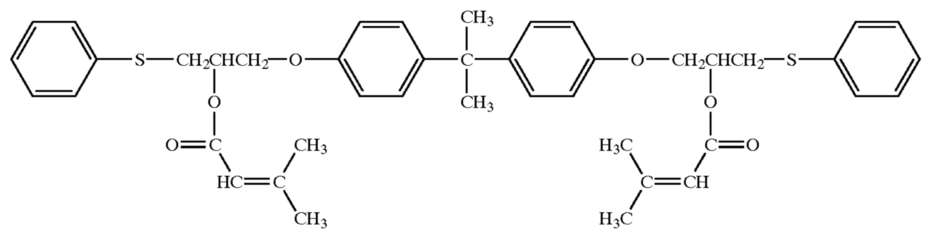 |
| 509 | 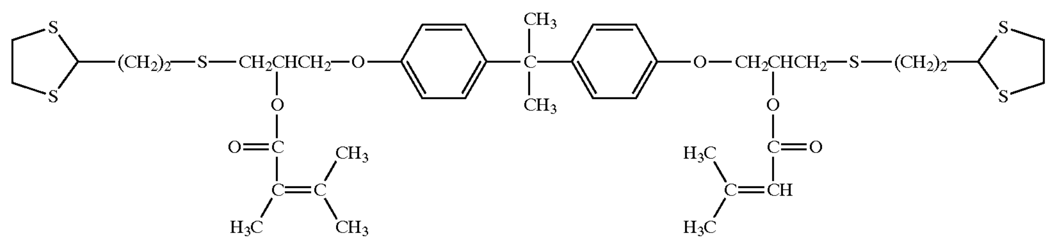 |
| 510 | 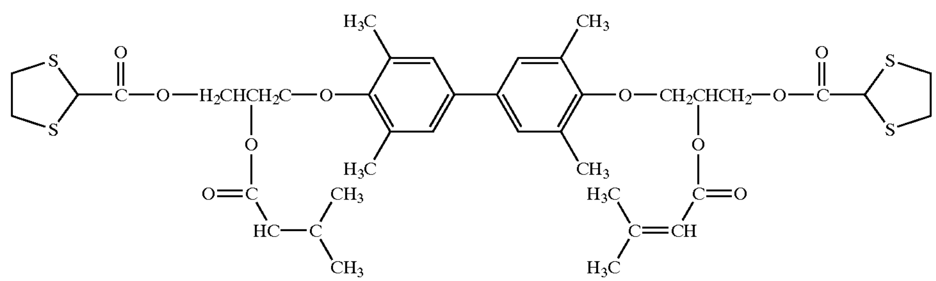 |

TABLE 1-continued

| No. of exemplified compounds | Structure |
|---|---|
| 511 | 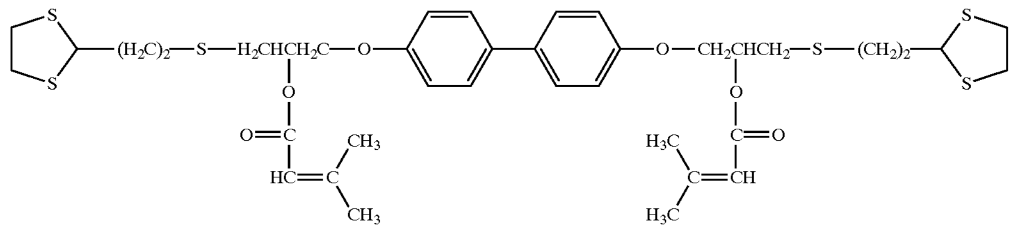 |
| 512 | 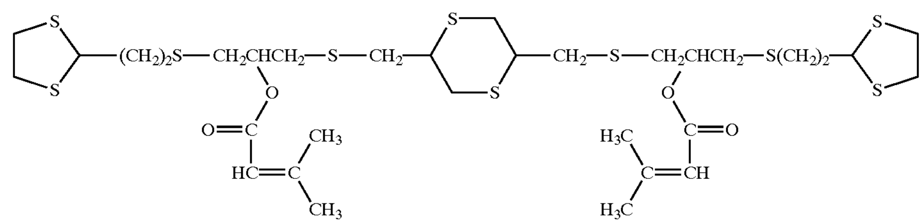 |
| 513 | 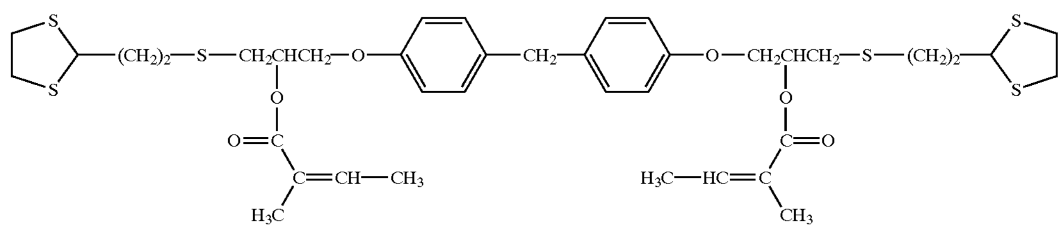 |
| 514 | 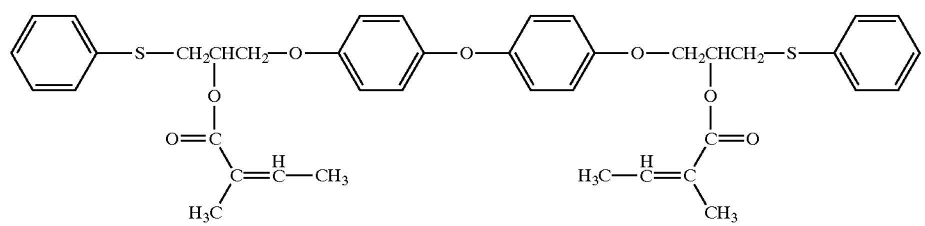 |

TABLE 1-continued
| No. of exemplified compounds | Structure |
|---|---|
| 515 | 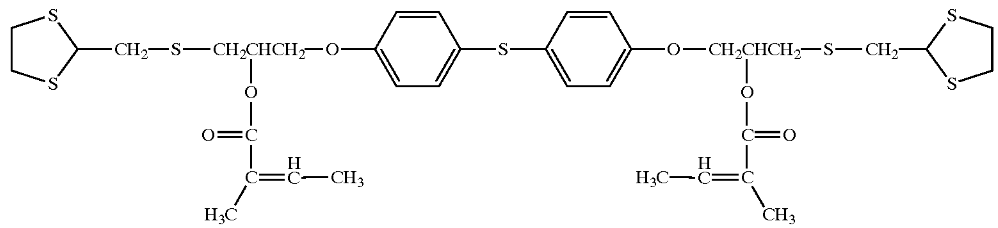 |
| 516 | 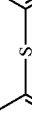 |
| 517 | 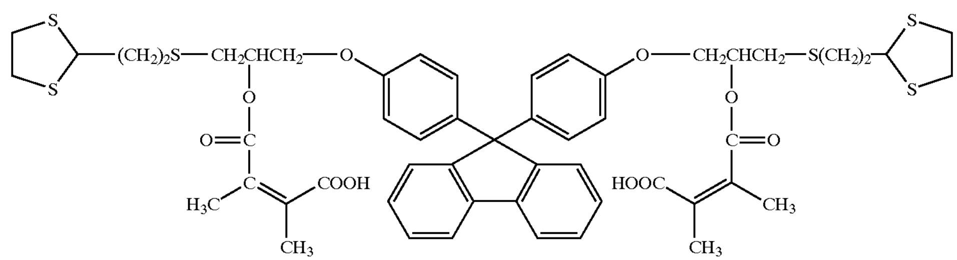 |

A sulfur-containing unsaturated carboxylate comprising a sulfur-containing substituent and at least two α,β-unsaturated carboxylic acid residues, which are each attached to a secondary or tertiary carbon atom via an oxygen atom, according to this invention is a novel compound, but may be suitably prepared by a well-known preparation process.

A sulfur-containing unsaturated carboxylate represented by general formula (1) as a typical example of the sulfur-containing unsaturated carboxylate according to this invention may be suitably prepared by a representative process, via a synthetic route illustrated in Scheme A.

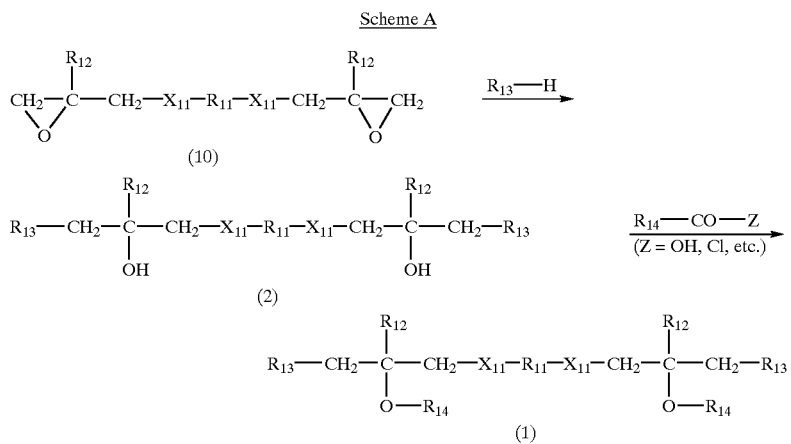

Scheme A wherein $R_{11}$, $R_{12}$, $R_{13}$, $R_{14}$ and $X_{11}$ are as defined above.

A sulfur-containing unsaturated carboxylate represented by general formula (1) according to this invention can be prepared by a unsaturated carboxylation process employing a well-known synthetic reaction; typically by reacting a sulfur-containing dihydroxy compound represented by general formula (2) with, for example, (a) an α,β-unsaturated carboxylic acid derivatives such as an α,β-unsaturated carboxylic acid and its ester, anhydride and halide, including (meth)acrylic acid, crotonic acid, tiglic acid, 3,3-dimethylacrylic acid, maleic acid, citraconic acid, 2,3-dimethylmaleic acid, itaconic acid and cinnamic acid derivatives; or (b) a halopropionic acid such as 3-chloropropionic acid, 3-bromopropionic acid, 3-chloro-2-methylpropionic acid and 3-bromo-2-methylpropionic acid, or its acid halide to form a halopropionate which is then dehydrohalogenated to provide a (meth)acrylate.

A sulfur-containing dihydroxy compound represented by general formula (2) according to this invention is a novel compound which is useful as a preparation intermediate for a sulfur-containing unsaturated carboxylate represented by general formula (1) according to this invention, in the synthetic route illustrated in Scheme A.

In general formula (2), $R_{11}$, $R_{12}$, $R_{13}$, $R_{14}$ and $X_{11}$ are as defined for general formula (1).

Specific examples of a sulfur-containing dihydroxy compound represented by general formula (2) according to this invention are listed in Table 2, but this invention is not limited to those specific compounds.

TABLE 2

| No. of exemplified compounds | Structure |
|---|---|
| 1 | 1,3-bis(2-hydroxy-3-(2-methylthioethoxy)propoxy)benzene |
| 2 | 1,3-bis(2-hydroxy-3-(2-(2-methylthioethylthio)ethoxy)propoxy)benzene |
| 3 | 1,3-bis(2-hydroxy-3-(2,2-bis(methylthio)ethoxy)propoxy)benzene |
| 4 | 1,3-bis(2-hydroxy-3-(2,2-bis(ethylthio)ethoxy)propoxy)benzene |
| 5 | 1,3-bis(2-hydroxy-3-((1,3-dithiolan-2-yl)methoxy)propoxy)benzene |
| 6 | 1,3-bis(2-hydroxy-3-((1,3-dithiolan-2-yl)methoxy)propoxy)benzene isomer |

TABLE 2-continued

| No. of exemplified compounds | Structure |
|---|---|
| 7 | (1,4-dithian-2-yl)-CH₂O-CH₂CHCH₂(OH)-O-[1,3-phenylene]-O-CH₂CHCH₂(OH)-OCH₂-(1,4-dithian-2-yl) |
| 8 | (1,4-dithian-2-yl)-(CH₂)₂O-CH₂CHCH₂(OH)-O-[1,3-phenylene]-O-CH₂CHCH₂(OH)-OCH₂-O(CH₂)₂-(1,4-dithian-2-yl) |
| 9 | (1,3-dithian-2-yl)-CH₂O-CH₂CHCH₂(OH)-O-[1,3-phenylene]-O-CH₂CHCH₂(OH)-OCH₂-(1,3-dithian-2-yl) |
| 10 | (1,3-dithian-2-yl)-(CH₂)₂O-CH₂CHCH₂(OH)-O-[1,3-phenylene]-O-CH₂CHCH₂(OH)-OCH₂-O(CH₂)₂-(1,3-dithian-2-yl) |
| 11 | (4-CH₃S-C₆H₄)-CH₂O-CH₂CHCH₂(OH)-O-[1,3-phenylene]-O-CH₂CHCH₂(OH)-OCH₂-(C₆H₄-4-SCH₃) |
| 12 | (2,6-bis(SCH₃)-4-CH₃S-C₆H₂)-CH₂O-CH₂CHCH₂(OH)-O-[1,3-phenylene]-O-CH₂CHCH₂(OH)-OCH₂-(C₆H₂-2,6-bis(SCH₃)-4-SCH₃) |

TABLE 2-continued

| No. of exemplified compounds | Structure |
|---|---|
| 13 | (structure) |
| 14 | (structure) |
| 15 | (structure) |
| 16 | (structure) |
| 17 | (structure) |
| 18 | (structure) |

TABLE 2-continued
| No. of exemplified compounds | Structure |
|---|---|
| 19 | 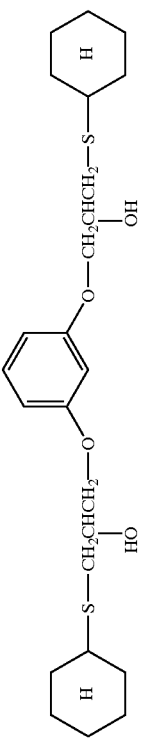 |
| 20 | 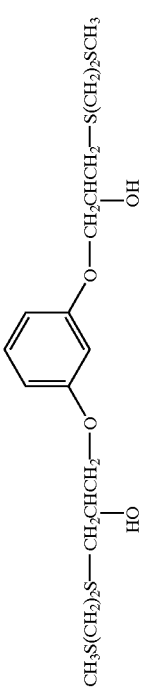 |
| 21 | 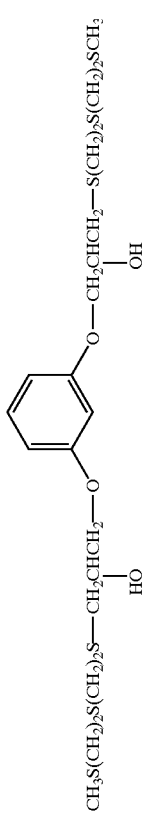 |
| 22 | 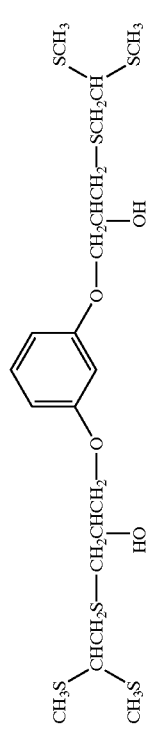 |
| 23 | 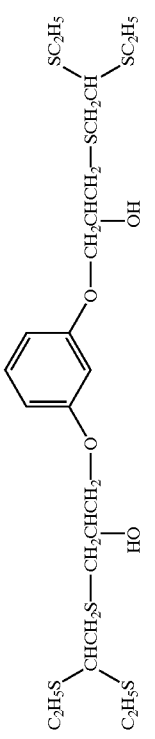 |
| 24 | 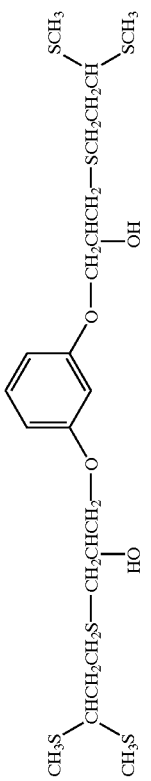 |

TABLE 2-continued

| No. of exemplified compounds | Structure |
|---|---|
| 25 | (structure) |
| 26 | (structure) |
| 27 | (structure) |
| 28 | (structure) |
| 29 | (structure) |
| 30 | (structure) |

TABLE 2-continued

| No. of exemplified compounds | Structure |
|---|---|
| 31 | (structure) |
| 32 | (structure) |
| 33 | (structure) |
| 34 | (structure) |
| 35 | (structure) |
| 36 | (structure) |

TABLE 2-continued

| No. of exemplified compounds | Structure |
|---|---|
| 37 | (chemical structure) |
| 38 | (chemical structure) |
| 39 | (chemical structure) |
| 40 | (chemical structure) |
| 41 | (chemical structure) |
| 42 | (chemical structure) |

TABLE 2-continued

| No. of exemplified compounds | Structure |
|---|---|
| 43 | 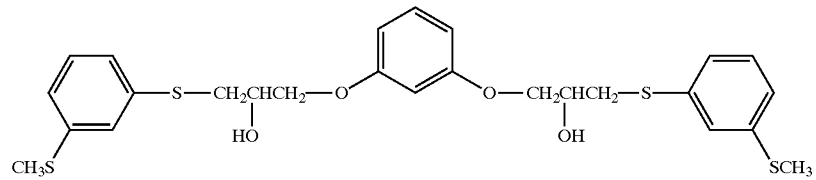 |
| 44 | 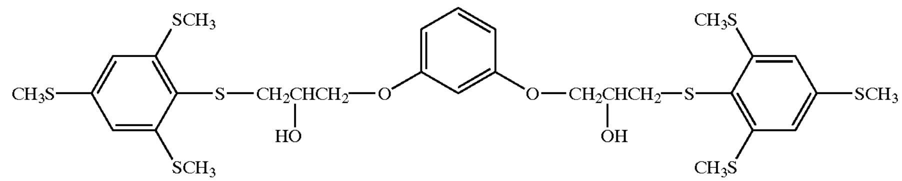 |
| 45 | 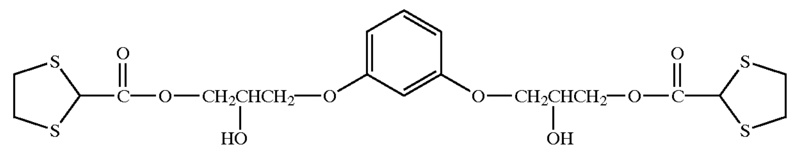 |
| 46 | 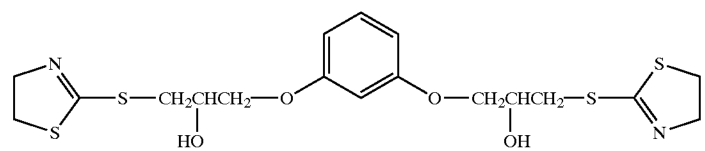 |
| 47 | 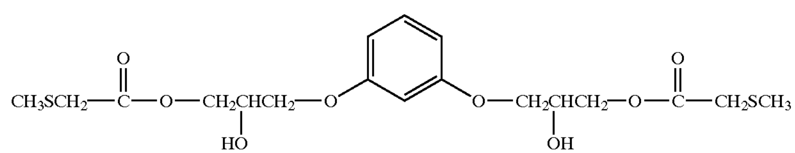 |
| 48 | 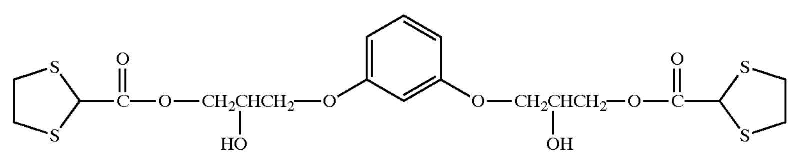 |

TABLE 2-continued

| No. of exemplified compounds | Structure |
| --- | --- |
| 49 | 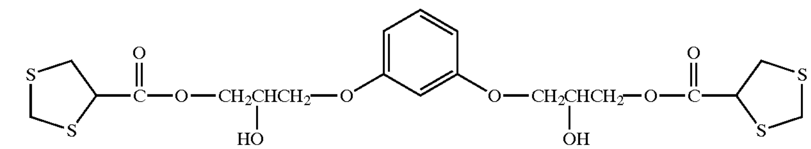 |
| 50 | 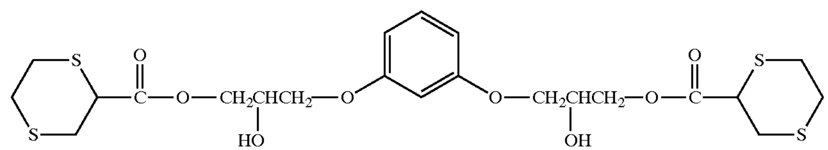 |
| 51 | 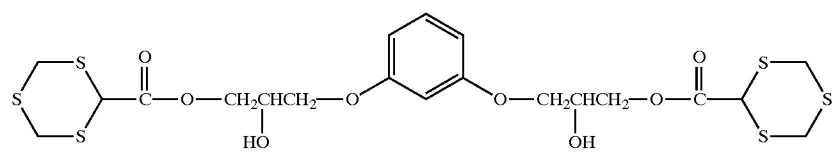 |
| 52 | 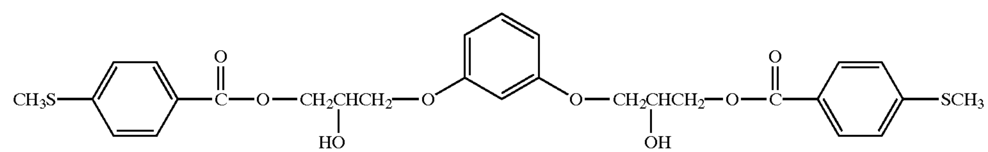 |
| 53 | 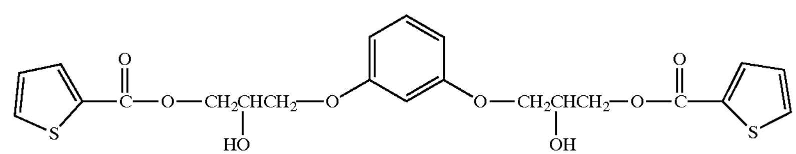 |
| 54 | 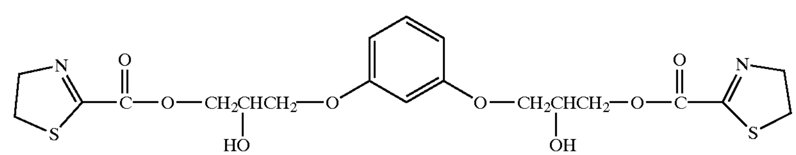 |

TABLE 2-continued

| No. of exemplified compounds | Structure |
|---|---|
| 55 | 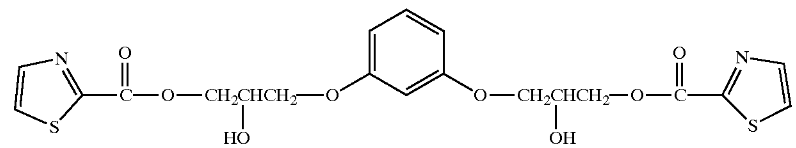 |
| 56 | 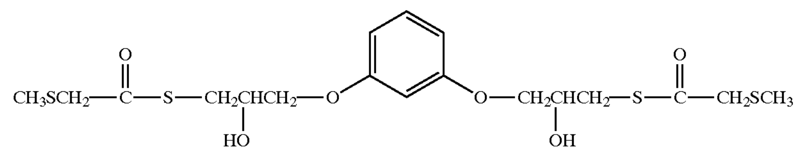 |
| 57 | 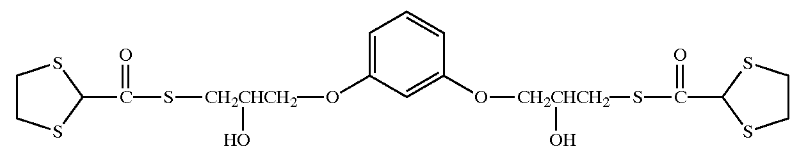 |
| 58 | 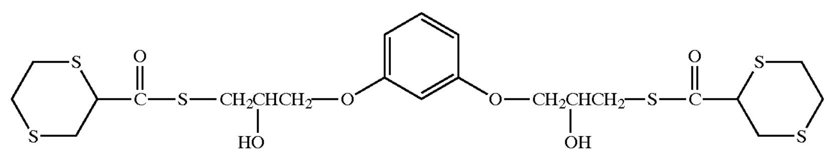 |
| 59 | 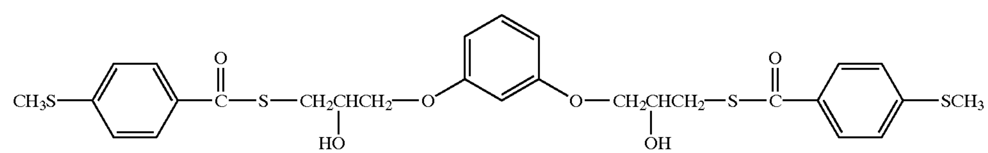 |
| 60 | 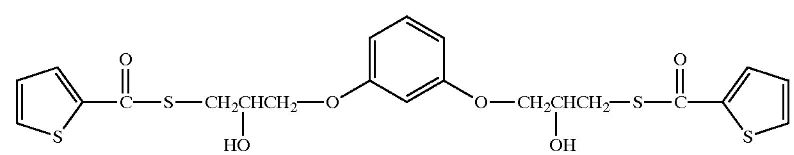 |

TABLE 2-continued

| No. of exemplified compounds | Structure |
|---|---|
| 61 | 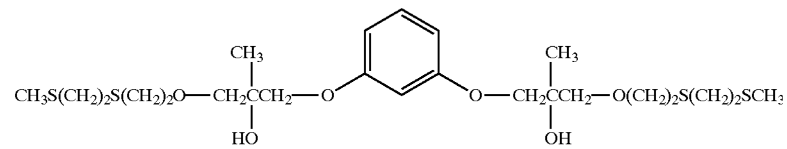 |
| 62 | 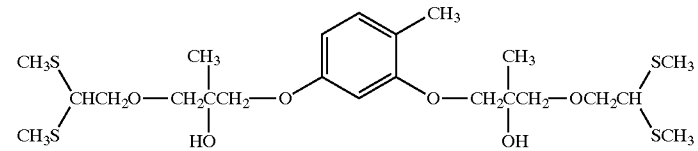 |
| 63 | 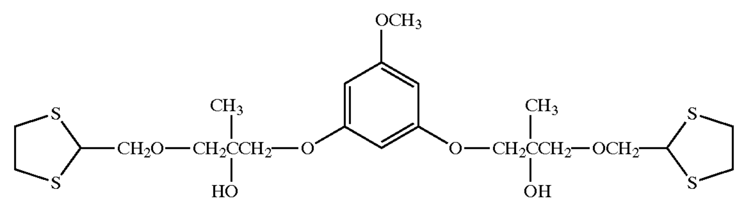 |
| 64 | 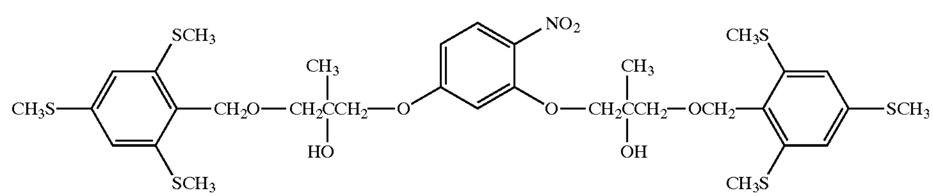 |
| 65 | 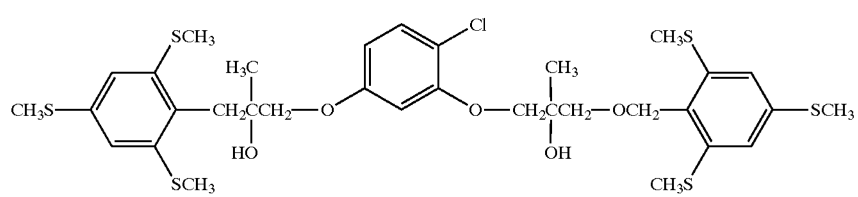 |

TABLE 2-continued

| No. of exemplified compounds | Structure |
|---|---|
| 66 | 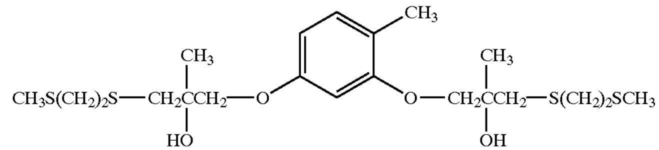 |
| 67 | 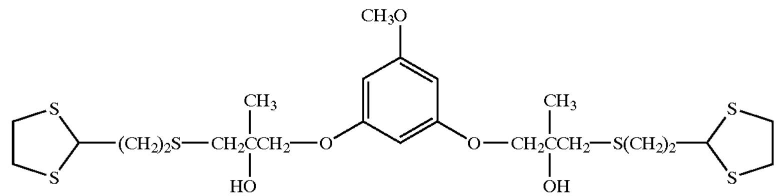 |
| 68 | 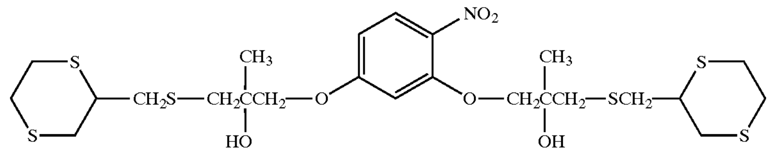 |
| 69 | 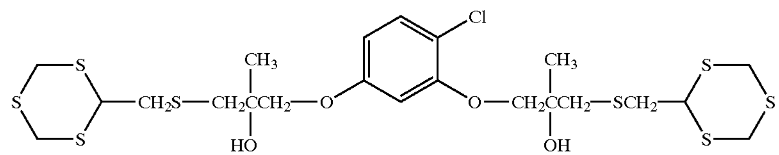 |
| 70 | 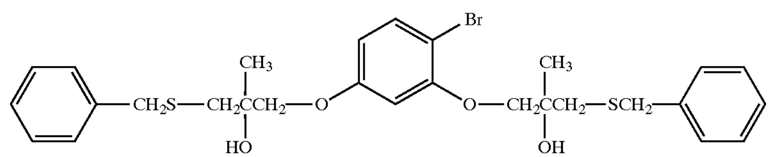 |
| 71 | 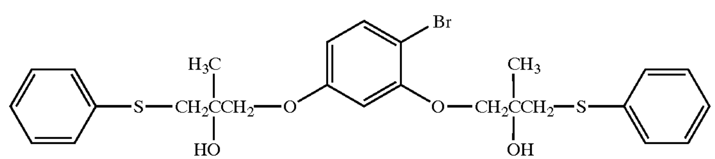 |

TABLE 2-continued

| No. of exemplified compounds | Structure |
|---|---|
| 72 | (chemical structure) |
| 73 | (chemical structure) |
| 74 | (chemical structure) |
| 75 | (chemical structure) |
| 76 | (chemical structure) |
| 77 | (chemical structure) |

TABLE 2-continued

| No. of exemplified compounds | Structure |
|---|---|
| 78 | 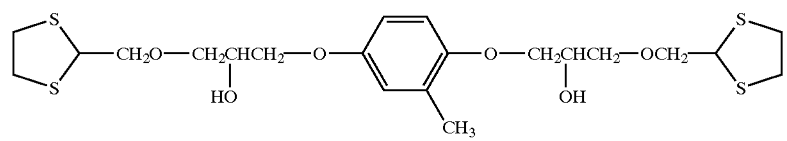 |
| 79 | 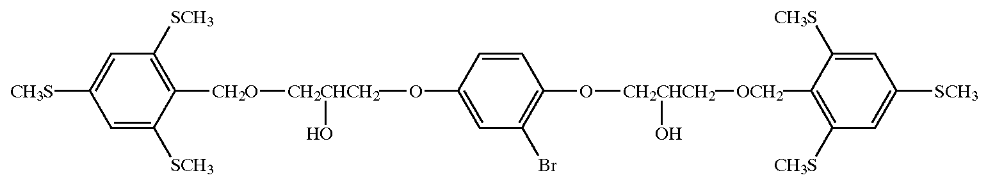 |
| 80 | 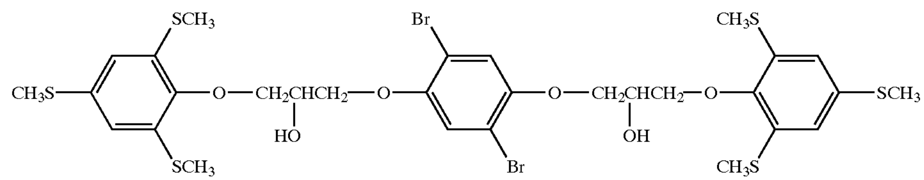 |
| 81 | 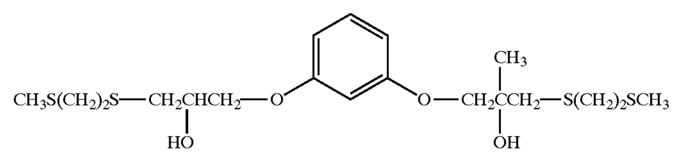 |
| 82 | 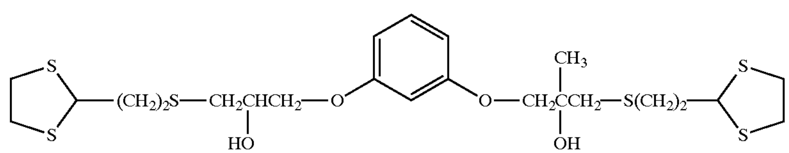 |
| 83 | 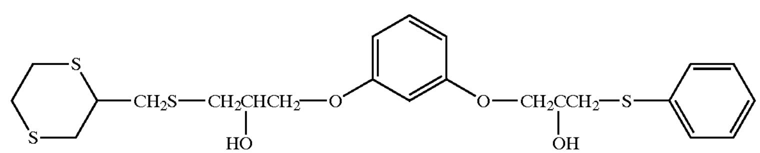 |

TABLE 2-continued

| No. of exemplified compounds | Structure |
|---|---|
| 84 | (structure) |
| 85 | (structure) |
| 86 | (structure) |
| 87 | (structure) |
| 88 | (structure) |
| 89 | (structure) |

TABLE 2-continued

| No. of exemplified compounds | Structure |
| --- | --- |
| 90 | 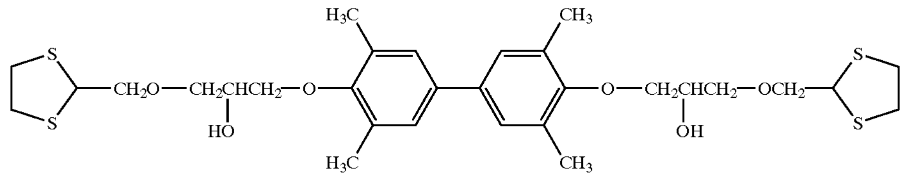 |
| 91 | 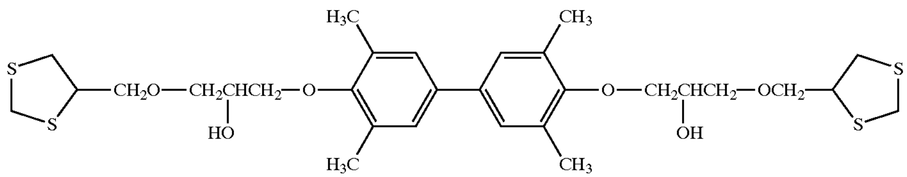 |
| 92 | 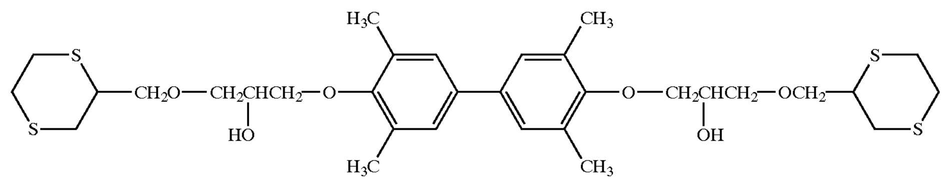 |
| 93 | 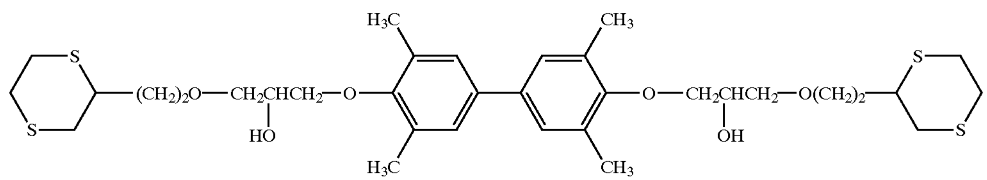 |
| 94 | 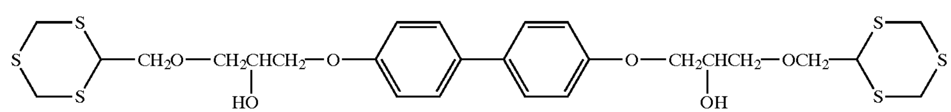 |
| 95 | 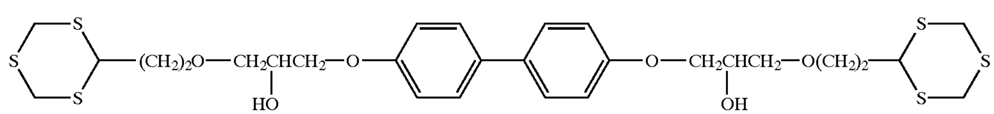 |

TABLE 2-continued

| No. of exemplified compounds | Structure |
|---|---|
| 96 | 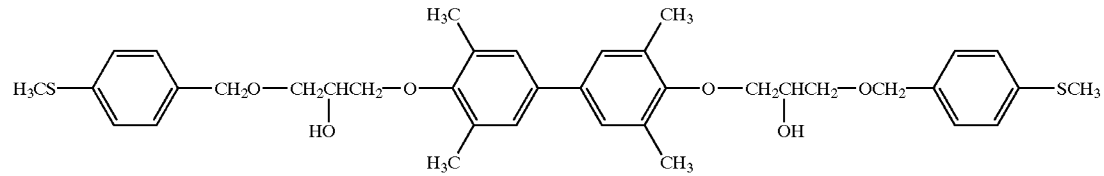 |
| 97 | 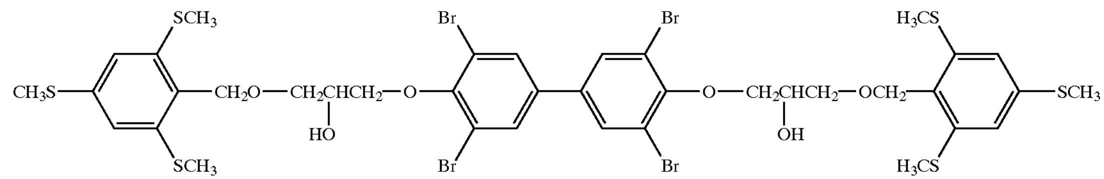 |
| 98 | 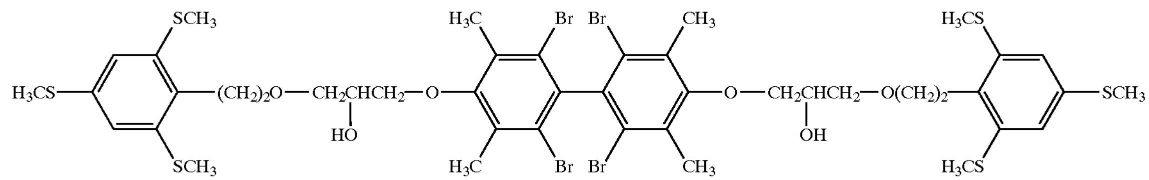 |
| 99 | 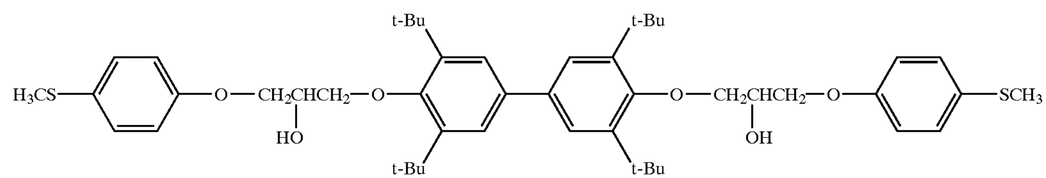 |
| 100 | 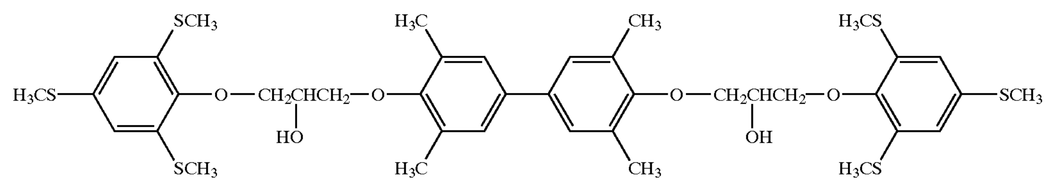 |

TABLE 2-continued
| No. of exemplified compounds | Structure |
|---|---|
| 101 | 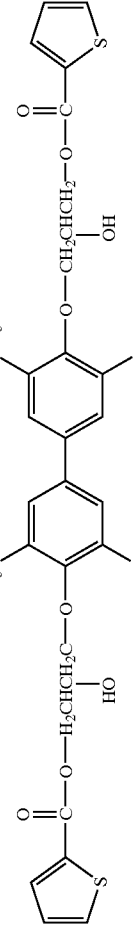 |
| 102 | 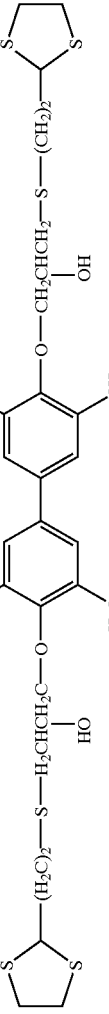 |
| 103 | 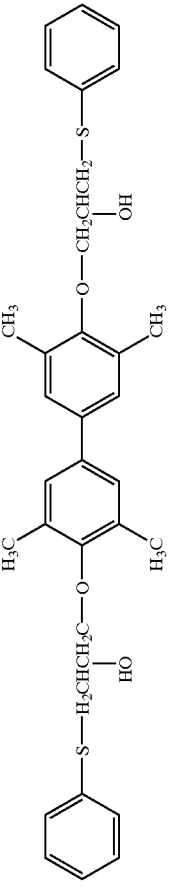 |
| 104 | 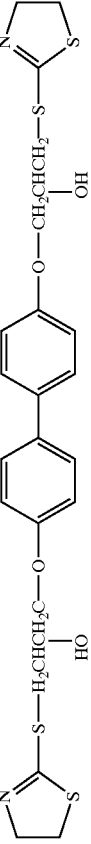 |
| 105 | 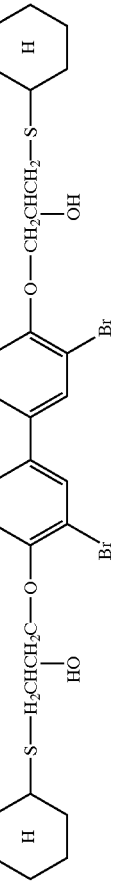 |

TABLE 2-continued

| No. of exemplified compounds | Structure |
|---|---|
| 106 | 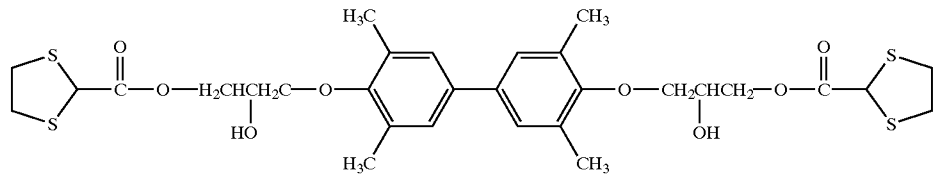 |
| 107 | 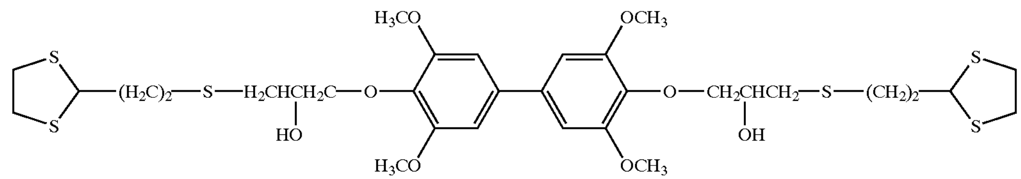 |
| 108 | 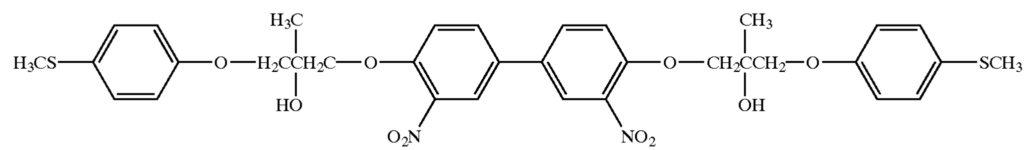 |
| 109 | 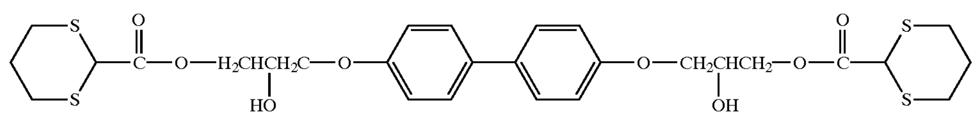 |
| 110 | 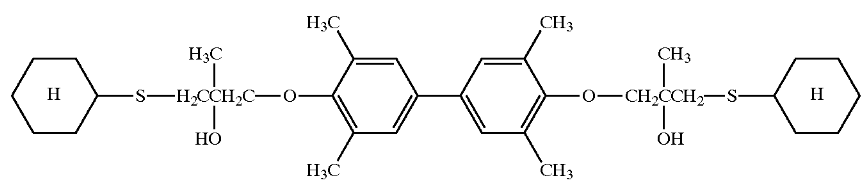 |
| 111 | 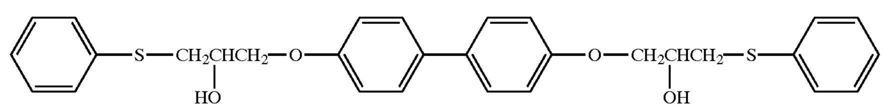 |

TABLE 2-continued

| No. of exemplified compounds | Structure |
|---|---|
| 112 | 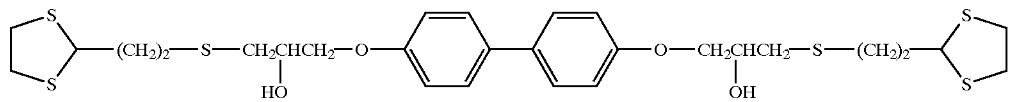 |
| 113 | 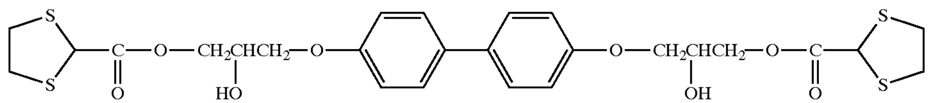 |
| 114 | 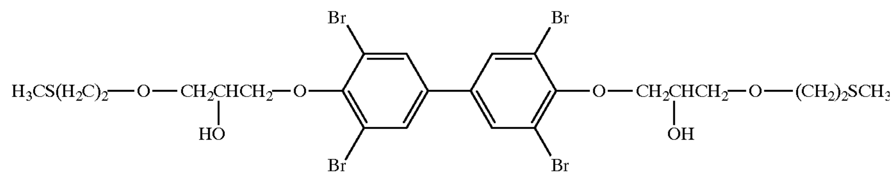 |
| 115 | 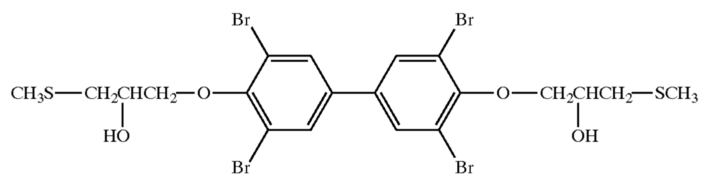 |
| 116 | 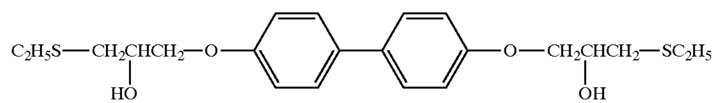 |
| 117 | 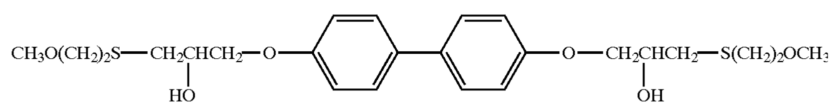 |
| 118 | 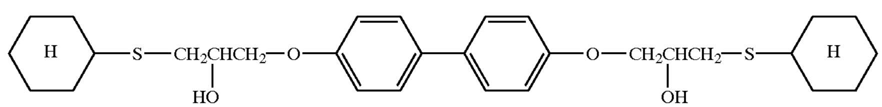 |

TABLE 2-continued

| No. of exemplified compounds | Structure |
|---|---|
| 119 | (structure) |
| 120 | (structure) |
| 121 | (structure) |
| 122 | (structure) |
| 123 | (structure) |
| 124 | (structure) |

TABLE 2-continued

| No. of exemplified compounds | Structure |
|---|---|
| 125 | 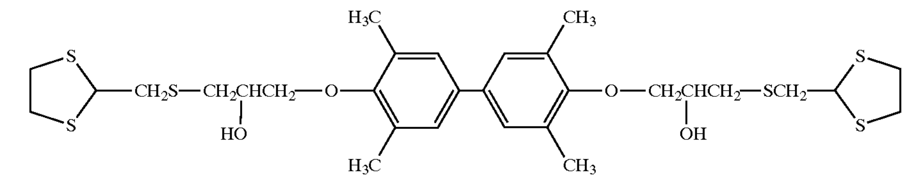 |
| 126 | 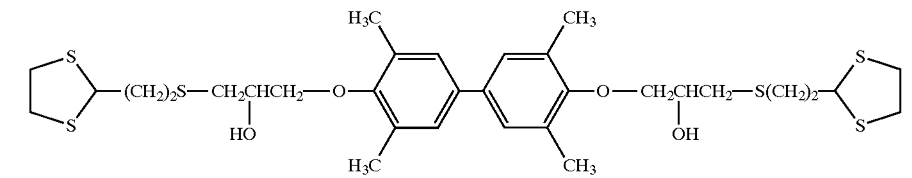 |
| 127 | 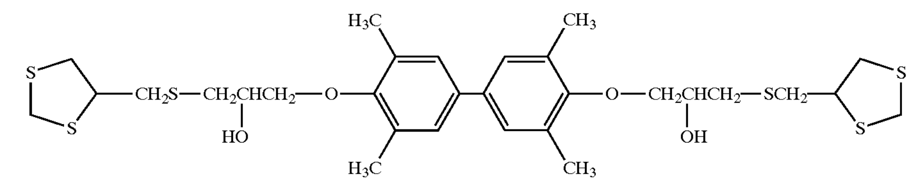 |
| 128 | 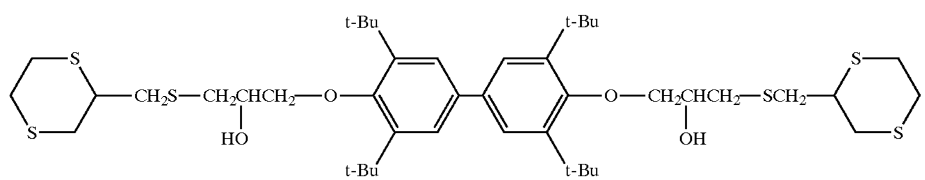 |
| 129 | 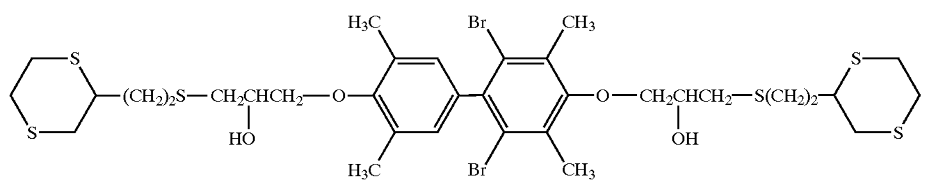 |

TABLE 2-continued

| No. of exemplified compounds | Structure |
|---|---|
| 130 | 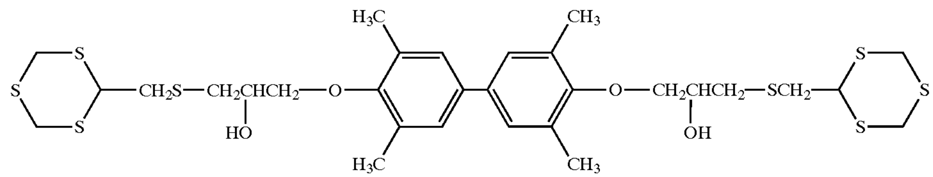 |
| 131 | 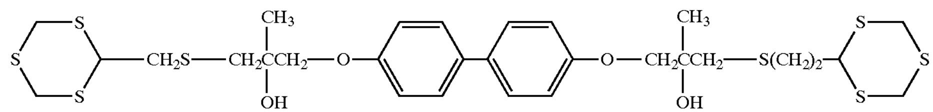 |
| 132 | 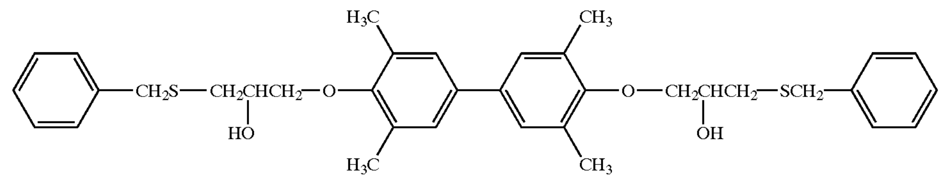 |
| 133 | 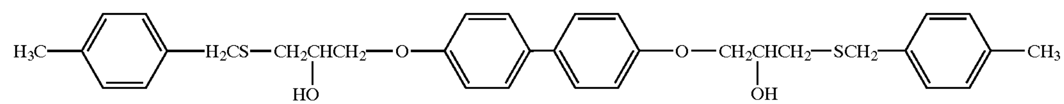 |
| 134 | 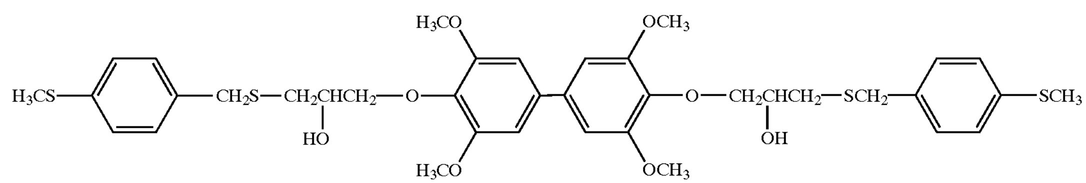 |
| 135 | 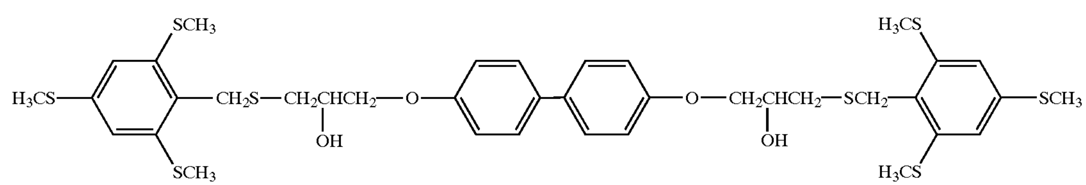 |

TABLE 2-continued

| No. of exemplified compounds | Structure |
|---|---|
| 136 | 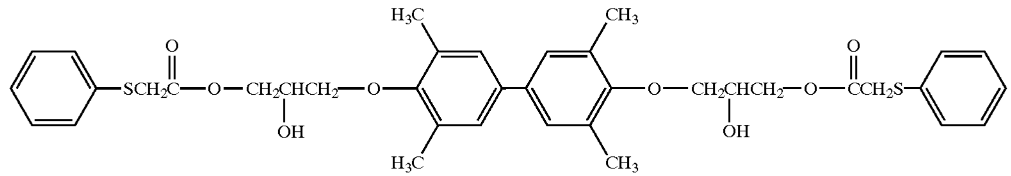 |
| 137 | 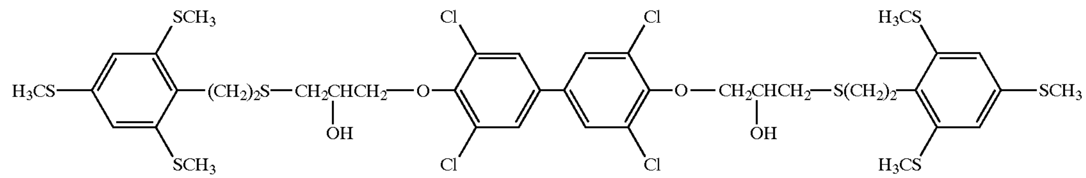 |
| 138 | 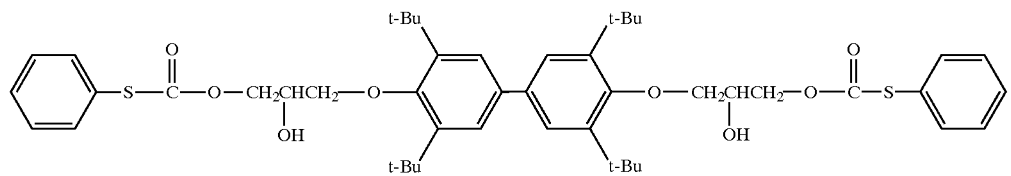 |
| 139 | 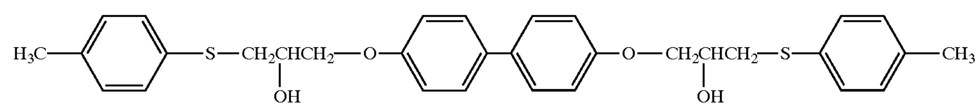 |
| 140 | 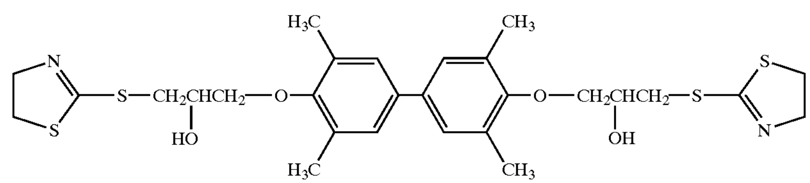 |
| 141 | 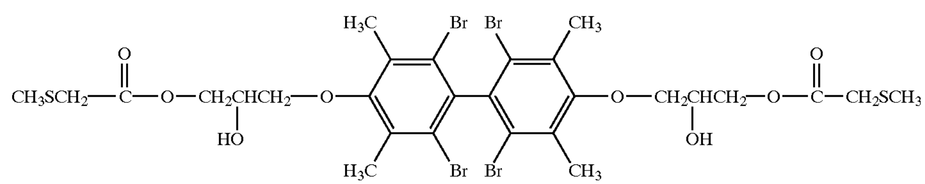 |

TABLE 2-continued

| No. of exemplified compounds | Structure |
|---|---|
| 142 | 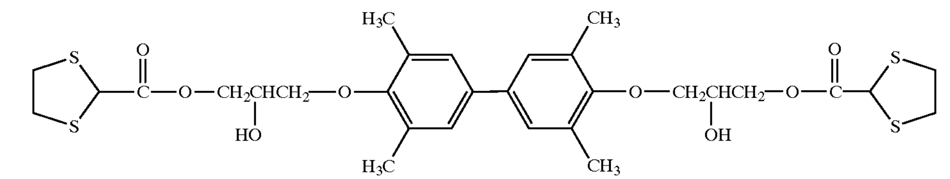 |
| 143 | 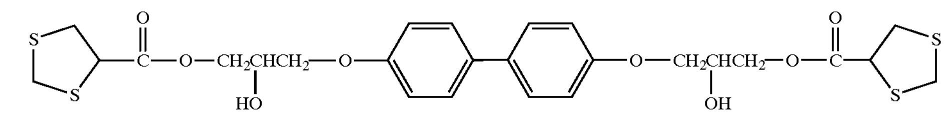 |
| 144 | 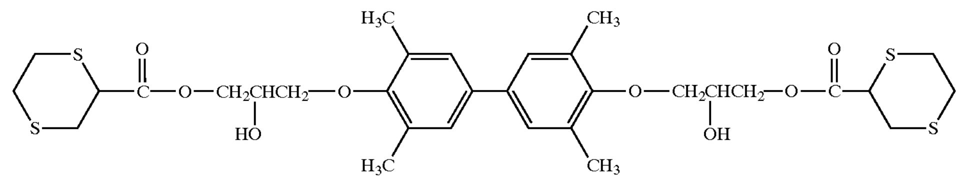 |
| 145 | 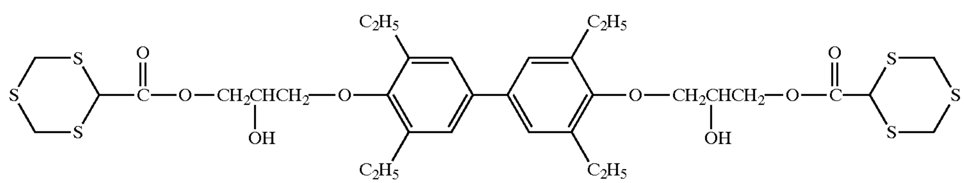 |
| 146 | 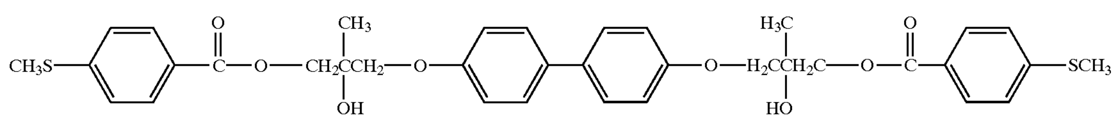 |
| 147 | 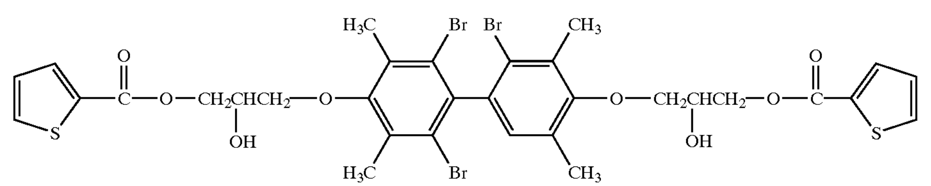 |

TABLE 2-continued

| No. of exemplified compounds | Structure |
|---|---|
| 148 | 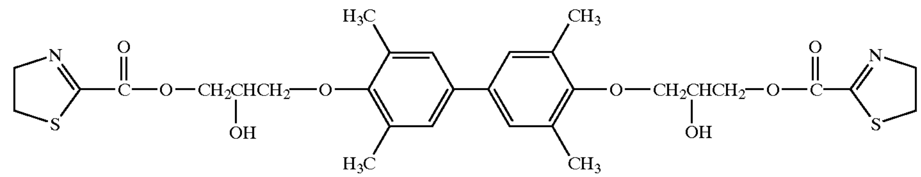 |
| 149 | 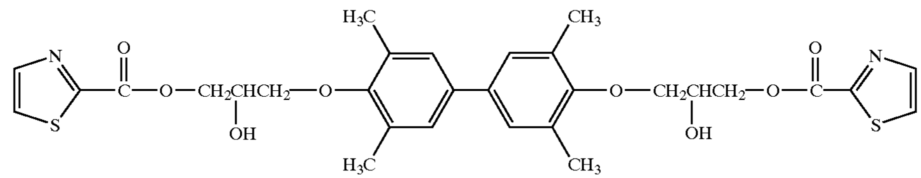 |
| 150 | 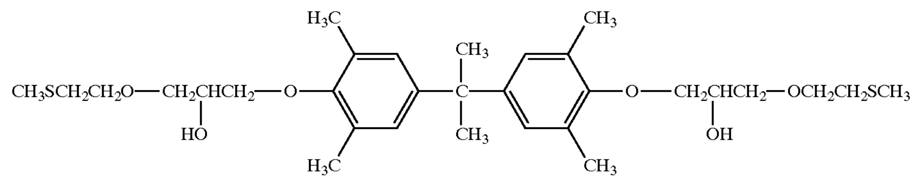 |
| 151 | 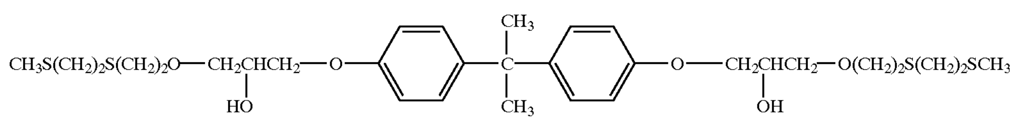 |
| 152 | 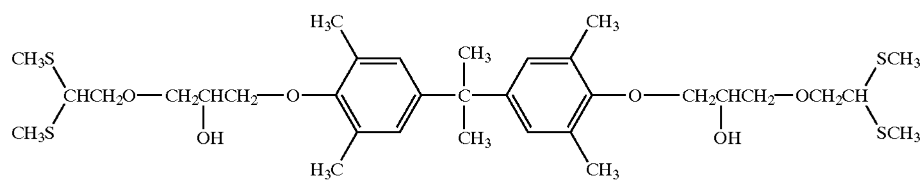 |

TABLE 2-continued

| No. of exemplified compounds | Structure |
|---|---|
| 153 | 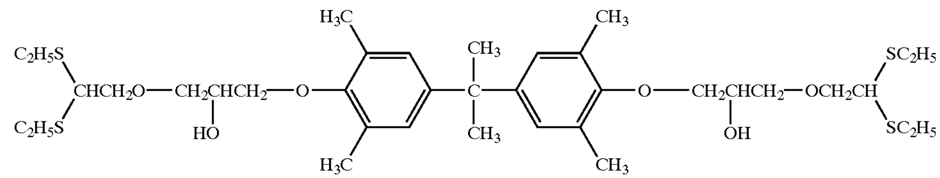 |
| 154 | 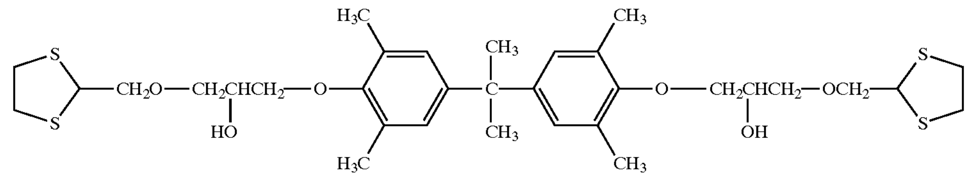 |
| 155 | 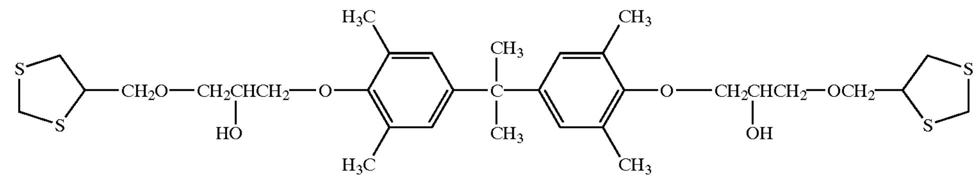 |
| 156 | 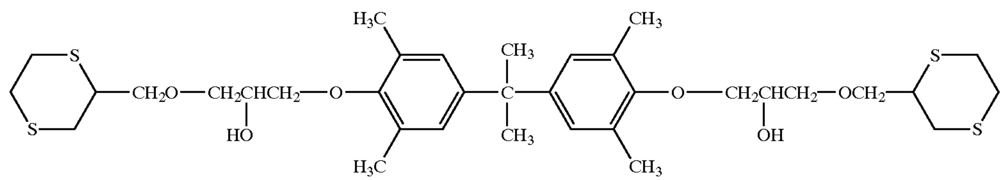 |
| 157 | 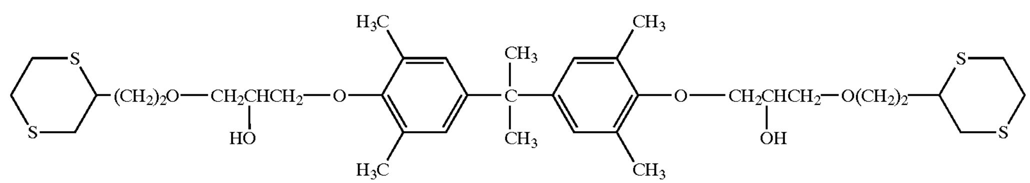 |

TABLE 2-continued

| No. of exemplified compounds | Structure |
|---|---|
| 158 | (structure) |
| 159 | (structure) |
| 160 | (structure) |
| 161 | (structure) |
| 162 | (structure) |
| 163 | (structure) |

TABLE 2-continued

| No. of exemplified compounds | Structure |
|---|---|
| 164 | (structure) |
| 165 | (structure) |
| 166 | (structure) |
| 167 | (structure) |
| 168 | (structure) |

TABLE 2-continued

| No. of exemplified compounds | Structure |
|---|---|
| 169 | 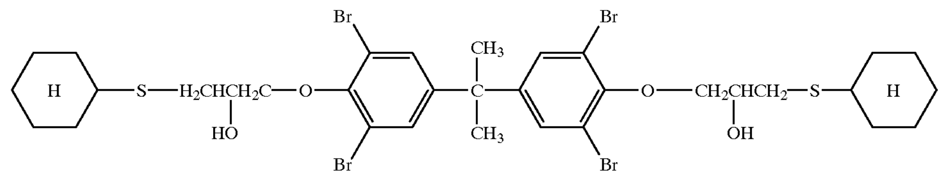 |
| 170 | 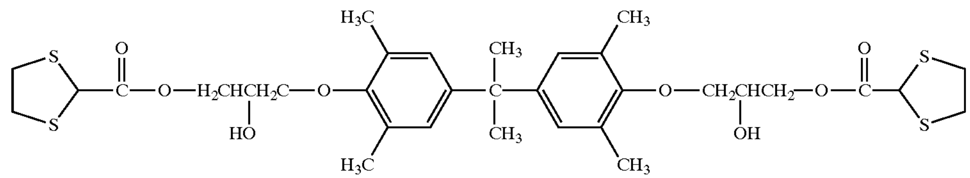 |
| 171 | 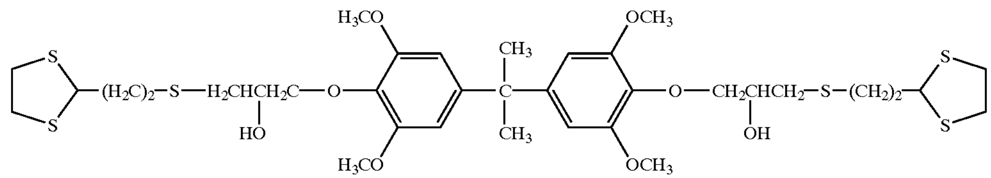 |
| 172 | 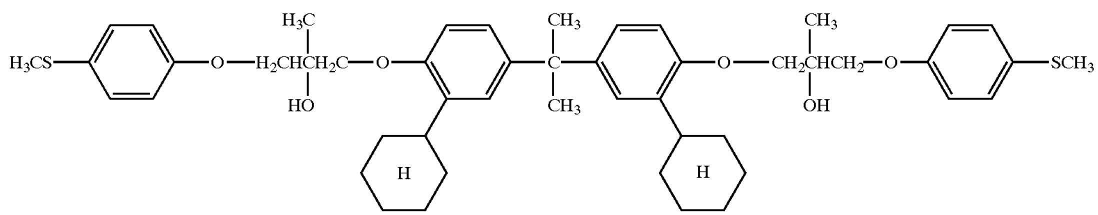 |
| 173 | 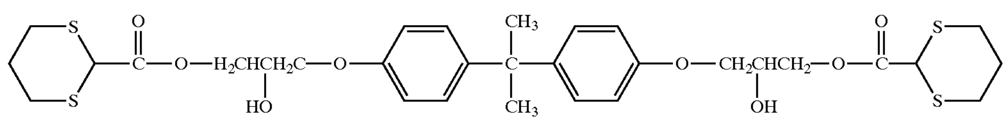 |

TABLE 2-continued

| No. of exemplified compounds | Structure |
|---|---|
| 174 | (chemical structure) |
| 175 | (chemical structure) |
| 176 | (chemical structure) |
| 177 | (chemical structure) |
| 178 | (chemical structure) |
| 179 | (chemical structure) |

TABLE 2-continued

| No. of exemplified compounds | Structure |
|---|---|
| 180 | 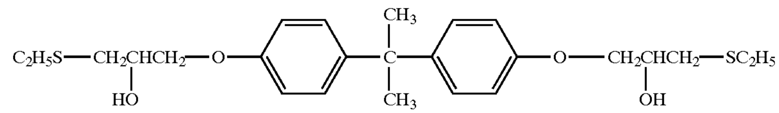 |
| 181 | 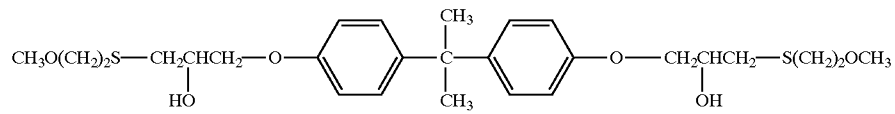 |
| 182 | 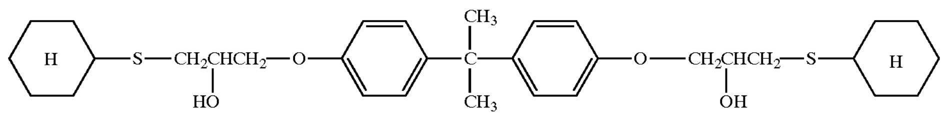 |
| 183 | 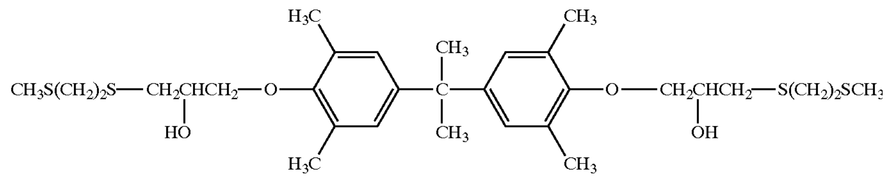 |
| 184 | 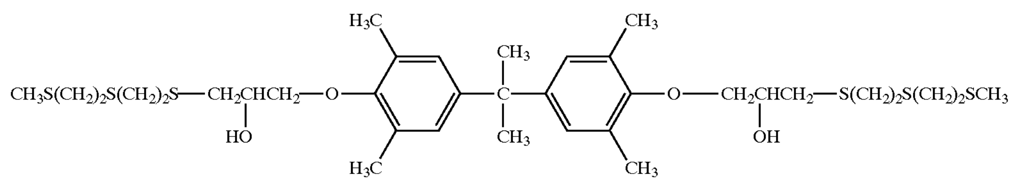 |
| 185 | 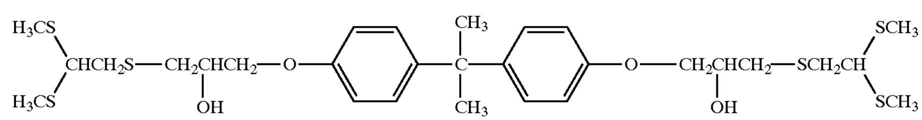 |
| 186 | 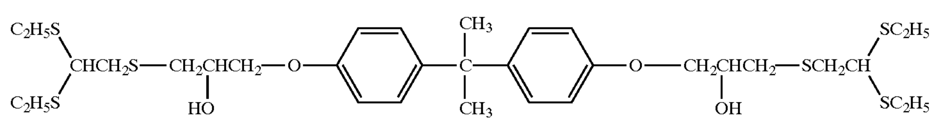 |

TABLE 2-continued

| No. of exemplified compounds | Structure |
|---|---|
| 187 | (structure) |
| 188 | (structure) |
| 189 | (structure) |
| 190 | (structure) |
| 191 | (structure) |
| 192 | (structure) |

TABLE 2-continued

| No. of exemplified compounds | Structure |
|---|---|
| 193 | 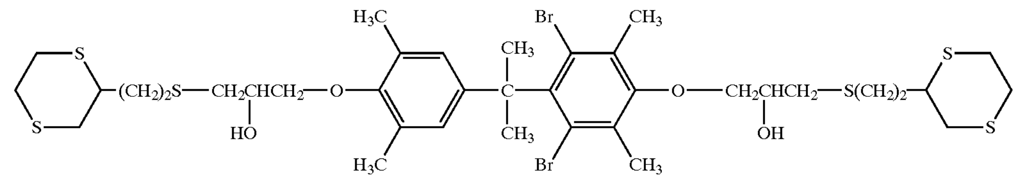 |
| 194 | 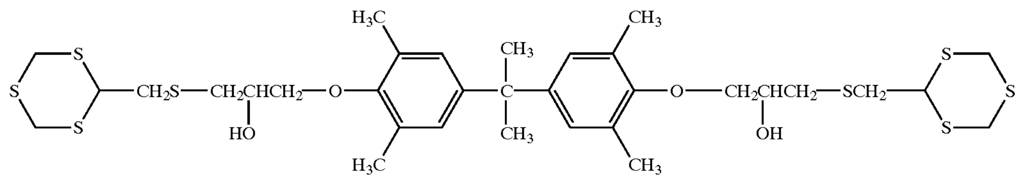 |
| 195 | 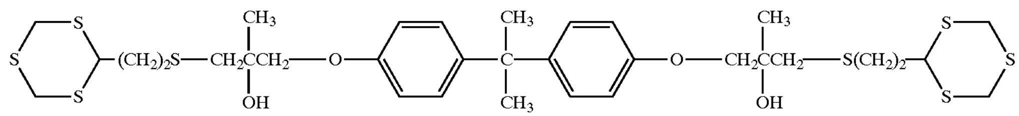 |
| 196 | 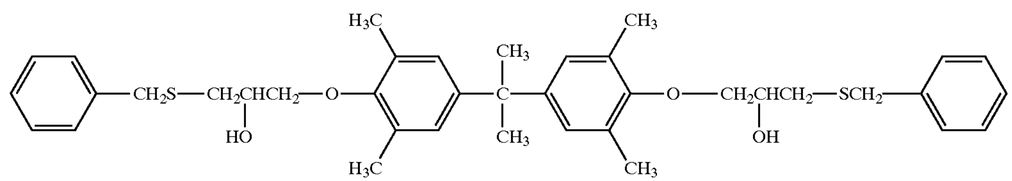 |
| 197 | 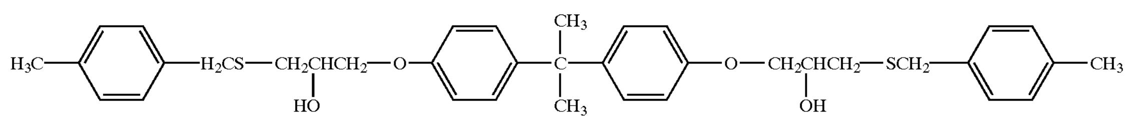 |
| 198 | 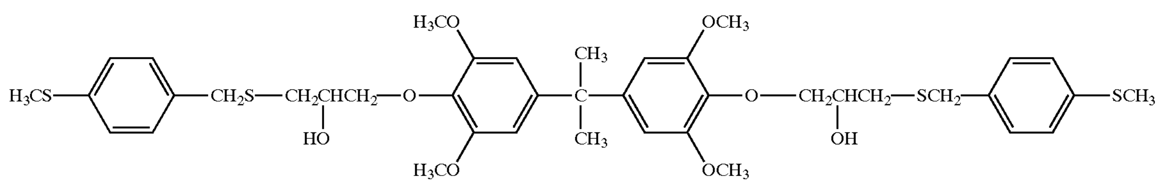 |

TABLE 2-continued

| No. of exemplified compounds | Structure |
|---|---|
| 199 | (structure) |
| 200 | (structure) |
| 201 | (structure) |
| 202 | (structure) |
| 203 | (structure) |

TABLE 2-continued

| No. of exemplified compounds | Structure |
|---|---|
| 204 | 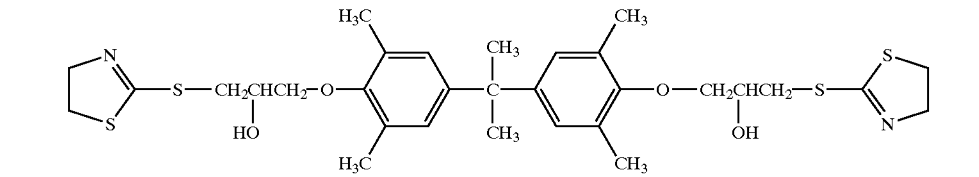 |
| 205 | 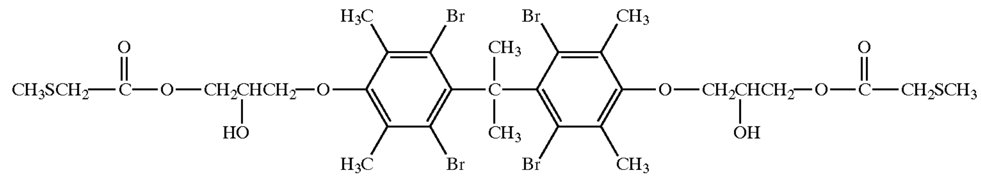 |
| 206 | 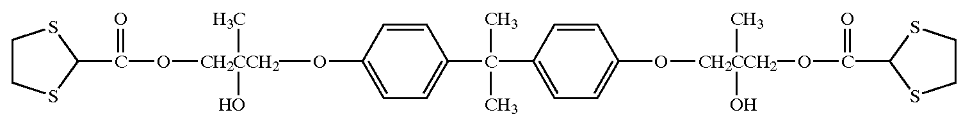 |
| 207 | 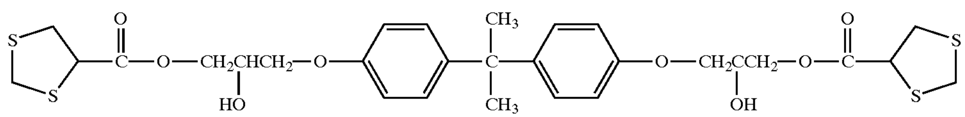 |
| 208 | 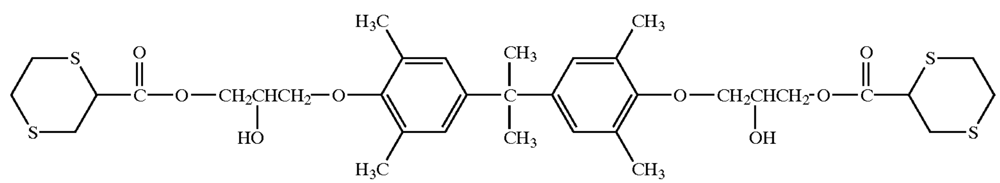 |
| 209 | 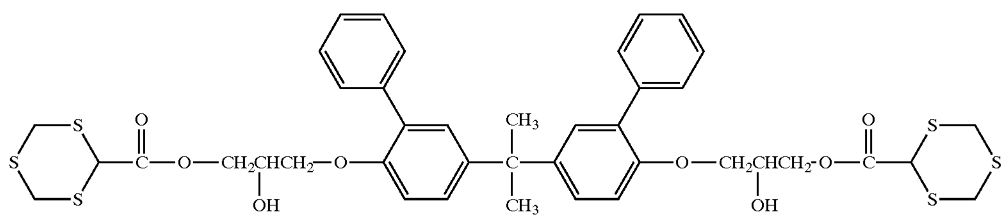 |

TABLE 2-continued

| No. of exemplified compounds | Structure |
|---|---|
| 210 | 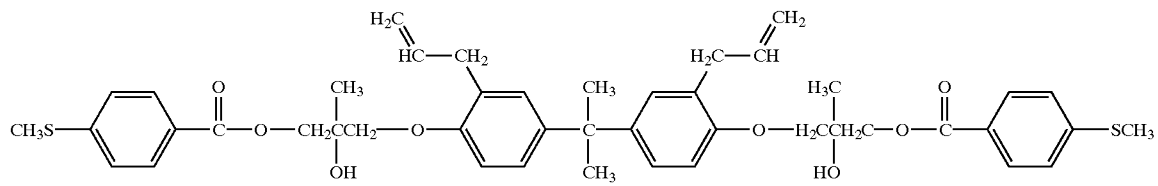 |
| 211 | 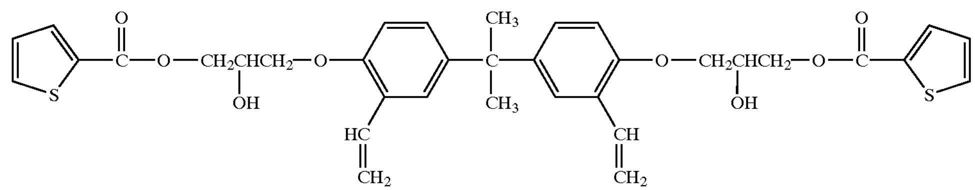 |
| 212 | 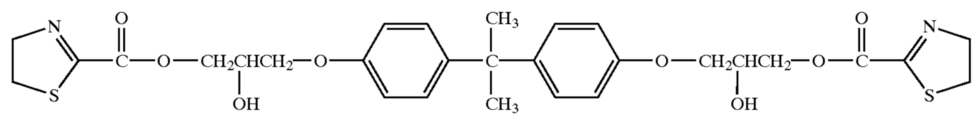 |
| 213 | 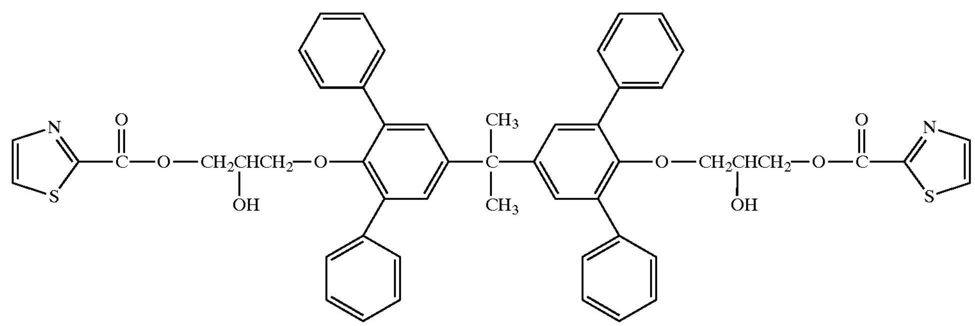 |

TABLE 2-continued

| No. of exemplified compounds | Structure |
|---|---|
| 214 | 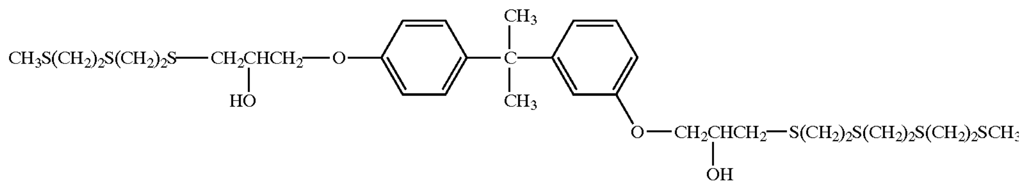 |
| 215 | 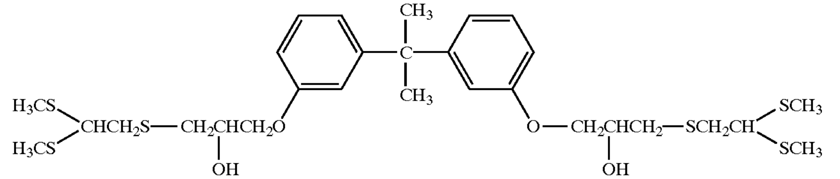 |
| 216 | 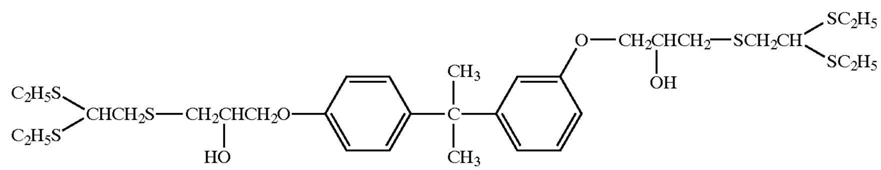 |
| 217 | 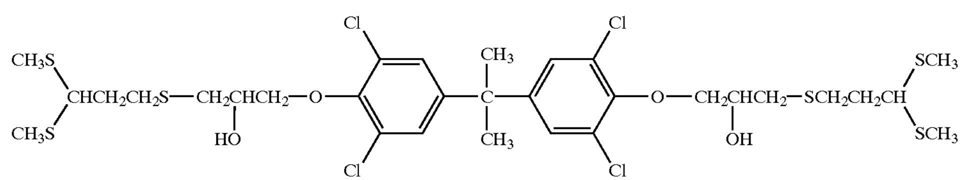 |
| 218 | 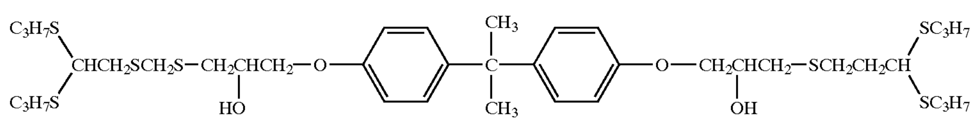 |
| 219 | 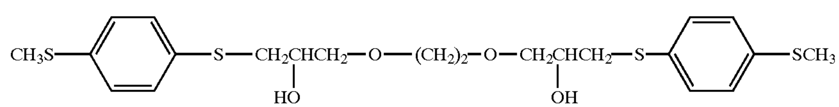 |

TABLE 2-continued

| No. of exemplified compounds | Structure |
|---|---|
| 220 | C6H5-S-CH2CHCH2-O-(CH2)2O(CH2)2-O-CH2CHCH2-S-C6H5, with OH on each CHCH2 |
| 221 | C6H5-S-CH2CHCH2-S-(CH2)2-S-CH2CHCH2-S-C6H5, with OH on each CHCH2 |
| 222 | C6H5-S-CH2CHCH2-S-(CH2)2S(CH2)2-S-CH2CHCH2-S-C6H5, with OH on each CHCH2 |
| 223 | C6H5-S-CH2CHCH2-OCH2-(trans-cyclohexyl)-CH2O-CH2CHCH2-S-C6H5, with OH on each CHCH2 |
| 224 | C6H5-S-CH2CHCH2-S-CH2-(1,3-dithiolane-2-yl)-CH2-S-CH2CHCH2-S-C6H5, with OH on each CHCH2 |
| 225 | (1,3-dithiolan-2-yl)-CH2O-CH2CHCH2-S-CH2-(1,3-dithiolan-2-yl)-CH2-S-CH2CHCH2-OCH2-(1,3-dithiolan-2-yl), with OH on each CHCH2 |
| 226 | (1,3-dithiolan-2-yl)-CH2S-CH2CHCH2-S-CH2-(1,3-dithiolan-2-yl)-CH2-SCH2-CH2CHCH2-SCH2-(1,3-dithiolan-2-yl), with OH on each CHCH2 |
| 227 | (1,3-dithiolan-2-yl)-(CH2)2S-CH2CHCH2-S-CH2-(1,3-dithiolan-2-yl)-CH2-S(CH2)2-CH2CHCH2-S(CH2)2-(1,3-dithiolan-2-yl), with OH on each CHCH2 |

TABLE 2-continued

| No. of exemplified compounds | Structure |
|---|---|
| 228 | (structure) |
| 229 | (structure) |
| 230 | (structure) |
| 231 | (structure) |
| 232 | (structure) |
| 233 | (structure) |
| 234 | (structure) |

TABLE 2-continued

| No. of exemplified compounds | Structure |
|---|---|
| 235 | (structure) |
| 236 | (structure) |
| 237 | (structure) |
| 238 | (structure) |
| 239 | (structure) |
| 240 | (structure) |
| 241 | (structure) |
| 242 | (structure) |

TABLE 2-continued

| No. of exemplified compounds | Structure |
|---|---|
| 243 | 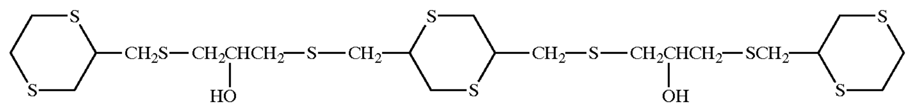 |
| 244 | 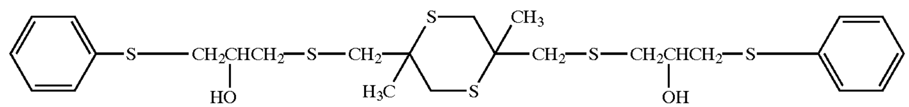 |
| 245 | 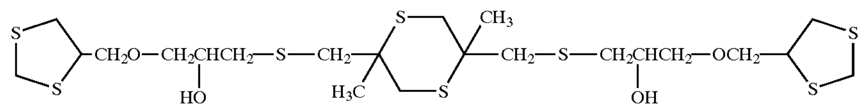 |
| 246 | 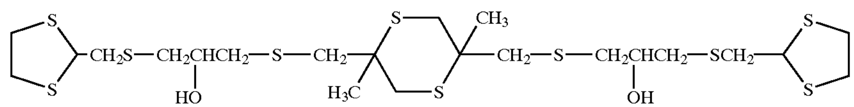 |
| 247 | 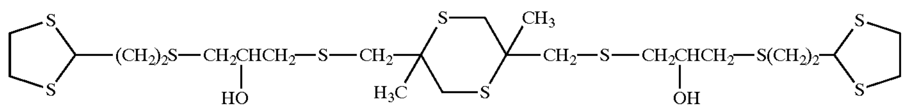 |
| 248 | 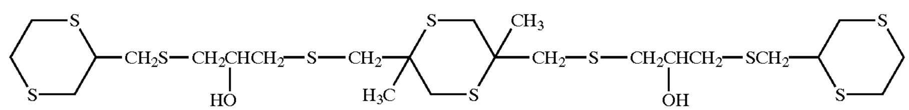 |
| 249 | 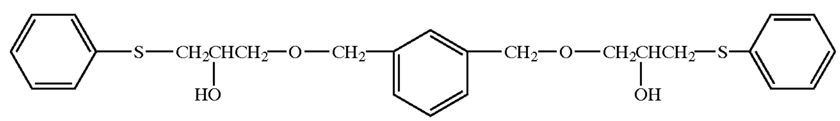 |
| 250 | 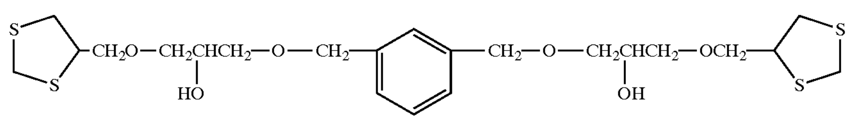 |

TABLE 2-continued

| No. of exemplified compounds | Structure |
|---|---|
| 251 | (1,3-dithiolan-2-yl)-CH₂S-CH₂CH(OH)CH₂-O-CH₂-(1,3-phenylene)-CH₂-O-CH₂CH(OH)CH₂-SCH₂-(1,3-dithiolan-2-yl) |
| 252 | (1,3-dithiolan-2-yl)-CH₂S-CH₂CH(OH)CH₂-O-CH₂-(1,3-phenylene)-CH₂-O-CH₂CH(OH)CH₂-S(CH₃)₂-... |
| 253 | (1,3-dithian-2-yl)-CH₂S-CH₂CH(OH)CH₂-O-CH₂-(1,3-phenylene)-CH₂-O-CH₂CH(OH)CH₂-SCH₂-(1,3-dithian-2-yl) |
| 254 | Ph-S-CH₂CH(OH)CH₂-O-CH₂-(1,4-phenylene)-CH₂-O-CH₂CH(OH)CH₂-S-Ph |
| 255 | (1,3-dithiolan-4-yl)-CH₂O-CH₂CH(OH)CH₂-O-CH₂-(1,4-phenylene)-CH₂-O-CH₂CH(OH)CH₂-OCH₂-(1,3-dithiolan-4-yl) |
| 256 | (1,3-dithiolan-2-yl)-CH₂S-CH₂CH(OH)CH₂-O-CH₂-(1,4-phenylene)-CH₂-O-CH₂CH(OH)CH₂-SCH₂-(1,3-dithiolan-2-yl) |
| 257 | (1,3-dithiolan-2-yl)-(CH₂)₂S-CH₂CH(OH)CH₂-O-CH₂-(1,4-phenylene)-CH₂-O-CH₂CH(OH)CH₂-S(CH₂)₂-(1,3-dithiolan-2-yl) |
| 258 | (1,3-dithian-2-yl)-CH₂S-CH₂CH(OH)CH₂-O-CH₂-(1,4-phenylene)-CH₂-O-CH₂CH(OH)CH₂-SCH₂-(1,3-dithian-2-yl) |

TABLE 2-continued

| No. of exemplified compounds | Structure |
|---|---|
| 259 | (structure) |
| 260 | (structure) |
| 261 | (structure) |
| 262 | (structure) |
| 263 | (structure) |
| 264 | (structure) |
| 265 | (structure) |
| 266 | (structure) |

TABLE 2-continued

| No. of exemplified compounds | Structure |
|---|---|
| 267 | 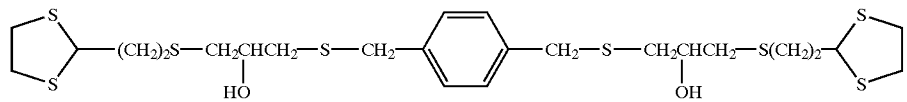 |
| 268 | 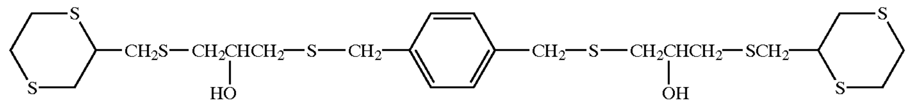 |
| 269 | 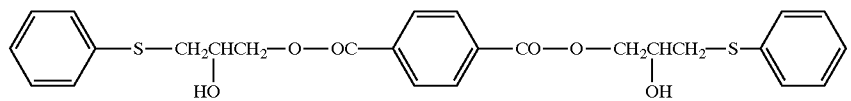 |
| 270 | 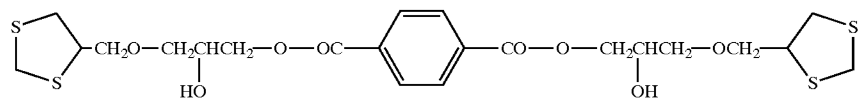 |
| 271 | 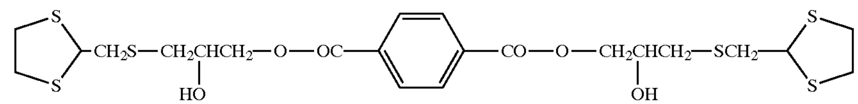 |
| 272 | 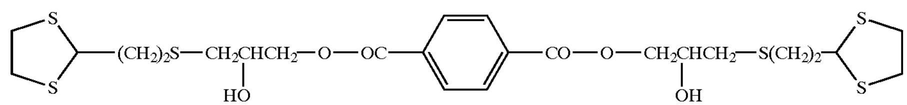 |
| 273 | 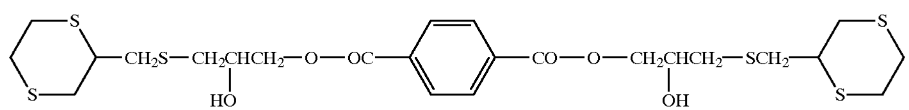 |
| 274 | 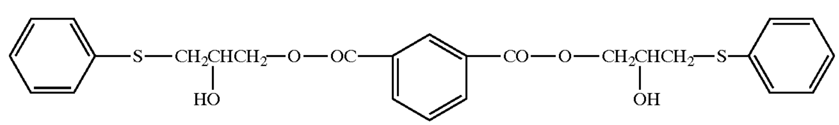 |

TABLE 2-continued

| No. of exemplified compounds | Structure |
| --- | --- |
| 275 | 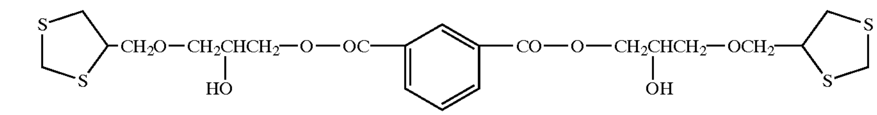 |
| 276 | 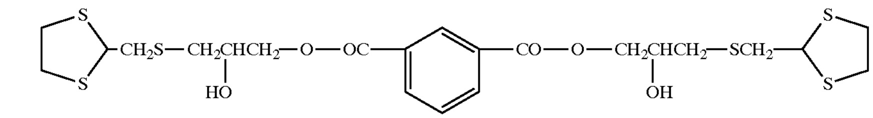 |
| 277 | 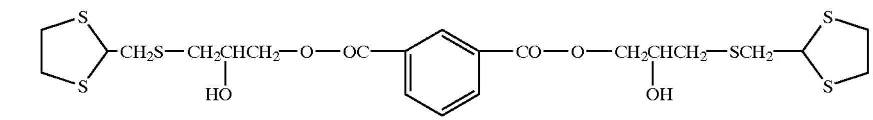 |
| 278 | 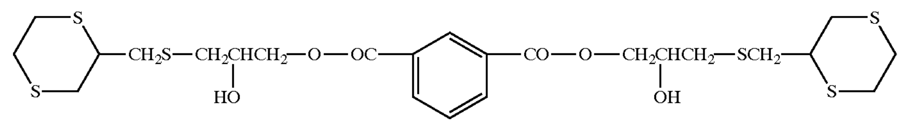 |
| 279 | 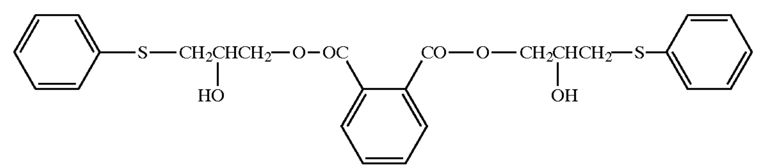 |
| 280 | 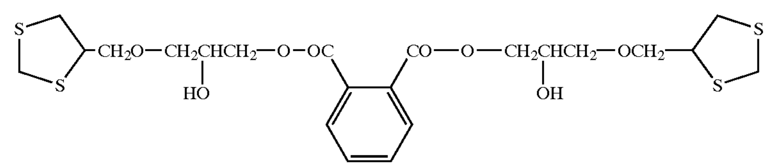 |
| 281 | 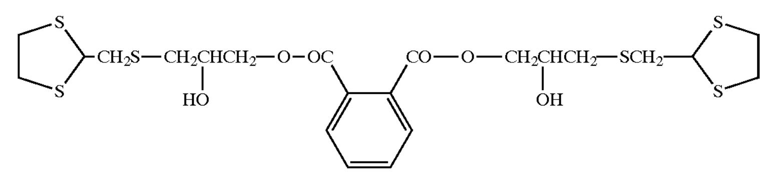 |

TABLE 2-continued

| No. of exemplified compounds | Structure |
|---|---|
| 282 | 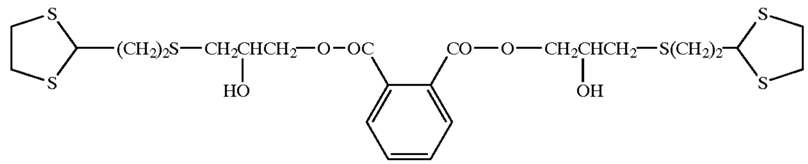 |
| 283 | 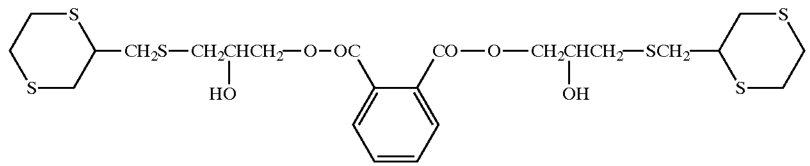 |
| 284 | 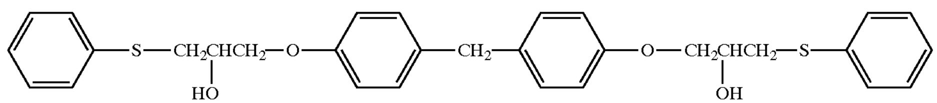 |
| 285 | 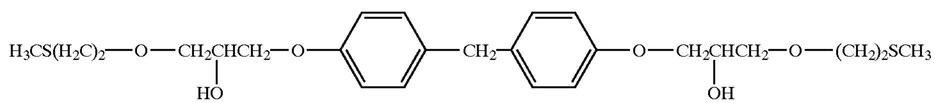 |
| 286 | 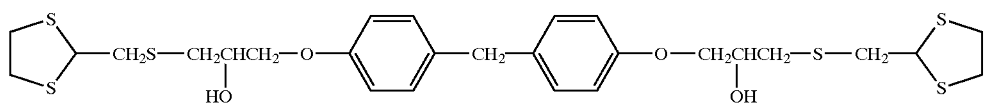 |
| 287 | 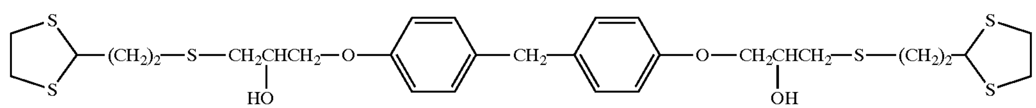 |
| 288 | 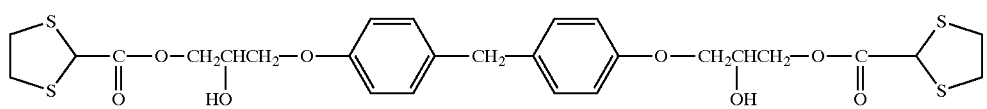 |

TABLE 2-continued

| No. of exemplified compounds | Structure |
|---|---|
| 289 | 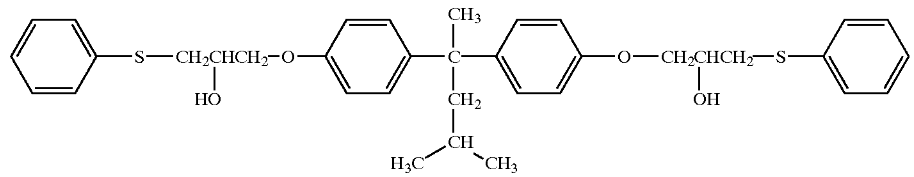 |
| 290 | 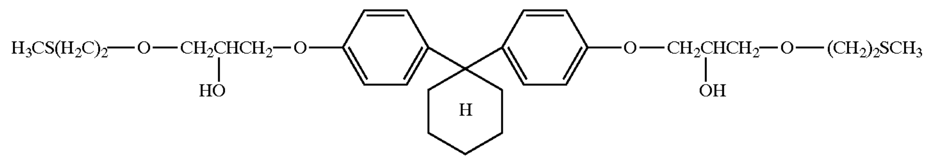 |
| 291 | 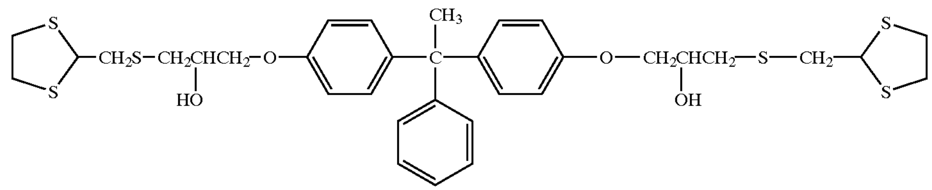 |
| 292 | 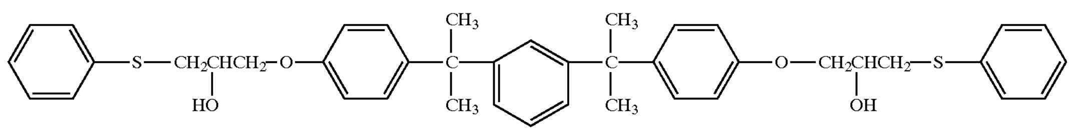 |
| 293 | 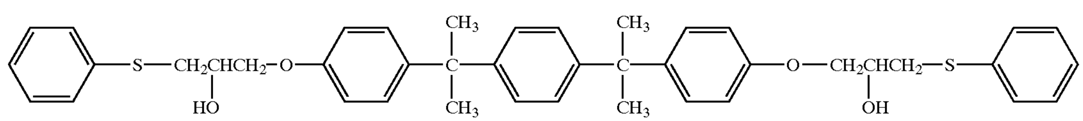 |
| 294 | 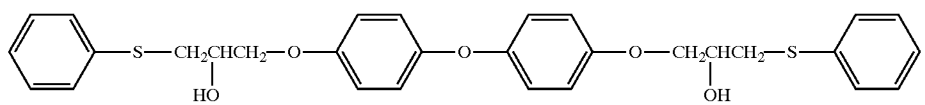 |

TABLE 2-continued

| No. of exemplified compounds | Structure |
|---|---|
| 295 | (structure) |
| 296 | (structure) |
| 297 | (structure) |
| 298 | (structure) |
| 299 | (structure) |
| 300 | (structure) |
| 301 | (structure) |
| 302 | (structure) |
| 303 | (structure) |

TABLE 2-continued

| No. of exemplified compounds | Structure |
|---|---|
| 304 | (structure) |
| 305 | (structure) |
| 306 | (structure) |
| 307 | (structure) |
| 308 | (structure) |
| 309 | (structure) |
| 310 | (structure) |

TABLE 2-continued

| No. of exemplified compounds | Structure |
|---|---|
| 311 | 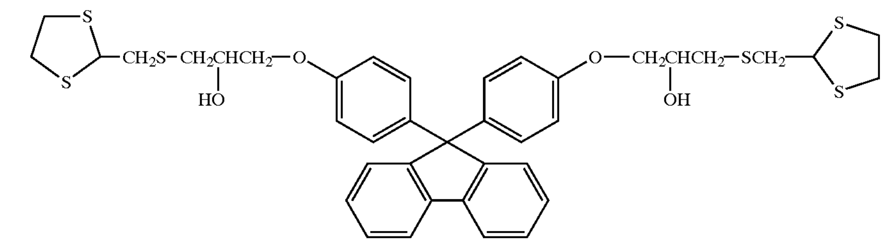 |
| 312 | 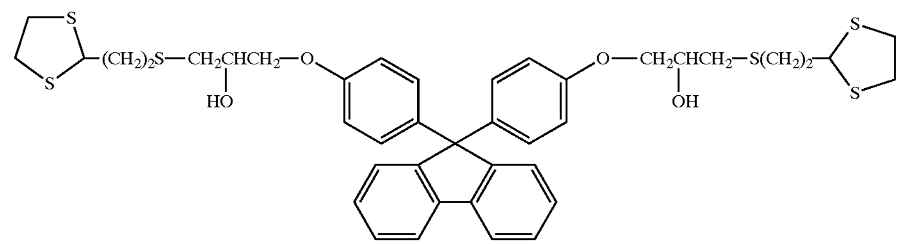 |
| 313 | 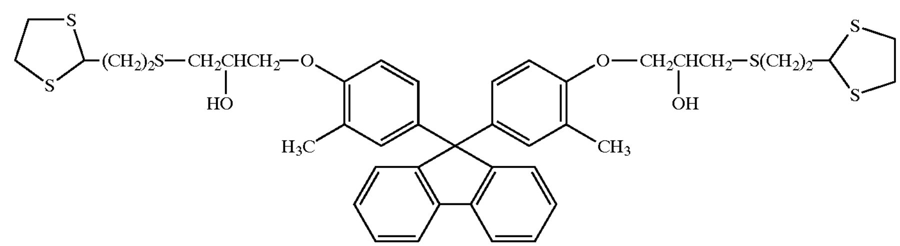 |
| 314 | 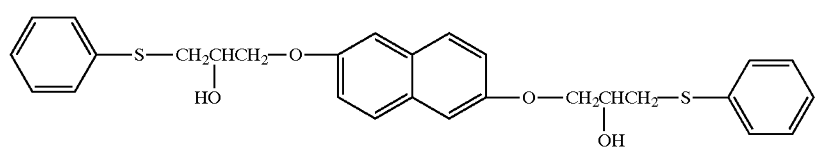 |

TABLE 2-continued

| No. of exemplified compounds | Structure |
|---|---|
| 315 | (structure) |
| 316 | (structure) |
| 317 | (structure) |
| 318 | (structure) |
| 319 | (structure) |
| 320 | (structure) |

TABLE 2-continued

| No. of exemplified compounds | Structure |
|---|---|
| 321 | 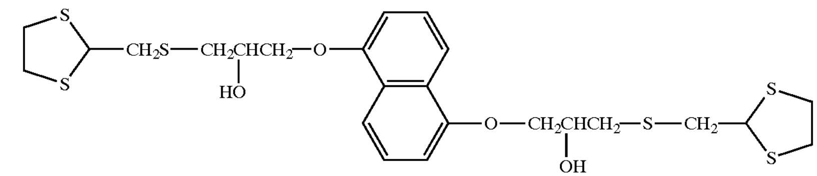 |
| 322 | 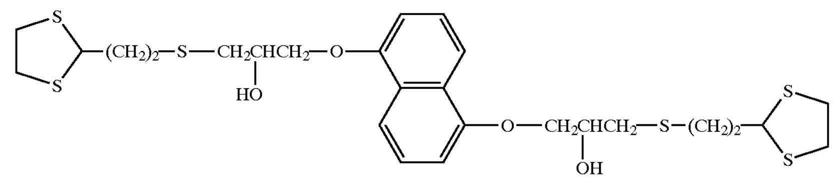 |
| 323 | 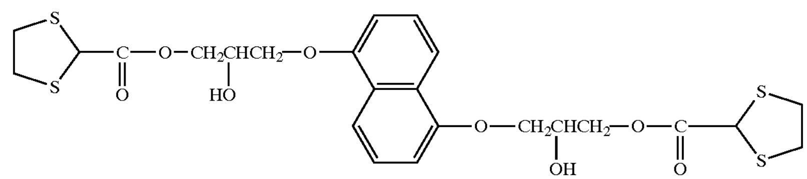 |
| 324 | 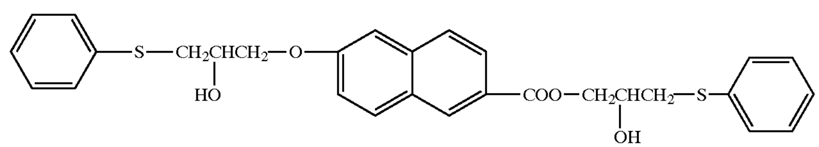 |
| 325 | 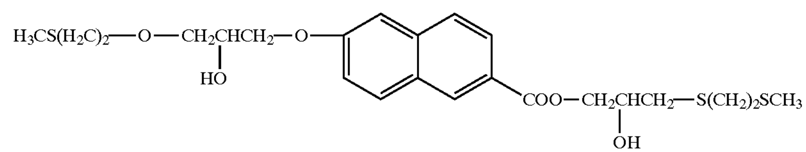 |

TABLE 2-continued
| No. of exemplified compounds | Structure |
|---|---|
| 326 | 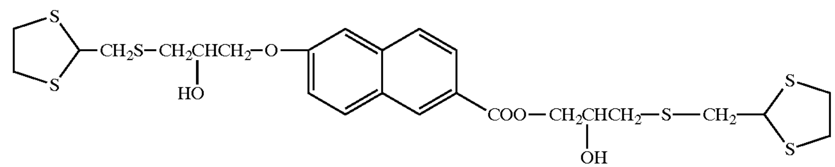 |
| 327 | 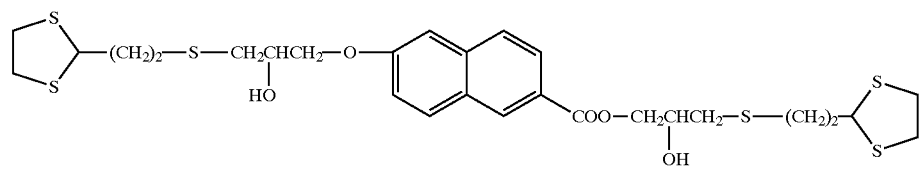 |
| 328 | 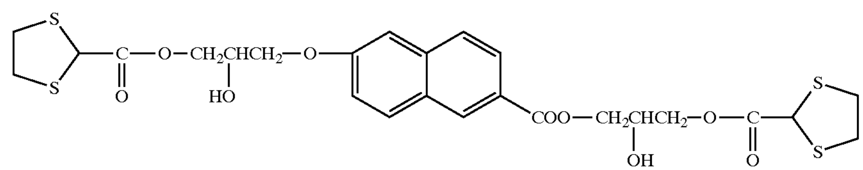 |
| 329 | 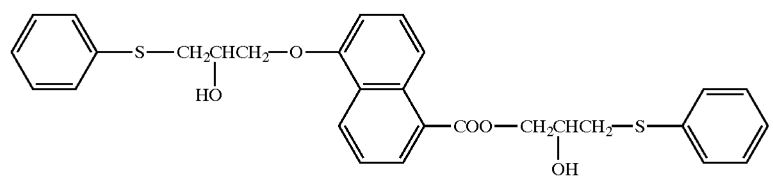 |
| 330 | 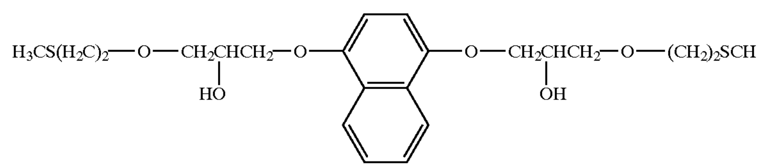 |

TABLE 2-continued

| No. of exemplified compounds | Structure |
|---|---|
| 331 | (structure) |
| 332 | (structure) |
| 333 | (structure) |

There will be described a process for preparing a sulfur-containing dihydroxy compound represented by general formula (2) in Scheme (A).

A sulfur-containing dihydroxy compound represented by general formula (2) of this invention may be suitably prepared by reacting a diepoxy compound represented by general formula (10) with a sulfur-containing compound $R_{13}$—H (specifically a sulfur-containing compound represented by formula (7) or (8), etc.) which is added to the epoxy group via ring opening. The reaction process itself is well known and conducted under conventional reaction conditions. For example, the reaction is suitably conducted in the presence of an appropriate catalyst such as acid or base catalyst, if necessary;

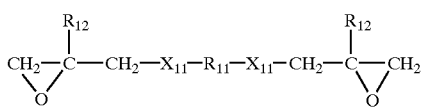

(10)

wherein $R_{11}$, $R_{12}$ and $X_{11}$ are as defined above;

 (7)

wherein $R_{71}$ is a monovalent organic group comprising at least one sulfur atom;

 (8)

wherein $R_{81}$ is a monovalent organic group optionally comprising a sulfur atom.

In this reaction, the amount of the sulfur-containing compound which is to be reacted with the diepoxy compound represented by general formula (10) is, but not limited to, per one mole of the diepoxy compound represented by general formula (10), generally 0.1 to 10 moles (0.05 to 5 epoxy equivalents), preferably 0.5 to 5 moles (0.25 to 2.5 epoxy equivalents), more preferably 0.8 to 3 moles (0.4 to 1.5 epoxy equivalents).

The reaction may be conducted neat or in a solvent inert to the reaction. Solvents which may be used include hydrocarbons such as n-hexane, benzene and toluene; ketones such as acetone, methyl ethyl ketone and methyl isobutyl ketone; esters such as ethyl acetate and butyl acetate; ethers such as diethylether, tetrahydrofuran and dioxane; halogenated solvents such as dichloromethane, chloroform, carbon tetrachloride, 1,2-dichloroethane and perchlene; and polar solvents such as acetonitrile, N,N-dimethylformamide, N,N-dimethylacetamide and N,N-dimethylimidazolidinone. These solvents may be used in combination of two or more.

A reaction temperature is generally, but not limited to, 0 to 200° C., preferably 0 to 100° C.

A reaction time depends on various conditions such as a reaction temperature, but generally several minutes to several ten hours.

A sulfur-containing compound represented by formula (9) of this invention is a novel halogenated, hydroxy or thiol compound characterized in that it has an intramolecular cyclic thioacetal structure:

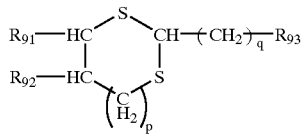

(9)

wherein $R_{91}$ and $R_{92}$ independently represent hydrogen or alkyl or $R_{91}$ and $R_{92}$ may be linked together to form a ring; $R_{93}$ represents halogen, hydroxyl or thiol; p represents an integer of 0 to 3; and q represents an integer of 1 to 4.

In formula (9), $R_{91}$ and $R_{92}$ independently represent hydrogen or alkyl or $R_{91}$ and $R_{92}$ may be linked together to form a ring.

The substituents $R_{91}$ and $R_{92}$ are preferably hydrogen or $C_1$–$C_4$ alkyl; more preferably hydrogen, methyl or ethyl. A ring formed by linking $R_{91}$ and $R_{92}$ together is preferably a cycloalkane ring, more preferably $C_5$–$C_7$ cycloalkane ring, more preferably cyclohexane.

In formula (9), p is an integer of 0 to 3, preferably 0 to 2, more preferably 0 or 1.

In formula (9), q is an integer of 1 to 4, preferably 1 to 3, more preferably 1 or 2.

In formula (9), $R_{93}$ represents halogen, hydroxyl or thiol; preferably, halogen or thiol; more preferably thiol. When $R_{93}$ represents hydroxyl or thiol, formula (9) is a subgroup of formula (7) or (8).

Specific examples of a sulfur-containing compound represented by formula (9) of this invention are listed in Table 3 below.

TABLE 3

| Compound No. | Structure |
|---|---|
| 9-1 | ![structure] |
| 9-2 | ![structure] |
| 9-3 | ![structure] |
| 9-4 | ![structure] |
| 9-5 | ![structure] |
| 9-6 | ![structure] |

TABLE 3-continued

| Compound No. | Structure |
|---|---|
| 9-7 | n-C₄H₉-[1,3-dithiolane]-(CH₂)₂-Br |
| 9-8 | 4,5-di(H₃C)-[1,3-dithiolane]-2-(CH₂)₂-Br |
| 9-9 | cyclohexane-fused [1,3-dithiolane]-(CH₂)₂-Br |
| 9-10 | [1,3-dithiane]-2-CH₂-Br |
| 9-11 | [1,3-dithiane]-2-(CH₂)₂-Br |
| 9-12 | [1,3-dithiane]-2-(CH₂)₃-Br |
| 9-13 | [1,3-dithiane]-2-(CH₂)₄-Br |
| 9-14 | [1,3-dithiepane]-2-(CH₂)₂-Br |
| 9-15 | [1,3-dithiolane]-2-(CH₂)₂-Cl |
| 9-16 | [1,3-dithiane]-2-(CH₂)₂-Cl |
| 9-17 | [1,3-dithiolane]-2-CH₂-SH |
| 9-18 | [1,3-dithiolane]-2-(CH₂)₂-SH |
| 9-19 | [1,3-dithiolane]-2-(CH₂)₃-SH |
| 9-20 | [1,3-dithiolane]-2-(CH₂)₄-SH |

TABLE 3-continued

| Compound No. | Structure |
|---|---|
| 9-21 | H₃C-[1,3-dithiolane]-2-(CH₂)₂-SH |
| 9-22 | C₂H₅-[1,3-dithiolane]-2-(CH₂)₂-SH |
| 9-23 | n-C₄H₉-[1,3-dithiolane]-2-(CH₂)₂-SH |
| 9-24 | 4,5-di(H₃C)-[1,3-dithiolane]-2-(CH₂)₂-SH |
| 9-25 | cyclohexane-fused [1,3-dithiolane]-(CH₂)₂-SH |
| 9-26 | [1,3-dithiane]-2-CH₂-SH |
| 9-27 | [1,3-dithiane]-2-(CH₂)₂-SH |
| 9-28 | [1,3-dithiane]-2-(CH₂)₃-SH |
| 9-29 | [1,3-dithiane]-2-(CH₂)₄-SH |
| 9-30 | [1,3-dithiepane]-2-(CH₂)₂-SH |
| 9-31 | [1,3-dithiolane]-2-CH₂-OH |
| 9-32 | [1,3-dithiolane]-2-(CH₂)₂-OH |
| 9-33 | [1,3-dithiolane]-2-(CH₂)₃-OH |

TABLE 3-continued

| Compound No. | Structure |
|---|---|
| 9-34 | ![structure] 1,3-dithiolane-(CH₂)₄-OH |
| 9-35 | H₃C-substituted 1,3-dithiolane-(CH₂)₂-OH |
| 9-36 | C₂H₅-substituted 1,3-dithiolane-(CH₂)₂-OH |
| 9-37 | n-C₄H₉-substituted 1,3-dithiolane-(CH₂)₂-OH |
| 9-38 | (H₃C)₂-substituted 1,3-dithiolane-(CH₂)₂-OH |
| 9-39 | cyclohexane-fused 1,3-dithiolane-(CH₂)₂-OH |
| 9-40 | 1,3-dithiane-CH₂-OH |
| 9-41 | 1,3-dithiane-(CH₂)₂-OH |
| 9-42 | 1,3-dithiane-(CH₂)₃-OH |
| 9-43 | 1,3-dithiane-(CH₂)₄-OH |
| 9-44 | 1,3-dithiepane-(CH₂)₂-OH |

A sulfur-containing compound represented by formula (9) of this invention in which $R_{93}$ is halogen can be suitably prepared typically by reacting an aldehyde represented by formula (11) or its acetal derivative with a dithiol represented by formula (12) in the presence of an acid catalyst.

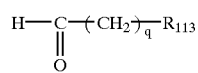

(11)

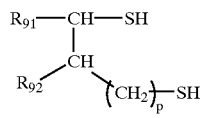

(12)

wherein $R_{91}$, $R_{92}$, p and q are as defined above, and $R_{113}$ represents halogen.

A sulfur-containing compound represented by formula (9) of this invention in which $R_{93}$ is hydroxyl or thiol can be suitably prepared typically by converting a circular thioacetal represented by formula (9) in which $R_{93}$ is halogen using a known synthetic chemistry such as alkaline hydrolysis of halogen into hydroxyl, or by reacting the halogen with a thiourea to form a thiuronium salt, which is then treated with an alkali to be converted into thiol.

There will be described in detail a process for preparing a sulfur-containing compound represented by formula (9) of this invention in which $R_{93}$ is halogen, by reacting an aldehyde represented by formula (11) or its acetal derivative with a dithiol represented by formula (12) in the presence of an acid catalyst.

Examples of an aldehyde represented by formula (11) or its acetal derivative include haloalkylaldehydes such as chloroacetaldehyde, 3-chloropropionaldehyde and 3-bromopropionaldehyde; and dialkylacetal or circular alkyleneacetal derivatives such as 2-chloroacetaldehyde dimethylacetal, 2-chloroacetaldehyde diethylacetal, 2-chloropropionaldehyde dimethylacetal, 2-chloropropionaldehyde diethylacetal, 2-bromopropionaldehyde dimethylacetal, 2-bromopropionaldehyde diethylacetal, 2-bromopropionaldehyde ethyleneacetal [or 2-(2'-bromoethyl)-1,3-dioxolane] and 2-bromopropionaldehyde trimethyleneacetal [or 2-(2'-bromoethyl)-1,3-dioxane].

Examples of a dithiol derivative represented by formula (12) include straight alkanedithiols such as ethanedithiol, 1,2-propanedithiol, 1,3-propanedithiol, 1,2-butanedithiol, 1,3-butanedithiol, 1,4-butanedithiol, 1,2-pentanedithiol, 1,3-pentanedithiol, 1,4-pentanedithiol, 1,2-hexanedithiol, 1,3-hexanedithiol, 1,4-hexanedithiol, 1,2-heptanedithiol, 1,2-octanedithiol, 1,2-nonanedithiol, 1,2-decanedithiol; and cycloalkanedithiols such as cyclopentane-1,2-dithiol and cyclohexane-1,2-dithiol.

In preparation of a compound represented by formula (9) of this invention where $R_{93}$ is halogen by reacting an aldehyde represented by formula (11) or its acetal derivative with a dithiol represented by formula (12), the amount of the dithiol is generally, but not limited to, 0.5 to 5 moles, preferably 0.8 to 2 moles, more preferably 0.9 to 1.2 moles per one mole of the aldehyde represented by formula (11) or its acetal derivative.

The reaction may be conducted in the absence or presence of a catalyst such as a protic acid including mineral acids (e.g., hydrochloric acid and sulfuric acid) and organic acids (e.g., acetic acid and propionic acid), and a Lewis acid. In the light of a reaction temperature and a reaction time, it is preferable to conduct the reaction in the presence of a catalyst for accelerating the reaction.

Examples of a reaction catalyst include protic acids such as sulfuric acid, hydrochloric acid, hydrobromic acid, nitric acid, methanesulfonic acid, trifluoromethanesulfonic In acid and p-toluenesulfonic acid; and Lewis acids such as titanium trichloride, titanium tetrachloride, tin dichloride, tin tetrachloride and boron trifluoride-etherate complex.

The amount of the reaction catalyst is generally, but not limited to, 0.001 to 20 moles, preferably 0.01 to 10 moles, more preferably 0.1 to 5 moles per one mole of the aldehyde represented by formula (11) or its acetal derivative.

These reaction catalysts may be used alone or in combination of two or more.

The reaction may be conducted neat or in the presence of a solvent. Examples of a solvent, if used, include hydrocarbons such as benzene, toluene and xylenes; halogenated solvents such as dichloromethane, chloroform, 1,2-dichloroethane, chlorobenzene and dichlorobenzene; and ethers such as diethylether, tetrahydrofuran, dioxane and diethyleneglycol dimethyl ether. These solvents may be used alone or in combination of two or more.

There are no restrictions for the amount of the solvent, but an extremely excessive amount of solvent is not preferable because of, for example, a manufacturing efficiency. It is generally 300-fold by weight or less, preferably 100-fold by weight or less, per the weight of the aldehyde represented by formula (11) or its acetal derivative.

The reaction may be conducted either under an ambient atmosphere or under an inert gas atmosphere. It is preferably conducted under an inert gas atmosphere such as nitrogen and argon for preventing, for example, coloring of a reaction product.

A reaction temperature is preferably, but not limited to, 0° C. to a boiling point of a solvent used.

A reaction time depends on a reaction temperature, but may be generally several minutes to several ten hours. A reaction end-point may be determined by tracing the reaction by a known analytical method such as liquid chromatography, thin layer chromatography and IR.

The substituent $R_{93}$, i.e., halogen, in the compound represented by formula (9) prepared as described above can be suitably converted into thiol by an appropriate known process such as those described in Journal of Organic Chemistry, Vol. 27, pp. 93–95 (1962); and Organic Synthesis, IV, pp. 401–403 (1963). Specifically, in a typical process, a compound represented by formula (9) in which $R_{93}$ is halogen is suitably reacted with thiourea, and a product is then hydrolyzed using an alkali such as aqueous ammonia and sodium hydroxide to give a compound represented by formula (9) in which $R_{93}$ is thiol.

The substituent $R_{93}$, i.e., halogen, in the compound represented by formula (9) prepared as described above can be suitably converted into hydroxyl by an appropriate known process such as those described in Jikken Kagaku Koza, 4th ed., Vol. 20, pp. 49–51 (edited by Japan Chemistry Association) and Synthesis, p. 763 (1986). Specifically, in a typical process, a compound represented by formula (9) in which $R_{93}$ is halogen is suitably hydrolyzed using an alkali such as sodium hydroxide to give a compound represented by formula (9) in which $R_{93}$ is hydroxyl.

A sulfur-containing compound represented by formula (9) of this invention can be isolated, after completion of the above reaction, from a reaction mixture by a usual work-up procedure such as neutralization, filtration, solvent extraction, washing with water, phase separation and evaporation. It can be, as necessary, purified by a known treatment or purification process such as distillation, recrystallization, column chromatography and charcoal treatment.

There will be described a process for preparing a sulfur-containing unsaturated carboxylate, especially a sulfur-containing (meth)acrylate using a sulfur-containing dihydroxy compound represented by general formula (2) as a starting material.

As described above, a sulfur-containing dihydroxy compound represented by general formula (2) can be converted into a sulfur-containing unsaturated carboxylate typically by (a) its reaction with (meth)acrylic acid, its ester or its acid halide and then esterification by dehydration, transesterification or dehydrohalogenation; or (b) its reaction with a chloropropionic acid such as chloropropionic acid, its ester and its acid halide to form a chloropropionate, which is then dehydrohalogenation to give a (meth)acrylate.

There will be further described, as the most typical process of the above processes, reaction of a sulfur-containing dihydroxy compound represented by general formula (2) with (meth)acrylic acid, its ester or its acid halide.

Specifically, the reaction can be conducted by an appropriate known process such as those described in J. Org. Chem., 4, 5364 (1980) and Eur. Polym. J., 19, 399 (1983). For example, (a) to a sulfur-containing dihydroxy compound represented by general formula (2) is reacted with (meth)acrylic acid halide (e.g., by adding dropwise) with stirring in the presence of a base; (b) a sulfur-containing dihydroxy compound represented by general formula (2) and (meth)acrylic acid are condensed with dehydration in the presence of a catalyst; or (c) in the presence of a catalyst such as an acid or base catalyst, a sulfur-containing dihydroxy compound is subject to transesterification with a (meth)acrylate derivative [e.g., an alkyl(meth)acrylate such as methyl (meth)acrylate and ethyl(meth)acrylate].

The amount of a (meth)acrylic compound [e.g., (meth) acrylic acid, its ester or its acid halide] to a sulfur-containing dihydroxy compound represented by general formula (2) is generally, but not limited to, per one mole of the dihydroxy compound, 0.1 to 10 moles (0.05 to 5 equivalents per one hydroxyl group), preferably 0.5 to 5 moles (0.25 to 2.5 equivalents per one hydroxyl group), more preferably 0.8 to 3 moles (0.4 to 1.5 equivalents per one hydroxyl group).

The reaction may be conducted neat or in a solvent inert to the reaction. Solvents which may be used include hydrocarbons such as n-hexane, benzene and toluene; ketones such as acetone, methyl ethyl ketone and methyl isobutyl ketone; esters such as ethyl acetate and butyl acetate; ethers such as diethylether, tetrahydrofuran and dioxane; halogenated solvents such as dichloromethane, chloroform, carbon tetrachloride, 1,2-dichloroethane and perchlene; and polar solvents such as acetonitrile, N,N-dimethylformamide, N,N-dimethylacetamide and N,N-dimethylimidazolidinone. These solvents may be used in combination of two or more.

A reaction temperature is, but not limited to, a temperature at which the raw material, the (meth)acrylic compound and a reaction product, a (meth)acrylate are not polymerized; generally −78 to 150° C., preferably −20 to 120° C., more preferably 0 to 100° C.

A reaction time depends on a reaction temperature, but may be generally several minutes to 100 hours, preferably 30 minutes to 50 hours, more preferably 1 to 20 hours. The reaction may be terminated in an appropriate conversion while checking a conversion by a known analytical method such as liquid chromatography, thin layer chromatography and IR.

In the reaction of a sulfur-containing dihydroxy compound represented by general formula (2) with (meth)acrylic acid halide, a hydrogen halide such as hydrogen chloride may be formed as a byproduct. A base can be, therefore, used as a dehydrohalogenation agent, including organic bases such as triethylamine, pyridine, picoline, dimethylaniline, diethylaniline, 1,4-diazabicyclo[2.2.2]octane (DABCO), 1,8-diazabicyclo[5.4.0]undec-7-ene (DBU) and inorganic bases such as sodium bicarbonate, sodium carbonate, potassium carbonate, lithium carbonate, sodium hydroxide, potassium hydroxide, calcium hydroxide and magnesium oxide.

The amount of such a dehydrohalogenation agent is generally, but not limited to, 0.1 to 10 moles, preferably 0.5 to 5 moles, more preferably 0.8 to 3 moles per one mole of the sulfur-containing dihydroxy compound represented by general formula (2).

In preparation of a sulfur-containing (meth) acrylate represented by general formula (1) of this invention by condensation with dehydration of a sulfur-containing dihydroxy compound represented by general formula (2) and (meth) acrylic acid, it is preferable to use a known esterification catalyst. Examples of such a catalyst include mineral acids such as hydrochloric acid, sulfuric acid, nitric acid, boric acid and phosphoric acid; organic acids such as methanesulfonic acid, benzenesulfonic acid, p-toluenesulfonic acid and trifluoromethanesulfonic acid; and Lewis acids such as boron trifluoride, aluminum trichloride, titanium tetrachloride, titanium dichloride, tin dichloride and tin tetrachloride.

The amount of the reaction catalyst is preferably, but not limited to, 0.001 to 50 wt %, preferably 0.01 to 30 wt % to the amount of reactants.

It is preferable to remove byproduced water outside the system for accelerating the reaction. It can be accomplished by azeotropic dehydration using a solvent among the above solvents which can be co-evaporated with water; using a dehydrating agent such as molecular sieves; or a combination thereof.

In the above process, an appropriate procedure, for example, as described in JP-A 10-67736 can be employed for reacting a sulfur-containing dihydroxy compound represented by general formula (2) with a halopropionic acid or its acid halide to form a halopropionate, which is then dehydrohalogenated to give a sulfur-containing (meth) acrylate represented by general formula (1).

An unsaturated carboxylate (e.g., crotonate, tiglate, 3,3-dimethylacrylate, maleate, citraconate, 2,3-dimethylmaleate, itaconate or cinnamate) represented by general formula (1) of this invention other than a sulfur-containing (meth)acrylate may be suitably prepared as described in the above process for a (meth)acrylate compound, except using, as a reactant, another unsaturated carboxylic acid such as a crotonic acid compound such as crotonic acid, its ester and its anhydride; a tiglic acid compound such as tiglic acid, its ester and its anhydride; a 3,3-dimethylacrylic acid compound such as 3,3-dimethylacrylic acid, its ester and its anhydride; a maleic acid compound such as maleic acid, its ester and its anhydride; a citraconic acid compound such as citraconic acid, its ester and its anhydride; a 2,3-dimethylmaleic acid compound such as 2,3-dimethylmaleic acid, its ester and its anhydride; an itaconic acid compound such as itaconic acid, its ester and its anhydride; and a cinnamic acid compound such as itaconic acid, its ester, its anhydride and its acid halide, instead of a (meth)acrylic acid compound.

In preparation of a sulfur-containing unsaturated carboxylate compound represented by general formula (1), it is preferable to use a polymerization inhibitor for preventing a product from being polymerized during or after the reaction. Examples of such an inhibitor include various known compounds such as 4-methoxyphenol, hydroquinone and phenothiazine.

The amount of the polymerization inhibitor is generally, but not limited to, 0.01 to 5 wt %, preferably 0.05 to 3 wt % to the amount of a reaction mixture or product in a reaction system.

A sulfur-containing unsaturated carboxylate compound represented by general formula (1) of this invention as a product can be isolated, after completion of the reaction, by a usual treatment or work-up procedure such as neutralization, solvent extraction, washing with water, phase separation and evaporation. The sulfur-containing unsaturated carboxylate compound represented by general formula (1) thus obtained can be also, as necessary, separated and purified by a known process such as distillation, recrystallization and chromatography, to be isolated as a highly pure compound.

When preparing a polymerizable composition, a cured product formed by polymerization of the polymerizable composition or an optical component of this invention, using a sulfur-containing unsaturated carboxylate compound represented by general formula (1) of this invention, the mixture as such may be used without separation or purification.

There will be detailed a polymerizable composition comprising a sulfur-containing unsaturated carboxylate compound represented by general formula (1) of this invention.

A polymerizable composition of this invention comprises a sulfur-containing unsaturated carboxylate compound represented by general formula (1) of this invention and photo- and/or thermal-polymerization initiators, as essential components. The sulfur-containing unsaturated carboxylate compound can be used alone or a plurality of different sulfur-containing unsaturated carboxylates compound can be combined.

A polymerizable composition of this invention may, as necessary, comprise a known polymerizable compound such as a photo- or thermal polymerizable monomer or oligomer, in addition to a sulfur-containing unsaturated carboxylate compound represented by general formula (1), as long as it does not affect desired effects of this invention.

The amount of a sulfur-containing unsaturated carboxylate compound represented by general formula (1) in the above polymerizable composition is generally, but not limited to, at least 10 wt %, preferably at least 20 wt %, more preferably at least 30 wt %, more preferably at least 50 wt % to the overall weight of the polymerizable composition.

There are no restrictions for a polymerization initiator used in a polymerizable composition of this invention, and a variety of known thermal- or photo-initiators may be used.

Photoinitiators includes benzoin, benzil, benzoin methyl ether, benzoin isopropyl ether, acetophenone, 1,1-dimethoxy-1-phenylaceto-phenone, 1,1-dichloroacetophenone, 1-hydroxycyclohexyl phenyl ketone, 2-hydroxy-2-methyl-1-phenylpropan-1-one, 2-methyl-1-(4-methylthiophenyl)-2-morpholinolpropan-1-one, N,N-dimethylaminoacetophenone, 2-methylanthraquinone, 2-ethylanthraquinone, 2-tert-butylanthraquinone, 1-chloroanthraquinone, 2-amylanthraquinone, 2-isopropylthioxanthone, 2,4-dimethylthioxanthone, 2,4-diethylthioxanthone, 2,4-diisopropylthioxanthone, acetophenone dimethyl ketal, benzophenone, 4-methylbenzophenone, 4,4'-dichlorobenzophenone, 4,4'-bisdiethylaminobenzophenone and Mihira's ketone. These may be used alone or in combination of two or more.

The amount of a photoinitiator is 0.001 to 50 parts by weight, preferably 0.01 to 30 parts by weight, more preferably 0.1 to 10 parts by weight, more preferably 0.2 to 5 parts by weight, to 100 parts by weight of a sulfur-containing unsaturated carboxylate compound represented by general formula (1).

Thermal initiators include peroxides such as benzoyl peroxide, p-chlorobenzoyl peroxide, diisopropyl peroxycarbonate, di-2-ethylhexyl peroxycarbonate and tert-butyl peroxypivalate; and azo compounds such as azobisisobutyronitrile.

The amount of a thermal initiator is generally 0.001 to 50 parts by weight, preferably 0.01 to 30 parts by weight, more preferably 0.1 to 10 parts by weight, more preferably 0.2 to 5 parts by weight, to 100 parts by weight of a sulfur-containing unsaturated carboxylate compound represented by general formula (1).

Known polymerizable compounds other than a sulfur-containing unsaturated carboxylate compound represented by general formula (1) which may be used as a polymerizable compound in a polymerizable composition of this invention, are, for example, known polymerizable monomers including monofunctional or polyfunctional (meth)acrylates such as methyl(meth)acrylate, butyl(meth)acrylate, 2-ethylhexyl(meth)acrylate, ethylcarbitol(meth)acrylate, lauryl(meth)acrylate, tetracyclododecyl(meth)acrylate, phenoxyethyl(meth)acrylate, nonylphenoxyethyl(meth)acrylate, dicyclopentenyl(meth)acrylate, isobornyl(meth)acrylate, N-n-butyl-O-(meth)acryloyloxyethyl carbamate, acryloylmorpholine, trifluoroethyl(meth)acrylate, tribromobenzyl(meth)acrylate and perfluorooctylethyl(meth)acrylate, ethylene glycol di(meth)acrylate, propylene glycol di(meth)acrylate, neopentyl glycol di(meth)acrylate, 1,6-hexanediol di(meth)acrylate, triethylene glycol di(meth)acrylate, tripropylene glycol di(meth)acrylate, polyethylene glycol di(meth)acrylate, polypropylene glycol di(meth)acrylate, 2,2-bis(4-acryloyloxyphenyl)propane, 2,2-bis(4-methacryloyloxyphenyl)propane, bis(4-acryloyloxyphenyl)methane, bis(4-methacryloyloxyphenyl)methane, 4,4'-bis(acryloyloxy)diphenyl sulfide, 4,4'-bis(methacryloyloxy)diphenyl sulfide, 2,2-bis[4-(acryloyloxyethoxy)phenyl]propane, 2,2-bis[4-(methacryloyloxyethoxy)phenyl]propane, 2,2-bis[4-(2-acryloyloxypropoxy)phenyl]propane, 2,2-bis[4-(2-methacryloyloxypropoxy)phenyl]propane, bis[4-(acryloyloxyethoxy)phenyl]methane, bis[4-(methacryloylethoxy)phenyl]methane, bis[4-(2-acryloyloxypropoxy)phenyl]methane, bis[4-(2-methacryloylpropoxy)phenyl]methane, 4,4'-bis(2-acryloyloxyethoxy)diphenyl sulfide, 4,4'-bis(2-methacryloyloxyethoxy)diphenyl sulfide, 4,4'-bis(2-acryloyloxypropoxy)diphenyl sulfide, 4,4'-bis(2-methacryloyloxypropoxy)diphenyl sulfide, 4,4'-bis(2-acryloyloxyethoxy)diphenyl sulfone, 4,4'-bis(2-methacryloyloxyethoxy)diphenyl sulfone, 4,4'-bis(2-acryloyloxypropoxy)diphenyl sulfone, 4,4'-bis(2-methacryloyloxypropoxy)diphenyl sulfone, di(meth)acrylate of ethylene oxide or propylene oxide adducts of 2,2-bis(4-hydroxyphenyl)propane, di(meth)acrylate of ethylene oxide or propylene oxide adducts of bis(4-hydroxyphenyl)methane, trimethylolpropane tri(meth)acrylate, di(pentaerythritol)pentaacrylate, pentaerythritol triacrylate, pentaerythritol tetraacrylate, di(trimethylol)tetraacrylate, di(pentaerythritol)hexaacrylate, 2-(meth)acryloyloxyethyl tris(isocyanulate) and (meth)acryloxypropyl-tris(methoxy)silane; epoxy(meth)acrylates as a reaction product of a (meth)acrylic acid and a various of known monofunctional or 2 or more functional epoxy compound such as phenol glycidyl ether, ethyleneglycol diglycidyl ether, propyleneglycol diglycidyl ether, resorcinol diglycidyl ether, hydroquinone diglycidyl ether, bis(4-hydroxyphenyl)methane (common name: bisphenol-F) diglycidyl ether, 2,2-bis(4-hydroxyphenyl)propane (common name: bisphenol-A) diglycidyl ether, 4,4'-bis(hydroxyphenyl)sulfide diglycidyl ether, 4,4'-bis(hydroxyphenyl)sulfone (common name: bisphenol-S) diglycidyl ether, 4,4'-biphenol diglycidyl ether, 3,3',5,5'-tetramethyl-4,4'-biphenol diglycidyl ether and tris(2,3-epoxypropyl)isocyanulate; epoxy(meth)acrylates as a reaction product of an epoxy compound such as phenol novolac epoxy resin, cresol novolac epoxy resin, phenol-aralkyl-resin-type epoxy resin, bisphenol epoxy resin with acrylic or methacrylic acid; vinyl compounds such as vinylbenzene, divinylbenzene, trivinylbenzene, isopropenylbenzene, diisopropenylbenzene, triisopropenylbenzene, N-vinylpyrrolidone and N-vinylcaprolactam; allyl-containing compounds such as ethyleneglycol diallyl carbonate, triallyl trimellite and triallyl isocyanurate; and various known polymerizable oligomers such as polyurethane(meth)acrylate, epoxy(meth)acrylate, polyester(meth)acrylate and polyether(meth)acrylate.

The amount of the compound is generally 300 parts by weight or less, preferably 200 parts by weight or less, more preferably 100 parts by weight or less, to 100 parts by weight of a sulfur-containing unsaturated carboxylate compound represented by general formula (1) for more effectively achieving the effects of this invention.

A polymerizable composition of this invention may be prepared specifically by using a sulfur-containing unsaturated carboxylate compound represented by formula (1) of this invention, as necessary, in combination with one or more of the various known polymerizable compounds described above, and after adding any of the above polymerization initiator, blending and/or dissolving them. After, if necessary, removing insolubles and/or foreign matters and fully defoaming at a reduced pressure before polymerization, the polymerizable composition can be used for polymerization and curing. For preparing the polymerizable composition, a variety of known additives can be, as necessary, added, including internal mold release agents, photostabilizers, ultraviolet absorbers, antioxidants, color pigments such as Cyanine Green and Cyanine Blue, dyes, fluidity-regulating agents, and inorganic fillers such as talc, silica, alumina, barium sulfate and magnesium oxide.

A cured product and an optical component comprising the product according to this invention can be prepared by polymerizing and curing the above polymerizable composition. They can be suitably prepared by a variety of known processes; typically by injecting a polymerizable composition obtained as described above into a mold and then polymerizing it by radical polymerization initiated by heat or light, i.e., cast molding.

The mold consists of two mirror-finished templates combined via a gasket made of a soft thermoplastic resin such as polyethylene, ethylene-vinyl acetate copolymer and polyvinyl chloride. The templates may be, for example, a combination of glass-glass, glass-plastic plate, or glass-metal plate. Instead of using the above gasket made of a soft thermoplastic resin, two templates may be combined and fixed with an appropriate fixing means such as a polyester sticky tape.

The templates may be treated by a known procedure such as application of a mold releasing agent.

Radical polymerization may be conducted by heating (thermal polymerization), irradiating light such as UV (photo polymerization) and irradiating γ-rays as well as a combination thereof, as described above.

For these processes, thermal polymerization takes several to several ten hours while photo polymerization with, e.g., UV allows curing to be completed several seconds to several minutes. The latter is preferable in the light of improvement in a yield for preparing an optical component of this invention.

For thermal polymerization, a polymerization temperature cannot be specifically defined because it varies depending on various polymerization conditions such as a type of an initiator, but generally 25 to 200° C., preferably 50 to 170° C.

An optical lens can be formed by, for example, cast molding using light and/or heating as described above (See, e.g., JP-A 60-135901, JP-A 10-67736 and JP-A 10-130250). It is suitably conducted by, as necessary, defoaming a polymerizable composition comprising a sulfur-containing unsaturated carboxylate compound represented by general formula (1) of this invention prepared as described above by an appropriate procedure; injecting it in a mold and generally polymerizing it by irradiation. Thermal polymerization may be suitably conducted by gradually heating the composition from a lower temperature to a higher temperature.

Furthermore, an optical lens thus obtained may be, if necessary, subject to a variety of physical or chemical treatments such as surface abrasion, antistatic treatment, hard coat treatment, non-reflection coating, dyeing and light-modulating treatment (e.g., photochromic-lens treatment), for improvements such as prevention of reflection; improvement in hardness, abrasion resistance or chemical resistance; and impartation of antifogy or cosmetic property.

A substrate for an optical disk or magneto-optical disk may be prepared by any of appropriate known processes such as injecting a polymerizable composition comprising a sulfur-containing unsaturated carboxylate compound represented by general formula (1) of this invention prepared as described above into the cavity of a mold for a disk substrate, polymerizing it by, e.g., radical polymerization and, as necessary, post-heating it (See, e.g., JP-As 58-130450, 58-137150 and 62-280008); photopolymerizing it in a mold whose both sides are made of glass (See JP-A 60-2025557); or injecting it optionally in vacuo and then compressing the liquid resin for thermal polymerization (See JP-A 60-203414).

The polymerizable composition of this invention may be photopolymerized to give a cured product or an optical component consisting of the cured product in as short as period of several minutes to several hours. That is, it has a feature that it may be polymerized and molded in a shorter time than an existing thermosetting optical resin such as poly(diethyleneglycoldiallyl carbonate) and polythiourethane.

Furthermore, a cured product and an optical component of this invention are characterized in that they exhibit excellent optical, mechanical and thermal properties as well as a higher refractive index. Examples of the optical component include a variety of plastic lenses (typically, an orthodontic eyeglass), substrates for optical information recording media, plastic substrates for a liquid crystal cell and coatings for optical fibers.

This invention will be more specifically described with reference to the following examples, but is not limited to these in any manner.

Preparation of a Sulfur-containing Compound Represented by General Formula (9) of This Invention

EXAMPLE 1

Preparation of Compound 9-2 in Table 3: a Compound Represented by Formula (9) Wherein $R_{91}$ and $R_{92}$ are Hydrogen; $R_{93}$ is Bromine; p is Zero; and q is 2

In a 500 mL glass vessel equipped with a mechanical stirrer were placed 25.4 g of ethane dithiol (0.27 mol), 25 mL of boron trifluoride etherate and 100 g of toluene. To the mixture at 20° C. was added dropwise 55.4 g of 90% 2-(2'-bromoethyl)-1,3-dioxolane (0.275 mol) over 1 hour. After stirring at 20° C. for additional 5 hours, to the mixture were added 150 g of ice-water and 50 g of toluene, and the mixture was stirred for 15 minutes, allowed to stand and separated into two phases. The extracted toluene phase was washed with 150 g of 3% aqueous sodium bicarbonate and washed with water until the pH of the aqueous phase became neutral.

The toluene phase was separated and evaporated in vacuo at 40° C. to give a crude product. The product was distilled at a reduced pressure to collect 51.8 g of 2-(2'-bromoethyl)-1,3-dithiolane as a colorless liquid.

Yield: 90%; Purity: higher than 99% (an area method based on a gas chromatogram). Boiling point: 93 to 96° C./0.22 mmHg. $^1$H-NMR δ (CDCl$_3$): 2.2–2.3 (m, 2H), 3.2 (s, 4H), 3.4–3.5 (m, 2H), 4.6–4.7 (t, 1H). FD-MS: 213 (M$^+$).

EXAMPLE 2

Preparation of Compound 9-18 in Table 3: a Compound Represented by Formula (9) Wherein $R_{91}$ and $R_{92}$ are Hydrogen; $R_{93}$ is Thiol; p is Zero; and q is 2

In a 500 mL glass vessel equipped with a mechanical stirrer were placed 32.0 g of thiourea (0.42 mol) and 175 g of ethanol. To the mixture at 50° C. was added dropwise 44.8 g of 2-(2'-bromoethyl)-1,3-dithiolane prepared in Example 1 over 35 minutes, and the mixture was reacted at 80° C. for 4 hours to form a thiuronium salt. The reaction solution was analyzed by high performance liquid chromatography to confirm that the starting bromide had been disappeared. To the reaction mixture at 50° C. was added dropwise 200 g of 18% aqueous ammonium hydroxide over 10 minutes, and then the mixture was reacted at 50° C. for additional 2 hours to hydrolyze the thiuronium salt. To the mixture was added toluene and the two phases were separated. The toluene phase was washed with water until a wastewater became neutral, separated and evaporated in vacuo at 40° C. to give a crude product. The crude product was distilled at a reduced pressure to collect 31.6 g of 2-(2'-mercaptoethyl)-1,3-dithiolane as a colorless liquid.

Yield: 95% Purity: higher than 99% (an area method based on a gas chromatogram). Boiling point: 98 to 100° C./0.25 mmHg. $^1$H-NMR δ (CDCl$_3$): 1.7–1.8 (br, 1H), 2.0–2.1 (m, 2H), 2.5–2.7 (m, 2H), 3.2–3.3 (m, 4H), 4.7–4.8 (t, 1H). FD-MS: 166 (M$^+$).

EXAMPLE 3

Preparation of Compound 9-32 in Table 3: a Compound Represented by Formula (9) Wherein $R_{91}$ and $R_{92}$ are Hydrogen; $R_{93}$ is Hydroxy; p is Zero; and q is 2

In a 100 mL glass vessel equipped with a mechanical stirrer were placed 21.3 g of 2-(2'-bromoethyl)-1,3-dithiolane (0.10 mol) prepared in Example 1, 13.6 g of sodium formate (0.20 mol) and 1.61 g of tetramethylammonium bromide (0.005 mol). The mixture was heated with stirring at 110° C. for 1.5 hours. After completion of the reaction, to the stirred reaction mixture was added dropwise 8.8 g of 50% aqueous solution of sodium hydroxide over 15 minutes. The reaction product was extracted with toluene. The toluene layer was washed with water and evaporated in vacuo at 40° C. The resulting crude product was distilled at a reduced pressure to give 13.5 g of 2-(2'-hydroxyethyl)-1,3-dithiolane as a colorless liquid.

Yield: 90% Purity: higher than 99% (an area method based on a gas chromatogram). Boiling point: 100 to 105° C./0.25 mmHg. $^1$H-NMR δ (CDCl$_3$): 2.0–2.1 (m, 2H), 2.5–2.6 (br, 1H), 2.8–2.9 (m, 2H), 3.2–3.3 (m, 4H), 4.7–4.8 (t, 1H). FD-MS: 150 (M$^+$).

EXAMPLE 4

Preparation of Compound 9-5 in Table 3: a Compound Represented by Formula (9) Wherein $R_{91}$ is Methyl; $R_{92}$ is Hydrogen; $R_{93}$ is Bromine; p is Zero; and q is 2

The procedure described in Example 1 was repeated, except substituting 1,2-propane dithiol for ethane dithiol to give 2-(2'-bromoethyl)-4-methyl-1,3-dithiolane as a colorless liquid.

EXAMPLE 5

Preparation of Compound 9-21 in Table 3: a Compound Represented by Formula (9) Wherein $R_{91}$ is Methyl; $R_{92}$ is Hydrogen; $R_{93}$ is Thiol; p is Zero; and q is 2

The procedure described in Example 2 was repeated, except substituting 2-(2'-bromoethyl)-4-methyl-1,3-dithiolane prepared in Example 4 for 2-(2'-bromoethyl)-1,3-dithiolane prepared in Example 1 to give 2-(2'-mercaptoethyl)-4-methyl-1,3-dithiolane as a colorless liquid.

Preparation of Sulfur-containing Dihydroxy Compounds Represented by General Formula (2) of This Invention

EXAMPLE 6

To a mixture of 220.4 g of benzene thiol (2.00 mol), 3.0 g of sodium hydroxide (0.075 mol) and 300 g of methanol at 10° C. were added dropwise a solution of 222.2 g of resorcinol diglycidyl ether (1.00 mol) represented by formula (10-1) below in 400 g of methanol over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water.

The oily product was extracted with 300 g of toluene. The toluene layer was washed with water until a wastewater became neutral and separated.

The toluene in the organic layer was evaporated in vacuo at 40° C. to give 420.0 g of the sulfur-containing dihydroxy compound represented by formula (2-1) (Compound 39 in Table 2) as a viscous slightly-yellowish transparent oil.

Yield: 95%; purity: 99% (an area method based on HPLC analysis). NMR and mass spectrometry results for the product are as follows. $^1$H-NMR (400 MHz) δ (CDCl$_3$): 2.8–2.9 (m, 2H), 3.1–3.3 (m, 4H), 3.9–4.1 (m, 4H), 4.1–4.4 (d, 2H), 6.4–6.5 (m, 3H), 7.1–7.4 (m, 11H). FD-MS: 442 (M$^+$).

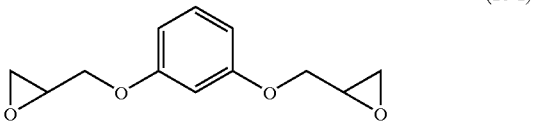

(10-1)

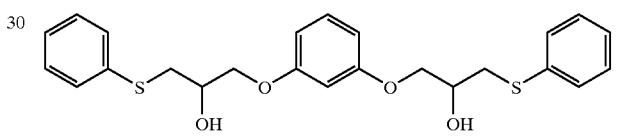

(2-1)

EXAMPLE 7

The procedure described in Example 6 was repeated except substituting 2-(2'-mercaptoethyl)-1,3-dithiolane prepared in Example 2 for benzene thiol to give a sulfur-containing dihydroxy compound represented by formula (2-2) (Compound 27 in Table 2) as a colorless transparent liquid.

FD-MS: 554 (M$^+$).

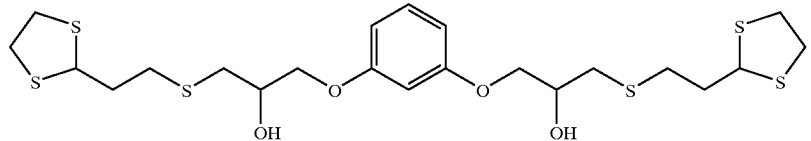

(2-2)

EXAMPLE 8

The procedure described in Example 6 was repeated except substituting 1,3-dithiolane-2-carboxylic acid for benzene thiol to give a sulfur-containing dihydroxy compound represented by formula (2-3) (Compound 45 in Table 2) as a colorless transparent liquid.

FD-MS: 522 (M$^+$).

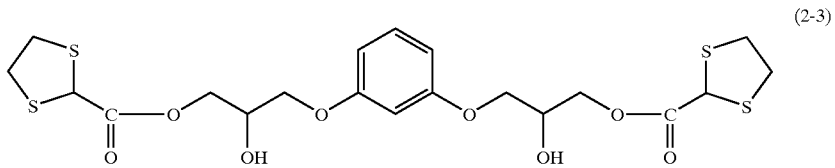

(2-3)

EXAMPLE 9

To a mixture of 22 g of benzene thiol (0.2 mol), 0.3 g of sodium hydroxide (0.0075 mol) and 30 g of methanol at 10° C. were added dropwise a solution of 29.8 g of 4,4'-diglycidyloxybiphenyl (0.1 mol) in 40 g of methyl ethyl ketone over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water.

The oily product was extracted with 250 g of toluene. The toluene layer was washed with water until a wastewater became neutral and separated. The toluene in the organic layer was evaporated in vacuo at 40° C. to give a crude product, which was purified by column chromatography (silica gel: 400 g, a mobile phase: toluene) to give 49.2 g of the sulfur-containing dihydroxy compound represented by formula (2-4) (Compound 111 in Table 2) as a viscous transparent oil.

Yield: 95%; purity: 99.6% (an area method based on HPLC analysis). Elementary analysis and mass spectrometry results for the product are as follows.

| | Analysis for $C_{30}H_{30}O_4S_2$ | | |
|---|---|---|---|
| | C | H | S |
| Calcd. (%) | 69.47 | 5.83 | 12.36 |
| Found (%) | 69.61 | 5.81 | 12.40 |

FD-MS: 519 ($M^+$).

(2-4)

EXAMPLE 10

The procedure described in Example 9 was repeated except substituting 33.3 g of 2-(2'-mercaptoethyl)-1,3-dithiolane (0.2 mol) for benzene thiol. The resulting product was purified by column chromatography to give 58.1 g of the dihydroxy compound represented by formula (2-5) (Compound 112 in Table 2) as a colorless transparent oil.

Yield: 92%; purity: 99.5% (an area method based on HPLC analysis). Elementary analysis and mass spectrometry results for the product are as follows.

| | Analysis for $C_{28}H_{38}O_4S_6$ | | |
|---|---|---|---|
| | C | H | S |
| Calcd. (%) | 53.30 | 6.07 | 30.49 |
| Found (%) | 53.33 | 6.11 | 30.43 |

-continued

FD-MS: 631 (M⁺).

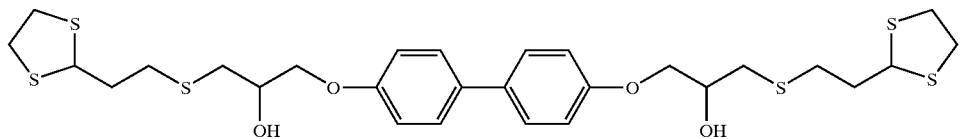

(2-5)

EXAMPLE 11

The procedure described in Example 9 was repeated except substituting 30.0 g of 1,3-dithiolane-2-carboxylic acid (0.2 mol) for benzene thiol. The resulting product was purified by column chromatography to give 49.1 g of the dihydroxy compound represented by formula (2-6) (Compound 113 in Table 2) as a viscous colorless transparent oil.

Yield: 94%; purity: 99.4% (an area method based on HPLC analysis). Elementary analysis and mass spectrometry results for the product are as follows.

| | Analysis for $C_{26}H_{30}O_8S_4$ | | |
|---|---|---|---|
| | C | H | S |
| Calcd. (%) | 52.15 | 5.05 | 21.42 |
| Found (%) | 52.11 | 5.01 | 21.40 |

FD-MS: 599 (M⁺).

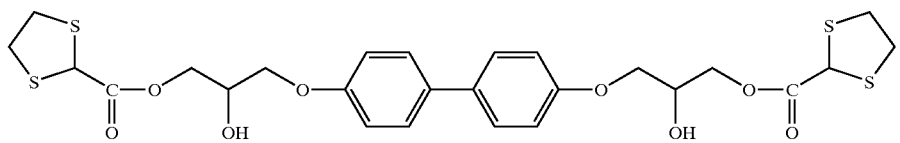

(2-6)

EXAMPLE 12

The procedure described in Example 9 was repeated except substituting 35.4 g of 3,3',5,5'-tetramethyl-4,4'-diglycidyloxybiphenyl (0.1 mol) for 4,4'-diglycidyloxybiphenyl. The resulting product was purified by column chromatography to give 54.6 g of the dihydroxy compound represented by formula (2-7) (Compound 103 in Table 2) as a viscous colorless transparent oil.

Yield: 90%; purity: 99.5% (an area method based on HPLC analysis). Elementary analysis and mass spectrometry results for the product are as follows.

| | Analysis for $C_{34}H_{38}O_4S_2$ | | |
|---|---|---|---|
| | C | H | S |
| Calcd. (%) | 71.05 | 6.66 | 11.16 |
| Found (%) | 71.09 | 6.61 | 11.20 |

-continued

FD-MS: 575 (M⁺).

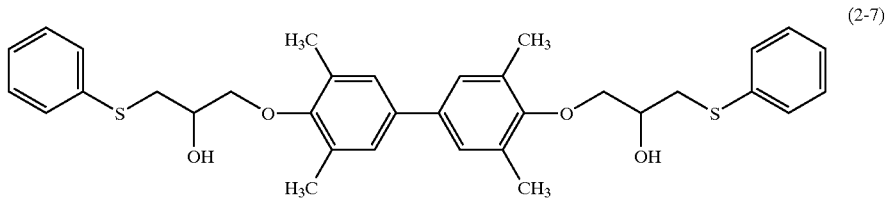

(2-7)

EXAMPLE 13

The procedure described in Example 10 was repeated except substituting 35.4 g of 3,3',5,5'-tetramethyl-4,4'-diglycidyloxybiphenyl (0.1 mol) for 4,4'-diglycidyloxybiphenyl. The resulting product was purified by column chromatography to give 62.5 g of the sulfur-containing dihydroxy compound represented by formula (2-8) (Compound 102 in Table 2) as a colorless transparent oil.

Yield: 91%; purity: 99.5% (an area method based on HPLC analysis). Elementary analysis and mass spectrometry results for the product are as follows.

| | Analysis for $C_{32}H_{46}O_4S_6$ | | |
|---|---|---|---|
| | C | H | S |
| Calcd. (%) | 55.94 | 6.75 | 28.02 |
| Found (%) | 55.88 | 6.73 | 28.07 |

FD-MS: 687 (M⁺).

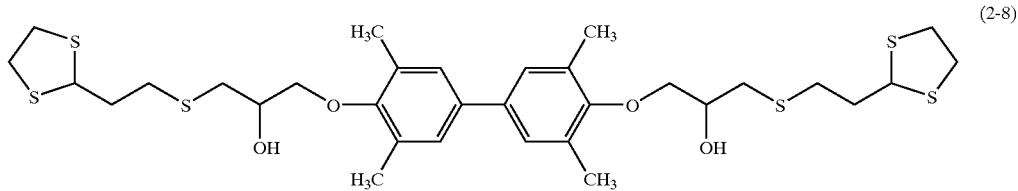

(2-8)

EXAMPLE 14

To a mixture of 18.4 g of methylthioethanol (0.2 mol), 0.3 g of sodium hydroxide (0.0075 mol) and 30 g of methanol at 10° C. were added dropwise a solution of 35.4 g of 3,3',5,5'-tetramethyl-4,4'-diglycidyloxybiphenyl (0.1 mol) in 40 g of methyl ethyl ketone over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water. The oily product was extracted with 300 g of toluene. The toluene layer was washed with water until a wastewater became neutral and separated. The toluene in the organic layer was evaporated in. vacuo at 40° C. to give a crude product, which was purified by column chromatography (silica gel: 400 g, a mobile phase: toluene) to give 51.6 g of the sulfur-containing dihydroxy compound represented by formula (2-9) (Compound 86 in Table 2) as a colorless transparent oil.

Yield: 96%; purity: 99.5% (an area method based on HPLC analysis). Elementary analysis and mass spectrometry results for the product are as follows.

| | Analysis for $C_{28}H_{42}O_6S_2$ | | |
|---|---|---|---|
| | C | H | S |
| Calcd. (%) | 62.42 | 7.86 | 11.90 |
| Found (%) | 62.51 | 7.82 | 11.86 |

-continued

FD-MS: 539 (M+).

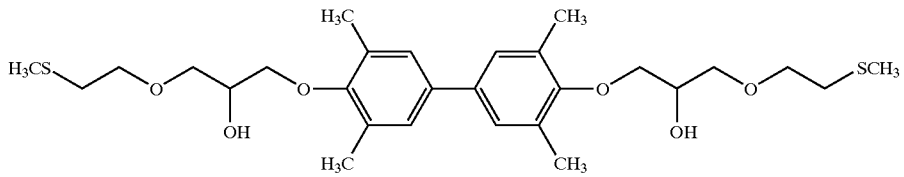

(2-9)

EXAMPLE 15

The procedure described in Example 10 was repeated except substituting 41.8 g of 3,3',5,5'-tetramethoxy- 4,4'-diglycidyloxybiphenyl (0.1 mol) for 4,4'-diglycidyloxybiphenyl. The resulting product was purified by column chromatography to give 66.1 g of the sulfur-containing dihydroxy compound represented by formula (2-10) (Compound 107 in Table 2) as a viscous colorless transparent oil.

Yield: 88%; purity: 99.7% (an area method based on HPLC analysis). Elementary analysis and mass spectrometry results for the product are as follows.

| | Analysis for $C_{32}H_{46}O_8S_6$ | | |
|---|---|---|---|
| | C | H | S |
| Calcd. (%) | 51.17 | 6.17 | 25.61 |
| Found (%) | 51.58 | 6.12 | 25.67 |

FD-MS: 751 (M+).

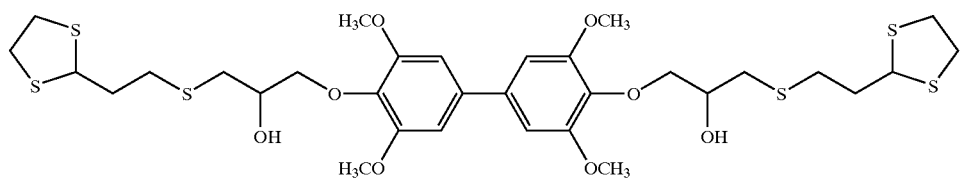

(2-10)

EXAMPLE 16

To a mixture of 18.4 g of methylthioethanol (0.2 mol), 0.3 g of sodium hydroxide (0.0075 mol) and 30 g of methanol at 10° C. were added dropwise a solution of 64.2 g of 3,3',5,5'-tetrabromo-4,4'-diglycidyloxybiphenyl (0.1 mol) in 100 g of methyl ethyl ketone over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water. The oily product was extracted with 400 g of toluene. The toluene layer was washed with water until a wastewater became neutral and separated. The toluene in the organic layer was evaporated in vacuo at 40° C. to give a crude product, which was purified by column chromatography (silica gel: 600 g, a mobile phase: toluene) to give 71.0 g of the sulfur-containing dihydroxy compound represented by formula (2-11) (Compound 114 in Table 2) as a viscous transparent oil.

Yield: 86%; purity: 99.2% (an area method based on HPLC analysis). Elementary analysis and mass spectrometry results for the product are as follows.

| | Analysis for $C_{24}H_{30}Br_4O_6S_2$ | | | |
|---|---|---|---|---|
| | C | H | Br | S |
| Calcd. (%) | 36.11 | 3.79 | 40.04 | 8.03 |
| Found (%) | 36.12 | 3.78 | 40.00 | 8.05 |

FD-MS: 799 (M⁺).

(2-11)

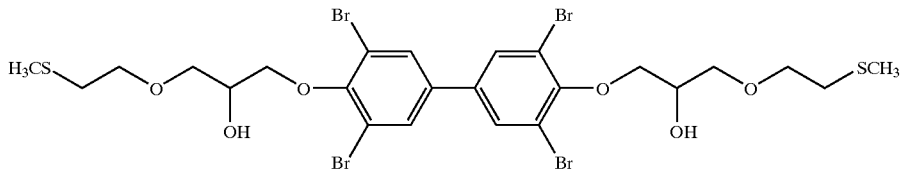

EXAMPLE 17

To a mixture of 22 g of benzene thiol (0.2 mol), 0.3 g of sodium hydroxide (0.0075 mol) and 30 g of methanol at 10° C. were added dropwise a solution of 34.0 g of 2,2-bis(4-glycidyloxyphenyl)propane (0.1 mol) in 50 g of methanol over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water. The oily product was extracted with 350 g of toluene. The toluene layer was washed with water until a wastewater became neutral and separated. The toluene in the organic layer was evaporated in vacuo at 40° C. to give a crude product, which was purified by column chromatography (silica gel: 500 g, a mobile phase: toluene) to give 53.8 g of the sulfur-containing dihydroxy compound represented by formula (2-12) (Compound 175 in Table 2) as a viscous transparent oil.

Yield: 96%; purity: 99.5% (an area method based on HPLC analysis). Elementary analysis and mass spectrometry results for the product are as follows.

| | Analysis for $C_{33}H_{36}O_4S_2$ | | |
|---|---|---|---|
| | C | H | S |
| Calcd. (%) | 70.68 | 6.47 | 11.44 |
| Found (%) | 70.63 | 6.44 | 11.42 |

FD-MS: 561 (M⁺).

(2-12)

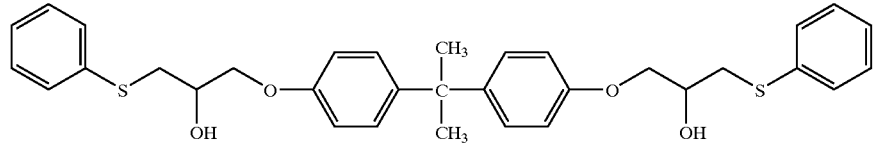

EXAMPLE 18

The procedure described in Example 17 was repeated except substituting 30.0 g of 1,3-dithiolane-2-carboxylic acid (0.2 mol) for benzene thiol. The resulting product was purified by column chromatography to give 62.2 g of the sulfur-containing dihydroxy compound represented by formula (2-13) (Compound 177 in Table 2) as a colorless transparent oil.

Yield: 97%; purity: 99.6% (an area method based on HPLC analysis). Elementary analysis and mass spectrometry results for the product are as follows.

| Analysis for $C_{29}H_{36}O_8S_4$ | | | |
|---|---|---|---|
| | C | H | S |
| Calcd. (%) | 54.35 | 5.66 | 20.01 |
| Found (%) | 54.37 | 5.61 | 20.03 |

FD-MS: 641 (M⁺).

(2-13)

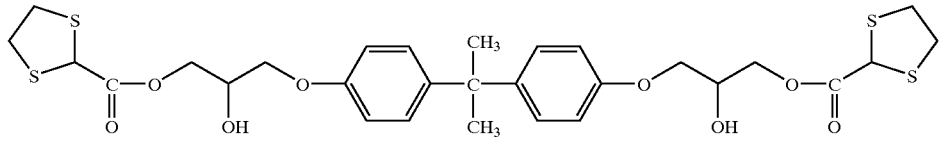

EXAMPLE 19

The procedure described in Example 17 was repeated except substituting 33.3 g of 2-(2'-mercaptoethyl)-1,3-dithiolane (0.2 mol) for benzene thiol. The resulting product was purified by column chromatography to give 62.5 g of the sulfur-containing dihydroxy compound represented by formula (2-14) (Compound 176 in Table 2) as a colorless transparent oil.

Yield: 93%; purity: 99.5% (an area method based on HPLC analysis). Elementary analysis and mass spectrometry results for the product are as follows.

| Analysis for $C_{31}H_{44}O_4S_6$ | | | |
|---|---|---|---|
| | C | H | S |
| Calcd. (%) | 55.32 | 6.59 | 28.58 |
| Found (%) | 55.35 | 6.57 | 28.53 |

FD-MS: 673 (M⁺).

(2-14)

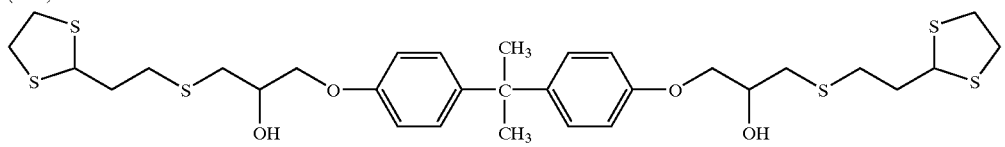

EXAMPLE 20

The procedure described in Example 17 was repeated except substituting 39.6 g of 2,2-bis(3,5-dimethyl-4-glycidyloxyphenyl)propane (0.1 mol) for 2,2-bis(4-glycidyloxyphenyl)propane. The resulting product was purified by column chromatography to give 56.7 g of the dihydroxy compound represented by formula (2-15) (Compound 167 in Table 2) as a viscous material.

Yield: 92%; purity: 99.6% (an area method based on HPLC analysis). Elementary analysis and mass spectrometry results for the product are as follows.

| Analysis for $C_{37}H_{44}O_4S_2$ | | | |
|---|---|---|---|
| | C | H | S |
| Calcd. (%) | 72.04 | 7.19 | 10.40 |
| Found (%) | 67.33 | 6.23 | 10.59 |

FD-MS: 617 (M⁺).

(2-15)

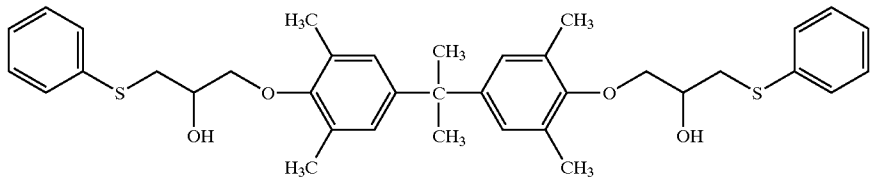

EXAMPLE 21

The procedure described in Example 18 was repeated except substituting 39.6 g of 2,2-bis(3,5-dimethyl-4-glycidyloxyphenyl)propane (0.1 mol) for 2,2-bis(4-glycidyloxyphenyl)propane. The resulting product was purified by column chromatography to give 65.5 g of the dihydroxy compound represented by formula (2-16) (Compound 170 in Table 2) as a colorless transparent oil.

Yield: 94%; purity: 99.8% (an area method based on HPLC analysis). Elementary analysis and mass spectrometry results for the product are as follows.

| Analysis for $C_{33}H_{44}O_8S_4$ | | | |
|---|---|---|---|
| | C | H | S |
| Calcd. (%) | 56.87 | 6.36 | 18.40 |
| Found (%) | 55.88 | 6.73 | 28.07 |

FD-MS: 697 (M⁺).

(2-16)

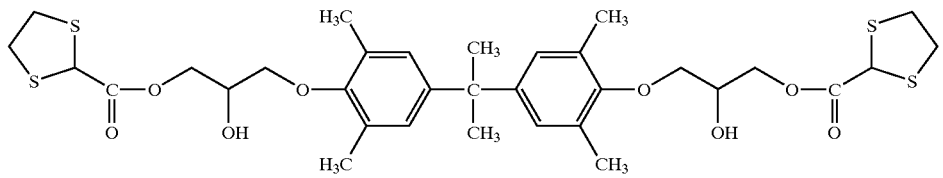

EXAMPLE 22

To a mixture of 18.4 g of methylthioethanol (0.2 mol), 0.3 g of sodium hydroxide (0.0075 mol) and 30 g of methanol at 10° C. were added dropwise a solution of 34.0 g of 2,2-bis(4-glycidyloxyphenyl)propane (0.1 mol) in 40 g of methyl ethyl ketone over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water. The oily product was extracted with 300 g of toluene. The toluene layer was washed with water until a wastewater became neutral and separated. The toluene in the organic layer was evaporated in vacuo at 40° C. to give a crude product, which was purified by column chromatography (silica gel: 400 g, a mobile phase: toluene) to give 53.5 g of the sulfur-containing dihydroxy compound represented by formula (2-17) as a colorless transparent oil.

Yield: 96%; purity: 99.5% (an area method based on HPLC analysis). Elementary analysis and mass spectrometry results for the product are as follows.

| Analysis for $C_{29}H_{40}O_6S_2$ | | | |
|---|---|---|---|
| | C | H | S |
| Calcd. (%) | 61.80 | 7.68 | 12.22 |
| Found (%) | 61.84 | 7.70 | 12.23 |

FD-MS: 525 (M⁺).

(2-17)

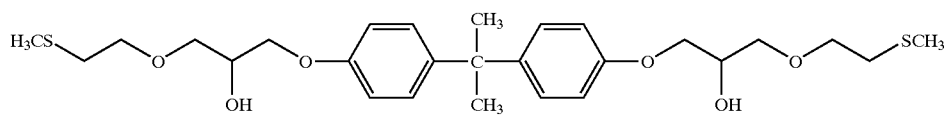

EXAMPLE 23

The procedure described in Example 19 was repeated except substituting 46.0 g of 2,2-bis(3,5-dimethoxy-4-glycidyloxyphenyl)propane (0.1 mol) for 2,2-bis(4-glycidyloxyphenyl)propane. The resulting product was purified by column chromatography to give 71.2 g of the sulfur-containing dihydroxy compound represented by formula (2-18) (Compound 171 in Table 2) as a viscous colorless transparent oil.

Yield: 90%; purity: 99.7% (an area method based on HPLC analysis). Elementary analysis and mass spectrometry results for the product are as follows.

water until a wastewater became neutral and separated. The toluene in the organic layer was evaporated in vacuo at 40° C. to give a crude product, which was purified by column chromatography (silica gel: 600 g, a mobile phase: toluene) to give 58.4 g of the sulfur-containing dihydroxy compound represented by formula (2-19) (Compound 178 in Table 2) as a viscous transparent oil.

Yield: 89%; purity: 99.2% (an area method based on HPLC analysis). Elementary analysis and mass spectrometry results for the product are as follows.

| Analysis for $C_{35}H_{52}O_8S_6$ | | | |
|---|---|---|---|
| | C | H | S |
| Calcd. (%) | 53.00 | 6.61 | 24.25 |
| Found (%) | 53.04 | 6.59 | 24.26 |

FD-MS: 793 (M⁺).

(2-18)

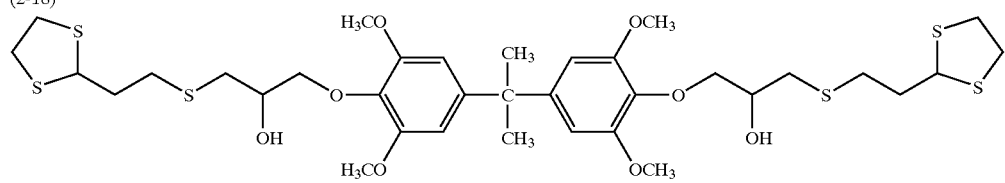

EXAMPLE 24

To a mixture of 18.4 g of methylthioethanol (0.2 mol), 0.3 g of sodium hydroxide (0.0075 mol) and 30 g of methanol at 10° C. were added dropwise a solution of 65.6 g of 2,2-bis(3,5-dibromo-4-glycidyloxyphenyl)propane (0.1 mol) in 100 g of methyl ethyl ketone over 1 hour. After addition, the mixture was stirred at a room temperature (25° C.) for 3 hours. It was confirmed by HPLC (high performance liquid chromatography) that the starting material had been completely consumed, and then the reaction solution was poured into ice-water. The oily product was extracted with 400 g of toluene. The toluene layer was washed with

| Analysis for $C_{27}H_{36}Br_4O_6S_2$ | | | | |
|---|---|---|---|---|
| | C | H | Br | S |
| Calcd. (%) | 38.59 | 4.32 | 38.03 | 7.63 |
| Found (%) | 37.82 | 4.18 | 38.70 | 7.69 |

FD-MS: 841 (M⁺).

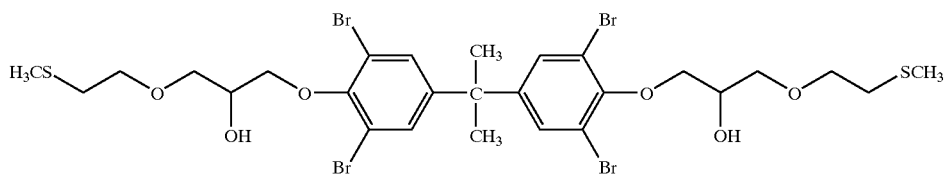
(2-19)
EXAMPLES 25 TO 66
As described in any of the above Examples 6 to 24, the sulfur-containing dihydroxy compounds represented by general formula (2) shown in Table 4 were prepared by reacting an appropriate diepoxy compound with an appropriate sulfur-containing compound.

TABLE 4

| Example No. | Structure | FS-MS |
|---|---|---|
| 25 | 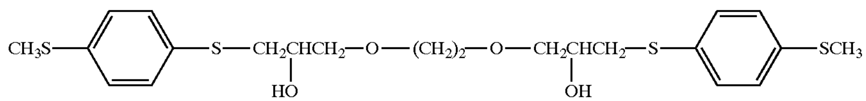 | 487 (M⁺) C₂₂H₃₀O₄S₄ |
| 26 | 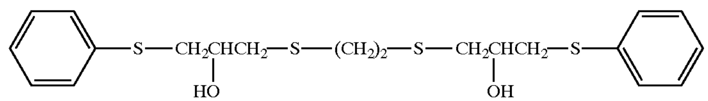 | 427 (M⁺) C₂₀H₂₆O₂S₄ |
| 27 | 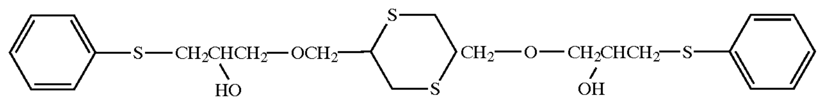 | 513 (M⁺) C₂₄H₃₂O₄S₄ |
| 28 | 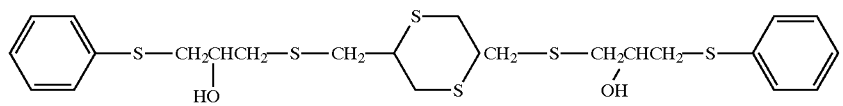 | 545 (M⁺) C₂₄H₃₂O₂S₆ |
| 29 | 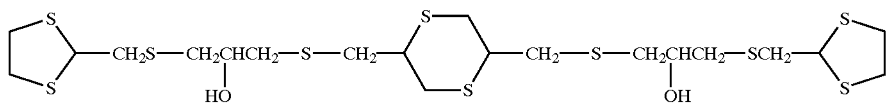 | 629 (M⁺) C₂₀H₃₆O₂S₁₀ |
| 30 | 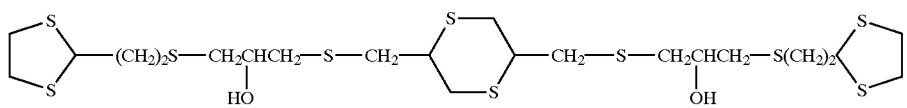 | 657 (M⁺) C₂₂H₄₀O₂S₁₀ |
| 31 | 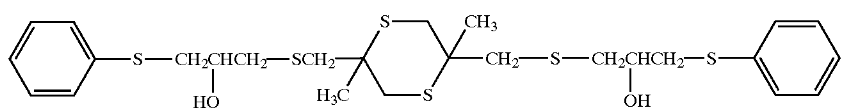 | 573 (M⁺) C₂₆H₃₆O₂S₆ |
| 32 | 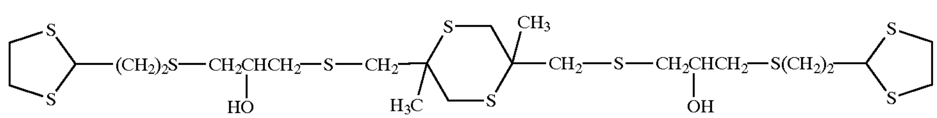 | 685 (M⁺) C₂₄H₄₄O₂S₁₀ |

TABLE 4-continued

| Example No. | Structure | FS-MS |
|---|---|---|
| 33 | 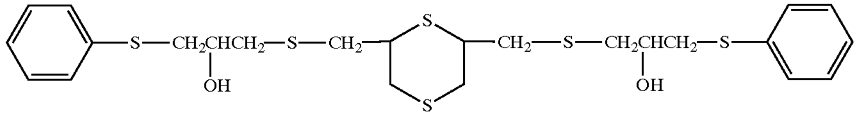 | 545 (M⁺) C₂₄H₃₂O₂S₆ |
| 34 | 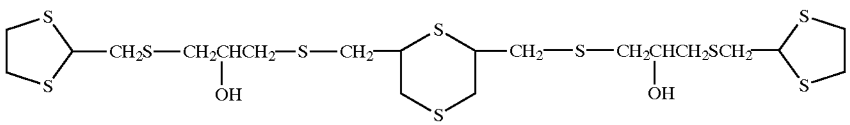 | 629 (M⁺) C₂₀H₃₆O₂S₁₀ |
| 35 | 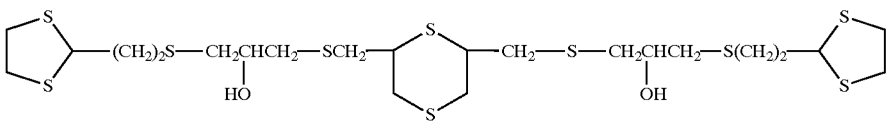 | 657 (M⁺) C₂₄H₄₀O₂S₁₀ |
| 36 | 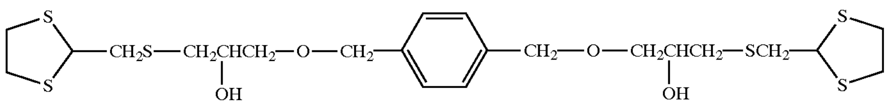 | 555 (M⁺) C₂₂H₃₄O₄S₆ |
| 37 | 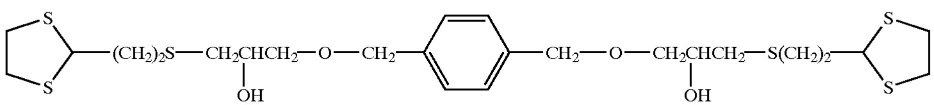 | 583 (M⁺) C₂₄H₃₈O₄S₆ |
| 38 | 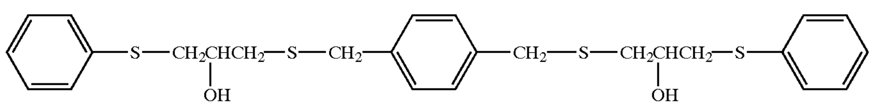 | 503 (M⁺) C₂₆H₃₀O₂S₄ |
| 39 | 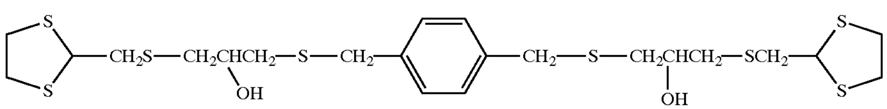 | 587 (M⁺) C₂₂H₃₄O₂S₈ |
| 40 | 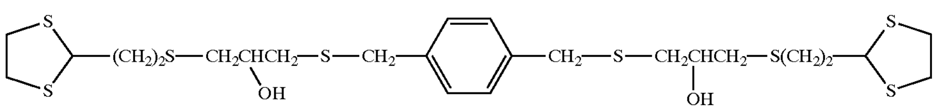 | 615 (M⁺) C₂₄H₃₈O₂S₈ |

TABLE 4-continued

| Example No. | Structure | FS-MS |
|---|---|---|
| 41 | (structure) | 555 (M+) $C_{22}H_{34}O_4S_6$ |
| 42 | (structure) | 503 (M+) $C_{26}H_{30}O_2S_4$ |
| 43 | (structure) | 587 (M+) $C_{22}H_{34}O_2S_8$ |
| 44 | (structure) | 615 (M+) $C_{24}H_{38}O_2S_8$ |
| 45 | (structure) | 583 (M+) $C_{22}H_{30}O_6S_6$ |
| 46 | (structure) | 611 (M+) $C_{24}H_{34}O_6S_6$ |
| 47 | (structure) | 583 (M+) $C_{22}H_{30}O_6S_6$ |
| 48 | (structure) | 611 (M+) $C_{24}H_{34}O_6S_6$ |

TABLE 4-continued

| Example No. | Structure | FS-MS |
|---|---|---|
| 49 | 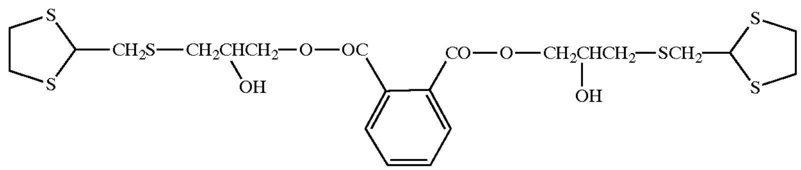 | 583 (M$^+$) C$_{22}$H$_{30}$O$_6$S$_6$ |
| 50 | 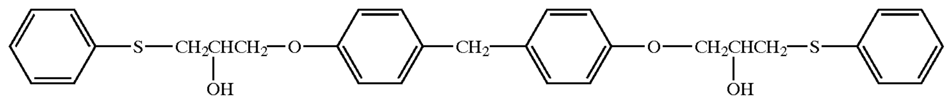 | 533 (M$^+$) C$_{31}$H$_{32}$O$_4$S$_2$ |
| 51 | 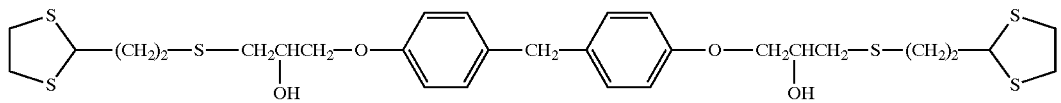 | 645 (M$^+$) C$_{29}$H$_{40}$O$_4$S$_6$ |
| 52 | 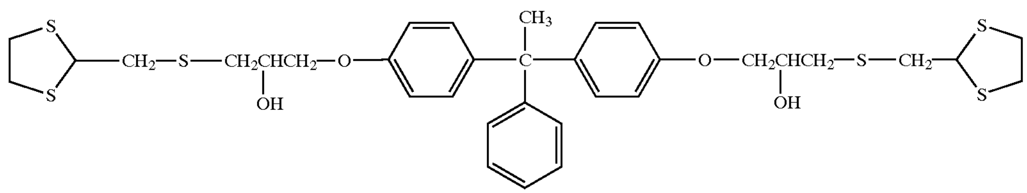 | 707 (M$^+$) C$_{34}$H$_{42}$O$_4$S$_6$ |
| 53 | 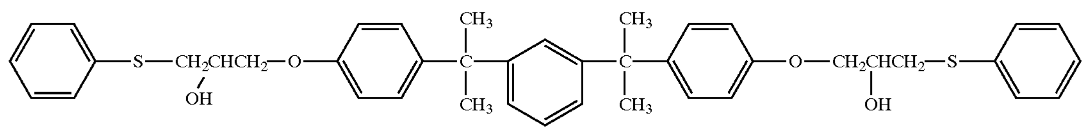 | 679 (M$^+$) C$_{42}$H$_{46}$O$_4$S$_2$ |
| 54 | 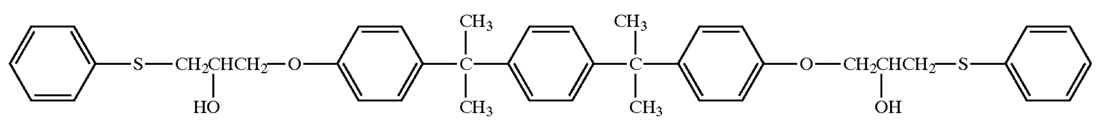 | 679 (M$^+$) C$_{42}$H$_{46}$O$_4$S$_2$ |
| 55 | 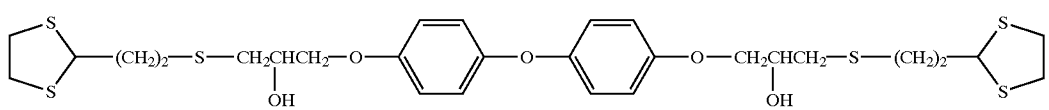 | 647 (M$^+$) C$_{28}$H$_{38}$O$_5$S$_6$ |

TABLE 4-continued

| Example No. | Structure | FS-MS |
|---|---|---|
| 56 | H₃CS(H₂C)₂—O—CH₂CHCH₂—O—⟨C₆H₄⟩—S—⟨C₆H₄⟩—O—CH₂CHCH₂—O—(CH₂)₂SCH₃ (with OH groups on CHCH₂) | 515 (M⁺) C₂₄H₃₄O₆S₃ |
| 57 | Bis(1,3-dithiolan-2-yl-(CH₂)₂-S-CH₂CHCH₂-O-) linked via -C₆H₄-S-C₆H₄- (with OH) | 663 (M⁺) C₂₈H₃₈O₄S₇ |
| 58 | PhS-CH₂CHCH₂-O-C₆H₄-SO₂-C₆H₄-O-CH₂CHCH₂-SPh (with OH) | 583 (M⁺) C₃₀H₃₀O₆S₃ |
| 59 | Bis(1,3-dithiolan-2-yl-(CH₂)₂-S-CH₂CHCH₂-O-) linked via -C₆H₄-SO₂-C₆H₄- (with OH) | 695 (M⁺) C₂₈H₃₈O₆S₇ |
| 60 | PhS-CH₂CHCH₂-O- (with OH) attached to 9,9-bis(4-phenyl)fluorene | 683 (M⁺) C₄₃H₃₈O₄S₂ |
| 61 | CH₃S-CH₂CHCH₂-O- (with OH) attached to 9,9-bis(4-phenyl)fluorene with 1,3-dithiolan-2-yl-CH₂-SCH₂ substituents | 767 (M⁺) C₃₉H₄₂O₄S₆ |

TABLE 4-continued

| Example No. | Structure | FS-MS |
|---|---|---|
| 62 | 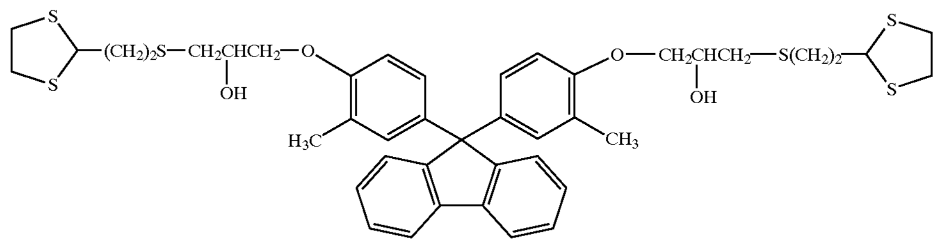 | 823 (M⁺) $C_{43}H_{50}O_4S_6$ |
| 63 | 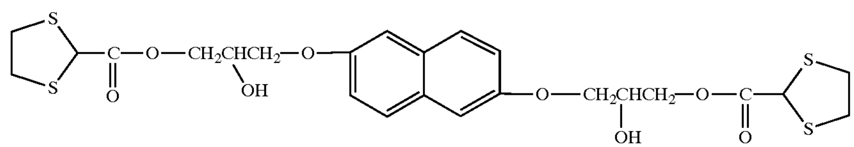 | 573 (M⁺) $C_{24}H_{28}O_8S_4$ |
| 64 | 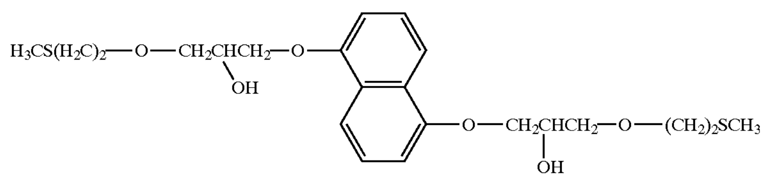 | 457 (M⁺) $C_{22}H_{32}O_6S_2$ |
| 65 | 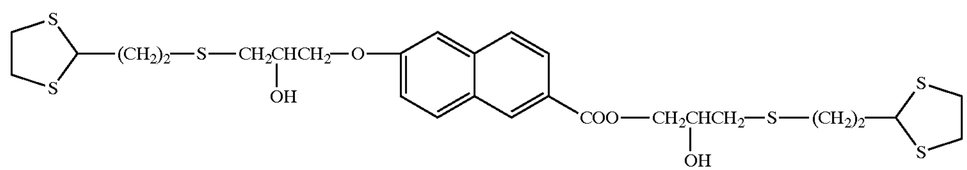 | 633 (M⁺) $C_{27}H_{36}O_6S_6$ |
| 66 | 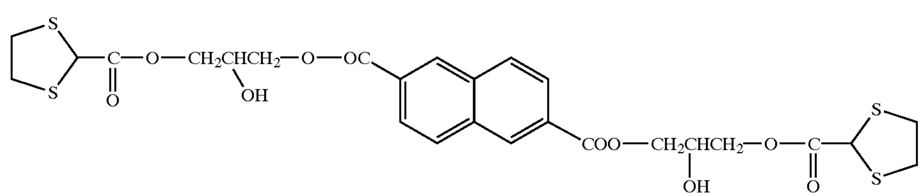 | 629 (M⁺) $C_{26}H_{28}O_{10}S_4$ |

Preparation of a Sulfur-containing Unsaturated Carboxylate Compound Represented by General Formula (1) of This Invention

EXAMPLE 67

To a solution of 55.5 g of the sulfur-containing dihydroxy compound represented by formula (2-1) prepared in Example 6 (0.10 mol) and 19.0 g of pyridine (0.24 mol) in 200 g of chloroform was added dropwise under ice-cooling (10° C.) 19.9 g of acrylic chloride (0.22 mol). After addition, the reaction mixture was stirred at 10° C. for additional 3 hours. Then, pyridine hydrochloride as a byproduct was removed by filtration. The filtrate (chloroform solution) was further washed with 200 g of a diluted aqueous hydrochloric acid solution, washed with water until a wastewater became neutral, and separated. The chloroform in the organic layer was evaporated in vacuo at 60° C. to give a crude product as pale yellow transparent oil. The crude product was purified by silica gel chromatography to give 63.0 g of a sulfur-containing acrylate compound represented by formula (1-1) (Compound 39 in Table 1) as a viscous colorless transparent oil.

Yield: 95%; purity: 99% or higher (an area method based on HPLC analysis). NMR and mass spectrometry results for the product are as follows. $^1$H-NMR (400 MHz) δ (CDCl$_3$): 3.3–3.4 (m, 4H), 4.1–4.3 (m, 4H), 5.3–5.4 (m, 2H), 5.8–5.9 (d, 2H), 6.0–6.1 (dd, 2H), 6.3–6.5 (m, 5H), 7.1–7.5 (m, 11H). FD-MS:550 (M$^+$).

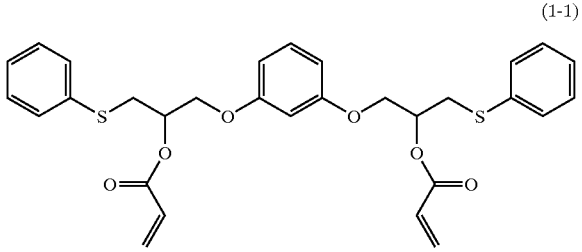

(1-1)

EXAMPLE 68

The procedure described in Example 67 was repeated except substituting the dihydroxy compound represented by formula (2-2) prepared in Example 7 for the dihydroxy compound represented by formula (2-1) to give a sulfur-containing acrylate compound represented by formula (1-2) (Compound 27 in Table 1) as a colorless transparent oil.

FD-MS: 663 (M$^+$).

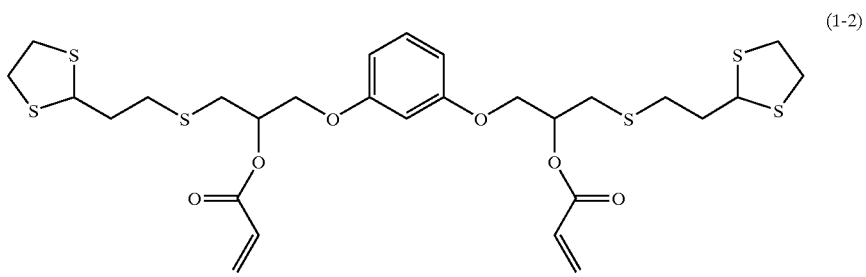

(1-2)

EXAMPLE 69

The procedure described in Example 67 was repeated except substituting the dihydroxy compound represented by formula (2-3) prepared in Example 8 for the dihydroxy compound represented by formula (2-1) to give a sulfur-containing acrylate compound represented by formula (1-3) (Compound 45 in Table 1) as a colorless transparent oil.

FD-MS: 630 (M$^+$).

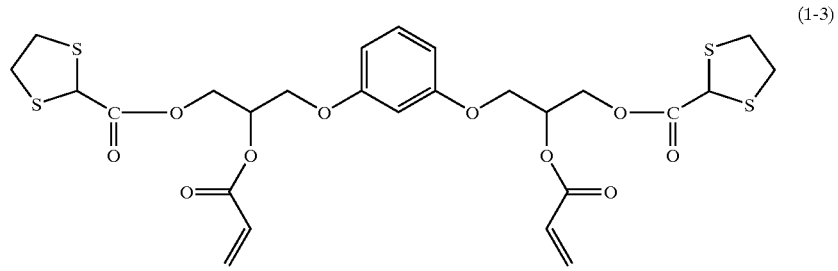

(1-3)

EXAMPLE 70

The procedure described in Example 67 was repeated except substituting methacrylic chloride for acrylic chloride to give a sulfur-containing methacrylate compound represented by formula (1-4) (Compound 71 in Table 1) as a colorless transparent oil.

FD-MS: 578 (M⁺).

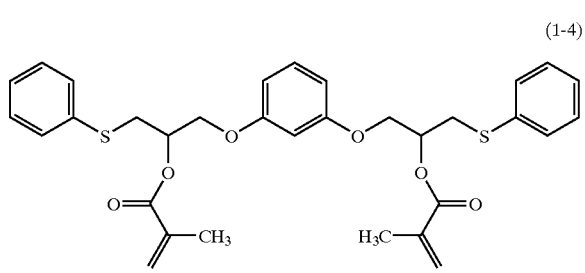

(1-4)

EXAMPLE 71

To a solution of 26.0 g of the sulfur-containing dihydroxy compound represented by formula (2-4) prepared in Example 9 (0.05 mol) and 9.5 g of pyridine (0.12 mol) in 100 g of chloroform was added dropwise under ice-cooling (10° C.) 9.95 g of acrylic chloride (0.11 mol). After addition, the reaction was stirred at 10° C. for additional 3 hours. Then, pyridine hydrochloride as a byproduct was removed by filtration. The filtrate (chloroform solution) was further washed with 100 g of a diluted aqueous hydrochloric acid solution, washed with water until a wastewater became neutral, and separated. The chloroform in the organic layer was evaporated in vacuo at 60° C. to give a crude product as pale yellow transparent oil. The crude product was purified by silica gel chromatography to give 29.4 g of a sulfur-containing acrylate compound represented by formula (1-5) (Compound 126 in Table 1) as a viscous colorless transparent oil.

Yield: 94%; purity: 99.2% or higher (an area method based on HPLC analysis). Elementary analysis and mass spectrometry results for the product are as follows.

| | Analysis for $C_{36}H_{34}O_6S_2$ | | |
|---|---|---|---|
| | C | H | S |
| Calcd. (%) | 68.99 | 5.47 | 10.23 |
| Found (%) | 69.01 | 5.45 | 10.20 |

FD-MS: 627 (M⁺).
(1-5)

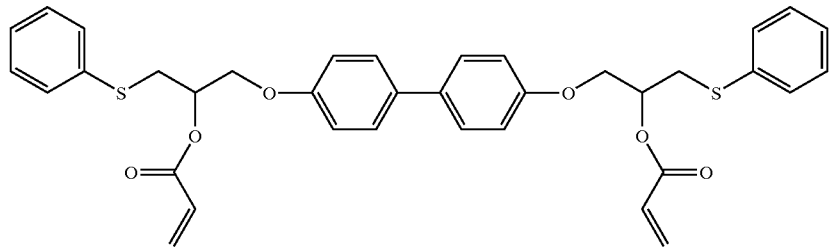

EXAMPLE 72

The procedure described in Example 71 was repeated except substituting 28.7 g of the sulfur-containing dihydroxy compound represented by formula (2-7) prepared in Example 12 (0.05 mol) for the sulfur-containing dihydroxy compound represented by formula (2-4). The resulting product was purified by column chromatography to give 32.4 g of a sulfur-containing acrylate compound represented by formula (1-6) (Compound 118 in Table 1) as a viscous colorless transparent oil.

Yield: 95%; purity: 99.7% (an area method based on HPLC analysis). Elementary analysis and mass spectrometry results for the product are as follows.

| Analysis for $C_{40}H_{42}O_6S_2$ | | | |
|---|---|---|---|
| | C | H | S |
| Calcd. (%) | 70.35 | 6.20 | 9.39 |
| Found (%) | 70.31 | 6.27 | 9.40 |

FD-MS: 683 (M+).

(1-6)

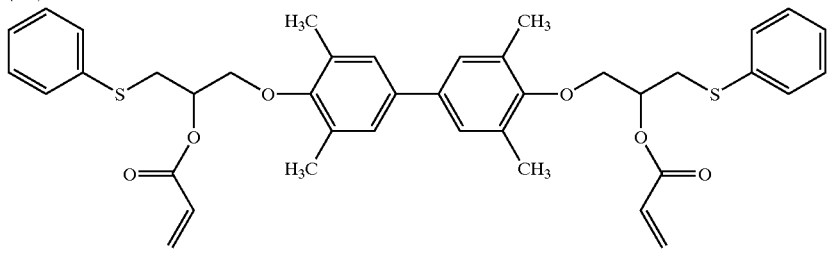

EXAMPLE 73

The sulfur-containing dihydroxy compound (31.6 g, 0.05 mol) represented by formula (2-5) prepared in Example 10 was reacted as described in Example 71 and then purified by column chromatography to give 34.7 g of a sulfur-containing acrylate compound represented by formula (1-7) (Compound 127 in Table 1) as a viscous colorless transparent oil.

Yield: 94%; purity: 99.6% (an area method based on HPLC analysis). Elementary analysis and mass spectrometry results for the product are as follows.

| Analysis for $C_{34}H_{42}O_6S_6$ | | | |
|---|---|---|---|
| | C | H | S |
| Calcd. (%) | 55.25 | 5.73 | 26.03 |
| Found (%) | 55.30 | 5.75 | 26.00 |

FD-MS: 739 (M+).

(1-7)

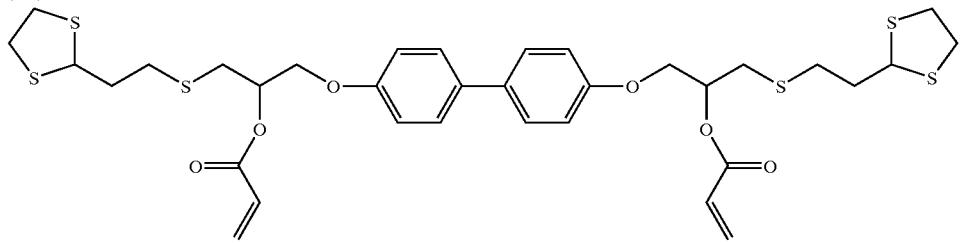

EXAMPLE 74

The sulfur-containing dihydroxy compound (34.4 g, 0.05 mol) represented by formula (2-8) prepared in Example 13 was reacted as described in Example 71 and then purified by column chromatography to give 32.4 g of a sulfur-containing acrylate compound represented by formula (1-8) (Compound 117 in Table 1) as a viscous colorless transparent oil.

Yield: 95%; purity: 99.7% (an area method based on HPLC analysis). Elementary analysis and mass spectrometry results for the product are as follows.

|  | Analysis for $C_{38}H_{50}O_6S_6$ | | |
|---|---|---|---|
|  | C | H | S |
| Calcd. (%) | 57.40 | 6.34 | 24.19 |
| Found (%) | 57.37 | 6.37 | 24.20 |

FD-MS: 795 (M⁺).

(1-8)

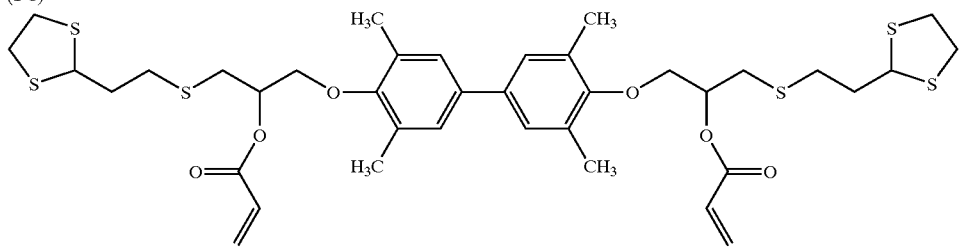

EXAMPLE 75

The procedure described in Example 74 was repeated except substituting methacrylic chloride for acrylic chloride to give a sulfur-containing methacrylate compound represented by formula (1-9) (Compound 141 in Table 1) as a colorless transparent oil.

Elementary analysis and mass spectrometry results for the product are as follows.

|  | Analysis for $C_{40}H_{54}O_6S_6$ | | |
|---|---|---|---|
|  | C | H | S |
| Calcd. (%) | 58.36 | 6.61 | 23.37 |
| Found (%) | 58.39 | 6.63 | 23.39 |

FD-MS: 823 (M⁺).

(1-9)

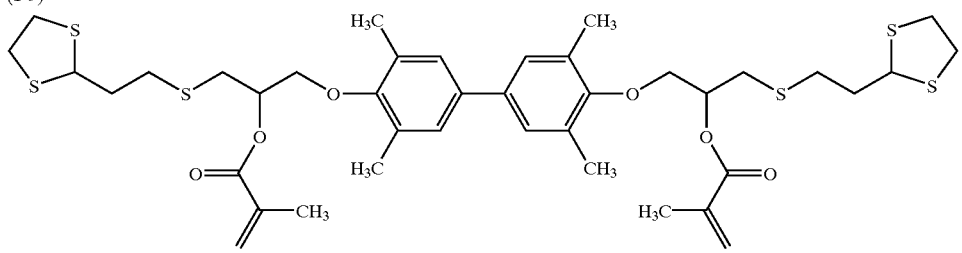

EXAMPLE 76

The sulfur-containing dihydroxy compound (41.3 g, 0.05 mol) represented by formula (2-11) prepared in Example 16 was reacted as described in Example 71 and then purified by column chromatography to give 44.4 g of a sulfur-containing acrylate compound represented by formula (1-10) (Compound 129 in Table 1) as a viscous colorless transparent oil.

Yield: 98%; purity: 99.8% (an area method based on HPLC analysis). Elementary analysis and mass spectrometry results for the product are as follows.

| Analysis for $C_{30}H_{34}Br_4O_8S_2$ | | | | |
|---|---|---|---|---|
| | C | H | Br | S |
| Calcd. (%) | 39.79 | 3.78 | 35.26 | 7.08 |
| Found (%) | 39.82 | 3.78 | 35.30 | 7.09 |

FD-MS: 907 (M⁺).

(1-10)

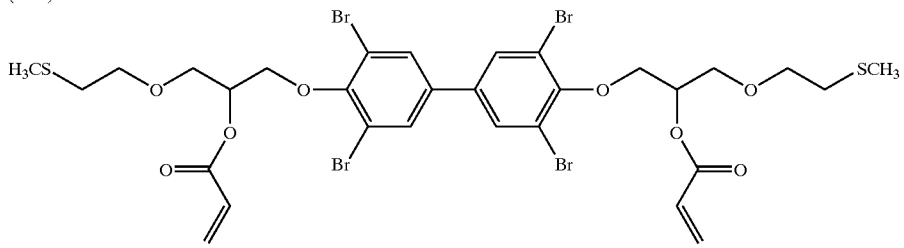

EXAMPLE 77

To a solution of 28.0 g of the sulfur-containing dihydroxy compound represented by formula (2-12) prepared in Example 17 (0.05 mol) and 9.5 g of pyridine (0.12 mol) in 100 g of chloroform was added dropwise under ice-cooling (10° C.) 9.95 g of acrylic chloride (0.11 mol). After addition, the reaction was stirred at 10° C. for additional 3 hours. Then, pyridine hydrochloride as a byproduct was removed by filtration. The filtrate (chloroform solution) was further washed with 100 g of a diluted aqueous hydrochloric acid solution, washed with water until a wastewater became neutral, and separated. The chloroform in the organic layer was evaporated in vacuo at 60° C. to give a crude product as pale yellow transparent oil. The crude product was purified by silica gel chromatography to give 30.7 g of a sulfur-containing acrylate compound represented by formula (1-11) (Compound 190 in Table 1) as a viscous colorless transparent oil.

Yield: 92%; purity: 99.0% or higher (an area method based on HPLC analysis). Elementary analysis and mass spectrometry results for the product are as follows.

EXAMPLE 78

The sulfur-containing dihydroxy compound (32.0 g, 0.05 mol) represented by formula (2-13) prepared in Example 18 was reacted as described in Example 77 and then purified by column chromatography to give 34.8 g of a sulfur-containing acrylate compound represented by formula (1-12) (Compound 192 in Table 1) as a viscous colorless transparent oil.

Yield: 93%; purity: 99.5% (an area method based on HPLC analysis). Elementary analysis and mass spectrometry results for the product are as follows.

| Analysis for $C_{39}H_{40}O_6S_2$ | | | |
|---|---|---|---|
| | C | H | S |
| Calcd. (%) | 70.03 | 6.03 | 9.59 |
| Found (%) | 70.06 | 6.05 | 9.60 |

FD-MS: 669 (M⁺).

(1-11)

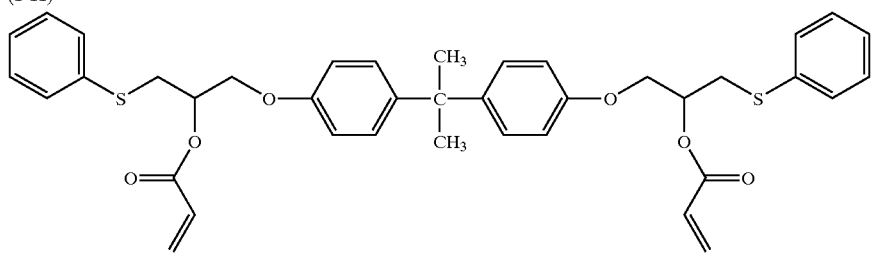

| Analysis for $C_{35}H_{40}O_{10}S_4$ | | | |
|---|---|---|---|
| | C | H | S |
| Calcd. (%) | 56.13 | 5.38 | 17.12 |
| Found (%) | 56.11 | 5.39 | 17.14 |

FD-MS: 749 (M$^+$).

(1-12)

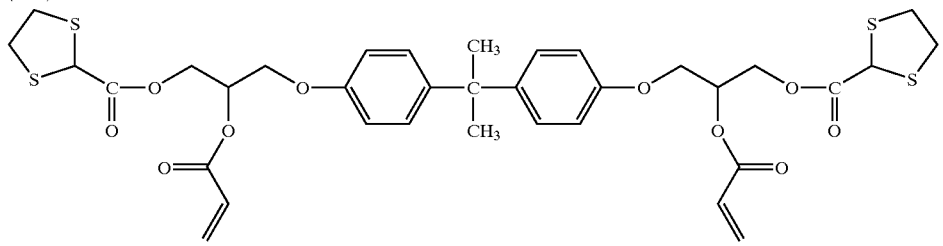

EXAMPLE 79

The sulfur-containing dihydroxy compound (33.6 g, 0.05 mol) represented by formula (2-14) prepared in Example 19 was reacted as described in Example 77 and then purified by column chromatography to give 36.7 g of a sulfur-containing acrylate compound represented by formula (1-13) (Compound 191 in Table 1) as a viscous colorless transparent oil.

Yield: 94%; purity: 99.5% (an area method based on HPLC analysis). Elementary analysis and mass spectrometry results for the product are as follows.

| Analysis for $C_{37}H_{48}O_6S_6$ | | | |
|---|---|---|---|
| | C | H | S |
| Calcd. (%) | 56.89 | 6.19 | 24.63 |
| Found (%) | 56.86 | 6.21 | 24.60 |

FD-MS: 781 (M$^+$).

(1-13)

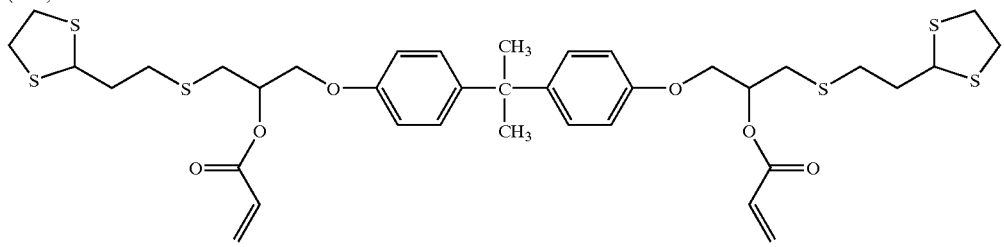

EXAMPLE 80

The sulfur-containing dihydroxy compound (30.8 g, 0.05 mol) represented by formula (2-15) prepared in Example 20 was reacted as described in Example 77 and then purified by column chromatography to give 32.9 g of a sulfur-containing acrylate compound represented by formula (1-14) (Compound 182 in Table 1) as a viscous colorless transparent oil.

Yield: 91%; purity: 99.2% (an area method based on HPLC analysis). Elementary analysis and mass spectrometry results for the product are as follows.

| Analysis for $C_{43}H_{48}O_6S_2$ | | | |
|---|---|---|---|
| | C | H | S |
| Calcd. (%) | 71.24 | 6.67 | 8.85 |
| Found (%) | 71.29 | 6.70 | 8.82 |
| FD-MS: 725 (M⁺). | | | |

(1-14)

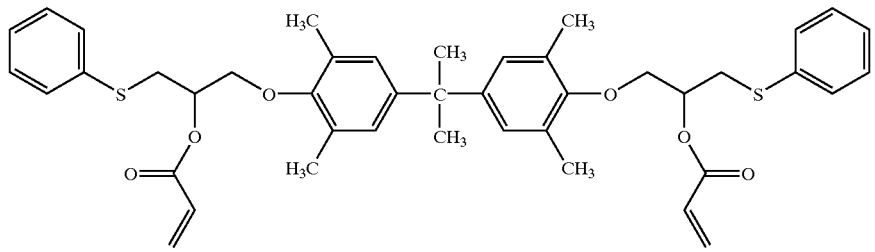

EXAMPLE 81

The procedure described in Example 79 was repeated except substituting methacrylic chloride for acrylic chloride to give a sulfur-containing methacrylate compound represented by formula (1-15) (Compound 205 in Table 1) as a colorless transparent oil.

Elementary analysis and mass spectrometry results for the product are as follows.

| Analysis for $C_{39}H_{52}O_6S_6$ | | | |
|---|---|---|---|
| | C | H | S |
| Calcd. (%) | 57.89 | 6.48 | 23.77 |
| Found (%) | 57.89 | 6.45 | 23.79 |
| FD-MS: 809 (M⁺). | | | |

(1-15)

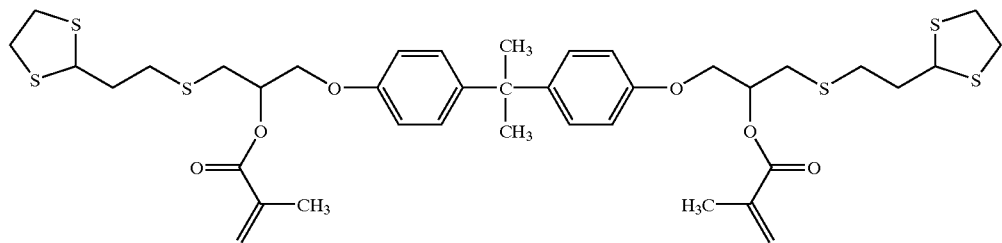

EXAMPLE 82

The sulfur-containing dihydroxy compound (34.8 g, 0.05 mol) represented by formula (2-16) prepared in Example 21 was reacted as described in Example 77 and then purified by column chromatography to give 38.2 g of a sulfur-containing acrylate compound represented by formula (1-16) (Compound 185 in Table 1) as a viscous colorless transparent oil.

Yield: 95%; purity: 99.1% (an area method based on HPLC analysis). Elementary analysis and mass spectrometry results for the product are as follows.

| Analysis for $C_{39}H_{48}O_{10}S_4$ | | | |
|---|---|---|---|
| | C | H | S |
| Calcd. (%) | 58.19 | 6.01 | 15.93 |
| Found (%) | 58.21 | 6.03 | 15.89 |
| FD-MS: 805 (M⁺). | | | |

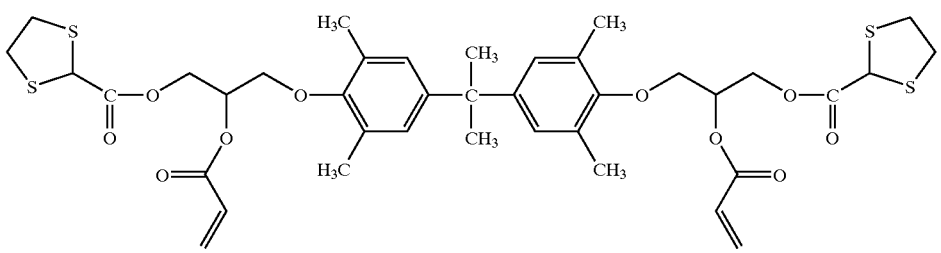

(1-16)

EXAMPLE 83

The sulfur-containing dihydroxy compound (26.2 g, 0.05 mol) represented by formula (2-17) prepared in Example 22 was reacted as described in Example 77 and then purified by column chromatography to give 30.4 g of a sulfur-containing acrylate compound represented by formula (1-17) as a viscous colorless transparent oil.

Yield: 96%; purity: 99.5% (an area method based on HPLC analysis). Elementary analysis and mass spectrometry results for the product are as follows.

| Analysis for $C_{33}H_{44}O_8S_2$ | | | |
|---|---|---|---|
| | C | H | S |
| Calcd. (%) | 62.63 | 7.01 | 10.13 |
| Found (%) | 62.62 | 7.05 | 10.09 |
| FD-MS: 633 (M⁺). | | | |

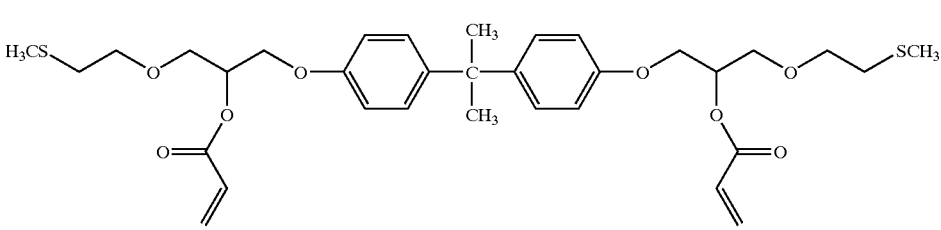

(1-17)

EXAMPLE 84

The sulfur-containing dihydroxy compound (39.6 g, 0.05 mol) represented by formula (2-18) prepared in Example 23 was reacted as described in Example 77 and then purified by column chromatography to give 42.8 g of a sulfur-containing acrylate compound represented by formula (1-18) as a viscous colorless transparent oil.

Yield: 95%; purity: 99.4% (an area method based on HPLC analysis). Elementary analysis and mass spectrometry results for the product are as follows.

| Analysis for $C_{41}H_{56}O_{10}S_6$ | | | |
|---|---|---|---|
| | C | H | S |
| Calcd. (%) | 54.64 | 6.26 | 21.35 |
| Found (%) | 54.63 | 6.28 | 21.39 |
| FD-MS: 901 (M⁺). | | | |

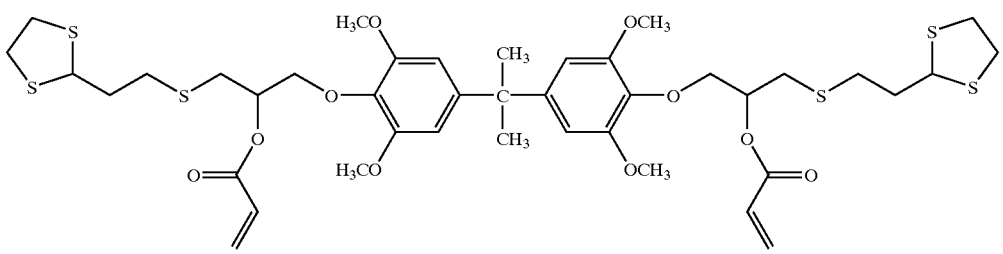

(1-18)

EXAMPLE 85

The sulfur-containing dihydroxy compound (32.8 g, 0.05 mol) represented by formula (2-19) prepared in Example 24 was reacted as described in Example 77 and then purified by column chromatography to give 42.7 g of a sulfur-containing acrylate compound represented by formula (1-19) (Compound 193 in Table 1) as a viscous colorless transparent oil.

Yield: 90%; purity: 99.1% (an area method based on HPLC analysis). Elementary analysis and mass spectrometry results for the product are as follows.

| Analysis for $C_{33}H_{40}Br_4O_8S_2$ | | | | |
|---|---|---|---|---|
| | C | H | Br | S |
| Calcd. (%) | 41.79 | 4.25 | 33.70 | 6.76 |
| Found (%) | 41.73 | 4.29 | 33.71 | 6.75 |
| FD-MS: 949 (M⁺). | | | | |

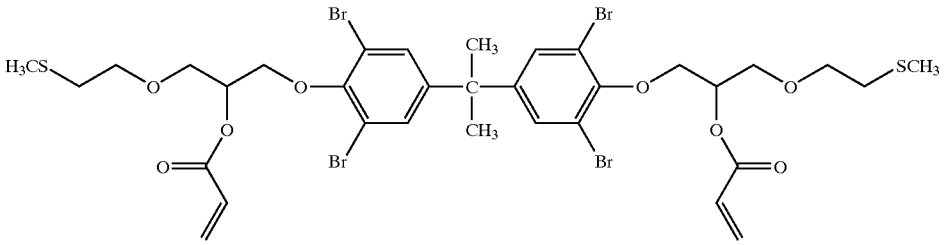

(1-19)

EXAMPLES 86 TO 142

Sulfur-containing unsaturated carboxylate compounds represented by general formula (1) of this invention shown in Table 5 were prepared as described in any of Examples 67 to 85.

TABLE 5

| Example No. | Structure | FD-MS |
|---|---|---|
| 86 | 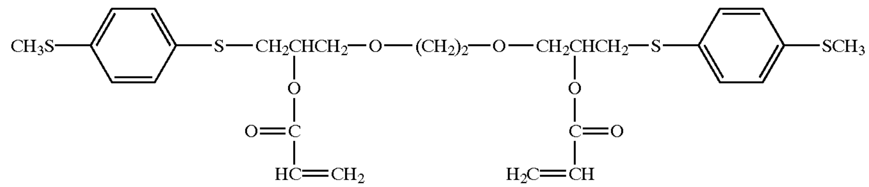 | 595 (M⁺) C₂₈H₃₄O₆S₄ |
| 87 | 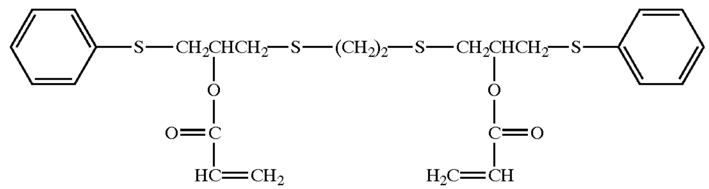 | 535 (M⁺) C₂₆H₃₀O₄S₄ |
| 88 | 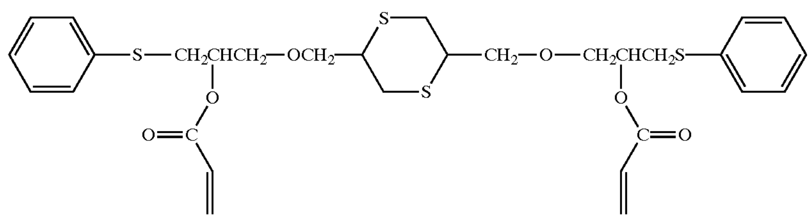 | 621 (M⁺) C₃₀H₃₆O₆S₄ |
| 89 | 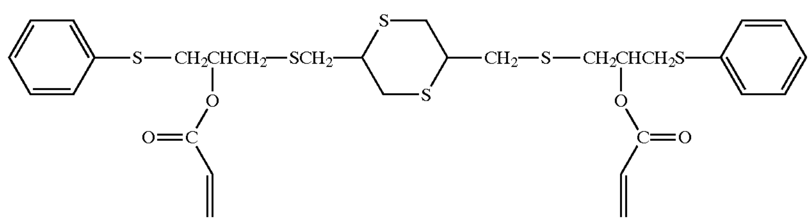 | 653 (M⁺) C₃₀H₃₆O₄S₆ |

TABLE 5-continued

| Example No. | Structure | FD-MS |
|---|---|---|
| 90 | 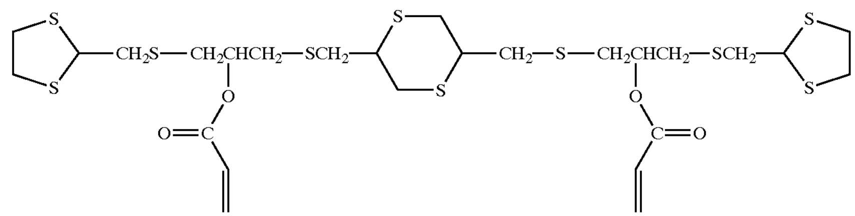 | 737 (M+) $C_{26}H_{40}O_4S_{10}$ |
| 91 | 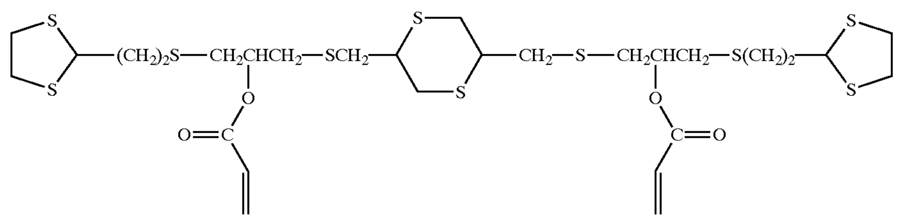 | 765 (M+) $C_{28}H_{44}O_4S_{10}$ |
| 92 | 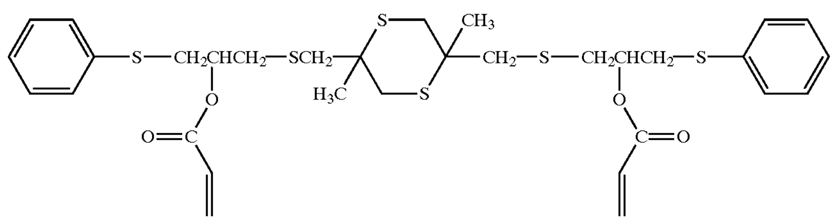 | 681 (M+) $C_{32}H_{40}O_4S_6$ |
| 93 | 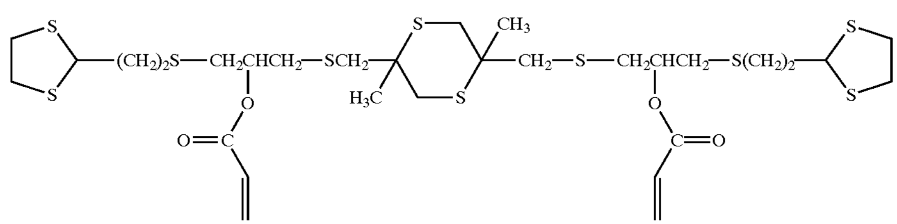 | 793 (M+) $C_{30}H_{48}O_4S_{10}$ |

TABLE 5-continued

| Example No. | Structure | FD-MS |
|---|---|---|
| 94 | 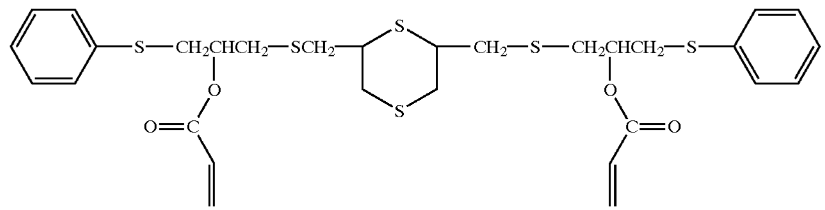 | 653 (M⁺) $C_{30}H_{36}O_4S_6$ |
| 95 | 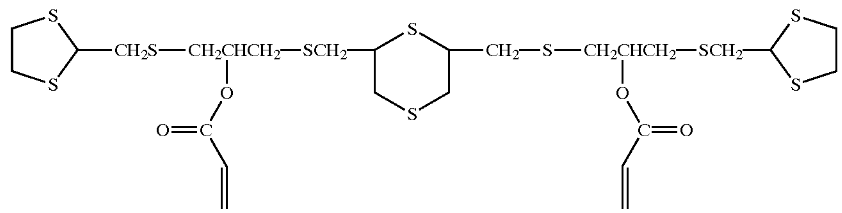 | 737 (M⁺) $C_{26}H_{40}O_4S_{10}$ |
| 96 | 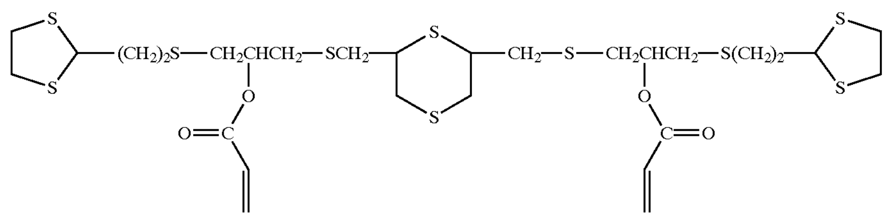 | 765 (M⁺) $C_{28}H_{44}O_4S_{10}$ |
| 97 | 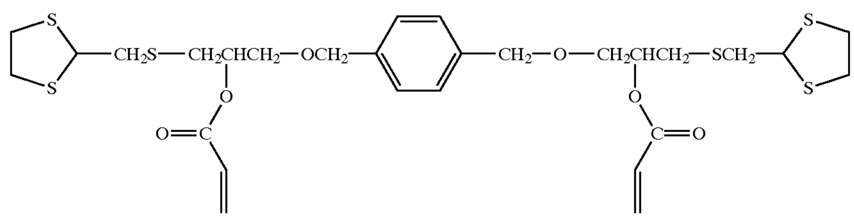 | 663 (M⁺) $C_{28}H_{38}O_6S_6$ |

TABLE 5-continued

| Example No. | Structure | FD-MS |
|---|---|---|
| 98 | 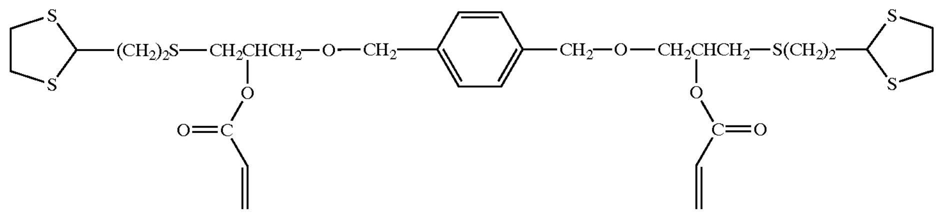 | 691 (M⁺) $C_{30}H_{42}O_6S_6$ |
| 99 | 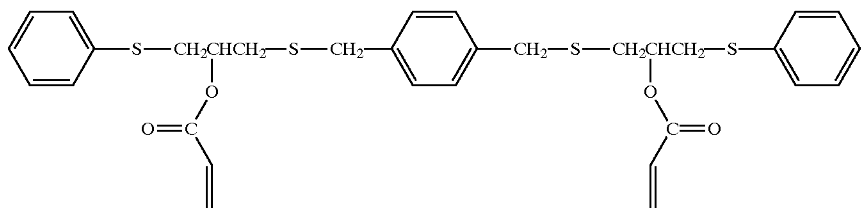 | 611 (M⁺) $C_{32}H_{34}O_4S_4$ |
| 100 | 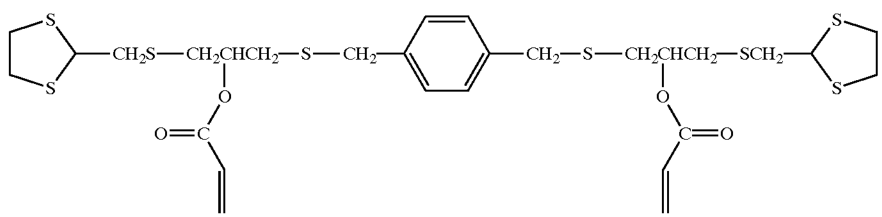 | 695 (M⁺) $C_{28}H_{38}O_4S_8$ |
| 101 | 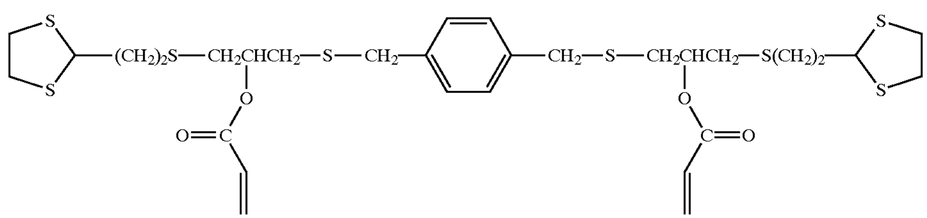 | 723 (M⁺) $C_{30}H_{42}O_4S_8$ |

TABLE 5-continued

| Example No. | Structure | FD-MS |
|---|---|---|
| 102 | 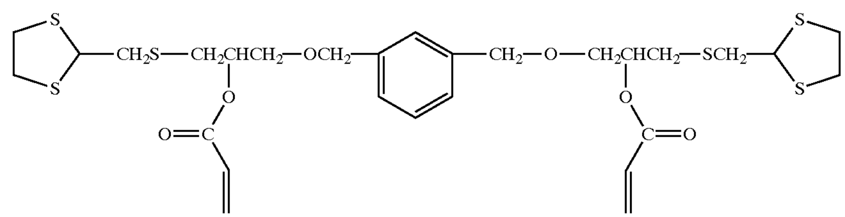 | 663 (M⁺) $C_{28}H_{38}O_6S_6$ |
| 103 | 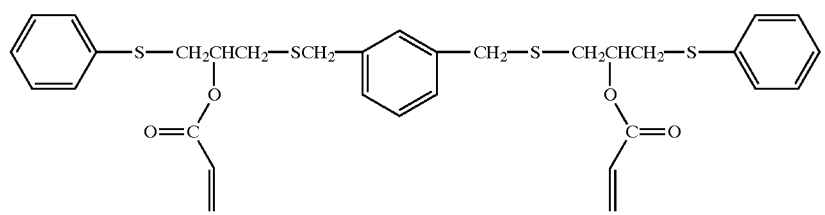 | 611 (M⁺) $C_{32}H_{34}O_4S_4$ |
| 104 | 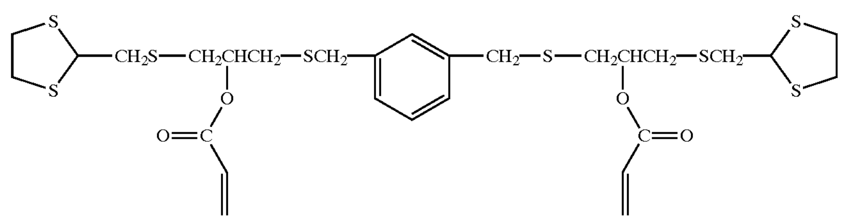 | 695 (M⁺) $C_{28}H_{38}O_4S_8$ |
| 105 | 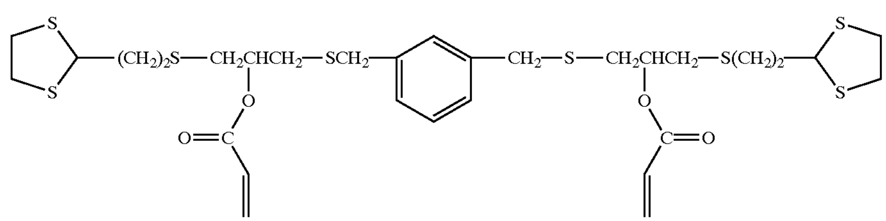 | 723 (M⁺) $C_{30}H_{42}O_4S_8$ |

TABLE 5-continued

| Example No. | Structure | FD-MS |
|---|---|---|
| 106 | (1,3-dithiolan-2-yl)-CH2S-CH2CHCH2-O-OC-C6H4(para)-CO-O-CH2CHCH2-SCH2-(1,3-dithiolan-2-yl), with acrylate esters on the CHCH2-O groups | 691 (M+) $C_{28}H_{34}O_8S_6$ |
| 107 | (1,3-dithiolan-2-yl)-(CH2)2S-CH2CHCH2-O-OC-C6H4(para)-CO-O-CH2CHCH2-S(CH2)2-(1,3-dithiolan-2-yl), with acrylate esters on the CHCH2-O groups | 719 (M+) $C_{30}H_{38}O_8S_6$ |
| 108 | (1,3-dithiolan-2-yl)-CH2S-CH2CHCH2-O-OC-C6H4(meta)-CO-O-CH2CHCH2-SCH2-(1,3-dithiolan-2-yl), with acrylate esters on the CHCH2-O groups | 691 (M+) $C_{28}H_{34}O_8S_6$ |
| 109 | (1,3-dithiolan-2-yl)-(CH2)2S-CH2CHCH2-O-OC-C6H4(meta)-CO-O-CH2CHCH2-S(CH2)2-(1,3-dithiolan-2-yl), with acrylate esters on the CHCH2-O groups | 719 (M+) $C_{30}H_{38}O_8S_6$ |

TABLE 5-continued

| Example No. | Structure | FD-MS |
|---|---|---|
| 110 | 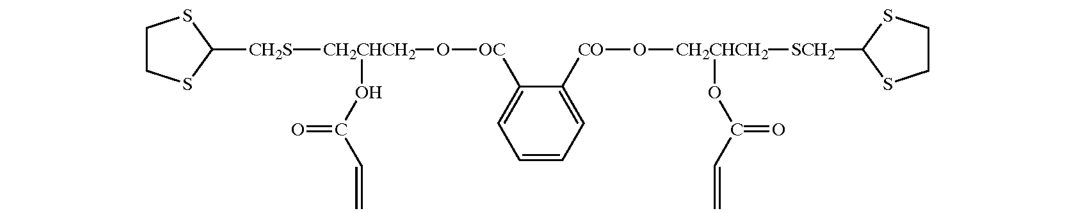 | 691 (M$^+$) C$_{28}$H$_{34}$O$_8$S$_6$ |
| 111 | 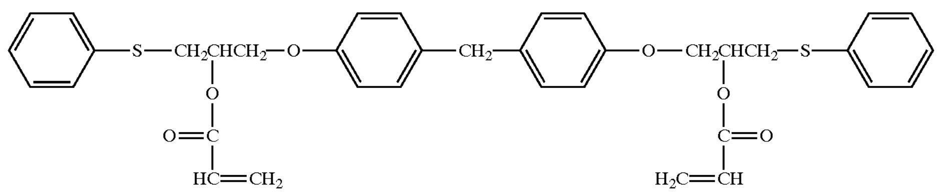 | 641 (M$^+$) C$_{37}$H$_{36}$O$_6$S$_2$ |
| 112 | 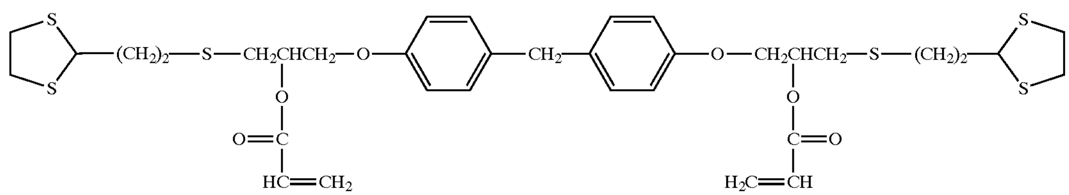 | 753 (M$^+$) C$_{35}$H$_{44}$O$_6$S$_6$ |
| 113 | 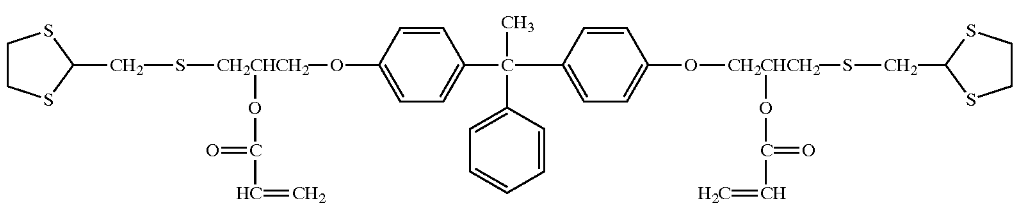 | 815 (M$^+$) C$_{40}$H$_{46}$O$_6$S$_6$ |
| 114 | 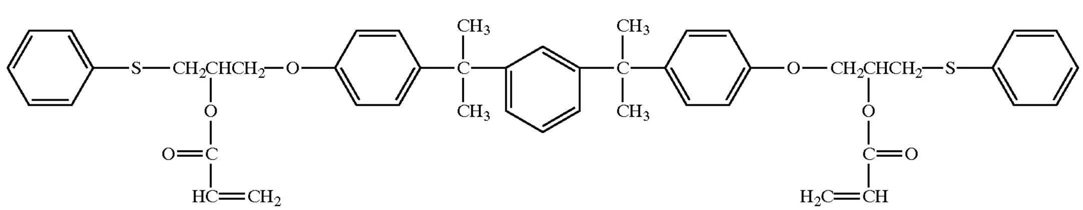 | 787 (M$^+$) C$_{48}$H$_{50}$O$_6$S$_2$ |

TABLE 5-continued

| Example No. | Structure | FD-MS |
|---|---|---|
| 115 | 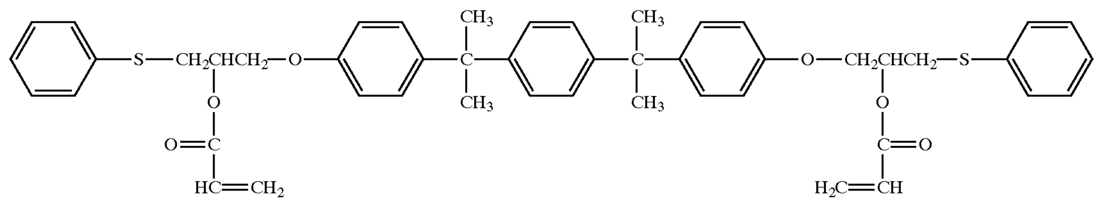 | 787 (M+) $C_{48}H_{50}O_6S_2$ |
| 116 | 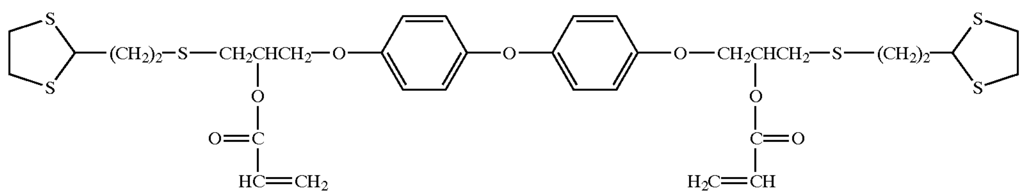 | 755 (M+) $C_{34}H_{42}O_7S_6$ |
| 117 | 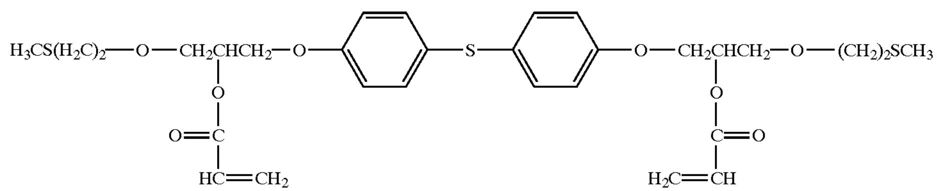 | 623 (M+) $C_{30}H_{38}O_8S_3$ |
| 118 | 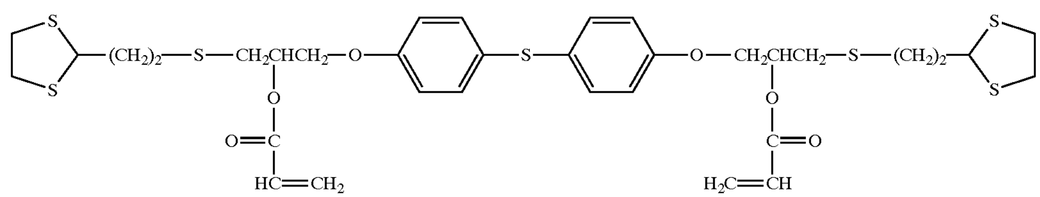 | 771 (M+) $C_{34}H_{42}O_6S_7$ |
| 119 | 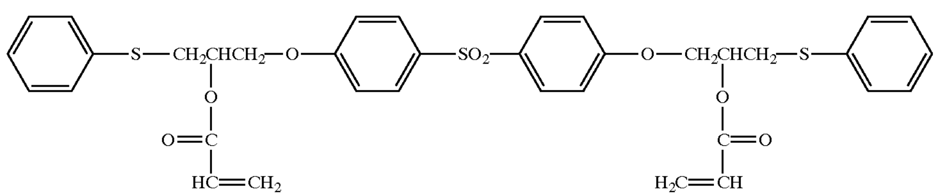 | 691 (M+) $C_{36}H_{34}O_8S_3$ |

TABLE 5-continued
| Example No. | Structure | FD-MS |
|---|---|---|
| 120 | 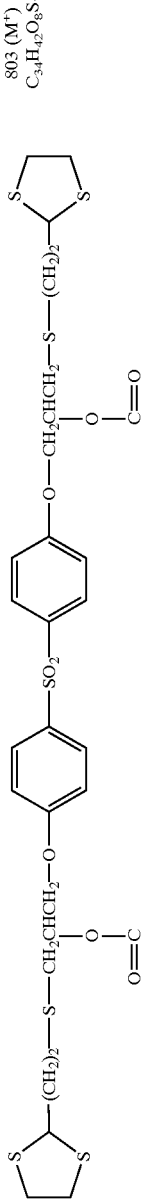 | 803 (M+) $C_{34}H_{42}O_8S_7$ |
| 121 | 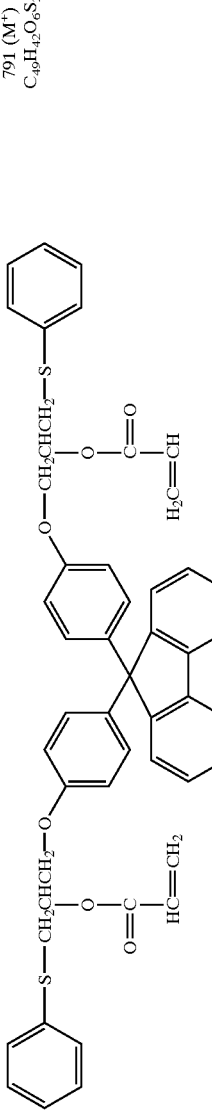 | 791 (M+) $C_{49}H_{42}O_6S_2$ |
| 122 | 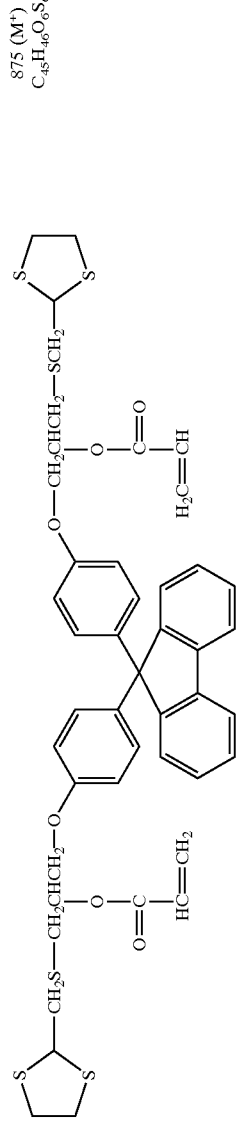 | 875 (M+) $C_{45}H_{46}O_6S_6$ |
| 123 | 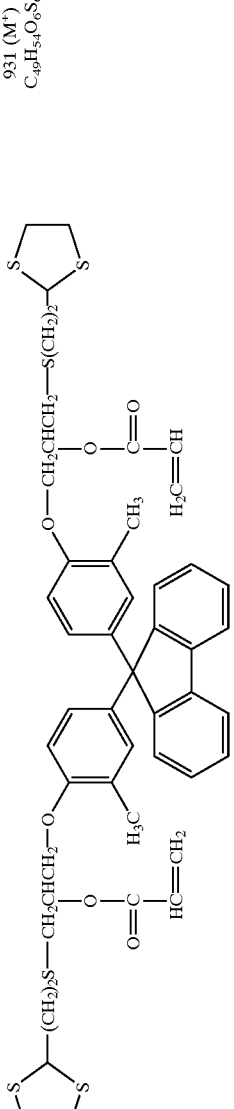 | 931 (M+) $C_{49}H_{54}O_6S_6$ |

TABLE 5-continued

| Example No. | Structure | FD-MS |
|---|---|---|
| 124 | 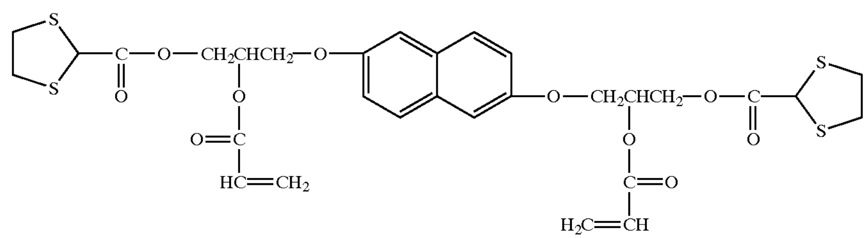 | 681 (M⁺) $C_{30}H_{32}O_{10}S_4$ |
| 125 | 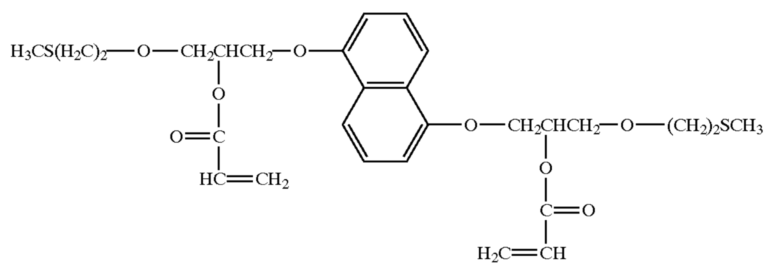 | 565 (M⁺) $C_{28}H_{36}O_8S_2$ |
| 126 | 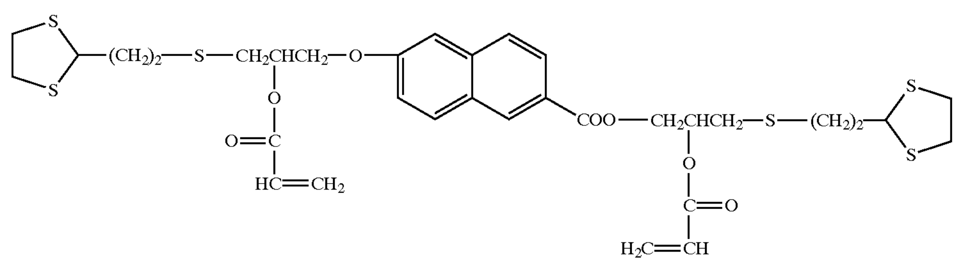 | 741 (M⁺) $C_{33}H_{40}O_7S_6$ |

TABLE 5-continued

| Example No. | Structure | FD-MS |
|---|---|---|
| 127 | 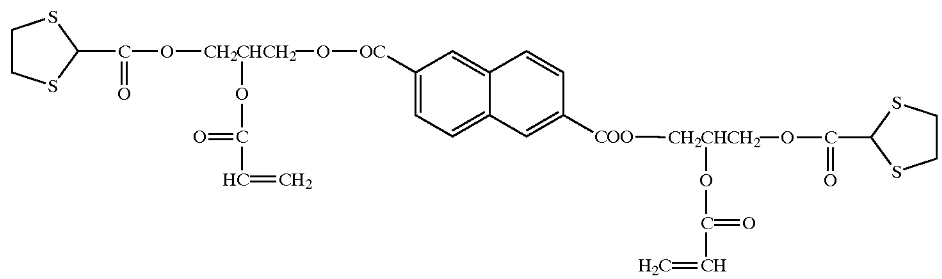 | 737 (M$^+$) C$_{32}$H$_{32}$O$_{12}$S$_4$ |
| 128 | 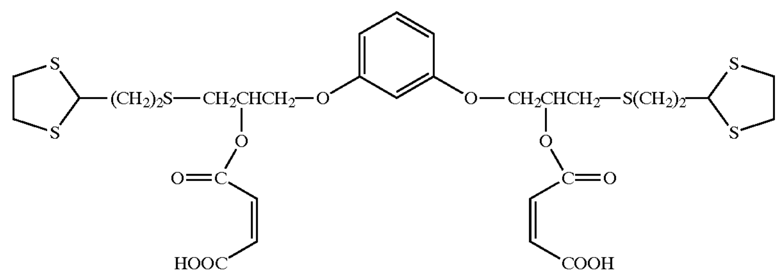 | 751 (M$^+$) C$_{30}$H$_{38}$O$_{10}$S$_6$ |
| 129 | 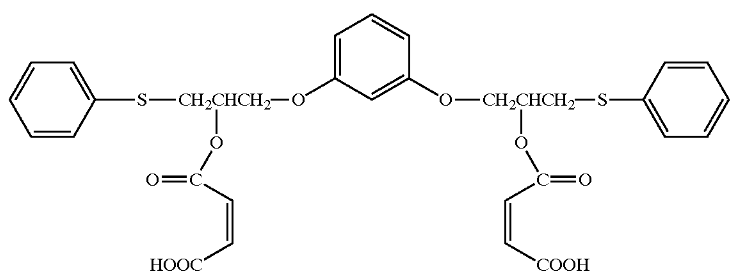 | 639 (M$^+$) C$_{32}$H$_{30}$O$_{10}$S$_2$ |

TABLE 5-continued

| Example No. | Structure | FD-MS |
|---|---|---|
| 130 | 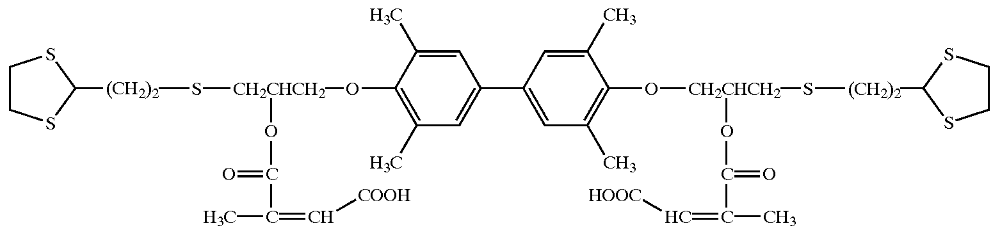 | 911 (M⁺) $C_{42}H_{54}O_{10}S_6$ |
| 131 | 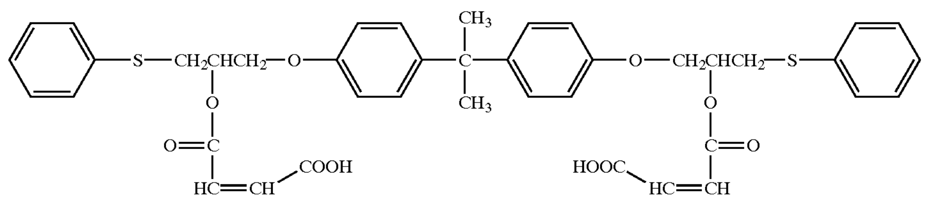 | 757 (M⁺) $C_{41}H_{40}O_{10}S_2$ |
| 132 | 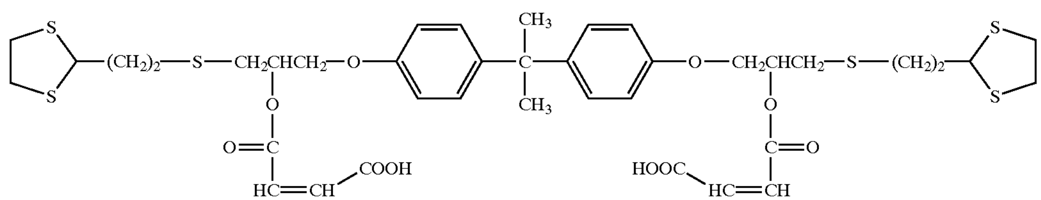 | 869 (M⁺) $C_{39}H_{48}O_{10}S_6$ |
| 133 | 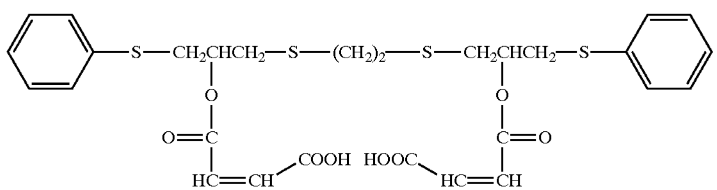 | 623 (M⁺) $C_{28}H_{30}O_8S_4$ |

TABLE 5-continued

| Example No. | Structure | FD-MS |
|---|---|---|
| 134 | 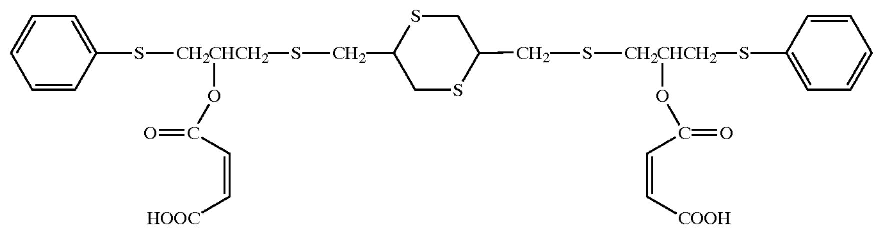 | 741 (M⁺) $C_{32}H_{36}O_8S_6$ |
| 135 | 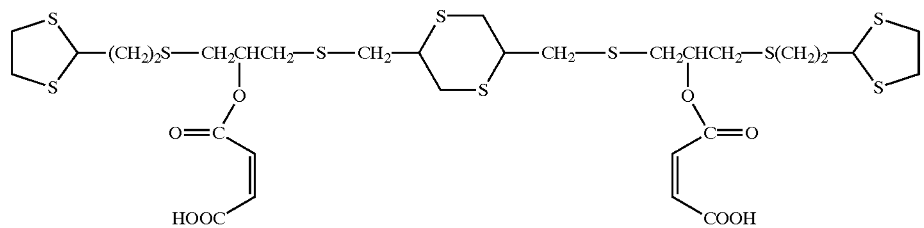 | 853 (M⁺) $C_{30}H_{44}O_8S_{10}$ |
| 136 | 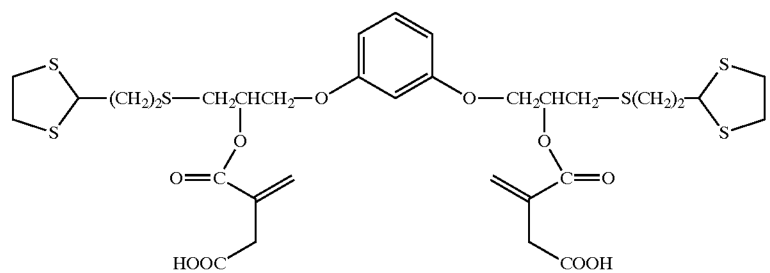 | 779 (M⁺) $C_{32}H_{42}O_{10}S_6$ |

TABLE 5-continued

| Example No. | Structure | FD-MS |
|---|---|---|
| 137 | 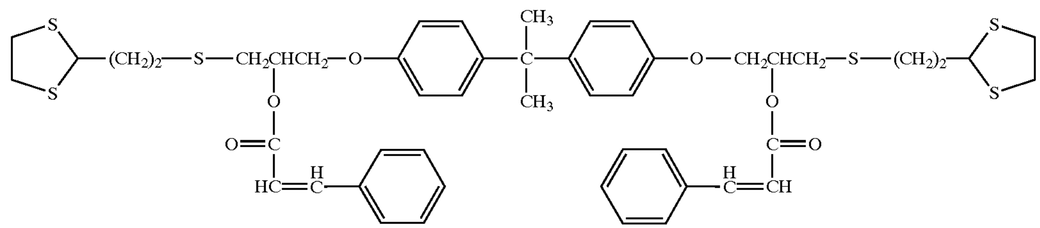 | 933 (M$^+$) C$_{49}$H$_{56}$O$_6$S$_6$ |
| 138 | 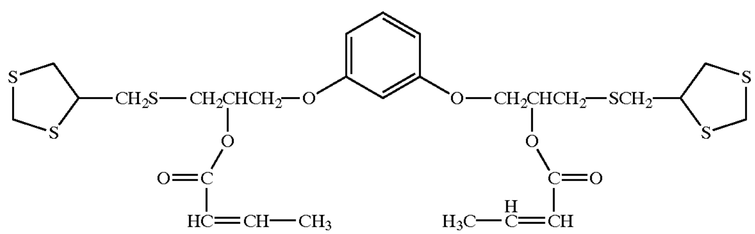 | 663 (M$^+$) C$_{28}$H$_{38}$O$_6$S$_6$ |
| 139 | 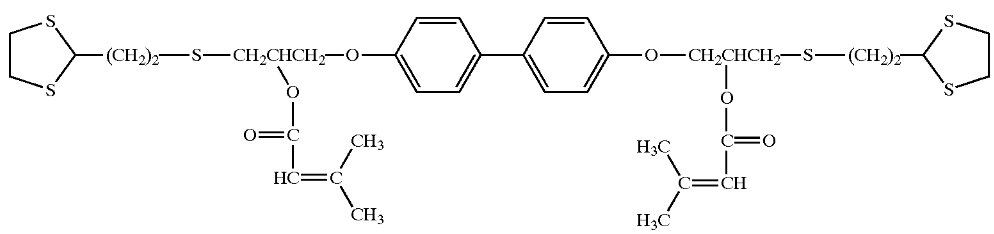 | 795 (M$^+$) C$_{38}$H$_{50}$O$_6$S$_6$ |
| 140 | 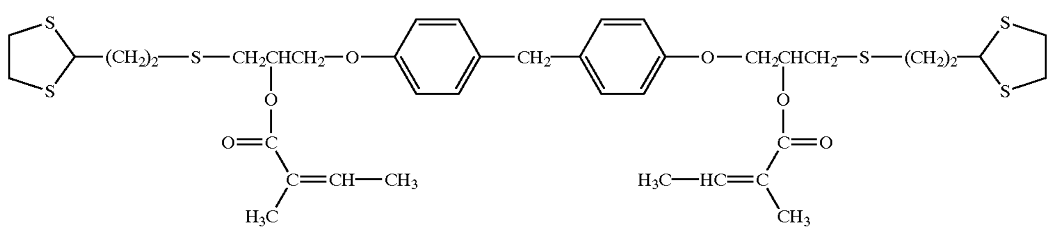 | 809 (M$^+$) C$_{39}$H$_{52}$O$_6$S$_6$ |

TABLE 5-continued

| Example No. | Structure | FD-MS |
|---|---|---|
| 141 | 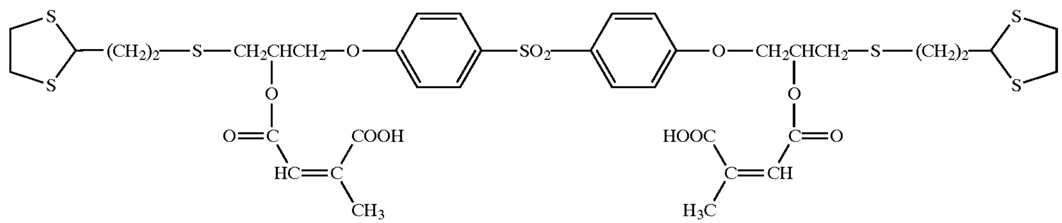 | 919 (M+) $C_{38}H_{46}O_{12}S_7$ |
| 142 | 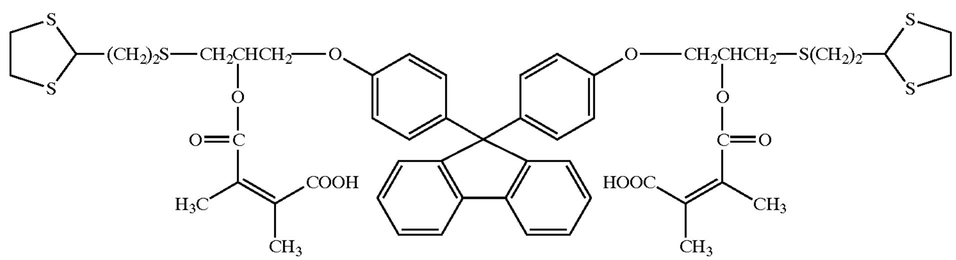 | 1047 (M+) $C_{53}H_{58}O_{10}S_6$ |

Preparation of a Polymerizable Composition Using a Sulfur-containing Unsaturated Carboxylate Compound Represented by General Formula (1) of This Invention, Preparation of a Cured Product by Curing the Composition, and Evaluation of the Physical Properties of the Cured Product Physical properties of cured products and optical components (lenses) prepared in the following examples were evaluated as follows.

Appearance: A color and transparency were visually determined.

Refractive index, Abbe number: these were determined at 20° C. using a Pulfrich refractometer.

EXAMPLE 143

To 30 g of the sulfur-containing acrylate compound represented by formula (1-1) prepared in Example 67 was added 30 mg of 2-hydroxy-2-methyl-1-phenylpropan-1-one (DAROCUR®-1173; Ciba-Geigy) as a photoinitiator, and the reaction was fully mixed to be a solution. The solution was fully defoamed in vacuo and injected in a mold consisting of glass templates and a gasket. The mold was irradiated by UV for 60 sec. using a metal halide lamp (80 W/cm) for polymerization. After polymerization, the mold was slowly cooled and then a cured molding was removed from the mold.

The cured product was colorless and transparent, and optical strain was not observed. A refractive index (nd) and an Abbe number (vd) were 1.614 and 30.0, respectively.

EXAMPLES 144 TO 172

A cured product was obtained as described in Example 143, except substituting each of the sulfur-containing unsaturated carboxylate compounds represented by formulas (1-2) to (1-19) prepared in Examples 68 to 85 and shown in Table 5.

Physical properties for the cured moldings after polymerization are shown in Table 6.

TABLE 6

| Ex. No. | Sulfur-containing unsaturated carboxylate of this invention | Appearance | Refractive index (nd) | Abbe number (vd) |
| --- | --- | --- | --- | --- |
| 144 | Compd. of formula (1-2) prepared in Example 68 | Colorless, transparent | 1.616 | 39.8 |
| 145 | Compd. of formula (1-3) prepared in Example 69 | Colorless, transparent | 1.593 | 34.5 |
| 146 | Compd. of formula (1-4) prepared in Example 70 | Colorless, transparent | 1.601 | 31.5 |
| 147 | Compd. of formula (1-5) prepared in Example 71 | Colorless, transparent | 1.605 | 30.3 |
| 148 | Compd. of formula (1-6) prepared in Example 72 | Colorless, transparent | 1.611 | 30.5 |
| 149 | Compd. of formula (1-7) prepared in Example 73 | Colorless, transparent | 1.612 | 30.7 |
| 150 | Compd. of formula (1-8) prepared in Example 74 | Colorless, transparent | 1.610 | 32.5 |
| 151 | Compd. of formula (1-9) prepared in Example 75 | Colorless, transparent | 1.612 | 32.9 |
| 152 | Compd. of formula (1-10) prepared in Example 76 | Colorless, transparent | 1.612 | 32.5 |
| 153 | Compd. of formula (1-11) prepared in Example 77 | Colorless, transparent | 1.609 | 31.5 |
| 154 | Compd. of formula (1-12) prepared in Example 78 | Colorless, transparent | 1.601 | 30.8 |
| 155 | Compd. of formula (1-13) prepared in Example 79 | Colorless, transparent | 1.607 | 35.8 |
| 156 | Compd. of formula (1-14) prepared in Example 80 | Colorless, transarent | 1.606 | 33.7 |
| 157 | Compd. of formula (1-15) prepared in Example 81 | Colorless, transparent | 1.606 | 35.9 |
| 158 | Compd. of formula (1-16) prepared in Example 82 | Colorless, transparent | 1.600 | 32.0 |
| 159 | Compd. of formula (1-17) prepared in Example 83 | Colorless, transparent | 1.595 | 32.6 |
| 160 | Compd. of formula (1-18) prepared in Example 84 | Colorless, transparent | 1.606 | 34.6 |
| 161 | Compd. of formula (1-19) prepared in Example 85 | Colorless, transparent | 1.609 | 31.9 |
| 162 | Compd. prepared in Example 89 | Colorless, transparent | 1.649 | 32.8 |
| 163 | Compd. prepared in Example 91 | Colorless, transparent | 1.640 | 37.2 |
| 164 | Compd. prepared in Example 101 | Colorless, transparent | 1.643 | 35.3 |
| 165 | Compd. prepared in Example 112 | Colorless, transparent | 1.624 | 35.0 |
| 166 | Compd. prepared in Example 116 | Colorless, transparent | 1.623 | 34.9 |
| 167 | Compd. prepared in Example 118 | Colorless, transparent | 1.632 | 34.0 |
| 168 | Compd. prepared in Example 119 | Colorless, transparent | 1.626 | 31.4 |
| 169 | Compd. prepared in Example 120 | Colorless, transparent | 1.623 | 35.4 |
| 170 | Compd. prepared in Example 121 | Colorless, transparent | 1.649 | 28.9 |
| 171 | Compd. prepared in Example 122 | Colorless, transparent | 1.642 | 31.9 |
| 172 | Compd. prepared in Example 126 | Colorless, transparent | 1.640 | 37.2 |

The sulfur-containing unsaturated carboxylates of this invention could be cured (photopolymerized) by photoirradiation for a short time. The cured products had a higher refractive index and a higher Abbe number, and exhibited excellent heat resistance and shock resistance.

The physical properties for the cured products or optical components (lenses) prepared in the following examples were evaluated as follows.

1) Appearance: visually observed for color and transparency.

2) Refractive index and Abbe number: determined at 20° C. using a Pulfrich refractometer.

3) Impact resistance: evaluated according to the following rating after falling 28.7 g of an iron ball on the center of a minus lens with a central thickness of 1.5 mm from the height of 127 cm and observing the presence of cracks.

○: no cracks in a lens x: crack(s) in a lens

EXAMPLE 173

To a mixture of 20 g of the sulfur-containing acrylate compound represented by formula (1-2) prepared in Example 68, 5 g of an epoxyacrylate of resolcinol diglycidyl ether represented by formula (13-1) and 5 g of divinyl-benene (hereinafter, referred to as "DVB") was added 60 mg of 2-hydroxy-2-methyl-1-phenylpropan-1-one (0.2 wt % to the polymerizable monomer), and the reaction was fully mixed to be a solution. The solution was fully defoamed in vacuo and injected in a mold consisting of glass templates and a tape, which was shaped into a minus lens. The mold was irradiated by UV for 60 sec. using a metal halide lamp and then heated at 80° C. for an hour for polymerization. After polymerization, the mold was allowed to be cooled to a room temperature to give a minus lens with a diameter of 30 mm and a central thickness of 1.5 mm.

The lens was colorless and transparent, and had a refractive index (nd) of 1.611 and an Abbe number (vd) of 36.5. It exhibited a glass-transition temperature (Tg) of 110° C. by a TMA technique and depression was not observed. In a shock-resistance test as described above, no cracks were observed in the lens.

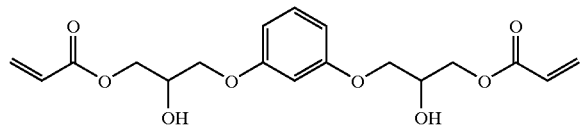

(13-1)

EXAMPLE 174

A minus lens was prepared as described in Example 173, except substituting 20 g of the sulfur-containing acrylate compound represented by formula (1-7) prepared in Example 73 and 5 g of an epoxyacrylate of 3,3',5,5'-tetramethyl-4,4'-diphenylglycidyloxybiphenyl represented by formula (13-2) for 20 g of the sulfur-containing acrylate compound represented by formula (1-2) and 5 g of the epoxyacrylate of resolcinol diglycidyl ether represented by formula (13-1).

The lens was colorless and transparent, and had a refractive index (nd) of 1.608 and an Abbe number (vd) of 33.3. It exhibited a glass-transition temperature (Tg) of 86° C. by a TMA technique and depression was not observed. In a shock-resistance test as described above, no cracks were observed in the lens.

EXAMPLE 175

A minus lens was prepared as described in Example 174, except substituting 5 g of ethyleneglycol dimethacrylate (hereinafter, referred to as "EGDMA") for DVB.

The lens was colorless and transparent, and had a refractive index (nd) of 1.595 and an Abbe number (vd) of 35.0. It exhibited a glass-transition temperature (Tg) of 71° C. by a TMA technique and depression was not observed. In a shock-resistance test as described above, no cracks were observed in the lens.

EXAMPLE 176

A minus lens was prepared as described in Example 174, except substituting 5 g of phenyl methacrylate (hereinafter, referred to as "PMA") for DVB.

The lens was colorless and transparent, and had a refractive index (nd) of 1.607 and an Abbe number (vd) of 34.9. It exhibited a glass-transition temperature (Tg) of 84° C. by a TMA technique and depression was not observed. In a shock-resistance test as described above, no cracks were observed in the lens.

EXAMPLE 177

A minus lens was prepared as described in Example 173, except substituting 20 g of the sulfur-containing acrylate compound represented by formula (1-13) prepared in Example 79 and 5 g of an epoxyacrylate of 2,2-bis(4-glycidyloxyphenyl)propane represented by formula (13-3) for 20 g of the sulfur-containing acrylate compound represented by formula (1-2) and 5 g of the epoxyacrylate of resolcinol diglycidyl ether represented by formula (13-1).

The lens was colorless and transparent, and had a refractive index (nd) of 1.607 and an Abbe number (vd) of 35.9. It exhibited a glass-transition temperature (Tg) of 81° C. by a TMA technique and depression was not observed. In a shock-resistance test as described above, no cracks were observed in the lens.

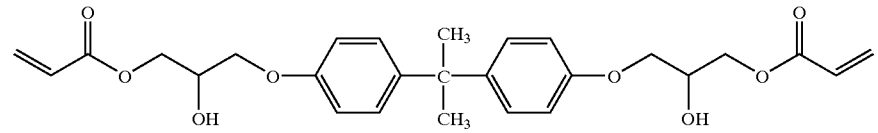

(13-3)

EXAMPLE 178

A minus lens was prepared as described in Example 177, except substituting 5 g of EGDMA for DVB.

The lens was colorless and transparent, and had a refractive index (nd) of 1.604 and an Abbe number (vd) of 36.4. It exhibited a glass-transition temperature (Tg) of 83° C. by a TMA technique and depression was not observed. In a shock-resistance test as described above, no cracks were observed in the lens.

EXAMPLE 179

A minus lens was prepared as described in Example 177, except substituting 5 g of PMA for DVB.

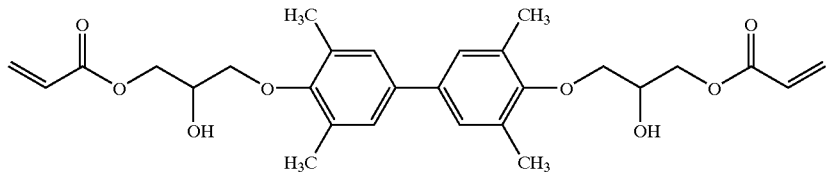

(13-2)

The lens was colorless and transparent, and had a refractive index (nd) of 1.610 and an Abbe number (vd) of 34.3. It exhibited a glass-transition temperature (Tg) of 80° C. by a TMA technique and depression was not observed. In a shock-resistance test as described above, no cracks were observed in the lens.

EXAMPLE 180

A minus lens was prepared as described in Example 177, except substituting 5 g of EGDMA for the epoxyacrylate represented by formula (13-3).

The lens was colorless and transparent, and had a refractive index (nd) of 1.607 and an Abbe number (vd) of 36.7. It exhibited a glass-transition temperature (Tg) of 89° C. by a TMA technique and. depression was not observed. In a shock-resistance test as described above, no cracks were observed in the lens.

EXAMPLES 181–186

A lens was prepared as described in Example 173, using each polymerizable composition with one of the composition ratios shown in Table 7. The lens was evaluated for physical properties, and the results are also shown in Table 7.

COMPARATIVE EXAMPLE 1

A polymerizable composition was prepared and a lens was formed as described in Example 173, except substituting 24 g of a known acrylate (described in JP-A 4-161410), 2,5-bis(acryloyloxyethylthiomethyl)-1,4-dithiane (hereinafter, referred to as "DTAET") and 6 g of dimethyloltricyclodecane acrylate (hereinafter, referred to as "DCPA"). The physical properties of the lens were evaluated and the results are shown in Table 7.

COMPARATIVE EXAMPLE 2

A polymerizable composition was prepared and a lens was formed as described in Example 173, except substituting 24 g of a known acrylate (described in JP-A 3-217412), 1,4-bis(2-methacryloyloxyethylthio)xylylene (hereinafter, referred to as "XDMET") and 6 g of 2,2-bis(4-methacryloxyethoxyphenyl)propane (hereinafter, referred to as "BSAM"). The physical properties of the lens were evaluated and the results are shown in Table 7.

COMPARATIVE EXAMPLE 3

A polymerizable composition was prepared and a lens was formed as described in Example 173, except substituting 18 g of a known acrylate (described in JP-A 63-248814), 1,3-bis[2-methacryloyloxy-3-(2,4,6-tribromophenoxy)propoxy]benzene (hereinafter, referred to as "BMPB") and 12 g of chlorostyrene (hereinafter, referred to as "CST"). The physical properties of the lens were evaluated and the results are shown in Table 7.

TABLE 7

| | Composition ratio of a polymerizable composition (by weight) | | Appearance | Ref. index (nd) | Abbe numb. (vd) | Tg (° C.) | Impact resistance |
|---|---|---|---|---|---|---|---|
| Ex. 181 | Compd of (1-1) Compd of (13-1) DVB | 20 5 5 | Colorless, Transparent | 1.609 | 31.3 | 110 | ○ |
| Ex. 182 | Compd of (1-2) Compd of (13-3) EGDMA | 30 5 5 | Colorless, Transparent | 1.601 | 40.0 | 100 | ○ |
| Ex. 183 | Compd of (1-3) Compd of (13-1) DVB | 20 5 5 | Colorless, Transparent | 1.593 | 34.4 | 90 | ○ |
| Ex. 184 | Compd of (1-4) Compd of (13-1) DVB | 20 5 5 | Colorless, Transparent | 1.605 | 32.0 | 115 | ○ |
| Ex. 185 | Compd of (1-1) Compd of (13-1) EGDMA | 20 5 5 | Colorless, Transparent | 1.595 | 33.1 | 90 | ○ |
| Ex. 186 | Compd of (1-4) Compd of (13-1) PMA | 20 5 2.5 | Colorless, Transparent | 1.605 | 33.0 | 110 | ○ |
| Comp. Ex. 1 | DTDET DCPA | 24 6 | Colorless, Transparent | 1.609 | 42.0 | 85 | x |
| Comp. Ex. 2 | XDMET BSAM | 24 6 | Colorless, Transparent | 1.588 | 39.0 | 85 | x |
| Comp. Ex. 3 | BMBP CST | 18 12 | Colorless, Transparent | 1.609 | 33.0 | 85 | x |

A cured product and an optical component prepared by polymerizing a polymerizable composition comprising a sulfur-containing unsaturated carboxylate of this invention has excellent optical, thermal and mechanical (Impact resistance) properties; can be produced by polymerization and molding/curing for a shorter period (a higher yield); and exhibits a higher refractive index.

What is claimed is:

1. A sulfur-containing unsaturated carboxylate compound represented by general formula (1):

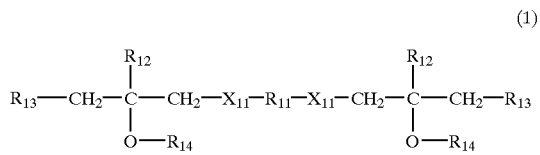

(1)

wherein $R_{11}$ represents a bivalent organic group represented by a formula selected from the group of formulas (3-a), (4-a), (5-a) and (6-a):

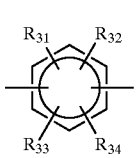

(3-a)

wherein $R_{31}$, $R_{32}$, $R_{33}$ and $R_{34}$ independently represents hydrogen, alkyl, alkoxy, nitro or halogen;

(4-a)

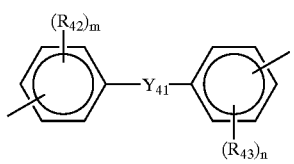

wherein $Y_{41}$ represents a single bond, $-C(R_{41})_2-$ (each $R_{41}$ independently represents hydrogen or methyl), $-O-$, $-S-$ or $-SO_2-$; $R_{42}$ and $R_{43}$ independently represent alkyl, alkenyl, aralkyl, aryl, alkoxy, alkylthio, nitro or halogen; m and n independently represent an integer of 0 to 4;

(5-a)

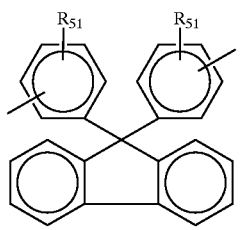

wherein each $R_{51}$ independently represents hydrogen or alkyl;

(6-a)

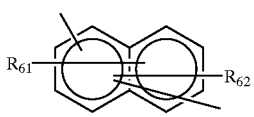

wherein $R_{61}$ and $R_{62}$ independently represent hydrogen or alkyl;
each $X_{11}$ independently represents oxygen, sulfur, $-COO-$ or $-(CH_2)_lX_{12}-$ ($X_{12}$ represents oxygen or sulfur and l is an integer of 1 to 3); each $R_{12}$ independently represents hydrogen or alkyl; each $R_{13}$ independently represents a sulfur-containing substituent represented by formula (7-a) or (8-a):

 (7-a)

wherein $R_{71}$ is a monovalent organic group containing at least one sulfur atom;

 (8-a)

wherein $R_{81}$ is a monovalent organic group optionally containing a sulfur atom; and each $R_{14}$ independently represents an $\alpha,\beta$-unsaturated carboxylate residue.

2. A process for preparing a sulfur-containing unsaturated carboxylate compound as claimed in claim 1 comprising reacting a sulfur-containing dihydroxy compound with an $\alpha,\beta$-unsaturated carboxylic acid derivative represented by general formula (2):

(2)

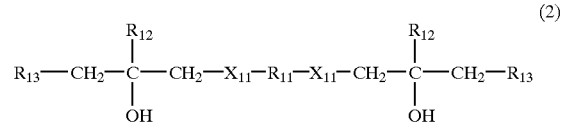

wherein $R_{11}$, $X_{11}$, $R_{12}$, and $R_{13}$ are same meanings of those of formula (1).

3. The sulfur-containing unsaturated carboxylate compound as claimed in claim 1 where the $\alpha,\beta$-unsaturated carboxylate residue is selected from the group consisting of (meth)acrylic acid, crotonic acid, tiglic acid, 3,3-dimethylacrylic acid, maleic acid, citraconic acid, 2,3-dimethylmaleic acid, itaconic acid and cinnamic acid residues.

4. The sulfur-containing unsaturated carboxylate compound as claimed in claim 1 where the sulfur-containing substituent $R_{13}$ is a moiety represented by formula (9-a):

(9-a)

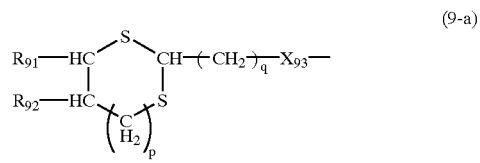

wherein $R_{91}$ and $R_{92}$ independently represent hydrogen or alkyl or $R_{91}$ and $R_{92}$ may be linked together to form a ring; $X_{93}$ represents oxygen or sulfur; p represents an integer of 0 to 3; and q represents an integer of 1 to 4.

5. The sulfur-containing unsaturated carboxylate compound as claimed in claim 1 where the bivalent organic group $R_{11}$ is represented by formula (3-a-i):

(3-a-i)

$X_{11}$ is oxygen, $-COO-$ or $-(CH_2)_lX_{12}$; and $R_{14}$ is a (meth)acrylic acid residue.

6. The sulfur-containing unsaturated carboxylate compound as claimed in claim 1 where the bivalent organic group $R_{11}$ is represented by formula (4a-i), (4-a-ii) or (4-a-iii):

(4-a-i)

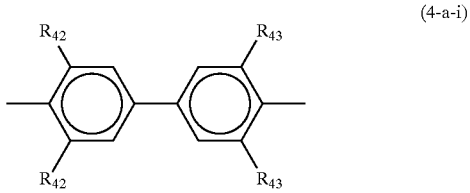

wherein $R_{42}$ and $R_{43}$ independently represent hydrogen or methyl;

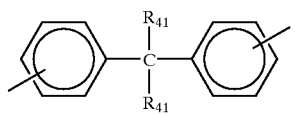

(4-a-ii)

wherein each $R_{41}$ independently represents hydrogen or methyl;

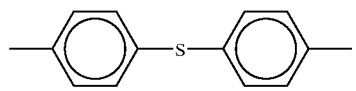

(4-a-iii)

$X_{11}$ is oxygen; and $R_{14}$ is a (meth)acrylic acid residue.

7. The sulfur-containing unsaturated carboxylate compound as claimed in claim 1 where the bivalent organic group $R_{11}$ is represented by formula (5-a-i):

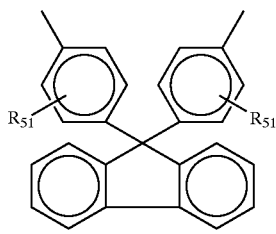

(5-a-i)

wherein each $R_{51}$ independently represents hydrogen or alkyl;

$X_{11}$ is oxygen; and $R_{14}$ is a (meth)acrylic acid residue.

8. The sulfur-containing unsaturated carboxylate compound as claimed in claim 1 where the bivalent organic group $R_{11}$ is represented by formula (6-a-i):

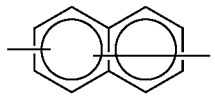

(6-a-i)

$X_{11}$ is oxygen or —COO—; and $R_{14}$ is a (meth)acrylic acid residue.

9. A polymerizable composition comprising the sulfur-containing unsaturated carboxylate compound as claimed in claim 1.

10. A polymerizable composition comprising the sulfur-containing unsaturated carboxylate compound as claimed in claim 3.

11. A polymerizable composition comprising the sulfur-containing unsaturated carboxylate compound as claimed in claim 4.

12. A polymerizable composition comprising the sulfur-containing unsaturated carboxylate compound as claimed in claim 5.

13. A polymerizable composition comprising the sulfur-containing unsaturated carboxylate compound as claimed in claim 6.

14. A polymerizable composition comprising the sulfur-containing unsaturated carboxylate compound as claimed in claim 7.

15. A polymerizable composition comprising the sulfur-containing unsaturated carboxylate compound as claimed in claim 8.

16. A cured product prepared by polymerizing the polymerizable composition as claimed in claim 9.

17. A cured product prepared by polymerizing the polymerizable composition as claimed in claim 10.

18. A cured product prepared by polymerizing the polymerizable composition as claimed in claim 11.

19. A cured product prepared by polymerizing the polymerizable composition as claimed in claim 12.

20. A cured product prepared by polymerizing the polymerizable composition as claimed in claim 13.

21. A cured product prepared by polymerizing the polymerizable composition as claimed in claim 14.

22. A cured product prepared by polymerizing the polymerizable composition as claimed in claim 15.

23. An optical component consisting of the cured product as claimed in claim 16.

24. An optical component consisting of the cured product as claimed in claim 17.

25. An optical component consisting of the cured product as claimed in claim 18.

26. An optical component consisting of the cured product as claimed in claim 19.

27. An optical component consisting of the cured product as claimed in claim 20.

28. An optical component consisting of the cured product as claimed in claim 21.

29. An optical component consisting of the cured product as claimed in claim 22.

* * * * *